US012269899B2

(12) United States Patent
Ji

(10) Patent No.: US 12,269,899 B2
(45) Date of Patent: Apr. 8, 2025

(54) PEPTIDOMIMETIC INHIBITORS OF β-CATENIN/Tcf PROTEIN-PROTEIN INTERACTION

(71) Applicant: H. LEE MOFFITT CANCER CENTER AND RESEARCH INSTITUTE, INC., Tampa, FL (US)

(72) Inventor: Haitao Ji, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 806 days.

(21) Appl. No.: 17/311,623

(22) PCT Filed: Dec. 6, 2019

(86) PCT No.: PCT/US2019/064929
§ 371 (c)(1),
(2) Date: Jun. 7, 2021

(87) PCT Pub. No.: WO2020/118179
PCT Pub. Date: Jun. 11, 2020

(65) Prior Publication Data
US 2022/0024977 A1 Jan. 27, 2022

Related U.S. Application Data

(60) Provisional application No. 62/776,726, filed on Dec. 7, 2018.

(51) Int. Cl.
*C07K 5/10* (2006.01)
*A61P 35/00* (2006.01)
*C07K 5/113* (2006.01)
*A61K 38/00* (2006.01)

(52) U.S. Cl.
CPC ............ *C07K 5/1021* (2013.01); *A61P 35/00* (2018.01); *A61K 38/00* (2013.01)

(58) Field of Classification Search
CPC ....... C07K 5/1021; A61P 35/00; A61K 38/00; C07D 209/42; C07D 403/12; C07D 405/12
See application file for complete search history.

(56) References Cited

U.S. PATENT DOCUMENTS

| | | | |
|---|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,960,648 B2 | 11/2005 | Bonny |
| 9,616,047 B2 | 4/2017 | Bode et al. |
| 2002/0035243 A1 | 3/2002 | Imfeld et al. |
| 2002/0120100 A1 | 8/2002 | Bonny |
| 2003/0032594 A1 | 2/2003 | Bonny |

FOREIGN PATENT DOCUMENTS

WO 2012040459 A2 3/2012

OTHER PUBLICATIONS

Huang et al, ACS Chemical Biology, 2014, 9(1), 193-201 (Year: 2014).*
Shroff et al (Bioorganic & Medicinal Chemistry Letters, 1998, 8(13), 1601-1606) (Year: 1998).*
Wang et al (J.Med.Chem.,2019,62,3617-3635) (Year: 2019).*
International Search Report and Written Opinion in PCT/US2019/064929. Mailed Feb. 25, 2020. 9 pages.
Huang et al., "Targeting the Tcf4 G13ANDE17 binding site to selctively disrupt beta-Catenin/T-Cell factor protein- protein interactions" ACS Chemical Biology. Nov. 5, 2013. vol 9, pp. 193-201.
Akhmetshina, A.; Palumbo, K.; Dees, C.; Bergmann, C.; Venalis, P.; Zerr, P.; Horn, A.; Kireva, T.; Beyer, C.; Zwerina, J.; Schneider, H.; Sadowski, A.; Riener, M. O.; MacDougald, O. A.; Distler, O.; Schett, G.; Distler, J. H., Activation of canonical Wnt signalling is required for TGF-beta-mediated fibrosis. Nature communications 2012, 3, 735.
Ambartsumian, N. S.; Grigorian, M. S.; Larsen, I. F.; Karlstrøm, O.; Sidenius, N.; Rygaard, J.; Georgiev, G.; Lukanidin, E., Metastasis of mammary carcinomas in GRS/A hybrid mice transgenic for the mts1 gene. Oncogene 1996, 13 (8), 1621-30.
Ashihara, E.; Kawata, E.; Nakagawa, Y.; Shimazaski, C.; Kuroda, J.; Taniguchi, K.; Uchiyama, H.; Tanaka, R.; Yokota, A.; Takeuchi, M.; Kamitsuji, Y.; Inaba, T.; Taniwaki, M.; Kimura, S.; Maekawa, T., beta-catenin small interfering RNA successfully suppressed progression of multiple myeloma in a mouse model. Clinical cancer research : an official journal of the American Association for Cancer Research 2009, 15 (8), 2731-8.
Bafico, A.; Liu, G.; Goldin, L.; Harris, V.; Aaronson, S. A., An autocrine mechanism for constitutive Wnt pathway activation in human cancer cells. Cancer cell 2004, 6 (5), 497-506.
Ban, F.; Leblanc, E.; Li, H.; Munuganti, R. S.; Frewin, K.; Rennie, P. S.; Cherkasov, A., Discovery of 1H-indole-2-carboxamides as novel inhibitors of the androgen receptor binding function 3 (BF3). Journal of medicinal chemistry 2014, 57 (15), 6867-72.
Banoglu, E.; Jha, G. G.; King, R. S., Hepatic microsomal metabolism of indole to indoxyl, a precursor of indoxyl sulfate. European journal of drug metabolism and pharmacokinetics 2001, 26 (4), 235-40.
Barker, N.; Ridgway, R. A.; van Es, J. H.; van de Wetering, M.; Begthel, H.; van den Born, M.; Danenberg, E.; Clarke, A. R.; Sansom, O. J.; Clevers, H., Crypt stem cells as the cells-of-origin of intestinal cancer. Nature 2009, 457 (7229), 608-11.
Beiter, K.; Hiendlmeyer, E.; Brabletz, T.; Hlubek, F.; Haynl, A.; Knoll, C.; Kirchner, T.; Jung, A., beta-Catenin regulates the expression of tenascin-C in human colorectal tumors. Oncogene 2005, 24 (55), 8200-8204.

(Continued)

*Primary Examiner* — Sudhakar Katakam
(74) *Attorney, Agent, or Firm* — Meunier Carlin & Curfman LLC

(57) ABSTRACT

Disclosed are inhibitors for the β-catenin/T-cell factor interaction. The inhibitors are selective for β-catenin/T-cell factor over β-catenin/phosphocadherin, and β-catenin/phosphoAPC interactions. Methods of using the disclosed compounds to treat cancer are also disclosed.

18 Claims, 2 Drawing Sheets

(56) References Cited

OTHER PUBLICATIONS

Brack, A. S.; Conboy, M. J.; Roy, S.; Lee, M.; Kuo, C. J.; Keller, C.; Rando, T. A., Increased Wnt signaling during aging alters muscle stem cell fate and increases fibrosis. Science (New York, N.Y.) 2007, 317 (5839), 807-10.
Catrow, J. L.; Zhang, Y.; Zhang, M.; Ji, H., Discovery of Selective Small-Molecule Inhibitors for the beta-Catenin/T-Cell Factor Protein-Protein Interaction through the Optimization of the Acyl Hydrazone Moiety. Journal of medicinal chemistry 2015, 58 (11), 4678-92.
Choi, H. J.; Huber, A. H.; Weis, W. I., Thermodynamics of beta-catenin-ligand interactions: the roles of the N- and C-terminal tails in modulating binding affinity. The Journal of biological chemistry 2006, 281 (2), 1027-38.
Clevers, H.; Nusse, R., Wnt/beta-catenin signaling and disease. Cell 2012, 149 (6), 1192-205.
Curcio, A.; Sasso, O.; Melisi, D.; Nieddu, M.; La Rana, G.; Russo, R.; Gavini, E.; Boatto, G.; Abignente, E.; Calignano, A.; Rimoli, M. G., Galactosyl prodrug of ketorolac: synthesis, stability, and pharmacological and pharmacokinetic evaluations. Journal of medicinal chemistry 2009, 52 (12), 3794-800.
Davies, M. P.; Rudland, P. S.; Robertson, L.; Parry, E. W.; Jolicoeur, P.; Barraclough, R., Expression of the calcium-binding protein S100A4 (p9Ka) in MMTV-neu transgenic mice induces metastasis of mammary tumours. Oncogene 1996, 13 (8), 1631-1637.
De Sa Alves, F. R.; Barreiro, E. J.; Fraga, C. A., From nature to drug discovery: the indole scaffold as a 'privileged structure'. Mini reviews in medicinal chemistry 2009, 9 (7), 782-93.
Dietrich, L.; Rathmer, B.; Ewan, K.; Bange, T.; Heinrichs, S.; Dale, T. C.; Schade, D.; Grossmann, T. N., Cell Permeable Stapled Peptide Inhibitor of Wnt Signaling that Targets beta-Catenin Protein-Protein Interactions. Cell chemical biology 2017, 24 (8), 958-968. e5.
Ding, Y.; Shen, S.; Lino, A. C.; Curotto de Lafaille, M. A.; Lafaille, J. J., Beta-catenin stabilization extends regulatory T cell survival and induces anergy in nonregulatory T cells. Nature medicine 2008, 14 (2), 162-9.
Dow, L. E.; O'Rourke, K. P.; Simon, J.; Tschaharganeh, D. F.; van Es, J. H.; Clevers, H.; Lowe, S. W., Apc Restoration Promotes Cellular Differentiation and Reestablishes Crypt Homeostasis in Colorectal Cancer. Cell 2015, 161 (7), 1539-1552.
Eklof Spink, K.; Fridman, S. G.; Weis, W. I., Molecular mechanisms of beta-catenin recognition by adenomatous polyposis coli revealed by the structure of an APC-beta-catenin complex. The EMBO journal 2001, 20 (22), 6203-12.
Emami, K. H.; Nguyen, C.; Ma, H.; Kim, D. H.; Jeong, K. W.; Eguchi, M.; Moon, R. T.; Teo, J. L.; Kim, H. Y.; Moon, S. H.; Ha, J. R.; Kahn, M., A small molecule inhibitor of beta-catenin/CREB-binding protein transcription [corrected]. Proceedings of the National Academy of Sciences of the United States of America 2004, 101 (34), 12682-7.
Fang, L.; Zhu, Q.; Neuenschwander, M.; Specker, E.; Wulf-Goldenberg, A.; Weis, W. I.; von Kries, J. P.; Birchmeier, W., A Small-Molecule Antagonist of the beta-Catenin/TCF4 Interaction Blocks the Self-Renewal of Cancer Stem Cells and Suppresses Tumorigenesis. Cancer research 2016, 76 (4), 891-901.
Gonsalves, F. C.; Klein, K.; Carson, B. B.; Katz, S.; Ekas, L. A.; Evans, S.; Nagourney, R.; Cardozo, T.; Brown, A. M.; DasGupta, R., An RNAi-based chemical genetic screen identifies three small-molecule inhibitors of the Wnt/wingless signaling pathway. Proceedings of the National Academy of Sciences of the United States of America 2011, 108 (15), 5954-63.
Graham, T. A.; Ferkey, D. M.; Mao, F.; Kimelman, D.; Xu, W., Tcf4 can specifically recognize beta-catenin using alternative conformations. Nature structural biology 2001, 8 (12), 1048-52.
Grossmann, T. N.; Yeh, J. T.; Bowman, B. R.; Chu, Q.; Moellering, R. E.; Verdine, G. L., Inhibition of oncogenic Wnt signaling through direct targeting of beta-catenin. Proceedings of the National Academy of Sciences of the United States of America 2012, 109 (44), 17942-7.
Ha, N. C.; Tonozuka, T.; Stamos, J. L.; Choi, H. J.; Weis, W. I., Mechanism of phosphorylation-dependent binding of APC to beta-catenin and its role in beta-catenin degradation. Molecular cell 2004, 15 (4), 511-21.
Halbedl, S.; Kratzer, M. C.; Rahm, K.; Crosta, N.; Masters, K. S.; Zippert, J.; Brase, S.; Gradl, D., Synthesis of novel inhibitors blocking Wnt signaling downstream of beta-catenin. FEBS letters 2013, 587 (5), 522-7.
Howe, L. R.; Watanabe, O.; Leonard, J.; Brown, A. M., Twist is up-regulated in response to Wnt1 and inhibits mouse mammary cell differentiation. Cancer research 2003, 63 (8), 1906-1913.
Hsieh, T. H.; Hsu, C. Y.; Tsai, C. F.; Chiu, C. C.; Liang, S. S.; Wang, T. N.; Kuo, P. L.; Long, C. Y.; Tsai, E. M., A novel cell-penetrating peptide suppresses breast tumorigenesis by inhibiting beta-catenin/LEF-1 signaling. Scientific reports 2016, 6, 19156.
Huang, Z.; Zhang, M.; Burton, S. D.; Katsakhyan, L. N.; Ji, H., Targeting the Tcf4 G13ANDE17 binding site to selectively disrupt beta-catenin/T-cell factor protein-protein interactions. ACS chemical biology 2014, 9 (1), 193-201.
Huber, A. H.; Weis, W. I., The structure of the beta-catenin/E-cadherin complex and the molecular basis of diverse ligand recognition by beta-catenin. Cell 2001, 105 (3), 391-402.
Hulsken, J.; Birchmeier, W.; Behrens, J., E-cadherin and APC compete for the interaction with beta-catenin and the cytoskeleton. The Journal of cell biology 1994, 127 (6 Pt 2), 2061-9.
Jenkinson, S. R.; Barraclough, R.; West, C. R.; Rudland, P. S., S100A4 regulates cell motility and invasion in an in vitro model for breast cancer metastasis. British journal of cancer 2004, 90 (1), 253-262.
Keerthivasan, S.; Aghajani, K.; Dose, M.; Molinero, L.; Khan, M. W.; Venkateswaran, V.; Weber, C.; Emmanuel, A. O.; Sun, T.; Bentrem, D. J.; Mulcahy, M.; Keshavarzian, A.; Ramos, E. M.; Blatner, N.; Khazaie, K.; Gounari, F., beta-Catenin promotes colitis and colon cancer through imprinting of proinflammatory properties in T cells. Science translational medicine 2014, 6 (225), 225ra28.
Kim, J. S.; Crooks, H.; Foxworth, A.; Waldman, T., Proof-of-principle: oncogenic beta-catenin is a valid molecular target for the development of pharmacological inhibitors. Molecular cancer therapeutics 2002, 1 (14), 1355-9.
Kondreddi, R. R.; Jiricek, J.; Rao, S. P.; Lakshminarayana, S. B.; Camacho, L. R.; Rao, R.; Herve, M.; Bifani, P.; Ma, N. L.; Kuhen, K.; Goh, A.; Chatterjee, A. K.; Dick, T.; Diagana, T. T.; Manjunatha, U. H.; Smith, P. W., Design, synthesis, and biological evaluation of indole-2-carboxamides: a promising class of antituberculosis agents. Journal of medicinal chemistry 2013, 56 (21), 8849-59.
Lancaster, M. A.; Louie, C. M.; Silhavy, J. L.; Sintasath, L.; Decambre, M.; Nigam, S. K.; Willert, K.; Gleeson, J. G., Impaired Wnt-beta-catenin signaling disrupts adult renal homeostasis and leads to cystic kidney ciliopathy. Nature medicine 2009, 15 (9), 1046-54.
Lepourcelet, M.; Chen, Y. N.; France, D. S.; Wang, H.; Crews, P.; Petersen, F.; Bruseo, C.; Wood, A. W.; Shivdasani, R. A., Small-molecule antagonists of the oncogenic Tcf/beta-catenin protein complex. Cancer cell 2004, 5 (1), 91-102.
Liljebris, C.; Larsen, S. D.; Ogg, D.; Palazuk, B. J.; Bleasdale, J. E., Investigation of potential bioisosteric replacements for the carboxyl groups of peptidomimetic inhibitors of protein tyrosine phosphatase 1B: identification of a tetrazole-containing inhibitor with cellular activity. Journal of medicinal chemistry 2002, 45 (9), 1785-98.
Lloyd, B. H.; Platt-Higgins, A.; Rudland, P. S.; Barraclough, R., Human S100A4 (p9Ka) induces the metastatic phenotype upon benign tumour cells. Oncogene 1998, 17 (4), 465-473.
Lu, D.; Zhao, Y.; Tawatao, R.; Cottam, H. B.; Sen, M.; Leoni, L. M.; Kipps, T. J.; Corr, M.; Carson, D. A., Activation of the Wnt signaling pathway in chronic lymphocytic leukemia. Proceedings of the National Academy of Sciences of the United States of America 2004, 101 (9), 3118-23.
Malanchi, I.; Peinado, H.; Kassen, D.; Hussenet, T.; Metzger, D.; Chambon, P.; Huber, M.; Hohl, D.; Cano, A.; Birchmeier, W.;

(56) References Cited

OTHER PUBLICATIONS

Huelsken, J., Cutaneous cancer stem cell maintenance is dependent on beta-catenin signalling. Nature 2008, 452 (7187), 650-3.
Nusse, R.; Clevers, H., Wnt/beta-Catenin Signaling, Disease, and Emerging Therapeutic Modalities. Cell 2017, 169 (6), 985-999.
Omer, C. A.; Miller, P. J.; Diehl, R. E.; Kral, A. M., Identification of Tcf4 residues involved in high-affinity beta-catenin binding. Biochemical and biophysical research communications 1999, 256 (3), 584-90.
Orsulic, S.; Huber, O.; Aberle, H.; Arnold, S.; Kemler, R., E-cadherin binding prevents beta-catenin nuclear localization and beta-catenin/LEF-1-mediated transactivation. Journal of cell science 1999, 112 ( Pt 8), 1237-45.
Oskarsson, T.; Acharyya, S.; Zhang, X. H.-F.; Vanharanta, S.; Tavazoie, S. F.; Morris, P. G.; Downey, R. J.; Manova-Todorova, K.; Brogi, E.; Massagué, J., Breast cancer cells produce tenascin C as a metastatic niche component to colonize the lungs. Nature medicine 2011, 17 (7), 867-874.
Piscitelli, F.; Ligresti, A.; La Regina, G.; Coluccia, A.; Morera, L.; Allara, M.; Novellino, E.; Di Marzo, V.; Silvestri, R., Indole-2-carboxamides as allosteric modulators of the cannabinoid CB(1) receptor. Journal of medicinal chemistry 2012, 55 (11), 5627-31.
Poy, F.; Lepourcelet, M.; Shivdasani, R. A.; Eck, M. J., Structure of a human Tcf4-beta-catenin complex. Nature structural biology 2001, 8 (12), 1053-7.
Rautio, J.; Meanwell, N. A.; Di, L.; Hageman, M. J., The expanding role of prodrugs in contemporary drug design and development. Nature reviews. Drug discovery 2018, 17 (8), 559-587.
Ravindranath, A.; Yuen, H.-F .; Chan, K.-K.; Grills, C.; Fennell, D. A.; Lappin, T. R.; El-Tanani, M., Wnt-beta-catenin-Tcf-4 signalling-modulated invasiveness is dependent on osteopontin expression in breast cancer. British journal of cancer 2011, 105 (4), 542-551.
Sampietro, J.; Dahlberg, C. L.; Cho, U. S.; Hinds, T. R.; Kimelman, D.; Xu, W., Crystal structure of a beta-catenin/BCL9/Tcf4 complex. Molecular cell 2006, 24 (2), 293-300.
Scheel, C.; Eaton, E. N.; Li, S. H.; Chaffer, C. L.; Reinhardt, F.; Kah, K. J.; Bell, G.; Guo, W.; Rubin, J.; Richardson, A. L.; Weinberg, R. A., Paracrine and autocrine signals induce and maintain mesenchymal and stem cell states in the breast. Cell 2011, 145 (6), 926-40.
Schneider, J. A.; Craven, T. W.; Kasper, A. C.; Yun, C.; Haugbro, M.; Briggs, E. M.; Svetlov, V.; Nudler, E.; Knaut, H.; Bonneau, R.; Garabedian, M. J.; Kirshenbaum, K.; Logan, S. K., Design of Peptoid-peptide Macrocycles to Inhibit the beta-catenin TCF Interaction in Prostate Cancer. Nature communications 2018, 9 (1), 4396.
Scholer-Dahirel, A.; Schlabach, M. R.; Loo, A.; Bagdasarian, L.; Meyer, R.; Guo, R.; Woolfenden, S.; Yu, K. K.; Markovits, J.; Killary, K.; Sonkin, D.; Yao, Y. M.; Warmuth, M.; Sellers, W. R.; Schlegel, R.; Stegmeier, F.; Mosher, R. E.; McLaughlin, M. E., Maintenance of adenomatous polyposis coli (APC)-mutant colorectal cancer is dependent on Wnt/beta-catenin signaling. Proceedings of the National Academy of Sciences of the United States of America 2011, 108 (41), 17135-40.
Shin, S. H.; Lim, D. Y.; Reddy, K.; Malakhova, M.; Liu, F.; Wang, T.; Song, M.; Chen, H.; Bae, K. B.; Ryu, J.; Liu, K.; Lee, M. H.; Bode, A. M.; Dong, Z., A Small Molecule Inhibitor of the beta-Catenin-TCF4 Interaction Suppresses Colorectal Cancer Growth In Vitro and In Vivo. EBioMedicine 2017, 25, 22-31.
Spranger, S.; Bao, R.; Gajewski, T. F., Melanoma-intrinsic beta-catenin signalling prevents anti-tumour immunity. Nature 2015, 523 (7559), 231-5.
Spranger, S.; Dai, D.; Horton, B.; Gajewski, T. F., Tumor-Residing Batf3 Dendritic Cells Are Required for Effector T Cell Trafficking and Adoptive T Cell Therapy. Cancer cell 2017, 31 (5), 711-723.e4.
Sravanthi, T. V.; Manju, S. L., Indoles—A promising scaffold for drug development. European journal of pharmaceutical sciences : official journal of the European Federation for Pharmaceutical Sciences 2016, 91, 1-10.
Stec, J.; Onajole, O. K.; Lun, S.; Guo, H.; Merenbloom, B.; Vistoli, G.; Bishai, W. R.; Kozikowski, A. P., Indole-2-carboxamide-based MmpL3 Inhibitors Show Exceptional Antitubercular Activity in an Animal Model of Tuberculosis Infection. Journal of medicinal chemistry 2016, 59 (13), 6232-47.
Stein, U.; Arlt, F.; Walther, W.; Smith, J.; Waldman, T.; Harris, E. D.; Mertins, S. D.; Heizmann, C. W.; Allard, D.; Birchmeier, W.; Schlag, P. M.; Shoemaker, R. H., The metastasis-associated gene S100A4 is a novel target of beta-catenin/T-cell factor signaling in colon cancer. Gastroenterology 2006, 131 (5), 1486-1500.
Sukhdeo, K.; Mani, M.; Zhang, Y.; Dutta, J.; Yasui, H.; Rooney, M. D.; Carrasco, D. E.; Zheng, M.; He, H.; Tai, Y. T.; Mitsiades, C.; Anderson, K. C.; Carrasco, D. R., Targeting the beta-catenin/TCF transcriptional complex in the treatment of multiple myeloma. Proceedings of the National Academy of Sciences of the United States of America 2007, 104 (18), 7516-21.
Sun, J.; Weis, W. I., Biochemical and structural characterization of beta-catenin interactions with nonphosphorylated and CK2-phosphorylated Lef-1. Journal of molecular biology 2011, 405 (2), 519-30.
Tian, W.; Han, X.; Yan, M.; Xu, Y.; Duggineni, S.; Lin, N.; Luo, G.; Li, Y. M.; Han, X.; Huang, Z.; An, J., Structure-based discovery of a novel inhibitor targeting the beta-catenin/Tcf4 interaction. Biochemistry 2012, 51 (2), 724-31.
Toyoizumi, et al., "Combined therapy with chemotherapeutic agents and herpes simplex virus type IICP34.5 mutant (HSV-1716) in human non-small cell lung cancer," Human Gene Therapy, 1999, 10(18):3013.
Trosset, J. Y.; Dalvit, C.; Knapp, S.; Fasolini, M.; Veronesi, M.; Mantegani, S.; Gianellini, L. M.; Catana, C.; Sundstrom, M.; Stouten, P. F.; Moll, J. K., Inhibition of protein-protein interactions: the discovery of druglike beta-catenin inhibitors by combining virtual and biophysical screening. Proteins 2006, 64 (1), 60-7.
van de Wetering, M.; Sancho, E.; Verweij, C.; de Lau, W.; Oving, I.; Hurlstone, A.; van der Horn, K.; Batlle, E.; Coudreuse, D.; Haramis, A. P.; Tjon-Pon-Fong, M.; Moerer, P.; van den Born, M.; Soete, G.; Pals, S.; Eilers, M.; Medema, R.; Clevers, H., The beta-catenin/TCF-4 complex imposes a crypt progenitor phenotype on colorectal cancer cells. Cell 2002, 111 (2), 241-50.
Wang, W.; Liu, H.; Wang, S.; Hao, X.; Li, L., A diterpenoid derivative 15-oxospiramilactone inhibits Wnt/beta-catenin signaling and colon cancer cell tumorigenesis. Cell research 2011, 21 (5), 730-40.
Wu, Z.-Q.; Li, X.-Y.; Hu, C. Y.; Ford, M.; Kleer, C. G.; Weiss, S. J., Canonical Wnt signaling regulates Slug activity and links epithelial-mesenchymal transition with epigenetic Breast Cancer 1, Early Onset (BRCA1) repression. Proceedings of the National Academy of Sciences of the United States of America 2012, 109 (41), 16654-16659.
Xing, Y.; Clements, W. K.; Le Trong, I .; Hinds, T. R.; Stenkamp, R.; Kimelman, D.; Xu, W., Crystal structure of a beta-catenin/APC complex reveals a critical role for APC phosphorylation in APC function. Molecular cell 2004, 15 (4), 523-33.
Yeung, J.; Esposito, M. T.; Gandillet, A.; Zeisig, B. B.; Griessinger, E.; Bonnet, D.; So, C. W., beta-Catenin mediates the establishment and drug resistance of MLL leukemic stem cells. Cancer cell 2010, 18 (6), 606-18.
Yook, J. I.; Li, X.-Y.; Ota, I.; Fearon, E. R.; Weiss, S. J., Wnt-dependent regulation of the E-cadherin repressor snail. The Journal of biological chemistry 2005, 280 (12), 11740-11748.
Yook, J. I.; Li, X.-Y.; Ota, I.; Hu, C.; Kim, H. S.; Kim, N. H.; Cha, S. Y.; Ryu, J. K.; Choi, Y. J.; Kim, J.; Fearon, E. R.; Weiss, S. J., A Wnt-Axin2-GSK3beta cascade regulates Snail1 activity in breast cancer cells. Nature cell biology 2006, 8 (12), 1398-1406.
Yu, B.; Huang, Z.; Zhang, M.; Dillard, D. R.; Ji, H., Rational design of small-molecule inhibitors for beta-catenin/T-cell factor protein-protein interactions by bioisostere replacement. ACS chemical biology 2013, 8 (3), 524-9.
Zhang, M.; Catrow, J. L.; Ji, H., High-Throughput Selectivity Assays for Small-Molecule Inhibitors of beta-Catenin/T-Cell Factor Protein-Protein Interactions. ACS medicinal chemistry letters 2013, 4 (2), 306-11.
Zhang, M.; Huang, Z.; Yu, B.; Ji, H., New homogeneous high-throughput assays for inhibitors of beta-catenin/Tcf protein-protein interactions. Analytical biochemistry 2012, 424 (1), 57-63.

(56) References Cited

OTHER PUBLICATIONS

International Preliminary Report on Patentability, issued for Application No. PCT/US2019/064929, dated Jun. 17, 2021.

* cited by examiner

PEPTIDOMIMETIC INHIBITORS OF β-CATENIN/Tcf PROTEIN-PROTEIN INTERACTION

CROSS-REFERENCE TO RELATED APPLICATIONS

This application is a United States National Phase Patent Application of International Patent Application Number PCT/US2019/064929, filed on Dec. 6, 2019, which claims benefit of U.S. Provisional Application No. 62/776,726 filed Dec. 7, 2018, which are hereby incorporated herein by reference in their entireties.

BACKGROUND

The Wnt/β-catenin signaling pathway plays a significant role in regulation of cell proliferation, differentiation, and survival. The aberrant activation of Wnt/β-catenin signaling has been implicated in the initiation and progression of many cancers, and fibroses. For instance, loss of adenomatous polyposis coli (APC) function could lead to the inappropriate stabilization of β-catenin and the formation of the constitutive complex between β-catenin and the T-cell factor (Tcf)/lymphoid enhancer-binding factor (Lef) family of transcriptional factors to transcribe specific Wnt target genes that produce crypt progenitor-like cells in the surface intestinal epithelium, which resulted in sporadic colorectal cancer. The autocrine activation of Wnt ligands can also stabilize β-catenin into the dephosphorylated state and result in an increased level of nuclear β-catenin to interact with Tcf/Lef to induce overexpression of Wnt target genes and cause initiation and progression of triple negative breast cancers (TNBCs). The hyperactivation of canonical Wnt signaling was also detected in cancer stem cells, which control tumor growth, seed metastases, and result in cancer recurrence after remission. In addition, the activation of β-catenin signaling was demonstrated to exclude CD8+ T cells from the tumor microenvironment and promote intratumoral regulator T cell (Treg) survival and infiltration, and thus impaired antitumor immunity. Therefore, the suppression of this signaling pathway holds great promise to design new targeted cancer therapy. Further biological studies demonstrated the formation of β-catenin/Tcf complex in the cell nucleus is the penultimate step of the canonical Wnt signaling pathway and the activation of canonical Wnt target genes is dependent on the formation of this complex. Therefore, the β-catenin/Tcf PPI emerges as an appealing therapeutic target to suppress the hyperactive Wnt/β-catenin signaling.

Significant efforts have been made to identify inhibitors for the β-catenin/Tcf PPI. Extensive compound screening has identified several small-molecule inhibitors for this PPI. The binding mode of these hit compounds remained unknown, making it difficult to further optimize these compounds. The large peptides or peptide-based macrocycles have also been designed as β-catenin/Tcf inhibitors. Hydrocarbon-stapled peptide, aStAx-35, designed based on the Axin sequence and the phage display result, was reported to bind with the Axin-binding site of β-catenin and inhibit the β-catenin/Tcf PPI. Further design offered a more cell-permeable derivative, NLS-StAx-h, by substituting all six arginine residues with homoarginine and introducing nuclear localization sequence (NLS) to the N-terminal end. Recently, Logan and coworkers disclosed the design of peptoid-peptide macrocycles as β-catenin/Tcf inhibitors, which showed promising efficacy in prostate cancer models. In the previous studies, our group reported small-molecule inhibitors for the β-catenin/Tcf PPI using different strategies. What are needed are new, potent and selective inhibitors for the β-catenin/Tcf PPI. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. The compounds can have a structure represented by Formula I or I-A below:

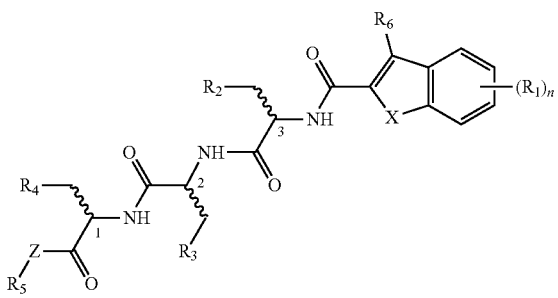

Formula I

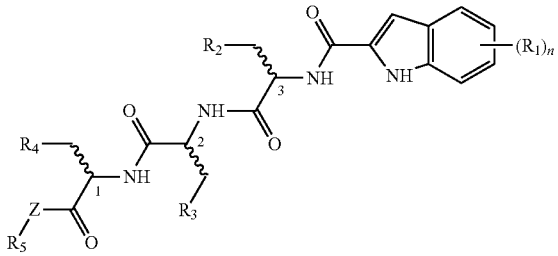

Formula I-A wherein

Z is selected from O or N—$R_a$, wherein $R_a$ is selected from hydrogen or $C_1$-$C_3$ alkyl;

$R_1$ is absent or independently for each occurrence, selected from halogen, $C_1$-$C_3$ alkyl, $C_1$-$C_3$ alkoxy, $C_1$-$C_3$ haloalkyl, $C_1$-$C_3$ haloalkoxy, $C_1$-$C_3$ alkoxy, hydroxyl, amino, cyano, nitro, or isocyano;

$R_2$ is $C_1$-$C_6$ alkyl, $C_3$-$C_{10}$ cycloalkyl, a $C_2$-$C_8$ heterocloalkyl, $C_5$-$C_{10}$ aryl, $C_2$-$C_8$ heteroaryl, alkylaryl, alkylheteroaryl, wherein $R_2$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ and $R_4$ are independently halogen, hydroxyl, amino, —CN, $C_1$-$C_6$ alkyl, $C_1$-$C_6$ haloalkyl, —R'$CO_2$H, —R'CONH$_2$, —R'CONHR", —R'CONR"R'", —R'$CO_2$R", —R'$SO_3$H, —R'$SO_2$NHCOR", —R'CONHSO$_2$R", —R'CONHOH, —R'CONHCN, —R'$SO_2$NHR", $C_3$-$C_6$ cycloalkyl, $C_1$-$C_8$ heterocloalkyl, $C_5$-$C_{10}$ aryl, $C_1$-$C_8$ heteroaryl, wherein $R_3$ and $R_4$ are optionally substituted with halogen, hydroxyl, amino, cyano, nitro, isocyano, carboxyl, hydroxyl, alkyl, alkoxy, alkenyl, haloalkyl, haloalkoxy, cyclopropyl, and wherein R', R", and R'" are independently absent or is hydrogen, halogen, $C_1$-$C_6$ alkyl, $C_1$-$C_6$ alkoxy, $C_1$-$C_6$ haloalkyl;

$R_5$ is $C_1$-$C_6$ alkyl, $C_1$-$C_6$ alkoxy, $C_3$-$C_8$ cycloalkyl, a $C_1$-$C_7$ heterocycloalkyl, $C_5$-$C_{10}$ aryl, alkylaryl, $C_1$-$C_8$ heteroaryl, alkylheteroaryl, wherein $R_5$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_6$ is hydrogen, $C_1$-$C_6$ alkyl, $C_1$-$C_6$ alkoxy, halogen, or $C_1$-$C_3$ haloalkyl, n is 0, 1, 2, 3, or 4;

wherein the positions labeled 1, 2, and 3 indicate chiral positions; or a pharmaceutically acceptable salt or ester thereof.

Pharmaceutical composition comprising a therapeutically effective amount of a compound described herein or a pharmaceutically acceptable salt thereof, and a pharmaceutically acceptable carrier are also disclosed.

In specific aspects, the disclosed subject matter relates to cancer therapy and to anti-cancer compounds. More specifically, the subject matter disclosed herein relates to inhibitors for the β-catenin/T-cell factor interaction. Further, the subject matter disclosed herein relates to inhibitors that are selective for β-catenin/T-cell factor interactions over β-catenin/phosphocadherin, and β-catenin/phosphoAPC interactions. Also disclosed are methods of inhibiting the β-catenin/T-cell factor interaction, as well as methods of treating certain cancers.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

FIG. 3B shows Matrigel invasion assays showed that inhibitor 56 (10 μM) inhibited invasion of human TNBC MDA-MB-231 cells. Control, 0.2% DMSO in 10% FBS. ICG-001 (5 μM) was assessed in parallel. Each set of data is expressed as mean±standard deviation (n=3).

DETAILED DESCRIPTION

Figure 1:
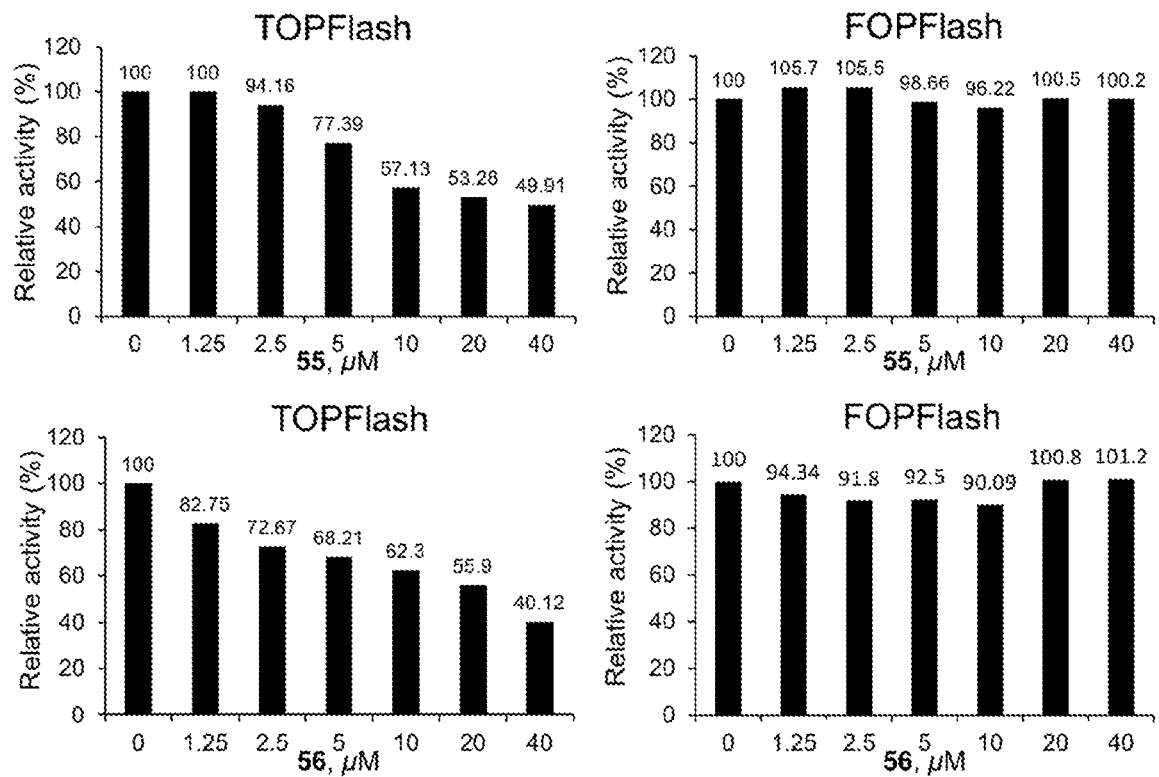
FIG. 1 shows graphs demonstrating Wnt-responsive TOPFlash and FOPFlash luciferase reporter assay results of inhibitors 55 and 56 in β-catenin activated HEK293 cells.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O—.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R—) or (S—) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R—) form is equivalent, for compounds that undergo epimerization in vivo, to administration of the compound in its (S—) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases.

Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Disclosed herein are compounds having Formula I,

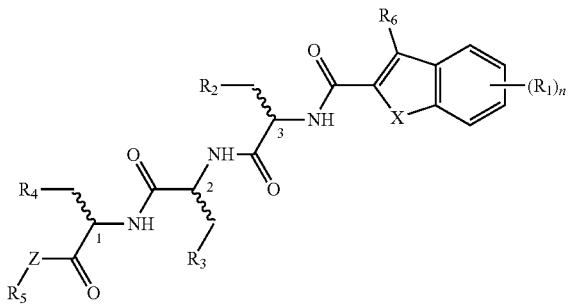

Formula I wherein

X is selected from O or N—$R_a$, wherein $R_a$ is selected from hydrogen or $C_1$-$C_3$ alkyl;

Z is selected from O or N—$R_a$, wherein $R_a$ is selected from hydrogen or $C_1$-$C_3$ alkyl;

$R_1$ is absent or independently for each occurrence, selected from halogen, $C_1$-$C_3$ alkyl, $C_1$-$C_3$ alkoxy, $C_1$-$C_3$ haloalkyl, $C_1$-$C_3$ haloalkoxy, $C_1$-$C_3$ alkoxy, hydroxyl, amino, cyano, nitro, or isocyano;

$R_2$ is $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, alkylaryl, alkylheteroaryl, wherein $R_2$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ and $R_4$ are independently halogen, hydroxyl, amino, —CN, $C_1$-$C_6$ alkyl, $C_1$-$C_6$ haloalkyl, —R'CO$_2$H, —R'CONH$_2$, —R'CONHR", —R'CONR"R''', —R'CO$_2$R", —R'SO$_3$H, —R'SO$_2$NHCOR", —R'CONHSO$_2$R", —R'CONHOH, —R'CONHCN, —R'SO$_2$NHR", $C_3$-$C_6$ cycloalkyl, $C_1$-$C_8$ heterocycloalkyl, $C_5$-$C_{10}$ aryl, $C_1$-$C_8$ heteroaryl, wherein $R_3$ and $R_4$ are optionally substituted with halogen, hydroxyl, amino, cyano, nitro, isocyano, carboxyl, hydroxyl, alkyl, alkoxy, alkenyl, haloalkyl, haloalkoxy, cyclopropyl, and wherein R', R", and R''' are independently absent or is hydrogen, halogen, $C_1$-$C_6$ alkyl, $C_1$-$C_6$ alkoxy, $C_1$-$C_6$ haloalkyl;

$R_5$ is $C_1$-$C_6$ alkyl, $C_1$-$C_6$ alkoxy, $C_3$-$C_8$ cycloalkyl, a $C_1$-$C_7$ heterocycloalkyl, $C_5$-$C_{10}$ aryl, alkylaryl, $C_1$-$C_8$ heteroaryl, alkylheteroaryl, wherein $R_5$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_6$ is hydrogen, $C_1$-$C_6$ alkyl, $C_1$-$C_6$ alkoxy, halogen, or $C_1$-$C_3$ haloalkyl, n is 0, 1, 2, 3, or 4;

wherein the positions labeled 1, 2, and 3 indicate chiral positions; or a pharmaceutically acceptable salt or ester thereof.

In certain aspects, the compounds can have a structure as defined by Formula I-A.

Formula I-A

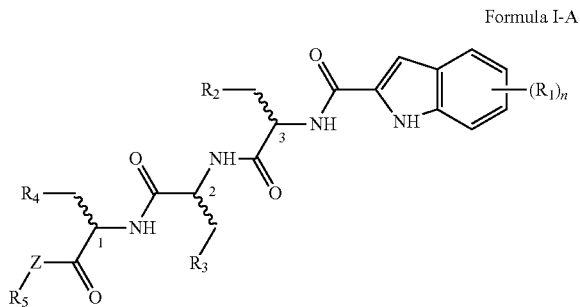

wherein

Z is selected from O or N—$R_a$, wherein $R_a$ is selected from hydrogen or $C_1$-$C_3$ alkyl;

$R_1$ is absent or independently for each occurrence, selected from halogen, $C_1$-$C_3$ alkyl, $C_1$-$C_3$ alkoxy, $C_1$-$C_3$ haloalkyl, $C_1$-$C_3$ haloalkoxy, $C_1$-$C_3$ alkoxy, hydroxyl, amino, cyano, nitro, or isocyano;

$R_2$ is $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, alkylaryl, alkylheteroaryl, wherein $R_2$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ and $R_4$ are independently halogen, hydroxyl, amino, —CN, $C_1$-$C_6$ alkyl, $C_1$-$C_6$ haloalkyl, —R'$CO_2$H, —R'$CONH_2$, —R'CONHR", —R'CONR"R'", —R'$CO_2$R", —R'$SO_3$H, —R'$SO_2$NHCOR", —R'CONHSO$_2$R", —R'CONHOH, —R'CONHCN, —R'$SO_2$NHR", $C_3$-$C_6$ cycloalkyl, $C_1$-$C_8$ heterocycloalkyl, $C_5$-$C_{10}$ aryl, $C_1$-$C_8$ heteroaryl, wherein $R_3$ and $R_4$ are optionally substituted with halogen, hydroxyl, amino, cyano, nitro, isocyano, carboxyl, hydroxyl, alkyl, alkoxy, alkenyl, haloalkyl, haloalkoxy, cyclopropyl, and wherein R', R", and R'" are independently absent or is hydrogen, halogen, $C_1$-$C_6$ alkyl, $C_1$-$C_6$ alkoxy, $C_1$-$C_6$ haloalkyl;

$R_5$ is $C_1$-$C_6$ alkyl, $C_1$-$C_6$ alkoxy, $C_3$-$C_8$ cycloalkyl, a $C_1$-$C_7$ heterocycloalkyl, $C_5$-$C_{10}$ aryl, alkylaryl, $C_1$-$C_8$ heteroaryl, alkylheteroaryl, wherein $R_5$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

n is 0, 1, 2, 3, or 4;

wherein the positions labeled 1, 2, and 3 indicate chiral positions; or a pharmaceutically acceptable salt or ester thereof.

Also disclosed are pharmaceutical compositions comprising a therapeutically effective amount of a disclosed compound, or a pharmaceutically acceptable salt thereof, and a pharmaceutically acceptable carrier.

In certain embodiments of Formula I or I-A, X can be N—$R_a$, wherein $R_a$ is selected from hydrogen, methyl, or ethyl. In some examples, X can be N—H.

In certain embodiments of Formula I or I-A, Z can be N—$R_a$, wherein $R_a$ is selected from hydrogen, methyl, or ethyl. In some examples, Z can be N—H. In certain embodiments of Formula I or I-A, Z can be O.

In certain embodiments of Formula I or I-A, $R_1$, independently for each occurrence, can be selected from a halogen, $C_1$-$C_3$ alkoxy, $C_1$-$C_3$ haloalkyl, $C_1$-$C_3$ alkoxy, $C_1$-$C_3$ alkyl, or nitro. In some examples, $R_1$ can be selected from a halogen, methoxy, ethoxy, trifluoromethoxy, methyl, ethyl, or nitro. For example, $R_1$ can be a halogen such as fluro, chloro, or bromo.

In certain embodiments of Formula I or I-A, $R_1$ can be absent. In other certain embodiments of Formula I or I-A, $R_1$ can occur once (that is, n is 1), twice (that is, n is 2), three times (that is, n is 3), or four times (that is, n is 4).

In certain embodiments of Formula I or I-A, $R_2$ is a $C_6$-$C_{10}$ aryl, wherein $R_2$ is optionally substituted with one or more groups selected from halogen, cyano, $C_1$-$C_6$ alkoxy, $C_1$-$C_6$ haloalkyl, $C_1$-$C_6$ haloalkoxy, or cyano. In some examples, $R_2$ is phenyl or naphthyl, optionally substituted with one or more groups selected from halogen, $C_1$-$C_3$ alkyl, $C_1$-$C_6$ alkoxy, $C_1$-$C_6$ haloalkyl, $C_1$-$C_6$ haloalkoxy, or cyano. In specific examples, $R_2$ is unsubstituted naphthyl. In other specific examples, $R_2$ is phenyl optionally substituted with one or more groups selected from halogen, $C_1$-$C_3$alkyl, cyano, $C_1$-$C_6$ alkoxy, $C_1$-$C_6$ haloalkyl, $C_1$-$C_6$ haloalkoxy. In some embodiments of Formula I or I-A, $R_2$ is $C_1$-$C_6$ alkyl, such as $C_1$-$C_3$ alkyl, methyl, ethyl, propyl, isopropyl.

In certain embodiments of Formula I or I-A, $R_3$ is selected from $C_1$-$C_5$ heterocycloalkyl, $C_1$-$C_5$ heteroaryl, R'$CO_2$H, or R'$CONH_2$, wherein R' is absent or selected from a $C_1$-$C_6$ alkyl. In some examples, $R_3$ is $C_1$-$C_2$ heterocycloalkyl, $C_1$-$C_2$ heteroaryl, $CO_2$H, or $CONH_2$. In some examples, $R_3$ is selected from an imidazole, pyrazole, triazole, or tetrazole. In specific examples, $R_3$ is selected from $CO_2$H, or $CONH_2$.

In certain embodiments of Formula I or I-A, $R_4$ can be selected from $C_1$-$C_5$ heterocycloalkyl, $C_1$-$C_5$ heteroaryl, R'$CO_2$H, R'$CO_2$R", or R'$CONH_2$, wherein R' and R" are independently absent or selected from hydrogen, a $C_1$-$C_6$ alkyl or a halogen. For example, $R_4$ can be R'$CO_2$H, —R'$CO_2$R", or R'$CONH_2$, wherein R' and R" are independently hydrogen, $C_1$-$C_6$ alkyl, or halogen. In some examples, $R_4$ is selected from an imidazole, pyrazole, triazole, or tetrazole. In specific examples, $R_4$ is selected from $CO_2$H, $CO_2$Cl, $CH_2CO_2$H, $CH_2CO_2C_1$, $CH_2CH_2CO_2$H, $CH_2CH_2CO_2C_1$, $CO_2CH_3$, $CO_2CH_2CH_3$, $CO_2CH_2CH_2CH_3$, $CH_2CO_2CH_3$, $CH_2CO_2CH_2CH_3$, $CH_2CO_2CH_2CH_2CH_3$, $CH_2CH_2CO_2CH_3$, $CH_2CH_2CO_2CH_2CH_3$, $CH_2CH_2CO_2CH_2CH_2CH_3$, $CONH_2$, $CH_2CONH_2$, $CH_2CH_2CONH_2$.

In certain embodiments of Formula I or I-A, $R_5$ is $C_1$-$C_6$ alkoxy, $C_1$-$C_6$ alkyl, $C_5$-$C_8$ aryl, alkylaryl, $C_2$-$C_8$ heteroaryl, or alkylheteroalkyl, wherein $R_5$ is optionally substituted with one or more groups selected from halogen, hydroxyl, amino, cyano, carboxyl, hydroxyl, alkyl, alkoxy, alkenyl, haloalkyl, haloalkoxy, cycloalkyl, heterocycloalkyl, aryl, or heteroaryl. In some examples, $R_5$ is $C_5$-$C_8$ aryl, optionally substituted with halogen, hydroxyl, alkoxy, haloalkyl, or haloalkoxy. In specific examples, $R_5$ is phenyl or benzyl, optionally substituted with one or more groups selected from halogen, hydroxyl, alkoxy, haloalkyl, or haloalkoxy. In some examples, $R_5$ is optionally substituted with one or more groups selected from halogen, hydroxyl, $C_1$-$C_6$ alkoxy, $C_1$-$C_6$ haloalkyl, or $C_1$-$C_6$ haloalkoxy. In some examples, $R_5$ is optionally substituted with one or more groups selected from methoxy, ethoxy, trifluromethoxy, methyl, ethyl, nitro, cyano, fluro, chloro, or bromo.

In some embodiments of Formula I or I-A, $R_5$ can be 1,3-benzodioxolane.

In some embodiments of Formula I or I-A, $R_5$ can be selected from a $C_1$-$C_{10}$ alkyl, such as a $C_2$-$C_8$ alkyl, or a $C_1$-$C_6$ alkyl.

In certain embodiments of Formula I or I-A, $R_6$ can be hydrogen. In certain embodiments of Formula I or I-A, $R_6$ can be selected from a halogen, methoxy, ethoxy, trifluromethoxy, methyl, ethyl, or nitro. For example, $R_6$ can be a halogen such as fluro, chloro, or bromo.

In certain embodiments of Formula I or I-A, the chiral designation of the compounds can be 1S,2S,3R; 1S,2R,3S; or 1R,2S,3S (See for example Table 4).

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is TNBC.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Examples

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Synthesis of the Peptidomimetic Inhibitors for the β-Catenin/Tcf Protein-Protein Interaction

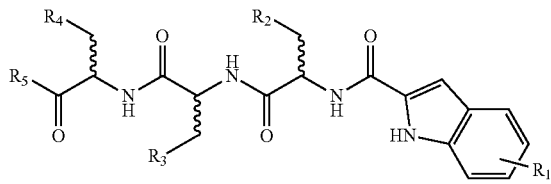

Abstract: The β-catenin/T-cell factor (Tcf) protein-protein interaction (PPI) plays a critical role in the Wnt/β-catenin signaling pathway which is hyperactivated in many cancers and fibroses. Based on compound 1, which was designed to target the Tcf4 G[13]ANDE[17] binding site of β-catenin, extensive structure-activity relationship (SAR) studies were conducted. As a result, compounds 53 and 57 were found to disrupt the β-catenin/Tcf PPI with the $K_i$ of 0.64 and 0.44 μM, respectively, and exhibit good selectivity for β-catenin/Tcf over β-catenin/E-cadherin and β-catenin/adenomatous polysis coli (APC) PPIs. Cell-based studies indicated that 56, the prodrug of 53, disrupted the β-catenin/Tcf PPI without affecting the β-catenin/E-cadherin and β-catenin/APC PPIs, suppressed transactivation of Wnt/β-catenin signaling in dose-dependent manners, and selectively inhibited viability, migration, and invasiveness of Wnt/β-catenin dependent cancer cells. The results described herein provides extensive SAR results for inhibitor optimization.

Chemical Synthesis

General Methods, Reagents, and Materials. All reagents were purchased from commercial sources and used without further purification unless stated otherwise. $^1$H NMR and $^{13}$C NMR spectra were recorded on the Bruker AVANCEIIIHD 500 (500 MHz) spectrometers (125.7 MHz for $^{13}$C NMR spectra) in $d_6$-DMSO, $d_6$-acetone, $d_4$-methanol, and CDCl$_3$. Chemical shifts were reported as values in parts per million (ppm), and the reference resonance peaks were set at 7.26 ppm (CHCl$_3$), 3.31 ppm (CD$_2$HOD), 2.50 ppm [(CD$_2$H)$_2$SO], 2.05 ppm [(CD$_2$H)$_2$CO] for $^1$H NMR spectra and 77.23 ppm (CDCl$_3$), 49.00 ppm (CD$_3$OD), 39.52 ppm ($d_6$-DMSO), and 29.84 ppm ($d_6$-acetone) for $^{13}$C NMR spectra. Low-resolution mass spectra were determined on the Agilent 6120 single quadrupole MS with 1220 infinity LC system (HPLC-MS) with an ESI source. High-resolution mass spectra were determined on the Agilent G6230BA TOF LCMS Mass Spectrometer with a TOF mass detector. Thin-layer chromatography was carried out on E. Merck pre-coated silica gel 60 F254 plates with a UV-visible lamp. Column chromatography was performed with SilicaFlash® F60 (230-400 mesh). The purity of final compounds 2-57 was determined by HPLC analysis with two different conditions (see the Supplementary Information). The instrument was an Agilent 1260 Infinity II HPLC system with a quaternary pump, a vial sampler, and a DAD detector. A Kromasil 300-5-C18 column (4.6×250 mm) was used. The DAD detector was set to 220, 254, and 280 nm. The purity of all tested compounds was >95%.

General peptide coupling procedure. a. CH$_2$Cl$_2$ as the solvent: At 0° C., to a suspension of carboxylic acid (1 equiv), amine (1 equiv), EDC.HCl (2 equiv), and HOAt (1.5 equiv) in dichloromethane (CH$_2$Cl$_2$) was added triethylamine (3 equiv) dropwise. The reaction mixture was warmed to room temperature and stirred overnight. After completion of the reaction, more CH$_2$Cl$_2$ was added. The CH$_2$Cl$_2$ phase was washed by 1 M HCl, saturated NaHCO$_3$, and brine, and was dried over Na$_2$SO$_4$ and concentrated under reduced pressure. Column chromatography was used to purify the target compound. b. DMF as the solvent: At 0° C., to a suspension of carboxylic acid (1 equiv), amine (1 equiv) in dimethylformamide (DMF) was added EDC.HCl (2 equiv) and HOAt (2 equiv). The reaction mixture was warmed to room temperature and stirred overnight. The mixture was poured into water and the solid was collected. The pure compound was obtained by recrystallization using hexane and ethyl acetate system or CH$_2$Cl$_2$ system.

General procedure for deprotection of the Cbz-protected amines. To the solution of the Cbz-protected amine in methanol was added 10% Pd/C under Ar. The mixture was stirred overnight at room temperature under H$_2$. The resulting product was collected by removal of the Pd/C catalyst and used directly in next step without further purification.

General procedure for deprotection of tert-butyl ester or Boc-protected indoles. At 0° C., to a solution of tert-butyl ester or Boc-protected indole in CH$_2$Cl$_2$ (5 mL) was added 5 mL of trifluoroacetic acid (TFA) dropwise. The reaction was kept at 0° C. for 4 h. Upon completion, the solvent was removed under reduced pressure, and TFA was totally removed by adding CH$_2$Cl$_2$ three times to afford the desired product.

General procedure for deprotection of Fmoc-protected amines. At 0° C., to a stirred solution of the Fmoc protected amine (1 mmol) in dichloromethane (10 mL), diethyl amine (10 mL) was added dropwise. The reaction was kept at 0° C. for 6 h until TLC showed no starting material left. Upon completion, the mixture was evaporated under reduced pressure. The diethyl amine residue was removed by adding dichloromethane at least three times. The residue was purified by flash column, except Asn and Gln-containing compounds, which were recrystallized in dichloromethane.

Synthesis of final products 20-21 and 30-38. The synthetic route for final products 20-21, and 30-38 is shown in Scheme 1. All the amide coupling reactions in Scheme 1 used CH$_2$Cl$_2$ as the solvent. The amide bond coupling reaction between N-Cbz-L-glutamic acid 5-tert-butyl ester and various amines generated intermediate 62, which underwent hydrogenation reaction to remove the Cbz protecting group and then coupled with N-Cbz-L-aspartic acid to yield 63. Hydrogenation of 63 and coupling with N-Cbz-L-2-naphthylalanine produced 64. Removal of the Cbz protecting group in 64 and then coupling with 5-chloroindole-2-carboxylic acid gave 65, in which the tert-butyl ester protecting group was removed by TFA in CH$_2$Cl$_2$ solution to offer the final products.

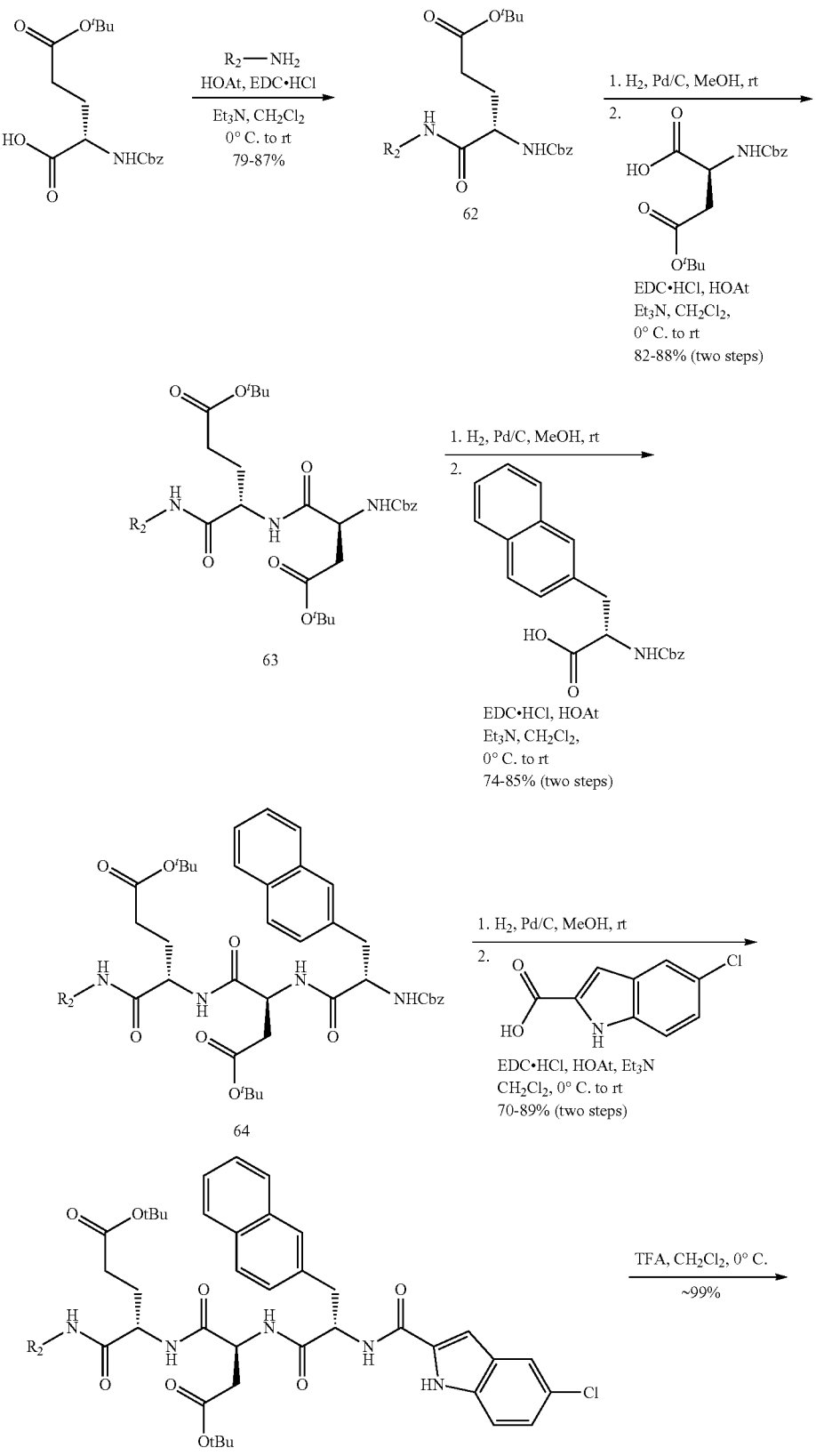
Scheme 1. Synthesis of 20-21 and 30-38.

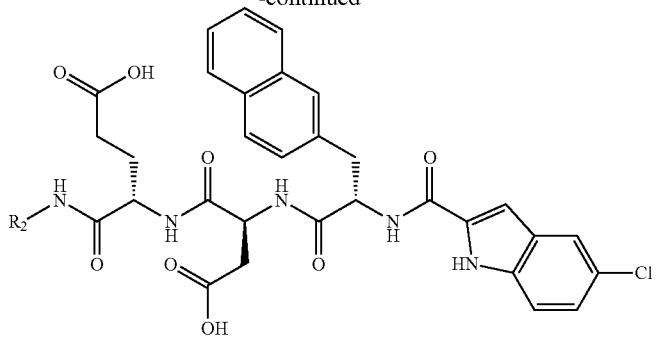

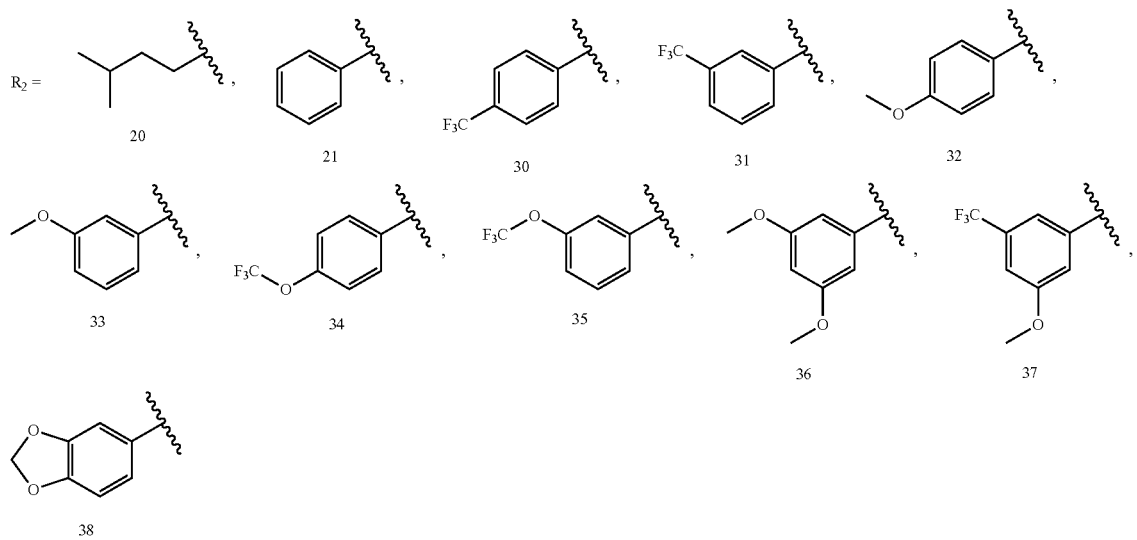

tert-Butyl (S)-4-(((benzyloxy)carbonyl)amino)-5-(isopentylamino)-5-oxopentanoate (62a). Yield, 87%. ¹H NMR (500 MHz, Chloroform-d) δ 7.41-7.27 (m, 5H), 6.35 (t, J=5.8 Hz, 1H), 5.76 (d, J=7.9 Hz, 1H), 5.08 (s, 2H), 4.17 (q, J=7.4 Hz, 1H), 3.30-3.16 (m, 2H), 2.40 (dt, J=16.5, 7.1 Hz, 1H), 2.28 (dt, J=16.6, 7.0 Hz, 1H), 2.05 (dtd, J=14.3, 7.2, 5.5 Hz, 1H), 1.91 (dt, J=14.4, 7.3 Hz, 1H), 1.66-1.51 (m, 1H), 1.43 (s, 11H), 0.89 (d, J=6.6 Hz, 6H). ¹³C NMR (126 MHz, Chloroform-d) δ 172.85, 171.03, 156.25, 136.23, 128.52, 128.16, 128.00, 80.96, 66.96, 54.36, 38.30, 37.89, 31.73, 28.22, 28.06, 25.83, 22.42 (d, J=2.8 Hz). MS (ESI) m/z=407.3 [M+H]⁺, MS (ESI) m/z=429.2 [M+Na]⁺.

tert-Butyl (S)-4-(((benzyloxy)carbonyl)amino)-5-oxo-5-(phenylamino)pentanoate (62b). Yield, 82%. ¹H NMR (500 MHz, Chloroform-d) δ 8.60 (s, 1H), 7.42 (d, J=8.0 Hz, 2H), 7.30-7.13 (m, 7H), 7.08-6.86 (m, 1H), 5.88 (d, J=7.8 Hz, 1H), 5.11-4.94 (m, 2H), 4.32 (d, J=6.9 Hz, 1H), 2.41 (dd, J=16.5, 7.2 Hz, 1H), 2.29 (dt, J=16.7, 6.9 Hz, 1H), 2.17-2.01 (m, 1H), 2.01-1.86 (m, 1H), 1.36 (s, 9H). ¹³C NMR (126 MHz, Chloroform-d) δ 173.09, 169.67, 156.57, 137.61, 136.09, 128.95, 128.55, 128.22, 128.02, 124.46, 119.98, 81.28, 67.20, 55.00, 53.46, 31.87, 28.08. MS (ESI) m/z=435.2 [M+Na]⁺.

tert-Butyl (S)-4-(((benzyloxy)carbonyl)amino)-5-oxo-5-((4-(trifluoromethyl)phenyl)amino)pentanoate (62c). Yield, 79%. ¹H NMR (500 MHz, Chloroform-d) δ 9.01 (s, 1H), 7.48 (d, J=8.4 Hz, 2H), 7.39 (d, J=8.4 Hz, 2H), 7.23 (q, J=4.1 Hz, 5H), 5.93 (d, J=7.7 Hz, 1H), 5.14-4.94 (m, 2H), 4.32 (d, J=7.0 Hz, 1H), 2.44 (dt, J=16.5, 7.0 Hz, 1H), 2.32-2.24 (m, 1H), 2.08 (ddt, J=13.8, 7.8, 6.0 Hz, 1H), 1.96-1.82 (m, 1H), 1.36 (s, 9H). ¹³C NMR (126 MHz, Chloroform-d) δ 173.15, 170.17, 156.80, 140.74, 135.96, 128.58, 128.30, 127.97, 126.11 (d, J=3.7 Hz), 125.92, 124.05 (d, J=271.5 Hz), 119.40, 81.51, 67.36, 55.16, 31.88, 28.05, 27.83. MS (ESI) m/z=503.2 [M+Na]⁺.

tert-Butyl (S)-4-(((benzyloxy)carbonyl)amino)-5-oxo-5-((3-(trifluoromethyl)phenyl)amino)pentanoate (62 d). Yield, 80%. ¹H NMR (500 MHz, Chloroform-d) δ 9.23 (s, 1H), 7.87 (s, 1H), 7.58 (s, 1H), 7.30 (t, J=6.2 Hz, 7H), 6.23 (d, J=12.1 Hz, 1H), 5.10 (q, J=12.4 Hz, 2H), 4.48 (d, J=9.3 Hz, 1H), 2.51-2.30 (m, 2H), 2.17 (p, J=7.4 Hz, 1H), 2.09-1.94 (m, 1H), 1.43 (s, 9H). ¹³C NMR (126 MHz, Chloroform-d) δ 172.85, 170.38, 156.87, 138.31 (d, J=2.5 Hz), 135.96, 131.16 (q, J=32.1 Hz), 129.36, 128.54, 128.25, 127.94, 123.85 (q, J=271.2 Hz), 122.84, 120.80, 116.55 (d, J=4.1 Hz), 81.30, 67.35, 55.15, 31.71, 28.01, 27.81. MS (ESI) m/z=503.2 [M+Na]⁺.

tert-Butyl (S)-4-(((benzyloxy)carbonyl)amino)-5-((4-methoxyphenyl)amino)-5-oxopentanoate (62e). Yield, 85%. ¹H NMR (500 MHz, Chloroform-d) δ 8.48 (s, 1H), 7.39 (d, J=8.5 Hz, 2H), 7.35-7.28 (m, 5H), 6.90-6.73 (m, 2H), 5.92 (d, J=7.8 Hz, 1H), 5.29-4.96 (m, 2H), 4.49-4.25 (m, 1H), 3.77 (s, 3H), 2.58-2.42 (m, 1H), 2.36 (dt, J=16.6, 6.9 Hz, 1H), 2.15 (dq, J=13.4, 6.3 Hz, 1H), 2.06-1.93 (m, 1H), 1.45 (s, 9H). ¹³C NMR (126 MHz, Chloroform-d) δ 173.06, 169.37, 156.52, 136.13, 130.68, 128.54, 128.20, 128.01, 121.75, 114.10, 81.22, 67.16, 55.47, 54.88, 31.87, 28.20, 28.08. MS (ESI) m/z=443.1 [M+H]$^+$, MS (ESI) m/z=465.2 [M+Na]$^+$.

tert-Butyl (S)-4-(((benzyloxy)carbonyl)amino)-5-((3-methoxyphenyl)amino)-5-oxopentanoate (62f). Yield, 87%. $^1$H NMR (500 MHz, Chloroform-d) δ 8.75 (s, 1H), 7.28-7.14 (m, 6H), 7.05 (t, J=8.1 Hz, 1H), 6.96-6.74 (m, 1H), 6.54 (dd, J=8.3, 2.5 Hz, 1H), 5.98 (d, J=8.2 Hz, 1H), 5.05-4.89 (m, 2H), 4.33 (d, J=8.4 Hz, 1H), 3.64 (s, 3H), 2.44-2.33 (m, 1H), 2.28 (dt, J=16.8, 7.0 Hz, 1H), 2.10-2.04 (m, 1H), 1.96-1.83 (m, 1H), 1.34 (s, 9H). $^{13}$C NMR (126 MHz, Chloroform-d) δ 172.90, 169.91, 160.06, 156.63, 138.90, 136.10, 129.58, 128.52, 128.18, 127.99, 112.15, 110.46, 105.54, 81.15, 67.19, 55.22, 55.08, 38.64, 31.80, 28.07. MS (ESI) m/z=465.2 [M+Na]$^+$, MS (ESI) m/z=907.4 [2M+Na]$^+$.

tert-Butyl (S)-4-(((benzyloxy)carbonyl)amino)-5-oxo-5-((4-(trifluoromethoxy)phenyl)amino)pentanoate (62 g). Yield, 82%. $^1$H NMR (500 MHz, Chloroform-d) δ 8.97 (s, 1H), 7.75-7.40 (m, 2H), 7.31 (d, J=4.1 Hz, 5H), 7.09 (d, J=8.6 Hz, 2H), 6.03 (d, J=7.8 Hz, 1H), 5.10 (d, J=5.2 Hz, 2H), 4.39 (t, J=7.2 Hz, 1H), 2.50 (dt, J=16.6, 7.1 Hz, 1H), 2.38 (dt, J=16.8, 6.8 Hz, 1H), 2.15 (ddt, J=13.9, 7.4, 5.9 Hz, 1H), 2.02 (dt, J=14.4, 7.2 Hz, 1H), 1.44 (s, 9H). $^{13}$C NMR (126 MHz, Chloroform-d) δ 173.07, 169.94, 156.74, 145.27, 136.35, 136.00, 128.56, 128.27, 127.96, 121.60, 120.96, 120.46 (q, J=190 Hz), 81.40, 67.29, 55.06, 31.84, 28.04, 27.92. MS (ESI) m/z=519.2 [M+Na]$^+$.

tert-Butyl (S)-4-(((benzyloxy)carbonyl)amino)-5-oxo-5-((3-(trifluoromethoxy)phenyl)amino)pentanoate (62 h). Yield, 80%. $^1$H NMR (500 MHz, Chloroform-d) δ 9.10 (s, 1H), 7.50 (s, 1H), 7.24-7.13 (m, 6H), 7.09 (t, J=8.2 Hz, 1H), 6.80 (d, J=8.2 Hz, 1H), 6.10 (d, J=7.9 Hz, 1H), 4.98 (q, J=12.3 Hz, 2H), 4.34 (t, J=7.3 Hz, 1H), 2.36 (dt, J=16.7, 7.3 Hz, 1H), 2.28 (dt, J=16.8, 6.9 Hz, 1H), 2.06 (dtd, J=14.5, 7.2, 5.5 Hz, 1H), 1.97-1.85 (m, 1H), 1.33 (s, 9H). $^{13}$C NMR (126 MHz, Chloroform-d) δ 172.87, 170.32, 156.84, 149.43 (d, J=1.9 Hz), 139.19, 135.99, 129.84, 128.53, 128.23, 127.93, 120.44 (d, J=257.2 Hz), 117.87, 116.29, 112.65, 81.27, 67.30, 55.13, 31.71, 28.00, 27.85. MS (ESI) m/z=519.2 [M+Na]$^+$, MS (ESI) m/z=495.3 [M−H]$^−$.

tert-Butyl (S)-4-(((benzyloxy)carbonyl)amino)-5-((3,5-dimethoxyphenyl)amino)-5-oxopentanoate (62i). Yield, 85%. $^1$H NMR (500 MHz, Chloroform-d) δ 8.62 (s, 1H), 7.33 (d, J=4.0 Hz, 5H), 6.77 (d, J=2.3 Hz, 2H), 6.23 (t, J=2.2 Hz, 1H), 5.88 (d, J=7.7 Hz, 1H), 5.27-4.84 (m, 2H), 4.55-4.22 (m, 1H), 3.75 (s, 6H), 2.51 (dt, J=14.7, 6.8 Hz, 1H), 2.42-2.31 (m, 1H), 2.15 (ddt, J=13.8, 7.5, 6.0 Hz, 1H), 2.01 (dt, J=14.4, 7.2 Hz, 1H), 1.45 (s, 9H). $^{13}$C NMR (126 MHz, Chloroform-d) δ 173.14, 169.67, 161.00, 156.56, 139.34, 136.04, 128.54, 128.22, 128.03, 98.08, 97.05, 81.35, 67.24, 55.36, 55.09, 31.89, 28.07. MS (ESI) m/z=473.3 [M+H]$^+$, MS (ESI) m/z=495.3 [M+Na]$^+$, MS (ESI) m/z=967.4 [2M+Na]$^+$.

tert-Butyl (S)-4-(((benzyloxy)carbonyl)amino)-5-((3-methoxy-5-(trifluoromethyl)phenyl)amino)-5-oxopentanoate (62j). Yield, 81%. $^1$H NMR (500 MHz, Chloroform-d) δ 9.06 (s, 1H), 7.39-7.11 (m, 7H), 6.72 (s, 1H), 6.02 (d, J=7.8 Hz, 1H), 5.01 (q, J=12.2 Hz, 2H), 4.34 (d, J=7.1 Hz, 1H), 3.65 (s, 3H), 2.49-2.34 (m, 1H), 2.29 (dt, J=16.7, 6.9 Hz, 1H), 2.11-2.00 (m, 1H), 2.02-1.88 (m, 1H), 1.34 (s, 9H). $^{13}$C NMR (126 MHz, Chloroform-d) δ 172.90, 170.28, 160.22, 156.84, 139.48, 135.90, 131.95 (q, J=32.6 Hz), 128.53, 128.27, 127.99, 123.70 (q, J=272.5 Hz), 108.72, 108.35, 106.94 (d, J=4.0 Hz), 81.34, 67.39, 55.46, 55.17, 31.71, 28.01, 27.80. MS (ESI) m/z=533.2 [M+Na]$^+$, MS (ESI) m/z=509.2 [M−H]$^−$.

tert-Butyl (S)-5-(benzo[d][1,3]dioxol-5-ylamino)-4-(((benzyloxy)carbonyl)amino)-5-oxopentanoate (62k). Yield, 85%. $^1$H NMR (500 MHz, Chloroform-d) δ 8.75 (s, 1H), 7.27-7.13 (m, 5H), 7.07 (d, J=2.2 Hz, 1H), 6.65 (dd, J=8.4, 2.1 Hz, 1H), 6.52 (d, J=8.3 Hz, 1H), 6.13 (d, J=8.0 Hz, 1H), 5.77 (s, 2H), 5.10-4.78 (m, 2H), 4.32 (d, J=7.3 Hz, 1H), 2.30 (qt, J=16.6, 7.3 Hz, 2H), 2.11-1.99 (m, 1H), 1.92 (dt, J=14.4, 7.4 Hz, 1H), 1.33 (s, 9H). $^{13}$C NMR (126 MHz, Chloroform-d) δ 172.71, 169.85, 156.68, 147.61, 144.24, 136.15, 131.93, 128.51, 128.15, 127.94, 113.31, 107.93, 102.81, 101.18, 80.99, 67.14, 55.01, 31.76, 28.07. MS (ESI) m/z=457.3 [M+H]$^+$, MS (ESI) m/z=479.2 [M+Na]$^+$, MS (ESI) m/z=935.4 [2M+Na]$^+$.

tert-Butyl (S)-4-((S)-2-(((benzyloxy)carbonyl)amino)-4-(tert-butoxy)-4-oxobutanamido)-5-(isopentylamino)-5-oxopentanoate (63a). Yield, 86%. $^1$H NMR (500 MHz, Chloroform-d) δ 7.46-7.28 (m, 6H), 6.57 (d, J=5.9 Hz, 1H), 5.86 (d, J=8.3 Hz, 1H), 5.12 (q, J=12.2 Hz, 2H), 4.46 (dt, J=8.5, 5.4 Hz, 1H), 4.35 (td, J=8.1, 4.7 Hz, 1H), 3.31-3.15 (m, 2H), 2.89 (dd, J=16.9, 4.7 Hz, 1H), 2.70 (dd, J=16.9, 6.1 Hz, 1H), 2.43-2.34 (m, 1H), 2.33-2.23 (m, 1H), 2.17-2.05 (m, 1H), 1.95 (dq, J=14.5, 7.1 Hz, 1H), 1.58 (td, J=13.3, 6.6 Hz, 1H), 1.42 (d, J=5.0 Hz, 20H), 0.89 (dd, J=6.6, 0.9 Hz, 6H). $^{13}$C NMR (126 MHz, Chloroform-d) δ 173.57, 170.93, 170.66, 170.38, 156.07, 136.01, 128.56, 128.27, 128.12, 81.94, 81.02, 67.30, 53.27, 51.67, 38.26, 37.93, 37.33, 31.71, 28.05, 28.03, 27.06, 25.85, 22.45. MS (ESI) m/z=600.3 [M+Na]$^+$.

tert-Butyl (S)-4-((S)-2-(((benzyloxy)carbonyl)amino)-4-(tert-butoxy)-4-oxobutanamido)-5-oxo-5-(phenylamino)pentanoate (63b). Yield, 83%. $^1$H NMR (500 MHz, Chloroform-d) δ 8.69 (s, 1H), 7.60 (t, J=8.9 Hz, 3H), 7.46-7.22 (m, 7H), 7.15-6.99 (m, 1H), 5.91 (d, J=8.2 Hz, 1H), 5.24-5.02 (m, 2H), 4.53 (tt, J=10.3, 5.3 Hz, 2H), 2.92 (dd, J=16.9, 4.8 Hz, 1H), 2.73 (dd, J=16.9, 6.1 Hz, 1H), 2.51 (ddd, J=17.1, 8.2, 5.6 Hz, 1H), 2.36 (ddd, J=17.1, 7.3, 5.6 Hz, 1H), 2.25-2.16 (m, 1H), 2.05 (dt, J=14.5, 7.4 Hz, 1H), 1.44 (s, 9H), 1.41 (s, 9H). $^{13}$C NMR (126 MHz, Chloroform-d) δ 173.82, 171.14, 170.90, 168.93, 156.19, 137.79, 135.96, 128.82, 128.57, 128.30, 128.17, 124.31, 120.10, 82.10, 81.33, 67.41, 53.91, 51.76, 37.26, 31.84, 28.06, 28.01, 26.88. MS (ESI) m/z=606.3 [M+Na]$^+$.

tert-Butyl (S)-4-((S)-2-(((benzyloxy)carbonyl)amino)-4-(tert-butoxy)-4-oxobutanamido)-5-oxo-5-((4-(trifluoromethyl)phenyl)amino)pentanoate (63c). Yield, 82%. $^1$H NMR (500 MHz, Acetone-d$_6$) δ 9.50 (s, 1H), 7.94 (d, J=8.4 Hz, 2H), 7.84 (d, J=8.0 Hz, 1H), 7.65 (d, J=8.5 Hz, 2H), 7.44-7.17 (m, 5H), 6.91 (d, J=7.6 Hz, 1H), 5.23-4.97 (m, 2H), 4.77-4.37 (m, 2H), 2.95-2.83 (m, 1H), 2.76 (dd, J=16.5, 6.8 Hz, 1H), 2.38 (ddd, J=11.3, 9.1, 6.3 Hz, 2H), 2.28-2.18 (m, 1H), 2.00-1.83 (m, 1H), 1.41 (s, 9H), 1.41 (s, 9H). $^{13}$C NMR (126 MHz, Acetone-d$_6$) δ 171.80, 171.03, 170.18, 170.04, 156.47, 142.33, 136.95, 128.36, 127.86, 127.79, 125.87 (q, J=3.8 Hz), 124.69 (d, J=32.5 Hz), 124.52 (d, J=268.7 Hz), 119.49, 119.41, 80.68, 79.69, 66.35, 53.46, 52.16, 37.05, 31.23, 27.37, 27.31, 26.80. MS (ESI) m/z=674.3 [M+Na]$^+$.

tert-Butyl (S)-4-((S)-2-(((benzyloxy)carbonyl)amino)-4-(tert-butoxy)-4-oxobutanamido)-5-oxo-5-((3-(trifluoromethyl)phenyl)amino)pentanoate (63 d). Yield, 83%. $^1$H NMR (500 MHz, Chloroform-d) δ 9.06 (s, 1H), 7.84 (s, 1H), 7.78-7.59 (m, 2H), 7.41-6.94 (m, 7H), 6.04 (d, J=9.7 Hz, 1H), 5.23-4.85 (m, 2H), 4.60-4.33 (m, 2H), 2.85-2.66 (m, 2H), 2.42-2.21 (m, 2H), 2.18-2.06 (m, 1H), 1.99-1.88 (m, 1H), 1.40-1.32 (m, 9H), 1.30 (d, J=2.3 Hz, 9H). $^{13}$C NMR (126 MHz, Chloroform-d) δ 173.45, 171.39, 170.80, 169.56, 156.32, 138.53, 135.96, 131.04 (q, J=32.5 Hz), 129.27, 128.52, 128.24, 128.02, 123.93 (q, J=271.2 Hz), 123.16, 120.66 (d, J=4.0 Hz), 116.81 (d, J=4.3 Hz), 82.14, 81.25, 67.34, 53.86, 51.86, 37.32, 31.68, 28.00, 27.91, 26.72. MS (ESI) m/z=674.2 [M+Na]$^+$.

tert-Butyl (S)-4-((S)-2-(((benzyloxy)carbonyl)amino-4-(tert-butoxy)-4-oxobutanamido)-5-((4-methoxyphenyl)amino)-5-oxopentanoate (63e). Yield, 82%. $^1$H NMR (500 MHz, Chloroform-d) δ 8.56 (s, 1H), 7.59 (d, J=7.4 Hz, 1H), 7.48 (d, J=8.6 Hz, 2H), 7.37-7.27 (m, 5H), 6.90-6.65 (m, 2H), 5.92 (d, J=8.1 Hz, 1H), 5.13 (q, J=12.2 Hz, 2H), 4.52 (tt, J=10.3, 5.3 Hz, 2H), 3.77 (s, 3H), 2.90 (dd, J=16.9, 4.9 Hz, 1H), 2.73 (dd, J=16.8, 6.1 Hz, 1H), 2.48 (ddd, J=17.0, 8.0, 5.9 Hz, 1H), 2.40-2.29 (m, 1H), 2.23-2.12 (m, 1H), 2.04 (d, J=2.7 Hz, 1H), 1.43 (s, 9H), 1.40 (s, 9H). $^{13}$C NMR (126 MHz, Chloroform-d) δ 173.71, 171.05, 170.87, 168.68, 156.39, 156.19, 135.98, 130.96, 128.56, 128.28, 128.14, 121.81, 113.97, 82.07, 81.23, 67.38, 55.46, 53.75, 51.79, 37.29, 31.82, 28.06, 28.01, 26.95. MS (ESI) m/z=614.3 [M+H]$^+$, MS (ESI) m/z=636.3 [M+Na]$^+$.

tert-Butyl (S)-4-((S)-2-(((benzyloxy)carbonyl)amino-4-(tert-butoxy)-4-oxobutanamido)-5-((3-methoxyphenyl)amino)-5-oxopentanoate (63f). Yield, 88%. $^1$H NMR (500 MHz, Chloroform-d) δ 8.79 (s, 1H), 7.61 (d, J=7.6 Hz, 1H), 7.33-7.13 (m, 6H), 7.08-6.92 (m, 2H), 6.53 (ddd, J=8.1, 2.5, 1.0 Hz, 1H), 6.05 (d, J=8.2 Hz, 1H), 5.18-4.94 (m, 2H), 4.61-4.41 (m, 2H), 3.65 (s, 3H), 2.77 (dd, J=16.8, 5.3 Hz, 1H), 2.65 (dd, J=16.8, 6.2 Hz, 1H), 2.39-2.30 (m, 1H), 2.26 (dt, J=16.8, 6.8 Hz, 1H), 2.11 (dt, J=13.4, 6.9 Hz, 1H), 1.94 (q, J=5.7, 4.2 Hz, 1H), 1.33 (s, 9H), 1.30 (s, 9H). $^{13}$C NMR (126 MHz, Chloroform-d) δ 173.25, 171.26, 170.72, 169.19, 160.00, 156.22, 139.07, 136.05, 129.44, 128.51, 128.20, 128.09, 112.37, 110.32, 105.72, 81.91, 81.01, 67.28, 55.20, 53.74, 51.77, 37.43, 31.67, 28.04, 27.98, 27.15. MS (ESI) m/z=636.3 [M+Na]$^+$.

tert-Butyl (S)-4-((S)-2-(((benzyloxy)carbonyl)amino-4-(tert-butoxy)-4-oxobutanamido)-5-oxo-5-((4-(trifluoromethoxy)phenyl)amino)pentanoate (63 g). Yield, 87%. $^1$H NMR (500 MHz, Chloroform-d) δ 8.95 (s, 1H), 7.70 (d, J=7.4 Hz, 1H), 7.54 (d, J=8.6 Hz, 2H), 7.38-7.15 (m, 5H), 7.08-6.87 (m, 2H), 6.04 (d, J=8.0 Hz, 1H), 5.36-4.93 (m, 2H), 4.49 (dp, J=18.7, 6.4, 5.7 Hz, 2H), 2.77 (dd, J=16.9, 5.2 Hz, 1H), 2.70 (d, J=6.3 Hz, 1H), 2.51-2.31 (m, 1H), 2.27 (dt, J=16.9, 6.6 Hz, 1H), 2.18-2.10 (m, 1H), 1.95 (q, J=7.3, 6.9 Hz, 1H), 1.33 (s, 9H), 1.30 (s, 9H). $^{13}$C NMR (126 MHz, Chloroform-d) δ 173.45, 171.39, 170.77, 169.33, 156.29, 145.18 (d, J=2.0 Hz), 136.63, 135.97, 128.52, 128.24, 128.03, 121.45, 121.22, 119.45, 82.04, 81.20, 67.33, 53.86, 51.81, 37.32, 31.68, 28.00, 27.94, 26.79. MS (ESI) m/z=690.3 [M+Na]$^+$.

tert-Butyl (S)-4-((S)-2-(((benzyloxy)carbonyl)amino-4-(tert-butoxy)-4-oxobutanamido)-5-oxo-5-((3-(trifluoromethoxy)phenyl)amino)pentanoate(63 h). Yield, 84%. 10 $^1$H NMR (500 MHz, Chloroform-d) δ 8.87 (s, 1H), 7.60 (d, J=19.4 Hz, 2H), 7.51-7.40 (m, 1H), 7.31-7.13 (m, 6H), 6.87 (ddt, J=8.2, 2.3, 1.1 Hz, 1H), 5.83 (d, J=7.7 Hz, 1H), 5.33-4.95 (m, 2H), 4.66-4.29 (m, 2H), 2.82 (dd, J=16.8, 4.9 Hz, 1H), 2.70 (dd, J=16.8, 6.2 Hz, 1H), 2.43 (ddd, J=17.2, 8.4, 5.3 Hz, 1H), 2.32-2.24 (m, 1H), 2.13 (ddd, J=13.8, 8.4, 4.3 Hz, 1H), 1.99 (dd, J=14.0, 6.6 Hz, 1H), 1.37 (s, 9H), 1.34 (s, 9H). $^{13}$C NMR (126 MHz, Chloroform-d) δ 173.97, 171.24, 170.87, 169.23, 156.29, 149.44, 139.35, 135.92, 129.79, 128.56, 128.31, 128.10, 120.45 (d, J=257.3 Hz), 118.11, 116.29, 112.89, 82.26, 81.50, 67.45, 54.01, 51.88, 37.19, 31.84, 28.03, 27.97, 26.49. MS (ESI) m/z=668.3 [M+H]$^+$, MS (ESI) m/z=690.3 [M+Na]$^+$.

tert-Butyl (S)-4-((S)-2-(((benzyloxy)carbonyl)amino-4-(tert-butoxy)-4-oxobutanamido)-5-((3,5-dimethoxyphenyl)amino)-5-oxopentanoate(63i). Yield, 87%. $^1$H NMR (500 MHz, Chloroform-d) δ 8.64 (s, 1H), 7.59 (d, J=7.4 Hz, 1H), 7.40-7.27 (m, 5H), 6.86 (d, J=2.3 Hz, 2H), 6.22 (t, J=2.3 Hz, 1H), 5.91 (d, J=8.1 Hz, 1H), 5.31-5.03 (m, 2H), 4.51 (td, J=7.8, 4.7 Hz, 2H), 3.76 (s, 6H), 2.92 (dd, J=16.9, 4.9 Hz, 1H), 2.72 (dd, J=16.9, 6.0 Hz, 1H), 2.50 (ddd, J=17.1, 8.2, 5.6 Hz, 1H), 2.35 (ddd, J=17.1, 7.2, 5.5 Hz, 1H), 2.23-2.09 (m, 1H), 2.11-1.96 (m, 1H), 1.44 (s, 9H), 1.41 (s, 9H). $^{13}$C NMR (126 MHz, Chloroform-d) δ 173.79, 171.16, 170.85, 168.98, 160.93, 156.22, 139.53, 135.95, 128.56, 128.29, 128.15, 98.28, 97.02, 82.09, 81.34, 67.42, 55.37, 53.93, 51.77, 37.24, 31.81, 28.06, 28.01, 26.86. MS (ESI) m/z=644.3 [M+H]$^+$, MS (ESI) m/z=666.3 [M+Na]$^+$.

tert-Butyl (S)-4-((S)-2-(((benzyloxy)carbonyl)amino-4-(tert-butoxy)-4-oxobutanamido)-5-((3-methoxy-5-(trifluoromethyl)phenyl)amino)-5-oxopentanoate (63j). Yield, 86%. $^1$H NMR (500 MHz, Chloroform-d) δ 8.98-8.91 (m, 1H), 7.71 (d, J=7.2 Hz, 1H), 7.63 (s, 1H), 7.43-7.27 (m, 6H), 6.94-6.80 (m, 1H), 6.00-5.76 (m, 1H), 5.30-5.06 (m, 2H), 4.66-4.35 (m, 2H), 3.82 (d, J=0.9 Hz, 3H), 2.95-2.84 (m, 1H), 2.79 (dd, J=16.8, 6.2 Hz, 1H), 2.50 (dtd, J=17.3, 5.9, 5.3, 2.9 Hz, 1H), 2.37 (ddd, J=17.2, 7.4, 5.2 Hz, 1H), 2.20 (ddd, J=13.4, 9.1, 4.5 Hz, 1H), 2.08 (dt, J=14.6, 7.4 Hz, 1H), 1.44 (s, 9H), 1.41 (s, 9H). $^{13}$C NMR (126 MHz, Chloroform-d) δ 173.98 (d, J=3.1 Hz), 171.23, 170.87, 169.38, 160.22, 156.31, 139.67, 135.90, 131.87 (d, J=32.5 Hz), 128.56, 128.09, 123.78 (d, J=272.5 Hz), 109.10, 108.65, 106.95 (d, J=3.9 Hz), 82.32, 81.54, 67.45, 55.60, 54.07, 51.91, 37.19, 31.83, 28.03, 27.95, 26.39. MS (ESI) m/z=682.3 [M+H]$^+$, MS (ESI) m/z=704.3 [M+Na]$^+$.

tert-Butyl (S)-5-(benzo[d][1,3]dioxol-5-ylamino)-4-((S)-2-(((benzyloxy)carbonyl)amino-4-(tert-butoxy)-4-oxobutanamido)-5-oxopentanoate (63k). Yield, 88%. $^1$H NMR (500 MHz, Chloroform-d) δ 8.61 (q, J=5.9, 4.6 Hz, 1H), 7.54 (d, J=7.4 Hz, 1H), 7.38-7.10 (m, 6H), 6.84 (d, J=8.4 Hz, 1H), 6.61 (dq, J=8.5, 1.7 Hz, 1H), 5.91 (d, J=8.8 Hz, 1H), 5.83 (q, J=1.6 Hz, 2H), 5.05 (q, J=12.4 Hz, 2H), 4.45 (q, J=6.8, 6.2 Hz, 2H), 2.79 (d, J=3.7 Hz, 1H), 2.67 (dd, J=16.9, 6.2 Hz, 1H), 2.48-2.31 (m, 1H), 2.27 (dt, J=16.8, 6.6 Hz, 1H), 2.16-2.05 (m, 1H), 2.04-1.84 (m, 1H), 1.35 (d, J=1.6 Hz, 9H), 1.33 (d, J=1.5 Hz, 9H). $^{13}$C NMR (126 MHz, Chloroform-d) δ 173.55, 171.12, 170.82, 168.79, 156.19, 147.60, 144.16, 136.00, 132.10, 128.54, 128.26, 128.12, 113.32, 107.89, 102.82, 101.13, 82.05, 81.18, 67.35, 53.73, 51.79, 37.33, 31.76, 28.05, 28.00, 26.96. MS (ESI) m/z=628.3 [M+H]$^+$, MS (ESI) m/z=650.3 [M+Na]$^+$.

tert-Butyl (5S,8S,11S)-8-(2-(tert-butoxy)-2-oxoethyl)-11-(isopentylcarbamoyl)-5-(naphthalen-2-ylmethyl)-3,6,9-trioxo-1-phenyl-2-oxa-4,7,10-triazatetradecan-14-oate (64a). Yield, 81%. $^1$H NMR (500 MHz, Chloroform-d) δ 7.75-7.59 (m, 3H), 7.58-7.52 (m, 2H), 7.44 (d, J=8.1 Hz, 1H), 7.40-7.28 (m, 2H), 7.26-7.01 (m, 6H), 6.67 (t, J=5.6 Hz, 1H), 5.54 (d, J=5.7 Hz, 1H), 4.94 (s, 2H), 4.61 (ddd, J=7.9, 6.4, 4.5 Hz, 1H), 4.54-4.41 (m, 1H), 4.33 (td, J=8.6, 4.5 Hz, 1H), 3.27 (dd, J=14.2, 5.0 Hz, 1H), 3.19-3.00 (m, 3H), 2.80 (dd, J=16.9, 4.4 Hz, 1H), 2.53 (dd, J=16.9, 6.5 Hz, 1H), 2.24-2.04 (m, 3H), 1.90-1.76 (m, 1H), 1.52 (dp, J=13.3, 6.6 Hz, 1H), 1.30 (s, 9H), 1.28 (s, 11H), 0.81 (dd, J=6.7, 3.0 Hz, 6H). $^{13}$C NMR (126 MHz, Chloroform-d) δ 172.62, 171.61, 170.97, 170.53, 170.24, 156.69, 135.73, 133.43, 132.53, 128.64, 128.51, 128.28, 128.18, 128.02, 127.70, 127.61, 126.97, 126.32, 125.90, 82.05, 80.50, 67.48, 56.75, 53.12, 50.22, 38.20, 37.96, 36.49, 31.94, 28.04, 27.99, 27.10, 22.52, 22.50. MS (ESI) m/z=775.2 [M+H]$^+$, MS (ESI) m/z=797.2 [M+Na]$^+$.

tert-Butyl (5S,8S,11S)-8-(2-(tert-butoxy)-2-oxoethyl)-5-(naphthalen-2-ylmethyl)-3,6,9-trioxo-1-phenyl-11-(phenylcarbamoyl)-2-oxa-4,7,10-triazatetradecan-14-oate (64b). Yield, 85%. ¹H NMR (500 MHz, DMSO-d₆) δ 9.92 (s, 1H), 8.55 (d, J=7.9 Hz, 1H), 8.07 (d, J=7.9 Hz, 1H), 7.88 (dd, J=6.9, 2.2 Hz, 1H), 7.86-7.75 (m, 3H), 7.69-7.58 (m, 3H), 7.56-7.41 (m, 3H), 7.37-7.27 (m, 2H), 7.27-7.11 (m, 5H), 7.09-6.98 (m, 1H), 4.90 (d, J=2.3 Hz, 2H), 4.66 (td, J=7.8, 6.1 Hz, 1H), 4.43 (tdd, J=10.9, 7.9, 4.3 Hz, 2H), 3.19 (dd, J=13.9, 3.7 Hz, 1H), 2.94 (dd, J=13.8, 10.9 Hz, 1H), 2.77 (dd, J=16.2, 6.0 Hz, 1H), 2.56 (dd, J=16.2, 7.8 Hz, 1H), 2.37-2.20 (m, 2H), 2.01 (ddd, J=14.0, 6.8, 3.4 Hz, 1H), 1.90-1.73 (m, 1H), 1.38 (s, 9H), 1.32 (s, 9H). ¹³C NMR (126 MHz, DMSO-d₆) δ 172.19, 171.96, 170.75, 170.10, 169.86, 156.35, 139.10, 137.37, 136.28, 133.39, 132.30, 129.17, 128.65, 128.27, 128.06, 127.99, 127.97, 127.91, 127.80, 127.79, 126.43, 125.88, 123.99, 119.81, 80.84, 80.19, 65.64, 56.56, 53.19, 50.08, 38.08, 37.59, 31.63, 28.13, 28.11, 27.80. MS (ESI) m/z=781.1 [M+H]⁺, MS (ESI) m/z=803.1 [M+Na]⁺.

tert-Butyl (5S,8S,11S)-8-(2-(tert-butoxy)-2-oxoethyl)-5-(naphthalen-2-ylmethyl)-3,6,9-trioxo-1-phenyl-11-((4-(trifluoromethyl)phenyl)carbamoyl)-2-oxa-4,7,10-triazatetradecan-14-oate (64c). Yield, 74%. ¹H NMR (500 MHz, Chloroform-d) δ 8.81 (d, J=7.1 Hz, 1H), 7.88 (d, J=8.2 Hz, 2H), 7.85-7.62 (m, 6H), 7.59-7.51 (m, 2H), 7.51-7.43 (m, 2H), 7.35-7.12 (m, 6H), 5.33 (t, J=9.6 Hz, 1H), 5.14-4.93 (m, 2H), 4.71-4.62 (m, 1H), 4.55 (d, J=8.6 Hz, 1H), 4.48 (q, J=5.1, 4.5 Hz, 1H), 3.43 (dd, J=14.5, 4.9 Hz, 1H), 3.15 (dd, J=14.2, 8.9 Hz, 1H), 3.00 (dd, J=17.2, 4.4 Hz, 1H), 2.70-2.56 (m, 1H), 2.33 (p, J=4.1 Hz, 3H), 2.01-1.91 (m, 1H), 1.41 (s, 9H), 1.36 (s, 9H). ¹³C NMR (126 MHz, Chloroform-d) δ 172.45, 172.24, 171.21, 170.51, 169.63, 157.07, 141.29, 135.29, 133.42, 132.85, 132.63, 128.99, 128.58, 128.51, 128.35, 127.95, 127.76, 127.56, 126.64, 126.58, 126.17, 126.02, 125.96, 125.90, 125.64, 125.32, 123.17, 119.69, 82.49, 80.72, 67.97, 57.20, 53.87, 50.80, 37.70, 35.66, 32.09, 28.02, 27.99, 26.54. MS (ESI) m/z=871.3 [M+Na]⁺.

tert-Butyl (5S,8S,11S)-8-(2-(tert-butoxy)-2-oxoethyl)-5-(naphthalen-2-ylmethyl)-3,6,9-trioxo-1-phenyl-11-((3-(trifluoromethyl)phenyl)carbamoyl)-2-oxa-4,7,10-triazatetradecan-14-oate (64 d). Yield, 76%. ¹H NMR (500 MHz, Chloroform-d) δ 8.95 (s, 1H), 7.95 (s, 1H), 7.89-7.70 (m, 3H), 7.65-7.53 (m, 3H), 7.48 (d, J=1.6 Hz, 1H), 7.28 (dd, J=6.2, 3.3 Hz, 2H), 7.22-7.14 (m, 3H), 7.14-6.99 (m, 5H), 5.85 (d, J=6.2 Hz, 1H), 4.89 (q, J=12.3 Hz, 2H), 4.78-4.69 (m, 1H), 4.66-4.56 (m, 1H), 4.51 (q, J=8.3, 5.8 Hz, 1H), 3.23 (dd, J=14.3, 4.9 Hz, 1H), 3.04 (dd, J=14.1, 8.8 Hz, 1H), 2.75 (dd, J=17.1, 4.6 Hz, 1H), 2.61 (dd, J=16.9, 7.0 Hz, 1H), 2.37-2.11 (m, 3H), 1.95-1.81 (m, 1H), 1.25 (s, 9H), 1.24 (s, 9H). ¹³C NMR (126 MHz, Chloroform-d) δ 172.44, 172.22, 170.91 (d, J=3.1 Hz), 169.74, 156.91, 138.77, 135.73, 133.50, 132.52, 131.03 (d, J=32.2 Hz), 129.30, 128.55, 128.51, 128.45, 128.26, 128.06, 127.70, 127.64, 127.03, 126.29, 125.88, 125.15, 123.24, 122.98, 120.62, 116.87 (d, J=4.0 Hz), 82.24, 80.78, 67.47, 56.80, 53.79, 50.38, 38.37, 36.73, 31.84, 28.03, 27.91, 26.92. MS (ESI) m/z=871.3 [M+Na]⁺.

tert-Butyl (5S,8S,11S)-8-(2-(tert-butoxy)-2-oxoethyl)-11-((4-methoxyphenyl)carbamoyl)-5-(naphthalen-2-ylmethyl)-3,6,9-trioxo-1-phenyl-2-oxa-4,7,10-triazatetradecan-14-oate (64e). Yield, 83%. ¹H NMR (500 MHz, Chloroform-d) δ 8.46 (s, 1H), 7.77-7.62 (m, 3H), 7.58-7.48 (m, 5H), 7.38-7.34 (m, 2H), 7.26-7.11 (m, 6H), 6.74 (d, J=9.0 Hz, 2H), 5.42 (d, J=5.5 Hz, 1H), 4.95 (d, J=2.7 Hz, 2H), 4.63 (ddd, J=7.7, 6.2, 4.4 Hz, 1H), 4.46 (q, J=5.5, 4.8 Hz, 1H), 3.68 (s, 3H), 3.40-3.20 (m, 1H), 3.07 (dd, J=14.2, 8.6 Hz, 1H), 2.85 (dd, J=17.4, 4.4 Hz, 1H), 2.54 (dd, J=17.0, 6.3 Hz, 1H), 2.31-2.15 (m, 3H), 1.90 (dt, J=11.9, 3.7 Hz, 1H), 1.29 (s, 9H), 1.28 (s, 9H). ¹³C NMR (126 MHz, Chloroform-d) δ 172.59, 171.87, 171.07, 170.45, 168.81, 156.82, 156.26, 135.59, 133.43, 133.24, 132.56, 131.33, 128.74, 128.52, 128.34, 128.23, 128.00, 127.71, 127.61, 126.89, 126.39, 125.98, 121.72, 113.95, 82.23, 80.62, 67.65, 56.87, 55.45, 53.66, 50.44, 37.94, 36.22, 32.04, 28.04, 27.98, 26.93. MS (ESI) m/z=833.3 [M+Na]⁺.

tert-Butyl (5S,8S,11S)-8-(2-(tert-butoxy)-2-oxoethyl)-11-((3-methoxyphenyl)carbamoyl)-5-(naphthalen-2-ylmethyl)-3,6,9-trioxo-1-phenyl-2-oxa-4,7,10-triazatetradecan-14-oate (64f). Yield, 80%. ¹H NMR (500 MHz, Chloroform-d) δ 8.65 (s, 1H), 7.81-7.55 (m, 5H), 7.54-7.47 (m, 1H), 7.37 (t, J=2.2 Hz, 1H), 7.32 (dd, J=6.2, 3.2 Hz, 2H), 7.23-6.99 (m, 8H), 6.58-6.45 (m, 1H), 5.64 (d, J=5.8 Hz, 1H), 4.92 (s, 2H), 4.73-4.63 (m, 1H), 4.51 (ddd, J=21.6, 10.8, 5.9 Hz, 2H), 3.63 (s, 3H), 3.26 (dd, J=14.2, 5.0 Hz, 1H), 3.05 (dd, J=14.1, 8.7 Hz, 1H), 2.80 (dd, J=17.2, 4.4 Hz, 1H), 2.55 (dd, J=17.0, 6.6 Hz, 1H), 2.30-2.11 (m, 3H), 1.91-1.77 (m, 1H), 1.27 (s, 9H), 1.27 (s, 9H). ¹³C NMR (126 MHz, Chloroform-d) δ 172.47, 171.91, 170.99, 170.67, 169.27, 160.00, 156.85, 139.33, 135.69, 133.42 (d, J=2.6 Hz), 132.53, 129.47, 128.62, 128.52, 128.29, 128.17, 128.04, 127.70, 127.64, 127.00, 126.33, 125.91, 112.37, 110.29, 105.65, 82.17, 80.64, 67.55, 56.81, 55.22, 53.78, 50.32, 38.16, 36.50, 31.93, 28.06, 27.98, 27.03. MS (ESI) m/z=833.4 [M+Na]⁺.

tert-Butyl (5S,8S,11S)-8-(2-(tert-butoxy)-2-oxoethyl)-5-(naphthalen-2-ylmethyl)-3,6,9-trioxo-1-phenyl-11-((4-(trifluoromethoxy)phenyl)carbamoyl)-2-oxa-4,7,10-triazatetradecan-14-oate (64 g). Yield, 79%. ¹H NMR (500 MHz, Chloroform-d) δ 8.64 (dd, J=11.5, 4.6 Hz, 1H), 7.84-7.64 (m, 5H), 7.59 (d, J=26.7 Hz, 3H), 7.44-7.32 (m, 2H), 7.25-7.13 (m, 6H), 7.07 (dd, J=8.9, 3.3 Hz, 2H), 5.30 (d, J=28.7 Hz, 1H), 5.11-4.84 (m, 2H), 4.68-4.54 (m, 1H), 4.50-4.25 (m, 2H), 3.44-3.26 (m, 1H), 3.07 (dd, J=14.2, 8.8 Hz, 1H), 2.90 (d, J=17.1 Hz, 1H), 2.54 (ddd, J=17.0, 5.9, 2.3 Hz, 1H), 2.32-2.16 (m, 2H), 1.96-1.81 (m, 2H), 1.32 (s, 9H), 1.28 (s, 9H). ¹³C NMR (126 MHz, Chloroform-d) δ 172.46, 172.19, 171.18, 170.44, 169.34, 157.04, 145.13, 136.92, 135.33, 133.42, 132.93, 132.62, 128.95, 128.57, 128.48, 128.34, 127.96, 127.75, 127.57, 126.68, 126.55, 126.14, 121.50, 121.16, 82.44, 80.68, 67.92, 57.16, 53.81, 50.73, 37.73, 35.74, 32.10, 28.02, 27.97, 26.61. MS (ESI) m/z=887.4 [M+Na]⁺.

tert-Butyl (5S,8S,11S)-8-(2-(tert-butoxy)-2-oxoethyl)-5-(naphthalen-2-ylmethyl)-3,6,9-trioxo-1-phenyl-11-((3-(trifluoromethoxy)phenyl)carbamoyl)-2-oxa-4,7,10-triazatetradecan-14-oate (64 h). Yield, 80%. ¹H NMR (500 MHz, Chloroform-d) δ 8.89 (s, 1H), 7.88 (d, J=7.6 Hz, 1H), 7.80 (d, J=8.1 Hz, 1H), 7.68-7.53 (m, 4H), 7.47 (dd, J=15.1, 5.0 Hz, 2H), 7.28 (dd, J=6.2, 3.2 Hz, 2H), 7.22-7.17 (m, 1H), 7.14-7.04 (m, 6H), 6.89-6.63 (m, 1H), 5.84 (d, J=6.2 Hz, 1H), 4.89 (q, J=12.3 Hz, 2H), 4.77-4.67 (m, 1H), 4.62-4.59 (m, 1H), 4.52-4.46 (m, 1H), 3.25 (dd, J=14.2, 4.8 Hz, 1H), 3.05 (dd, J=14.1, 8.8 Hz, 1H), 2.76 (dd, J=17.1, 4.6 Hz, 1H), 2.60 (dd, J=16.9, 6.9 Hz, 1H), 2.30-2.11 (m, 3H), 1.89 (s, 1H), 1.25 (s, 18H). ¹³C NMR (126 MHz, Chloroform-d) δ 172.35, 172.13, 170.87, 170.86, 169.65, 156.91, 149.43, 149.41, 139.68, 135.74, 133.50, 133.44, 132.53, 129.77, 128.55, 128.50, 128.26, 128.07 (d, J=2.2 Hz), 127.69, 127.63, 127.02, 126.29, 125.87, 120.53 (d, J=257.1 Hz), 118.21, 116.10, 112.89, 82.19, 80.71, 67.47, 56.79, 53.78, 50.32, 38.42, 36.74, 31.85, 28.03, 27.91, 26.95. MS (ESI) m/z=887.4 [M+Na]⁺.

tert-Butyl (5S,8S,11S)-8-(2-(tert-butoxy)-2-oxoethyl)-11-((3,5-dimethoxyphenyl)carbamoyl)-5-(naphthalen-2-ylmethyl)-3,6,9-trioxo-1-phenyl-2-oxa-4,7,10-triazatetradecan-14-oate (64i). Yield, 81%. ¹H NMR (500 MHz, Chloroform-d) δ 8.55 (s, 1H), 7.84-7.55 (m, 5H), 7.52 (d, J=1.6 Hz, 1H), 7.38-7.29 (m, 2H), 7.21-7.11 (m, 6H), 6.92 (s, 2H), 6.13 (t, J=2.3 Hz, 1H), 5.49 (d, J=5.4 Hz, 1H), 4.94 (s, 2H), 4.63 (ddd, J=7.6, 6.1, 4.4 Hz, 1H), 4.47 (h, J=4.8 Hz, 2H), 3.64 (s, 6H), 3.27 (dd, J=14.1, 5.1 Hz, 1H), 3.05 (dd, J=14.2, 8.6 Hz, 1H), 2.84 (dd, J=17.6, 4.2 Hz, 1H), 2.53 (dd, J=17.3, 6.4 Hz, 1H), 2.29-2.13 (m, 3H), 1.91 (d, J=24.4 Hz, 1H), 1.29 (s, 9H), 1.27 (s, 9H). $^{13}$C NMR (126 MHz, Chloroform-d) δ 172.51, 171.92, 171.07, 170.57, 169.23, 160.89, 156.89, 139.87, 135.58, 133.43, 133.26, 132.56, 128.72, 128.53, 128.35, 128.24, 127.99, 127.71, 127.61, 126.89, 126.39, 125.97, 98.28, 96.99, 82.25, 80.65, 67.68, 56.95, 55.33, 53.80, 50.48, 37.96, 36.19, 31.97, 28.05, 27.99, 26.89. MS (ESI) m/z=863.4 [M+Na]$^+$.

tert-Butyl (5S,8S,11S)-8-(2-(tert-butoxy)-2-oxoethyl)-11-((3-methoxy-5-(trifluoromethyl)phenyl)carbamoyl)-5-(naphthalen-2-ylmethyl)-3,6,9-trioxo-1-phenyl-2-oxa-4,7,10-triazatetradecan-14-oate (64j). Yield, 82%. $^1$H NMR (500 MHz, Chloroform-d) δ 8.82 (s, 1H), 7.75-7.54 (m, 6H), 7.50 (t, J=2.5 Hz, 2H), 7.40-7.24 (m, 2H), 7.24-7.02 (m, 6H), 6.75 (t, J=1.8 Hz, 1H), 5.58 (d, J=5.6 Hz, 1H), 4.92 (s, 2H), 4.62 (td, J=7.0, 4.8 Hz, 1H), 4.55-4.36 (m, 2H), 3.65 (s, 3H), 3.27 (dd, J=14.2, 5.0 Hz, 1H), 3.04 (dd, J=14.2, 8.7 Hz, 1H), 2.81 (dd, J=17.1, 4.4 Hz, 1H), 2.58 (dd, J=17.0, 6.5 Hz, 1H), 2.26-2.11 (m, 3H), 1.92 (s, 1H), 1.28 (s, 9H), 1.26 (s, 9H). $^{13}$C NMR (126 MHz, Chloroform-d) δ 172.45, 172.20, 171.04, 170.68, 169.65, 160.20, 156.97, 140.00, 135.53, 133.43, 133.23, 132.56, 131.80 (q, J=32.3 Hz), 128.73, 128.53, 128.37, 128.20, 127.99, 127.71, 127.59, 126.85, 126.40, 125.98, 125.00, 122.83, 109.10 (d, J=4.3 Hz), 108.59, 106.86 (d, J=4.1 Hz), 82.38, 80.75, 67.70, 57.04, 55.51, 53.79, 50.64, 38.05, 36.22, 31.91, 28.03, 27.94, 26.71. MS (ESI) m/z=901.4 [M+Na]$^+$, MS (ESI) m/z=877.2 [M−H]$^-$.

tert-Butyl (5S,8S,11S)-11-(benzo[d][1,3]dioxol-5-ylcarbamoyl)-8-(2-(tert-butoxy)-2-oxoethyl)-5-(naphthalen-2-ylmethyl)-3,6,9-trioxo-1-phenyl-2-oxa-4,7,10-triazatetradecan-14-oate (64k). Yield, 80%. $^1$H NMR (500 MHz, Chloroform-d) δ 8.54 (s, 1H), 7.65 (ddt, J=17.6, 13.4, 5.0 Hz, 5H), 7.52 (d, J=1.7 Hz, 1H), 7.43-7.31 (m, 2H), 7.30-7.26 (m, 1H), 7.22-7.09 (m, 6H), 6.93-6.85 (m, 1H), 6.59 (d, J=8.4 Hz, 1H), 5.79 (s, 2H), 5.58 (d, J=5.7 Hz, 1H), 4.93 (s, 2H), 4.76-4.58 (m, 1H), 4.48 (ddd, J=19.7, 9.4, 5.0 Hz, 2H), 3.36-3.21 (m, 1H), 3.05 (dd, J=14.2, 8.7 Hz, 1H), 2.81 (dd, J=17.1, 4.5 Hz, 1H), 2.62-2.46 (m, 1H), 2.33-2.14 (m, 3H), 1.90 (dd, J=14.9, 8.6 Hz, 1H), 1.28 (s, 9H), 1.27 (s, 9H). $^{13}$C NMR (126 MHz, Chloroform-d) δ 172.48, 171.92, 170.98, 170.55, 168.94, 156.84, 147.55, 144.03, 135.67, 133.43, 133.36, 132.54, 132.44, 128.65, 128.50, 128.29, 128.16, 128.02, 127.70, 127.62, 126.96, 126.33, 125.91, 113.29, 107.90, 102.80, 101.08, 82.19, 80.62, 67.56, 56.82, 53.66, 53.49, 50.38, 38.06, 36.40, 31.97, 28.05, 27.97, 26.98. MS (ESI) m/z=825.3 [M+H]$^+$, MS (ESI) m/z=847.4 [M+Na]$^+$.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-(isopentylamino)-5-oxopentanoate (65a). Yield, 89%. $^1$H NMR (500 MHz, Chloroform-d) δ 7.76-7.61 (m, 3H), 7.59-7.50 (m, 2H), 7.44 (d, J=8.1 Hz, 1H), 7.39-7.31 (m, 2H), 7.26-7.08 (m, 6H), 6.67 (t, J=5.6 Hz, 1H), 5.54 (d, J=5.7 Hz, 1H), 4.94 (s, 2H), 4.61 (ddd, J=7.9, 6.4, 4.5 Hz, 1H), 4.53-4.42 (m, 1H), 4.33 (td, J=8.6, 4.5 Hz, 1H), 3.27 (dd, J=14.2, 5.0 Hz, 1H), 3.20-2.92 (m, 3H), 2.80 (dd, J=16.9, 4.4 Hz, 1H), 2.53 (dd, J=16.9, 6.5 Hz, 1H), 2.28-2.00 (m, 3H), 1.84 (tt, J=15.7, 7.0 Hz, 1H), 1.52 (dt, J=13.4, 6.7 Hz, 1H), 1.30 (s, 9H), 1.28 (s, 9H), 0.81 (dd, J=6.7, 3.0 Hz, 6H). $^{13}$C NMR (126 MHz, Chloroform-d) δ 172.62, 171.61, 170.97, 170.53, 170.24, 156.69, 135.73, 133.43, 132.53, 128.64, 128.51, 128.28, 128.17, 128.02, 127.70, 127.61, 126.97, 126.32, 125.90, 82.05, 80.50, 67.48, 56.75, 53.12, 50.22, 38.20, 38.05, 37.96, 36.49, 31.94, 28.04, 27.99, 27.10, 25.82, 22.52, 22.50. MS (ESI) m/z=775.2 [M+H]$^+$, MS (ESI) m/z=797.2 [M+Na]$^+$.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-oxo-5-(phenylamino)pentanoate (65b). Yield, 84%. $^1$H NMR (500 MHz, DMSO-d$_6$) δ 9.92 (s, 1H), 8.55 (d, J=7.9 Hz, 1H), 8.07 (d, J=7.9 Hz, 1H), 7.88 (dd, J=6.9, 2.2 Hz, 1H), 7.86-7.75 (m, 3H), 7.73-7.56 (m, 3H), 7.55-7.35 (m, 3H), 7.36-7.27 (m, 2H), 7.27-7.19 (m, 3H), 7.19-7.13 (m, 2H), 7.12-6.92 (m, 1H), 5.00-4.81 (m, 2H), 4.66 (td, J=7.8, 6.1 Hz, 1H), 4.43 (tdd, J=10.9, 7.9, 4.3 Hz, 2H), 3.23-3.09 (m, 1H), 2.94 (dd, J=13.8, 10.9 Hz, 1H), 2.77 (dd, J=16.2, 6.0 Hz, 1H), 2.56 (dd, J=16.2, 7.8 Hz, 1H), 2.38-2.18 (m, 2H), 2.11-1.97 (m, 1H), 1.86 (ddt, J=10.6, 5.2, 2.9 Hz, 1H), 1.38 (s, 9H), 1.32 (s, 9H). $^{13}$C NMR (126 MHz, DMSO-d$_6$) δ 172.19, 171.96, 170.75, 170.10, 169.86, 156.35, 139.10, 137.37, 136.28, 133.39, 132.30, 129.17, 128.65, 128.27, 128.06, 127.99, 127.97, 127.91, 127.79, 126.43, 125.88, 119.81, 80.84, 80.19, 65.64, 56.56, 53.19, 50.08, 38.08, 37.59, 31.63, 28.13, 28.11, 27.80. MS (ESI) m/z=781.1 [M+H]$^+$, MS (ESI) m/z=803.1 [M+Na]$^+$.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-oxo-5-((4-(trifluoromethyl)phenyl)amino)pentanoate (65c). Yield, 72%. $^1$H NMR (500 MHz, Chloroform-d) δ 11.05-10.69 (m, 1H), 8.90 (s, 1H), 8.10 (d, J=7.5 Hz, 1H), 8.00 (d, J=7.5 Hz, 1H), 7.89 (d, J=8.5 Hz, 2H), 7.84-7.69 (m, 4H), 7.59-7.49 (m, 3H), 7.49-7.43 (m, 2H), 7.40-7.33 (m, 2H), 7.18 (dd, J=8.8, 2.0 Hz, 1H), 6.87 (d, J=4.5 Hz, 1H), 6.62 (d, J=2.2 Hz, 1H), 4.87 (dd, J=9.5, 4.9 Hz, 1H), 4.69 (ddd, J=7.6, 6.0, 4.5 Hz, 1H), 4.44 (ddd, J=11.0, 7.3, 3.5 Hz, 1H), 3.56 (dd, J=14.2, 5.3 Hz, 1H), 3.28 (dd, J=14.2, 9.1 Hz, 1H), 2.96 (dd, J=16.9, 4.5 Hz, 1H), 2.82-2.58 (m, 1H), 2.53-2.32 (m, 3H), 2.30-2.21 (m, 1H), 1.49 (s, 9H), 1.20 (s, 9H). $^{13}$C NMR (126 MHz, Chloroform-d) δ 174.30, 172.12, 170.94, 170.76, 169.82, 163.11, 141.13, 135.78, 133.49, 132.83, 132.66, 129.94, 129.16, 127.99, 127.78, 127.77, 127.46, 126.74, 126.52, 126.31, 126.28, 125.95 (d, J=3.9 Hz), 125.76, 125.52, 125.28, 123.12, 121.02, 119.79, 113.68, 103.00, 82.54, 81.70, 56.38, 54.45, 50.97, 37.72, 35.70, 33.27, 28.09, 27.74, 27.55. MS (ESI) m/z=914.3 [M+Na]$^+$, MS (ESI) m/z=890.3 [M−H]$^-$.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-oxo-5-((3-(trifluoromethyl)phenyl)amino)pentanoate (65 d). Yield, 70%. $^1$H NMR (500 MHz, Acetone-d$_6$) δ 11.18-10.69 (m, 1H), 9.28 (s, 1H), 8.26 (dd, J=7.2, 4.4 Hz, 1H), 8.10 (d, J=2.0 Hz, 1H), 7.99-7.73 (m, 2H), 7.64 (d, J=1.7 Hz, 1H), 7.61-7.49 (m, 3H), 7.47 (d, J=2.0 Hz, 1H), 7.42-7.28 (m, 3H), 7.28-7.16 (m, 3H), 7.14-6.85 (m, 2H), 4.96 (ddd, J=8.9, 6.9, 5.7 Hz, 1H), 4.66 (q, J=6.8 Hz, 1H), 4.38 (ddd, J=9.5, 7.7, 4.8 Hz, 1H), 3.33 (dd, J=14.0, 5.7 Hz, 1H), 3.23 (dd, J=14.0, 9.0 Hz, 1H), 2.75 (dd, J=16.5, 6.5 Hz, 1H), 2.59 (dd, J=16.5, 6.6 Hz, 1H), 2.27 (td, J=9.3, 6.1 Hz, 2H), 2.21-2.08 (m, 1H), 1.98-1.87 (m, 1H), 1.25 (s, 9H), 1.17 (s, 9H). $^{13}$C NMR (126 MHz, Acetone-d$_6$) δ 172.31, 172.08, 170.89, 170.14, 170.10, 162.00, 139.60, 135.34, 135.00, 133.56, 132.45, 132.01, 130.38 (q, J=31.9 Hz), 129.58, 128.64, 127.91, 127.78, 127.52, 127.48, 127.47, 125.89, 125.45, 125.39, 125.29, 124.24, 123.23, 123.07, 120.01 (q, J=3.8 Hz), 116.04 (q, J=4.1 Hz), 113.80, 103.08, 80.89, 80.04, 55.91, 53.85, 50.78, 37.43, 36.83, 31.69, 27.40, 27.26, 26.99. MS (ESI) m/z=914.3 [M+Na]⁺, MS (ESI) m/z=890.3 [M−H]⁻.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-((4-methoxyphenyl)amino)-5-oxopentanoate (65e). Yield, 86%. ¹H NMR (500 MHz, Acetone-d₆) δ 11.13-10.78 (m, 1H), 9.00 (s, 1H), 8.29 (t, J=7.0 Hz, 2H), 7.88 (d, J=8.0 Hz, 1H), 7.68 (d, J=1.6 Hz, 1H), 7.62-7.43 (m, 3H), 7.38-7.31 (m, 3H), 7.24 (dd, J=6.3, 3.2 Hz, 2H), 7.16-6.97 (m, 2H), 6.92-6.56 (m, 2H), 5.17-4.93 (m, 1H), 4.76 (q, J=6.9 Hz, 1H), 4.59-4.29 (m, 1H), 3.63 (s, 3H), 3.38 (dd, J=14.0, 5.7 Hz, 1H), 3.27 (dd, J=14.0, 9.0 Hz, 1H), 2.79 (dd, J=16.4, 6.6 Hz, 1H), 2.62 (dd, J=16.4, 6.6 Hz, 1H), 2.38-2.25 (m, 2H), 2.23-2.12 (m, 1H), 2.00-1.90 (m, 1H), 1.29 (s, 9H), 1.21 (s, 9H). ¹³C NMR (126 MHz, Acetone-d₆) δ 172.31, 171.81, 170.76, 170.01, 169.10, 161.88, 156.20, 135.35, 135.06, 133.56, 132.43, 132.10, 131.93, 128.66, 127.88, 127.82, 127.59, 127.50, 127.45, 125.85, 125.40, 125.24, 124.18, 121.31, 120.88, 113.84, 113.69, 103.02, 80.79, 79.94, 55.70, 54.76, 53.64, 50.63, 37.59, 37.06, 31.73, 27.45, 27.41, 27.29. MS (ESI) m/z=876.2 [M+Na]⁺.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-((3-methoxyphenyl)amino)-5-oxopentanoate (65f). Yield, 81%. ¹H NMR (500 MHz, Chloroform-d) δ 10.75 (s, 1H), 8.76 (s, 1H), 8.61 (s, 1H), 8.31 (s, 1H), 7.62 (s, 1H), 7.49-7.35 (m, 5H), 7.33-7.26 (m, 1H), 7.24-7.08 (m, 4H), 7.08-6.93 (m, 3H), 6.87 (s, 1H), 6.50 (dt, J=5.8, 2.7 Hz, 1H), 5.38 (s, 1H), 4.98 (s, 1H), 4.38 (s, 1H), 3.56 (s, 3H), 3.31 (t, J=7.1 Hz, 1H), 3.23 (dd, J=14.0, 7.8 Hz, 1H), 2.70 (qd, J=17.1, 6.6 Hz, 2H), 2.42-2.07 (m, 3H), 1.94 (s, 1H), 1.33 (s, 9H), 1.05 (s, 9H). ¹³C NMR (126 MHz, Chloroform-d) δ 173.44, 171.51, 171.19, 170.35, 169.57, 161.97, 160.00, 138.85, 135.52, 133.60, 133.33, 132.33, 130.87, 129.47, 128.28, 128.25, 127.92, 127.45, 127.40, 127.13, 126.05, 125.93, 125.65, 124.99, 121.09, 113.74, 112.87, 110.27, 106.49, 103.62, 81.90, 81.31, 55.16, 54.89, 54.15, 49.98, 38.92, 37.65, 32.17, 28.10, 27.75, 27.49. MS (ESI) m/z=876.3 [M+Na]⁺.

tert-Butyl (S)-4-((S)-4-(tert-butoxy)-2-((S)-2-(5-chloro-1H-indole-2-carboxamido)-3-(naphthalen-2-yl)propanamido)-4-oxo-5-((4-(trifluoromethoxy)phenyl)amino)pentanoate (65 g). Yield, 86%. ¹H NMR (500 MHz, Chloroform-d) δ 10.99 (s, 1H), 8.76 (s, 1H), 8.07 (d, J=7.6 Hz, 1H), 7.90-7.69 (m, 7H), 7.52 (dt, J=5.4, 2.9 Hz, 3H), 7.45-7.35 (m, 2H), 7.23-7.02 (m, 3H), 6.69 (d, J=4.9 Hz, 1H), 6.55 (d, J=2.6 Hz, 1H), 4.76 (s, 1H), 4.70-4.60 (m, 1H), 4.45 (ddd, J=10.7, 7.6, 3.6 Hz, 1H), 3.61 (dd, J=14.3, 4.9 Hz, 1H), 3.28 (dd, J=14.3, 9.4 Hz, 1H), 3.00 (dd, J=17.0, 4.4 Hz, 1H), 2.62-2.55 (m, 1H), 2.54-2.44 (m, 1H), 2.44-2.24 (m, 3H), 1.49 (s, 9H), 1.18 (s, 9H). ¹³C NMR (126 MHz, Chloroform-d) δ 174.48, 172.16, 171.00, 170.56, 169.51, 163.31, 145.21, 136.86, 135.85, 133.54, 132.74, 132.70, 129.81, 129.37, 127.93, 127.86, 127.76, 127.49, 126.88, 126.42, 126.30, 125.58, 121.50, 121.22, 120.99, 119.50, 113.70, 102.91, 82.56, 81.67, 56.65, 54.35, 51.12, 37.48, 35.28, 33.55, 29.29, 28.10, 27.71. MS (ESI) m/z=930.3 [M+Na]⁺, MS (ESI) m/z=906.2 [M−H]⁻.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-oxo-5-((3-(trifluoromethoxy)phenyl)amino)pentanoate (65 h). Yield, 76%. ¹H NMR (500 MHz, Chloroform-d) δ 10.93 (s, 1H), 8.96-8.75 (m, 1H), 8.13-7.98 (m, 2H), 7.90-7.62 (m, 6H), 7.53 (d, J=2.1 Hz, 1H), 7.48-7.31 (m, 4H), 7.31-7.24 (m, 1H), 7.17 (dt, J=8.8, 2.3 Hz, 1H), 6.94 (d, J=8.3 Hz, 2H), 6.68 (s, 1H), 4.99 (s, 1H), 4.77-4.61 (m, 1H), 4.43 (t, J=8.0 Hz, 1H), 3.54 (d, J=15.1 Hz, 1H), 3.34-3.20 (m, 1H), 2.92 (d, J=17.6 Hz, 1H), 2.67 (dd, J=20.8, 12.6 Hz, 1H), 2.49-2.31 (m, 3H), 2.23 (d, J=9.1 Hz, 1H), 1.48 (d, J=2.4 Hz, 9H), 1.20 (d, J=3.3 Hz, 9H). ¹³C NMR (126 MHz, Chloroform-d) δ 174.23, 171.95, 170.93, 170.79, 169.57, 162.81, 149.42, 139.49, 135.76, 133.46, 132.97, 132.63, 130.14, 129.75, 129.01, 128.03, 127.77, 127.45, 126.60, 126.25, 125.47, 121.51, 121.00, 119.46, 118.20, 116.22, 113.69, 112.87, 102.96, 82.50, 81.65, 56.16, 54.34, 50.87, 37.99, 36.12, 33.03, 28.09, 27.72, 27.43. MS (ESI) m/z=930.3 [M+Na]⁺, MS (ESI) m/z=906.3 [M−H]⁻.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-((3,5-dimethoxyphenyl)amino)-5-oxopentanoate (65i). Yield, 83%. ¹H NMR (500 MHz, Chloroform-d) δ 10.86 (s, 1H), 8.73 (s, 1H), 8.40 (s, 1H), 8.22 (s, 1H), 7.61 (q, J=11.7, 9.7 Hz, 4H), 7.51 (d, J=2.0 Hz, 1H), 7.31 (t, J=8.3 Hz, 5H), 7.15 (dd, J=8.7, 2.0 Hz, 1H), 6.95 (d, J=2.2 Hz, 2H), 6.85 (s, 1H), 6.19 (t, J=2.2 Hz, 1H), 5.28 (s, 1H), 4.93 (s, 1H), 4.45 (s, 1H), 3.67 (s, 6H), 3.44 (dd, J=14.0, 6.1 Hz, 1H), 3.31 (dd, J=14.0, 8.1 Hz, 1H), 2.84 (dd, J=16.7, 4.9 Hz, 1H), 2.74 (dd, J=16.7, 7.4 Hz, 1H), 2.48-2.24 (m, 3H), 2.18-2.07 (m, 1H), 1.45 (s, 9H), 1.19 (s, 9H). ¹³C NMR (126 MHz, Chloroform-d) δ 173.74, 171.55, 171.00, 170.54, 169.46, 162.28, 160.88, 139.50, 135.59, 133.38, 133.36, 132.44, 130.59, 128.53, 128.18, 127.87, 127.55, 127.44, 126.97, 126.24, 126.03, 125.84, 125.14, 121.05, 113.71, 103.31, 98.75, 96.90, 82.09, 81.41, 55.30, 55.26, 54.28, 50.30, 38.57, 37.05, 32.51, 28.10, 27.75, 27.54. MS (ESI) m/z=906.4 [M+Na]⁺.

tert-Butyl (S)-4-((S)-4-(tert-butoxy)-2-((S)-2-(5-chloro-1H-indole-2-carboxamido)-3-(naphthalen-2-yl)propanamido)-4-oxobutanamido)-5-((3-methoxy-5-(trifluoromethyl)phenyl)amino)-5-oxopentanoate (65j). Yield, 80%. ¹H NMR (500 MHz, Chloroform-d) δ 10.86 (s, 1H), 8.92 (s, 1H), 8.31 (s, 1H), 8.14 (d, J=7.3 Hz, 1H), 7.73-7.58 (m, 5H), 7.54 (d, J=2.0 Hz, 1H), 7.50 (s, 1H), 7.42-7.27 (m, 4H), 7.16 (dd, J=8.7, 2.0 Hz, 2H), 6.88-6.52 (m, 2H), 5.15 (d, J=8.6 Hz, 1H), 4.80 (td, J=7.5, 4.6 Hz, 1H), 4.49-4.30 (m, 1H), 3.74 (s, 3H), 3.46 (dd, J=14.0, 6.1 Hz, 1H), 3.28 (dd, J=14.0, 8.4 Hz, 1H), 2.92-2.78 (m, 1H), 2.81-2.69 (m, 1H), 2.48-2.28 (m, 3H), 2.17 (d, J=6.1 Hz, 1H), 1.48 (s, 9H), 1.20 (s, 9H). ¹³C NMR (126 MHz, Chloroform-d) δ 174.08, 171.84, 170.91, 170.85, 169.67, 162.51, 160.12, 139.66, 135.64, 133.38, 133.11, 132.49, 131.72 (d, J=32.3 Hz), 130.29, 128.70, 128.10, 127.78, 127.59, 127.37, 126.74, 126.40, 126.15, 125.99, 125.30, 123.80 (q, J=272.5 Hz), 121.01, 113.71, 109.18 (d, J=4.1 Hz), 108.89, 106.78, 103.05, 82.45, 81.64, 55.63, 55.48, 54.40, 50.57, 38.39, 36.61, 32.68, 28.09, 27.70, 27.21. MS (ESI) m/z=944.3 [M+Na]⁺.

tert-Butyl (S)-5-(benzo[d][1,3]dioxol-5-ylamino)-4-((S)-4-(tert-butoxy)-2-((S)-2-(5-chloro-1H-indole-2-carboxamido)-3-(naphthalen-2-yl)propanamido)-4-oxobutanamido)-5-oxopentanoate (65k). Yield, 88%. ¹H NMR (500 MHz, Chloroform-d) δ 10.75 (s, 1H), 8.73 (s, 1H), 8.63 (s, 1H), 8.36 (s, 1H), 7.65 (s, 1H), 7.49-7.33 (m, 5H), 7.27-7.09 (m, 5H), 7.05 (dd, J=8.7, 2.0 Hz, 1H), 6.88 (s, 1H), 6.82 (dd, J=8.4, 2.1 Hz, 1H), 6.51 (d, J=8.3 Hz, 1H), 5.75 (d, J=1.5 Hz, 1H), 5.70 (s, 1H), 5.39 (s, 1H), 5.01 (s, 1H), 4.40 (s, 1H), 3.33 (dd, J=14.2, 6.3 Hz, 1H), 3.23 (d, J=14.1 Hz, 1H), 2.76 (dd, J=16.7, 8.0 Hz, 1H), 2.66 (d, J=13.0 Hz, 1H), 2.42-2.10 (m, 3H), 1.94 (s, 1H), 1.33 (s, 9H), 1.05 (s, 9H). ¹³C NMR (126 MHz, Chloroform-d) δ 173.35, 171.49, 171.15, 170.35, 169.49, 161.94, 147.58, 144.42, 135.53, 133.60, 133.32, 132.32, 131.80, 130.90, 128.26, 128.22, 127.94, 127.42, 127.38, 127.12, 126.02, 125.91, 125.62, 124.96, 121.05, 114.02, 113.73, 107.81, 103.84, 103.35, 101.21, 81.85, 81.23, 54.89, 53.90, 49.95, 38.95, 37.66, 32.14, 28.10, 27.74, 27.41. MS (ESI) m/z=890.3 [M+Na]⁺, MS (ESI) m/z=866.3 [M−H]⁻.

(S)-4-((S)-3-carboxy-2-((S)-2-(5-chloro-1H-indole-2-carboxamido)-3-(naphthalen-2-yl)propanamido)propanamido)-5-(isopentylamino)-5-oxopentanoic acid (20). ¹H NMR (500 MHz, DMSO-d$_6$) δ 12.27 (s, 2H), 11.63 (d, J=2.2 Hz, 1H), 8.80 (d, J=8.5 Hz, 1H), 8.66 (d, J=7.6 Hz, 1H), 7.92 (d, J=8.0 Hz, 1H), 7.85 (d, J=1.6 Hz, 1H), 7.83-7.73 (m, 4H), 7.70 (d, J=2.1 Hz, 1H), 7.56 (dd, J=8.5, 1.7 Hz, 1H), 7.42 (pd, J=6.8, 1.6 Hz, 2H), 7.36 (d, J=8.7 Hz, 1H), 7.24-7.19 (m, 1H), 7.14 (dd, J=8.7, 2.1 Hz, 1H), 4.99-4.78 (m, 1H), 4.62 (q, J=7.2 Hz, 1H), 4.21 (td, J=8.3, 5.0 Hz, 1H), 3.27 (d, J=3.6 Hz, 1H), 3.20-2.96 (m, 3H), 2.78 (dd, J=16.6, 6.1 Hz, 1H), 2.60 (dd, J=16.7, 7.4 Hz, 1H), 2.24 (dd, J=9.6, 7.0 Hz, 2H), 2.05-1.89 (m, 1H), 1.84-1.69 (m, 1H), 1.55 (dt, J=13.4, 6.7 Hz, 1H), 1.29 (q, J=7.2 Hz, 2H), 0.85 (d, J=6.6 Hz, 6H). ¹³C NMR (126 MHz, DMSO-d$_6$) δ 174.45, 172.40, 172.03, 170.87, 170.75, 161.05, 136.48, 135.23, 133.38, 133.06, 132.23, 128.46, 128.32, 127.91, 127.89, 127.84, 127.76, 126.40, 125.83, 124.63, 123.92, 121.10, 114.29, 103.33, 54.82, 52.53, 50.18, 38.40, 37.95, 37.27, 36.41, 30.48, 27.93, 25.55, 22.83, 22.80. HRMS (ESI) Calcd for C$_{36}$H$_{40}$ClN$_5$O$_8$(M−H)⁻ 704.2487, found 704.2492.

(S)-4-((S)-3-carboxy-2-((S)-2-(5-chloro-1H-indole-2-carboxamido)-3-(naphthalen-2-yl)propanamido)propanamido)-5-oxo-5-(phenylamino)pentanoic acid (21). ¹H NMR (500 MHz, DMSO-d$_6$) δ 12.30 (s, 2H), 11.63 (d, J=2.3 Hz, 1H), 9.86 (s, 1H), 8.81 (d, J=8.5 Hz, 1H), 8.67 (d, J=7.6 Hz, 1H), 8.13 (d, J=7.8 Hz, 1H), 7.85 (d, J=1.6 Hz, 1H), 7.83-7.75 (m, 3H), 7.70 (d, J=2.1 Hz, 1H), 7.62 (d, J=1.4 Hz, 1H), 7.60 (d, J=1.2 Hz, 1H), 7.56 (dd, J=8.5, 1.7 Hz, 1H), 7.48-7.39 (m, 2H), 7.36 (d, J=8.7 Hz, 1H), 7.33-7.27 (m, 2H), 7.21 (d, J=2.0 Hz, 1H), 7.15 (dd, J=8.7, 2.1 Hz, 1H), 7.10-7.03 (m, 1H), 5.12-4.82 (m, 1H), 4.67 (td, J=7.5, 6.0 Hz, 1H), 4.43 (td, J=8.2, 5.0 Hz, 1H), 3.31 (d, J=8.8 Hz, 1H), 3.16 (dd, J=13.9, 11.0 Hz, 1H), 2.81 (dd, J=16.7, 6.0 Hz, 1H), 2.63 (dd, J=16.6, 7.6 Hz, 1H), 2.32 (td, J=10.2, 6.2 Hz, 2H), 2.05 (ddt, J=15.0, 9.9, 5.7 Hz, 1H), 1.89 (ddt, J=13.6, 8.7, 4.7 Hz, 1H). ¹³C NMR (126 MHz, DMSO-d$_6$) δ 174.32, 172.37, 172.06, 171.08, 170.26, 161.06, 139.10, 136.49, 135.24, 133.39, 133.07, 132.23, 129.17, 128.47, 128.32, 127.91, 127.89, 127.85, 127.76, 126.40, 125.83, 124.64, 123.99, 123.92, 121.10, 119.91, 114.29, 103.34, 54.83, 53.34, 50.17, 37.97, 36.43, 30.56, 27.79. HRMS (ESI) Calcd for C$_{37}$H$_{34}$ClN$_5$O$_8$(M−H)⁻ 710.2018, found 710.2024.

(S)-4-((S)-3-carboxy-2-((S)-2-(5-chloro-1H-indole-2-carboxamido)-3-(naphthalen-2-yl)propanamido)propanamido)-5-oxo-5-((4-(trifluoromethyl)phenyl)amino)pentanoic acid (30). ¹H NMR (500 MHz, DMSO-d$_6$) δ 12.31 (s, 2H), 11.64 (s, 1H), 10.24 (s, 1H), 8.82 (d, J=8.5 Hz, 1H), 8.67 (d, J=7.6 Hz, 1H), 8.23 (d, J=7.5 Hz, 1H), 7.98-7.74 (m, 6H), 7.74-7.59 (m, 3H), 7.56 (d, J=8.4 Hz, 1H), 7.48-7.30 (m, 3H), 7.21 (s, 1H), 7.14 (d, J=8.8 Hz, 1H), 4.90 (d, J=8.1 Hz, 1H), 4.66 (q, J=7.1 Hz, 1H), 4.42 (q, J=7.1 Hz, 1H), 3.44-3.22 (m, 1H), 3.16 (t, J=12.5 Hz, 1H), 2.80 (dd, J=16.8, 5.9 Hz, 1H), 2.62 (dd, J=16.6, 7.6 Hz, 1H), 2.33 (td, J=10.2, 6.3 Hz, 2H), 2.11-2.03 (m, 1H), 1.95-1.80 (m, 1H). ¹³C NMR (126 MHz, DMSO-d$_6$) δ 174.30, 172.37, 172.04, 171.24, 171.02, 161.06, 142.71, 136.48, 135.24, 133.38, 133.07, 132.23, 128.45, 128.31, 127.87, 127.75, 126.45, 126.40, 125.83, 124.64, 123.92, 121.08, 119.81, 114.29, 103.34, 54.84, 53.56, 50.21, 37.97, 36.54, 30.56, 27.48. HRMS (ESI) Calcd for C$_{38}$H$_{33}$ClF$_3$N$_5$O$_8$ (M−H)⁻ 778.1892, found 778.1894.

(S)-4-((S)-3-carboxy-2-((S)-2-(5-chloro-1H-indole-2-carboxamido)-3-(naphthalen-2-yl)propanamido)propanamido)-5-oxo-5-((3-(trifluoromethyl)phenyl)amino)pentanoic acid (31). ¹H NMR (500 MHz, DMSO-d$_6$) δ 12.32 (s, 2H), 11.63 (s, 1H), 10.23 (s, 1H), 8.81 (d, J=8.6 Hz, 1H), 8.66 (d, J=7.6 Hz, 1H), 8.19 (d, J=7.6 Hz, 1H), 8.12 (s, 1H), 7.93-7.73 (m, 5H), 7.70 (s, 1H), 7.55 (t, J=7.7 Hz, 2H), 7.47-7.33 (m, 4H), 7.21 (s, 1H), 7.15 (d, J=8.8 Hz, 1H), 4.97-4.86 (m, 1H), 4.75-4.59 (m, 1H), 4.42 (t, J=7.0 Hz, 1H), 3.40-3.31 (m, 1H), 3.16 (t, J=12.5 Hz, 1H), 2.80 (dd, J=16.8, 5.8 Hz, 1H), 2.63 (dd, J=16.7, 7.8 Hz, 1H), 2.34 (dt, J=16.2, 7.7 Hz, 2H), 2.15-2.03 (m, 1H), 1.95-1.76 (m, 1H). ¹³C NMR (126 MHz, DMSO-d$_6$) δ 174.26, 172.33, 172.08, 171.21, 170.94, 161.07, 139.88, 136.47, 135.24, 133.39, 133.06, 132.23, 130.45, 128.46, 128.30, 127.90, 127.86, 127.75, 126.40, 125.83, 124.64, 123.92, 123.47, 121.09, 120.32, 115.92, 114.29, 103.35, 54.84, 53.52, 50.18, 37.96, 36.46, 30.52, 27.50. HRMS (ESI) Calcd for C$_{38}$H$_{33}$ClF$_3$N$_5$O$_8$ (M−H)⁻ 778.1892, found 778.1898.

(S)-4-((S)-3-carboxy-2-((S)-2-(5-chloro-1H-indole-2-carboxamido)-3-(naphthalen-2-yl)propanamido)propanamido)-5-((4-methoxyphenyl)amino)-5-oxopentanoic acid (32). ¹H NMR (500 MHz, DMSO-d$_6$) δ 12.31 (s, 2H), 11.63 (d, J=2.2 Hz, 1H), 9.72 (s, 1H), 8.81 (d, J=8.5 Hz, 1H), 8.69 (d, J=7.5 Hz, 1H), 8.09 (d, J=7.9 Hz, 1H), 7.93-7.73 (m, 4H), 7.70 (d, J=2.1 Hz, 1H), 7.56 (dd, J=8.5, 1.7 Hz, 1H), 7.54-7.48 (m, 2H), 7.47-7.39 (m, 2H), 7.36 (d, J=8.7 Hz, 1H), 7.21 (d, J=2.2 Hz, 1H), 7.15 (dd, J=8.7, 2.1 Hz, 1H), 6.91-6.81 (m, 2H), 4.93-4.82 (m, 1H), 4.66 (q, J=7.1 Hz, 1H), 4.40 (td, J=8.3, 5.1 Hz, 1H), 3.71 (s, 3H), 3.30 (s, 1H), 3.16 (dd, J=13.9, 11.0 Hz, 1H), 2.81 (dd, J=16.6, 6.0 Hz, 1H), 2.63 (dd, J=16.6, 7.6 Hz, 1H), 2.31 (dq, J=16.6, 10.5 Hz, 2H), 2.11-1.99 (m, 1H), 1.87 (dq, J=10.2, 5.3, 4.2 Hz, 1H). ¹³C NMR (126 MHz, DMSO-d$_6$) δ 174.33, 172.38, 172.07, 170.99, 169.71, 161.06, 155.87, 136.48, 135.24, 133.39, 133.07, 132.23, 132.20, 128.47, 128.31, 127.91, 127.89, 127.85, 127.76, 126.40, 125.83, 124.64, 123.92, 121.49, 121.10, 114.28, 103.33, 55.62, 54.83, 53.19, 50.19, 37.97, 36.39, 30.55, 27.86. HRMS (ESI) Calcd for C$_{38}$H$_{36}$ClN$_5$O$_9$(M−H)⁻ 740.2123, found 740.2128.

(S)-4-((S)-3-carboxy-2-((S)-2-(5-chloro-1H-indole-2-carboxamido)-3-(naphthalen-2-yl)propanamido)propanamido)-5-((3-methoxyphenyl)amino)-5-oxopentanoic acid (33). ¹H NMR (500 MHz, DMSO-d$_6$) δ 12.31 (s, 2H), 11.63 (d, J=2.2 Hz, 1H), 9.86 (s, 1H), 8.81 (d, J=8.5 Hz, 1H), 8.68 (d, J=7.5 Hz, 1H), 8.11 (d, J=7.8 Hz, 1H), 7.94-7.73 (m, 4H), 7.70 (d, J=2.1 Hz, 1H), 7.56 (dd, J=8.4, 1.7 Hz, 1H), 7.42 (pd, J=6.9, 1.6 Hz, 2H), 7.37 (d, J=8.7 Hz, 1H), 7.31 (t, J=2.2 Hz, 1H), 7.25-7.18 (m, 2H), 7.17-7.10 (m, 2H), 6.65 (dd, J=8.2, 2.5 Hz, 1H), 4.91 (ddd, J=11.8, 8.6, 3.7 Hz, 1H), 4.67 (q, J=7.1 Hz, 1H), 4.41 (td, J=8.3, 5.1 Hz, 1H), 3.71 (s, 3H), 3.32 (s, 1H), 3.17 (dd, J=13.9, 11.0 Hz, 1H), 2.81 (dd, J=16.7, 5.9 Hz, 1H), 2.63 (dd, J=16.7, 7.7 Hz, 1H), 2.31 (dq, J=16.6, 10.4 Hz, 2H), 2.14-1.91 (m, 1H), 1.88 (dq, J=10.3, 5.3, 4.3 Hz, 1H). ¹³C NMR (126 MHz, DMSO-d$_6$) δ 174.30, 172.33, 172.08, 171.06, 170.30, 161.08, 159.94, 140.27, 136.48, 135.24, 133.39, 133.06, 132.23, 129.98, 128.47, 128.31, 127.91, 127.88, 127.76, 126.40, 125.83, 124.64, 123.93, 121.10, 114.29, 112.16, 109.48, 105.66, 103.35, 55.43, 54.86, 53.37, 50.19, 37.96, 36.41, 30.55, 27.80. HRMS (ESI) Calcd for C$_{38}$H$_{36}$ClN$_5$O$_9$(M−H)⁻ 740.2123, found 740.2127.

(S)-4-((S)-3-carboxy-2-((S)-2-(5-chloro-1H-indole-2-carboxamido)-3-(naphthalen-2-yl)propanamido)propanamido)-5-oxo-5-((4-(trifluoromethoxy)phenyl)amino)pentanoic acid (34). ¹H NMR (500 MHz, DMSO-d$_6$) δ 12.30 (s, 2H), 11.64 (s, 1H), 10.07 (s, 1H), 8.82 (d, J=8.5 Hz, 1H), 8.67 (d, J=7.5 Hz, 1H), 8.19 (d, J=7.7 Hz, 1H), 7.97-7.65 (m, 7H), 7.56 (d, J=8.4 Hz, 1H), 7.50-7.26 (m, 5H), 7.23-7.01 (m, 2H), 4.91 (ddd, J=11.9, 8.4, 3.7 Hz, 1H), 4.66 (q, J=7.1 Hz, 1H), 4.40 (td, J=8.1, 5.0 Hz, 1H), 3.31 (s, 1H), 3.16 (dd, J=13.9, 10.9 Hz, 1H), 2.80 (dd, J=16.7, 6.0 Hz, 1H), 2.62 (dd, J=16.6, 7.5 Hz, 1H), 2.32 (pd, J=10.1, 3.2 Hz, 2H), 2.05 (ddt, J=15.0, 11.1, 5.8 Hz, 1H), 1.89 (dt, J=14.5, 4.3 Hz, 1H). $^{13}$C NMR (126 MHz, DMSO-$d_6$) δ 174.30, 172.38, 172.07, 171.16, 170.55, 161.06, 138.33, 136.49, 135.24, 133.39, 133.07, 132.23, 128.46, 128.32, 127.91, 127.88, 127.85, 127.76, 126.40, 125.83, 124.63, 123.92, 122.06, 121.27, 121.10, 114.29, 103.34, 54.83, 53.41, 50.18, 37.97, 36.47, 30.53, 27.58. HRMS (ESI) Calcd for $C_{38}H_{33}ClF_3N_5O_9$ (M−H)$^−$ 794.1841, found 794.1846.

(S)-4-((S)-3-carboxy-2-((S)-2-(5-chloro-1H-indole-2-carboxamido)-3-(naphthalen-2-yl)propanamido)propanamido)-5-oxo-5-((3-(trifluoromethoxy)phenyl)amino)pentanoic acid (35). $^1$H NMR (500 MHz, DMSO-$d_6$) δ 12.30 (s, 2H), 11.62 (d, J=2.2 Hz, 1H), 10.16 (s, 1H), 8.80 (d, J=8.5 Hz, 1H), 8.66 (d, J=7.5 Hz, 1H), 8.16 (d, J=7.6 Hz, 1H), 7.97-7.76 (m, 5H), 7.70 (d, J=2.1 Hz, 1H), 7.55 (ddd, J=10.6, 8.3, 1.8 Hz, 2H), 7.48-7.34 (m, 4H), 7.21 (d, J=2.2 Hz, 1H), 7.15 (dd, J=8.7, 2.1 Hz, 1H), 7.05 (dd, J=8.3, 2.3 Hz, 1H), 4.91 (ddd, J=11.8, 8.6, 3.7 Hz, 1H), 4.67 (td, J=7.6, 5.7 Hz, 1H), 4.41 (td, J=8.3, 5.2 Hz, 1H), 3.46-3.27 (m, 1H), 3.16 (dd, J=13.9, 10.9 Hz, 1H), 2.81 (dd, J=16.7, 5.8 Hz, 1H), 2.63 (dd, J=16.7, 7.8 Hz, 1H), 2.39-2.24 (m, 2H), 2.05 (td, J=8.8, 4.5 Hz, 1H), 1.90 (ddt, J=13.5, 8.7, 4.7 Hz, 1H). $^{13}$C NMR (126 MHz, DMSO-$d_6$) δ 174.24, 172.33, 172.08, 171.18, 170.84, 161.08, 148.92, 140.75, 136.47, 135.25, 133.39, 133.06, 132.24, 130.94, 128.47, 128.30, 127.90, 127.87, 127.84, 127.75, 126.39, 125.82, 124.65, 123.92, 121.55, 121.10, 119.52, 118.50, 116.01, 114.29, 111.96, 103.35, 54.84, 53.48, 50.18, 37.96, 36.43, 30.52, 27.55. HRMS (ESI) Calcd for $C_{38}H_{33}ClF_3N_5O_9$ (M−H)$^−$ 794.1841, found 794.1854.

(S)-4-((S)-3-carboxy-2-((S)-2-(5-chloro-1H-indole-2-carboxamido)-3-(naphthalen-2-yl)propanamido)propanamido)-5-((3,5-dimethoxyphenyl)amino)-5-oxopentanoic acid (36). $^1$H NMR (500 MHz, DMSO-$d_6$) δ 12.30 (s, 2H), 11.62 (d, J=2.2 Hz, 1H), 9.84 (s, 1H), 8.81 (d, J=8.5 Hz, 1H), 8.68 (d, J=7.5 Hz, 1H), 8.08 (d, J=7.8 Hz, 1H), 7.94-7.74 (m, 4H), 7.70 (d, J=2.0 Hz, 1H), 7.56 (dd, J=8.5, 1.7 Hz, 1H), 7.49-7.32 (m, 3H), 7.21 (dd, J=2.1, 0.9 Hz, 1H), 7.15 (dd, J=8.7, 2.1 Hz, 1H), 6.87 (d, J=2.3 Hz, 2H), 6.23 (t, J=2.3 Hz, 1H), 5.01-4.83 (m, 1H), 4.66 (td, J=7.6, 5.8 Hz, 1H), 4.40 (td, J=8.3, 5.1 Hz, 1H), 3.70 (s, 6H), 3.30 (d, J=3.7 Hz, 1H), 3.17 (dd, J=13.9, 11.0 Hz, 1H), 2.80 (dd, J=16.7, 5.8 Hz, 1H), 2.63 (dd, J=16.7, 7.8 Hz, 1H), 2.38-2.23 (m, 2H), 2.11-1.96 (m, 1H), 1.87 (ddt, J=13.6, 8.7, 4.8 Hz, 1H). $^{13}$C NMR (126 MHz, DMSO-$d_6$) δ 174.28, 172.29, 172.11, 171.05, 170.34, 161.09, 160.92, 140.75, 136.48, 135.24, 133.39, 133.05, 132.24, 128.47, 128.31, 127.91, 127.88, 127.85, 127.76, 126.40, 125.83, 124.65, 123.93, 121.11, 114.29, 103.36, 98.17, 96.04, 55.54, 54.88, 53.41, 50.20, 37.96, 36.38, 30.54, 27.80. HRMS (ESI) Calcd for $C_{39}H_{38}ClN_5O_{10}$ (M−H)$^−$ 770.2229, found 770.2237.

(S)-4-((S)-3-carboxy-2-((S)-2-(5-chloro-1H-indole-2-carboxamido)-3-(naphthalen-2-yl)propanamido)propanamido)-5-((3-methoxy-5-(trifluoromethyl)phenyl)amino)-5-oxopentanoic acid (37). $^1$H NMR (500 MHz, DMSO-$d_6$) δ 12.30 (s, 2H), 11.62 (s, 1H), 10.19 (s, 1H), 8.80 (d, J=8.5 Hz, 1H), 8.66 (d, J=7.6 Hz, 1H), 8.16 (d, J=7.6 Hz, 1H), 7.92-7.75 (m, 4H), 7.74-7.68 (m, 1H), 7.66 (s, 1H), 7.55 (s, 1H), 7.51-7.35 (m, 4H), 7.31-7.19 (m, 1H), 7.15 (dd, J=8.7, 2.1 Hz, 1H), 6.95 (s, 1H), 4.99-4.82 (m, 1H), 4.67 (q, J=7.1 Hz, 1H), 4.40 (q, J=7.3 Hz, 1H), 3.80 (s, 3H), 3.42-3.28 (m, 1H), 3.25-3.05 (m, 1H), 2.81 (dd, J=16.7, 5.7 Hz, 1H), 2.63 (dd, J=16.6, 7.9 Hz, 1H), 2.33 (td, J=9.9, 6.3 Hz, 2H), 2.06 (td, J=11.2, 8.9, 5.3 Hz, 1H), 2.00-1.83 (m, 1H). $^{13}$C NMR (126 MHz, DMSO-$d_6$) δ 174.24, 172.28, 172.10, 171.18, 170.94, 161.09, 160.43, 141.14, 136.46, 135.25, 133.39, 133.05, 132.23, 130.91 (d, J=31.8 Hz), 128.46, 128.29, 127.90, 127.87, 127.86, 127.75, 126.39, 125.82, 125.44, 124.65, 123.93, 123.27, 121.09, 114.29, 108.93, 108.42, 105.95, 103.36, 56.07, 54.87, 53.57, 50.22, 37.95, 36.45, 30.51, 27.50. HRMS (ESI) Calcd for $C_{39}H_{35}ClF_3N_5O_9$ (M−H)$^−$ 808.1997, found 808.2004.

(S)-5-(benzo[d][1,3]dioxol-5-ylamino)-4-((S)-3-carboxy-2-((S)-2-(5-chloro-1H-indole-2-carboxamido)-3-(naphthalen-2-yl)propanamido)propanamido)-5-oxopentanoic acid (38). $^1$H NMR (500 MHz, DMSO-$d_6$) δ 12.30 (s, 2H), 11.62 (s, 1H), 9.76 (s, 1H), 8.80 (d, J=8.4 Hz, 1H), 8.67 (d, J=7.5 Hz, 1H), 8.09 (d, J=7.7 Hz, 1H), 7.93-7.74 (m, 4H), 7.70 (s, 1H), 7.56 (d, J=8.4 Hz, 1H), 7.42 (p, J=6.9 Hz, 2H), 7.37 (d, J=8.7 Hz, 1H), 7.29 (s, 1H), 7.21 (s, 1H), 7.15 (d, J=8.8 Hz, 1H), 7.00 (d, J=8.4 Hz, 1H), 6.84 (d, J=8.3 Hz, 1H), 5.98 (s, 2H), 5.00-4.79 (m, 1H), 4.66 (q, J=7.1 Hz, 1H), 4.38 (q, J=7.4 Hz, 1H), 3.31 (s, 1H), 3.16 (t, J=12.5 Hz, 1H), 2.81 (dd, J=16.8, 6.0 Hz, 1H), 2.63 (dd, J=16.7, 7.5 Hz, 1H), 2.39-2.21 (m, 2H), 2.10-1.95 (m, 1H), 1.87 (dt, J=15.3, 7.8 Hz, 1H). $^{13}$C NMR (126 MHz, DMSO-$d_6$) δ 174.30, 172.38, 172.07, 171.01, 169.86, 161.07, 147.48, 143.57, 136.47, 135.24, 133.42, 133.39, 133.06, 132.24, 128.47, 128.31, 127.89, 127.88, 127.85, 127.76, 126.40, 125.83, 124.64, 123.92, 121.10, 114.29, 112.84, 108.46, 103.34, 102.12, 101.45, 54.83, 53.24, 50.17, 37.96, 36.39, 30.51, 27.79. HRMS (ESI) Calcd for $C_{38}H_{34}ClN_5O_{10}$ (M−H)$^−$ 754.1916, found 754.1924.

Synthesis of final products 9-19. The synthetic route for final products 9-19 is shown in Scheme 2.

Scheme 2. Synthesis of Final Compounds 9-19.

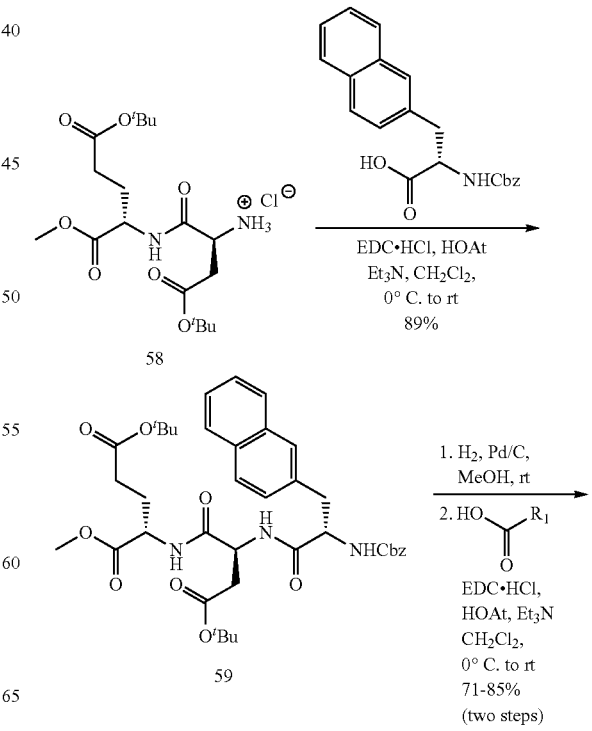

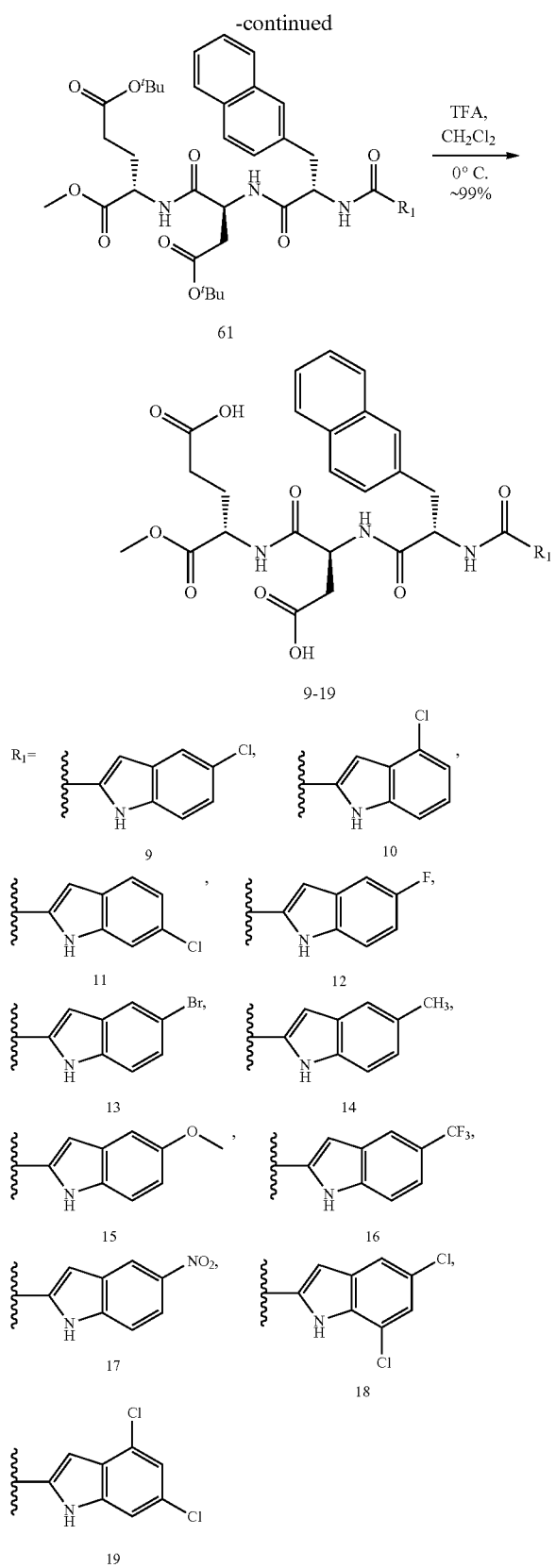

5-(tert-Butyl) 1-methyl ((S)-2-((S)-2-(((benzyloxy)carbonyl)amino)-3-(naphthalen-2-yl)propanamido)-4-(tert-butoxy)-4-oxobutanoyl)-L-glutamate (59). Yield, 89%. 1H NMR (500 MHz, CDCl₃) δ 7.85-7.63 (m, 3H), 7.60-7.54 (m, 1H), 7.46-7.33 (m, 2H), 7.29-7.13 (m, 8H), 7.09 (d, J=8.1 Hz, 1H), 4.99 (d, J=2.8 Hz, 2H), 4.72-4.61 (m, 1H), 4.47 (q, J=6.7 Hz, 1H), 4.39 (td, J=8.2, 5.1 Hz, 1H), 3.64 (s, 3H), 3.26 (dd, J=14.2, 5.8 Hz, 1H), 3.17 (dd, J=14.2, 7.6 Hz, 1H), 2.88 (d, J=17.3 Hz, 1H), 2.38 (dd, J=17.2, 6.4 Hz, 1H), 2.18-2.09 (m, 2H), 2.04-1.97 (m, 1H), 1.76 (dtd, J=14.6, 8.7, 6.1 Hz, 1H), 1.33 (s, 9H), 1.31 (s, 9H). 13C NMR (126 MHz, CDCl₃) δ 171.41, 170.69, 135.87, 133.47, 133.43, 132.56, 128.71, 128.52, 128.25, 128.09, 128.01, 127.70, 127.62, 127.00, 126.32, 125.90, 81.96, 80.61, 67.34, 56.40, 52.40, 51.90, 49.14, 38.05, 36.72, 31.28, 28.06, 27.97, 27.10. MS (ESI) m/z 742.3 [M+Na]⁺. The Cbz protecting group of compound 59 was removed by Pd/C under H₂ in MeOH. The resulting product was used directly in next step without further purification. 1H NMR (500 MHz, CDCl₃) δ 8.33 (d, J=8.4 Hz, 1H), 7.91-7.72 (m, 3H), 7.67 (d, J=1.6 Hz, 1H), 7.47 (tt, J=6.8, 5.2 Hz, 2H), 7.37 (dd, J=8.4, 1.8 Hz, 1H), 7.29 (d, J=7.7 Hz, 1H), 4.79 (ddd, J=8.5, 6.6, 4.6 Hz, 1H), 4.51 (td, J=7.9, 5.1 Hz, 1H), 3.95-3.77 (m, 1H), 3.71 (s, 3H), 3.42 (dd, J=13.7, 4.0 Hz, 1H), 2.93 (dd, J=13.7, 9.2 Hz, 1H), 2.86 (dd, J=17.0, 4.6 Hz, 1H), 2.55 (dd, J=17.0, 6.6 Hz, 1H), 2.27 (td, J=8.1, 6.7 Hz, 2H), 2.19-2.03 (m, 1H), 1.98-1.80 (m, 1H), 1.42 (s, 9H), 1.42 (s, 9H). MS (ESI) m/z=586.3 [M+H]⁺, 608.3 [M+Na]⁺.

5-(tert-Butyl) 1-methyl ((S)-4-(tert-butoxy)-2-((S)-2-(5-chloro-1H-indole-2-carboxamido)-3-(naphthalen-2-yl)propanamido)-4-oxobutanoyl)-L-glutamate (61 h). Yield, 85%. ¹H NMR (500 MHz, CDCl₃) δ 10.42 (s, 1H), 8.51 (s, 1H), 7.95 (s, 1H), 7.70-7.30 (m, 6H), 7.27-6.92 (m, 5H), 6.86 (s, 1H), 5.28 (d, J=11.3 Hz, 1H), 5.05 (d, J=9.9 Hz, 1H), 4.39 (q, J=6.8 Hz, 1H), 3.74 (s, 3H), 3.31-3.08 (m, 2H), 2.88 (t, J=25.0 Hz, 2H), 2.48-2.22 (m, 2H), 2.04 (dp, J=34.9, 7.5 Hz, 2H), 1.45 (d, J=2.6 Hz, 9H), 1.39 (s, 9H). ¹³C NMR (126 MHz, CDCl₃) δ 172.14, 171.58, 171.26, 170.27, 161.49, 135.17, 134.02, 133.26, 132.20, 131.47, 128.34, 128.00, 127.78, 127.16, 125.83, 125.40, 124.17, 120.88, 113.51, 101.95, 82.06, 80.98, 55.14, 52.45, 52.16, 48.75, 38.71, 36.18, 31.40, 28.08, 27.94, 27.12. MS (ESI) m/z=785.3 [M+Na]⁺.

5-(tert-Butyl) 1-methyl ((S)-4-(tert-butoxy)-2-((S)-2-(4-chloro-1H-indole-2-carboxamido)-3-(naphthalen-2-yl)propanamido)-4-oxobutanoyl)-L-glutamate (61i). Yield, 82%. ¹H NMR (500 MHz, Chloroform-d) δ 10.79 (s, 1H), 8.35 (d, J=8.5 Hz, 1H), 7.57-7.41 (m, 6H), 7.24-7.07 (m, 6H), 7.05 (d, J=2.2 Hz, 1H), 5.48 (q, J=7.4 Hz, 1H), 4.97 (td, J=8.4, 4.2 Hz, 1H), 4.36 (td, J=7.8, 5.6 Hz, 1H), 3.67 (s, 3H), 3.42-3.17 (m, 2H), 2.83 (dd, J=17.4, 4.2 Hz, 1H), 2.62 (dd, J=17.3, 8.4 Hz, 1H), 2.41-2.25 (m, 2H), 2.11 (ddt, J=14.7, 9.0, 6.0 Hz, 1H), 2.04-1.96 (m, 1H), 1.46 (s, 9H), 1.31 (s, 9H). ¹³C NMR (126 MHz, Chloroform-d) δ 172.24, 171.65, 171.13, 170.94, 170.81, 161.35, 137.55, 133.83, 133.33, 132.33, 130.54, 128.14, 128.00, 127.36, 127.28, 126.88, 126.53, 125.86, 125.43, 124.53, 119.77, 111.16, 101.34, 81.79, 81.07, 54.57, 52.41, 52.24, 48.94, 39.35, 38.49, 31.55, 28.11, 27.88, 26.91. MS (ESI) m/z=763.4 [M+H]⁺, 785.3 [M+Na]⁺.

5-(tert-Butyl) 1-methyl ((S)-4-(tert-butoxy)-2-((S)-2-(6-chloro-1H-indole-2-carboxamido)-3-(naphthalen-2-yl)propanamido)-4-oxobutanoyl)-L-glutamate (61j). Yield, 79%. ¹H NMR (500 MHz, Chloroform-d) δ 10.73 (s, 1H), 8.33 (d, J=8.5 Hz, 1H), 7.67-7.41 (m, 6H), 7.35 (d, J=1.8 Hz, 1H), 7.29-7.16 (m, 4H), 7.08 (dd, J=8.6, 1.8 Hz, 1H), 6.91 (d, J=2.1 Hz, 1H), 5.48 (q, J=7.3 Hz, 1H), 4.94 (td, J=8.3, 4.4 Hz, 1H), 4.34-4.25 (m, 1H), 3.71 (s, 3H), 3.45-3.21 (m, 2H), 2.79 (dd, J=17.3, 4.4 Hz, 1H), 2.61 (dd, J=17.3, 8.3 Hz, 1H), 2.43-2.24 (m, 2H), 2.11 (ddt, J=14.8, 9.0, 6.3 Hz, 1H), 2.04-1.95 (m, 1H), 1.46 (s, 9H), 1.31 (s, 9H). ¹³C NMR (126

MHz, Chloroform-d) δ 172.20, 171.65, 170.98, 170.80, 161.44, 137.28, 133.67, 133.30, 132.32, 130.70, 130.05, 128.15, 127.95, 127.44, 127.32, 127.25, 125.94, 125.89, 125.46, 122.78, 121.25, 112.27, 102.95, 81.84, 81.10, 54.38, 52.44, 52.25, 48.95, 39.34, 38.36, 31.54, 28.08, 27.85, 26.76. MS (ESI) m/z=785.3 [M+Na]+.

5-(tert-Butyl) 1-methyl ((S)-4-(tert-butoxy)-2-((S)-2-(5-fluoro-1H-indole-2-carboxamido)-3-(naphthalen-2-yl)propanamido)-4-oxobutanoyl)-L-glutamate (61k). Yield, 74%. ¹H NMR (500 MHz, Chloroform-d) δ 10.34 (s, 1H), 8.80 (s, 1H), 8.44 (s, 1H), 7.64 (d, J=7.5 Hz, 1H), 7.52-7.28 (m, 5H), 7.16 (dd, J=6.3, 3.2 Hz, 2H), 7.08-6.88 (m, 4H), 5.40-5.32 (m, 1H), 5.16 (d, J=7.6 Hz, 1H), 4.41 (q, J=7.0 Hz, 1H), 3.77 (s, 3H), 3.31-2.85 (m, 4H), 2.43-2.24 (m, 2H), 2.12-2.07 (m, 1H), 2.05-1.90 (m, 1H), 1.46 (s, 9H), 1.44 (s, 9H). ¹³C NMR (126 MHz, Chloroform-d) δ 172.26, 172.03, 171.63, 171.28, 170.35, 161.56, 158.84, 156.98, 134.40, 133.51, 133.29, 132.17, 132.03, 125.66, 125.21, 113.32 (d, J=9.6 Hz), 112.51, 112.30, 105.91, 105.73, 102.38, 82.11, 80.92, 55.31, 52.44, 52.17, 48.72, 39.56, 38.78, 31.47, 28.11, 27.98, 27.30. MS (ESI) m/z=769.3 [M+Na]+.

5-(tert-Butyl) 1-methyl ((S)-2-((S)-2-(5-bromo-1H-indole-2-carboxamido)-3-(naphthalen-2-yl)propanamido)-4-(tert-butoxy)-4-oxobutanoyl)-L-glutamate (61l). Yield, 78%. ¹H NMR (500 MHz, Chloroform-d) δ 10.43 (s, 1H), 8.51 (s, 1H), 7.96 (s, 1H), 7.70 (d, J=2.0 Hz, 1H), 7.49 (d, J=7.3 Hz, 1H), 7.41-7.25 (m, 4H), 7.20 (d, J=1.9 Hz, 1H), 7.13-7.06 (m, 2H), 6.99 (t, J=9.6 Hz, 2H), 6.89-6.72 (m, 1H), 5.42-5.24 (m, 1H), 4.97 (q, J=7.3 Hz, 1H), 4.29 (q, J=6.9 Hz, 1H), 3.65 (s, 3H), 3.21-3.00 (m, 2H), 2.77 (td, J=24.2, 21.5, 9.8 Hz, 2H), 2.30-2.14 (m, 2H), 1.97 (d, J=9.7 Hz, 1H), 1.92-1.87 (m, 1H), 1.37 (s, 9H), 1.29 (s, 9H). ¹³C NMR (126 MHz, Chloroform-d) δ 172.10, 171.82, 171.64, 171.17, 170.42, 161.41, 135.44, 134.09, 133.28, 132.21, 131.41, 129.12, 127.96, 127.83, 127.29, 127.25, 126.68, 125.80, 125.37, 124.06, 113.96, 113.15, 101.90, 82.02, 81.01, 55.01, 52.46, 52.23, 48.83, 39.10, 38.92, 31.40, 28.11, 27.99, 27.04. MS (ESI) m/z=829.3 [M+Na]+.

5-(tert-Butyl) 1-methyl ((S)-4-(tert-butoxy)-2-((S)-2-(5-methyl-1H-indole-2-carboxamido)-3-(naphthalen-2-yl)propanamido)-4-oxobutanoyl)-L-glutamate (61m). Yield, 83%. ¹H NMR (500 MHz, CDCl₃) δ 10.54-10.31 (m, 1H), 8.25 (d, J=8.5 Hz, 1H), 7.48 (ddd, J=11.3, 5.9, 2.4 Hz, 4H), 7.38 (d, J=7.7 Hz, 1H), 7.34-7.28 (m, 1H), 7.24-7.07 (m, 5H), 7.01 (dd, J=8.5, 1.6 Hz, 1H), 6.78 (dd, J=2.2, 0.9 Hz, 1H), 5.41 (q, J=7.2 Hz, 1H), 4.85 (td, J=8.1, 4.6 Hz, 1H), 4.29 (td, J=7.8, 5.7 Hz, 1H), 3.59 (s, 3H), 3.23 (qd, J=13.7, 6.9 Hz, 2H), 2.71 (dd, J=17.2, 4.6 Hz, 1H), 2.52 (dd, J=17.2, 7.9 Hz, 1H), 2.41-2.31 (m, 3H), 2.27-2.17 (m, 2H), 2.01 (ddt, J=14.8, 9.1, 6.2 Hz, 1H), 1.87 (dtd, J=9.4, 7.9, 4.6 Hz, 1H), 1.36 (s, 9H), 1.21 (s, 9H). ¹³C NMR (126 MHz, CDCl₃) δ 172.22, 171.76, 171.06, 170.81 (d, J=1.6 Hz), 161.91, 135.54, 133.85, 133.39, 132.39, 130.02, 129.53, 128.20, 128.03, 127.77, 127.52, 127.48, 127.41, 126.31, 125.91, 125.48, 121.18, 112.17, 102.60, 81.73, 80.97, 54.31, 52.41, 52.20, 49.11, 39.35, 38.23, 31.52, 28.12, 27.89, 26.92, 21.54. MS (ESI) m/z=765.3 [M+Na]+.

5-(tert-Butyl) 1-methyl ((S)-4-(tert-butoxy)-2-((S)-2-(5-methoxy-1H-indole-2-carboxamido)-3-(naphthalen-2-yl)propanamido)-4-oxobutanoyl)-L-glutamate (61n). Yield, 80%. ¹H NMR (500 MHz, CDCl₃) δ 10.57-10.40 (m, 1H), 8.18 (d, J=8.5 Hz, 1H), 7.63-7.47 (m, 4H), 7.36 (d, J=7.7 Hz, 1H), 7.28-7.13 (m, 4H), 7.05 (d, J=7.6 Hz, 1H), 6.94 (d, J=2.4 Hz, 1H), 6.86 (dd, J=8.9, 2.4 Hz, 1H), 6.79-6.71 (m, 1H), 5.38 (q, J=7.2 Hz, 1H), 4.84 (td, J=8.1, 4.5 Hz, 1H), 4.29 (td, J=7.8, 5.6 Hz, 1H), 3.76 (s, 3H), 3.59 (s, 3H), 3.24 (qd, J=13.8, 6.9 Hz, 2H), 2.73 (dd, J=17.2, 4.4 Hz, 1H), 2.51 (dd, J=17.2, 7.9 Hz, 1H), 2.34-2.15 (m, 2H), 2.01 (q, J=4.6, 3.2 Hz, 1H), 1.91-1.82 (m, 1H), 1.37 (s, 9H), 1.21 (s, 9H). ¹³C NMR (126 MHz, CDCl₃) δ 172.26, 171.72, 170.97, 170.87, 170.79, 161.82, 154.50, 133.77, 133.39, 132.54, 132.41, 130.30, 128.25, 128.01, 127.73, 127.53, 127.46, 127.34, 125.95, 125.52, 115.93, 113.39, 102.66, 101.99, 81.77, 81.01, 55.69, 54.34, 52.41, 52.20, 49.08, 39.28, 38.12, 31.53, 28.11, 27.88, 26.91. MS (ESI) m/z=781.1 [M+Na]+.

5-(tert-Butyl) 1-methyl ((S)-4-(tert-butoxy)-2-((S)-3-(naphthalen-2-yl)-2-(5-(trifluoromethyl)-1H-indole-2-carboxamido)propanamido)-4-oxobutanoyl)-L-glutamate (61o). Yield, 75%. ¹H NMR (500 MHz, Chloroform-d) δ 10.87 (s, 1H), 8.48 (d, J=8.4 Hz, 1H), 7.96 (s, 1H), 7.74 (s, 1H), 7.57 (d, J=7.5 Hz, 1H), 7.52-7.33 (m, 6H), 7.23-6.97 (m, 4H), 5.51 (q, J=7.6, 7.1 Hz, 1H), 5.01 (td, J=8.2, 4.2 Hz, 1H), 4.35 (td, J=7.5, 5.8 Hz, 1H), 3.69 (s, 3H), 3.25 (ddd, J=37.9, 13.5, 7.1 Hz, 2H), 2.83 (dd, J=17.4, 4.2 Hz, 1H), 2.68 (dd, J=17.4, 8.4 Hz, 1H), 2.45-2.25 (m, 2H), 2.09 (ddt, J=12.4, 8.5, 4.2 Hz, 1H), 2.01-1.93 (m, 1H), 1.46 (s, 9H), 1.33 (s, 9H). ¹³C NMR (126 MHz, Chloroform-d) δ 172.11, 171.64, 171.37, 170.89, 170.73, 161.25, 138.08, 133.86, 133.29, 132.27, 131.95, 128.49, 128.05, 127.94, 127.33, 127.28, 126.63, 126.33, 125.83, 125.43, 124.17, 122.54 (q, J=31.6 Hz), 122.02, 120.51, 119.74 (d, J=4.6 Hz), 112.87, 103.53, 81.92, 81.09, 54.63, 52.42, 52.28, 49.00, 39.29, 38.78, 31.47, 28.09, 27.87, 26.90. MS (ESI) m/z=819.3 [M+Na]+.

5-(tert-Butyl) 1-methyl ((S)-4-(tert-butoxy)-2-((S)-3-(naphthalen-2-yl)-2-(5-nitro-1H-indole-2-carboxamido)propanamido)-4-oxobutanoyl)-L-glutamate (61p). Yield, 71%. ¹H NMR (500 MHz, Chloroform-d) δ 11.00 (s, 1H), 8.58 (dd, J=36.9, 5.3 Hz, 2H), 8.09 (dt, J=13.5, 6.8 Hz, 2H), 7.63 (d, J=7.5 Hz, 1H), 7.48-7.33 (m, 4H), 7.22 (d, J=9.0 Hz, 1H), 7.17-7.03 (m, 4H), 5.49 (q, J=7.7 Hz, 1H), 5.05 (td, J=8.4, 4.4 Hz, 1H), 4.33 (q, J=7.0 Hz, 1H), 3.71 (s, 3H), 3.27 (dd, J=13.2, 7.1 Hz, 1H), 3.17 (dd, J=13.4, 7.6 Hz, 1H), 2.84 (dd, J=17.6, 4.3 Hz, 1H), 2.75 (dd, J=17.5, 8.6 Hz, 1H), 2.45-2.25 (m, 2H), 2.10-1.98 (m, 2H), 1.46 (s, 9H), 1.35 (s, 9H). ¹³C NMR (126 MHz, Chloroform-d) δ 172.05, 171.59, 171.45, 170.97, 170.73, 160.79, 142.09, 139.48, 133.87, 133.49, 133.25, 132.22, 127.97, 127.94, 127.22, 126.56, 125.82, 125.45, 119.34, 119.11, 112.49, 104.72, 82.11, 81.19, 54.91, 52.52, 52.34, 48.98, 39.18, 39.08, 31.42, 28.10, 27.91, 26.87. MS (ESI) m/z=796.3 [M+Na]+.

5-(tert-Butyl) 1-methyl ((S)-4-(tert-butoxy)-2-((S)-2-(5,7-dichloro-1H-indole-2-carboxamido)-3-(naphthalen-2-yl)propanamido)-4-oxobutanoyl)-L-glutamate (61q). Yield, 79%. ¹H NMR (500 MHz, Acetone-d₆) δ 10.75 (s, 1H), 8.31 (d, J=7.7 Hz, 1H), 8.12 (d, J=8.2 Hz, 1H), 7.92-7.72 (m, 4H), 7.62 (dd, J=1.8, 0.6 Hz, 1H), 7.57-7.46 (m, 2H), 7.42-7.34 (m, 2H), 7.30 (d, J=1.8 Hz, 1H), 5.01 (ddd, J=9.5, 7.6, 5.0 Hz, 1H), 4.81 (dt, J=8.2, 6.4 Hz, 1H), 4.51 (td, J=8.4, 5.1 Hz, 1H), 3.70 (s, 3H), 3.50 (dd, J=14.0, 5.0 Hz, 1H), 3.30 (dd, J=14.1, 9.4 Hz, 1H), 2.82 (dd, J=16.4, 6.1 Hz, 1H), 2.69 (dd, J=16.4, 6.6 Hz, 1H), 2.42-2.25 (m, 2H), 2.14-2.06 (m, 1H), 1.90 (dtd, J=13.9, 8.7, 6.2 Hz, 1H), 1.38 (s, 9H), 1.37 (s, 9H). ¹³C NMR (126 MHz, Acetone-d₆) δ 171.84, 171.66, 171.00, 170.18, 169.87, 160.66, 135.37, 133.64, 133.59, 132.54, 132.44, 129.62, 127.87, 127.84, 127.66, 127.50, 127.49, 125.90, 125.43, 125.23, 123.30, 120.02, 117.79, 104.42, 80.44, 79.73, 55.37, 51.62, 50.00, 37.33, 37.09, 30.95, 27.36, 27.29, 26.96. MS (ESI) m/z=818.9 [M+Na]+.

5-(tert-Butyl) 1-methyl ((S)-4-(tert-butoxy)-2-((S)-2-(4,6-dichloro-1H-indole-2-carboxamido)-3-(naphthalen-2-yl)propanamido)-4-oxobutanoyl)-L-glutamate (61r). Yield, 76%. ¹H NMR (500 MHz, Chloroform-d) δ 10.78 (s, 1H), 8.72 (d, J=8.6 Hz, 1H), 8.34 (s, 1H), 7.68 (d, J=7.2 Hz, 1H), 7.50-7.29 (m, 4H), 7.20-6.97 (m, 6H), 5.54 (q, J=7.9 Hz, 1H), 5.16 (td, J=8.7, 4.5 Hz, 1H), 4.31 (q, J=7.0 Hz, 1H), 3.72 (s, 3H), 3.24 (dd, J=13.3, 7.3 Hz, 1H), 3.14 (dd, J=13.3, 7.6 Hz, 1H), 2.90 (dd, J=17.7, 4.3 Hz, 1H), 2.79 (dd, J=17.5, 9.2 Hz, 1H), 2.39 (td, J=7.8, 7.3, 2.4 Hz, 2H), 2.19-2.08 (m, 1H), 2.08-1.99 (m, 1H), 1.46 (s, 9H), 1.39 (s, 9H). $^{13}$C NMR (126 MHz, Chloroform-d) δ 172.09, 171.99, 171.64, 171.00, 170.92, 160.91, 137.09, 134.18, 133.24, 132.13, 131.49, 129.14, 127.94, 127.81, 127.29, 127.26, 127.23, 127.12, 125.60, 125.27, 125.13, 120.13, 111.01, 101.16, 81.81, 81.10, 54.94, 52.45, 48.88, 39.28, 31.60, 26.77. MS (ESI) m/z=818.9 [M+Na]$^+$.

(S)-4-((S)-3-Carboxy-2-((S)-2-(5-chloro-1H-indole-2-carboxamido)-3-(naphthalen-2-yl)propanamido)propanamido)-5-methoxy-5-oxopentanoic acid (9). $^1$H NMR (500 MHz, DMSO-d$_6$) δ 12.28 (s, 2H), 11.64 (d, J=2.1 Hz, 1H), 8.79 (d, J=8.5 Hz, 1H), 8.59 (d, J=7.7 Hz, 1H), 8.25 (d, J=7.6 Hz, 1H), 7.94-7.74 (m, 4H), 7.70 (d, J=2.0 Hz, 1H), 7.55 (dd, J=8.5, 1.7 Hz, 1H), 7.48-7.32 (m, 3H), 7.20 (d, J=2.4 Hz, 1H), 7.15 (dd, J=8.7, 2.1 Hz, 1H), 4.88 (ddd, J=11.8, 8.5, 3.6 Hz, 1H), 4.65 (td, J=8.0, 5.2 Hz, 1H), 4.30 (ddd, J=9.2, 7.5, 5.2 Hz, 1H), 3.63 (s, 3H), 3.42-3.27 (m, 1H), 3.14 (dd, J=13.9, 10.9 Hz, 1H), 2.72 (dd, J=16.6, 5.2 Hz, 1H), 2.58 (dd, J=16.6, 8.3 Hz, 1H), 2.40-2.28 (m, 2H), 2.00-1.94 (m, 1H), 1.84-1.75 (m, 1H). $^{13}$C NMR (126 MHz, DMSO-d$_6$) δ 174.24, 172.46, 172.03, 171.84, 171.24, 161.04, 136.53, 135.24, 133.39, 133.08, 132.23, 128.46, 128.33, 127.91, 127.88, 127.85, 127.76, 126.40, 125.82, 124.63, 123.91, 121.09, 114.29, 103.32, 54.86, 52.40, 51.83, 50.03, 37.96, 36.60, 30.23, 26.54. HRMS (ESI) Calcd for C$_{32}$H$_{31}$ClN$_4$O$_9$ (M−H)$^−$ 649.1701, found 649.1700.

(S)-4-((S)-3-Carboxy-2-((S)-2-(4-chloro-1H-indole-2-carboxamido)-3-(naphthalen-2-yl)propanamido)propanamido)-5-methoxy-5-oxopentanoic acid (10). $^1$H NMR (500 MHz, DMSO-d$_6$) δ 12.28 (s, 2H), 11.80 (d, J=2.3 Hz, 1H), 8.88 (d, J=8.6 Hz, 1H), 8.57 (d, J=7.7 Hz, 1H), 8.24 (d, J=7.6 Hz, 1H), 7.94-7.71 (m, 4H), 7.56 (dd, J=8.4, 1.7 Hz, 1H), 7.42 (pd, J=6.9, 1.5 Hz, 2H), 7.39-7.26 (m, 2H), 7.19-6.97 (m, 2H), 4.96-4.83 (m, 1H), 4.65 (td, J=8.0, 5.1 Hz, 1H), 4.30 (ddd, J=9.2, 7.5, 5.2 Hz, 1H), 3.62 (s, 3H), 3.43-3.23 (m, 1H), 3.14 (dd, J=13.9, 11.0 Hz, 1H), 2.72 (dd, J=16.6, 5.2 Hz, 1H), 2.58 (dd, J=16.6, 8.3 Hz, 1H), 2.38-2.21 (m, 2H), 1.98 (dtd, J=13.0, 7.7, 5.1 Hz, 1H), 1.92-1.76 (m, 1H). $^{13}$C NMR (126 MHz, DMSO-d$_6$) δ 174.22, 172.46, 172.02, 171.82, 171.24, 160.92, 137.52, 136.57, 133.39, 132.39, 132.23, 128.31, 127.92, 127.86, 127.85, 127.74, 126.41, 126.13, 125.82, 124.59, 119.67, 111.93, 101.79, 54.87, 52.40, 51.83, 50.00, 37.95, 30.21, 26.54. HRMS (ESI) Calcd for C$_{32}$H$_{31}$ClN$_4$O$_9$(M−H)$^−$ 649.1701, found 649.1713.

(S)-4-((S)-3-Carboxy-2-((S)-2-(6-chloro-1H-indole-2-carboxamido)-3-(naphthalen-2-yl)propanamido)propanamido)-5-methoxy-5-oxopentanoic acid (11). $^1$H NMR (500 MHz, DMSO-d$_6$) δ 12.29 (s, 2H), 11.57 (d, J=2.2 Hz, 1H), 8.77 (d, J=8.5 Hz, 1H), 8.59 (d, J=7.7 Hz, 1H), 8.25 (d, J=7.6 Hz, 1H), 7.93-7.71 (m, 4H), 7.64 (d, J=8.5 Hz, 1H), 7.55 (dd, J=8.5, 1.7 Hz, 1H), 7.50-7.33 (m, 3H), 7.24 (dd, J=2.2, 0.9 Hz, 1H), 7.03 (dd, J=8.5, 2.0 Hz, 1H), 5.01-4.77 (m, 1H), 4.65 (td, J=8.0, 5.2 Hz, 1H), 4.30 (ddd, J=9.2, 7.5, 5.2 Hz, 1H), 3.63 (s, 3H), 3.32 (dd, J=13.9, 3.7 Hz, 1H), 3.13 (dd, J=13.9, 10.9 Hz, 1H), 2.72 (dd, J=16.6, 5.1 Hz, 1H), 2.58 (dd, J=16.7, 8.3 Hz, 1H), 2.30 (dp, J=9.0, 3.1, 2.6 Hz, 2H), 2.07-1.93 (m, 1H), 1.85-1.72 (m, 1H). $^{13}$C NMR (126 MHz, DMSO-d$_6$) δ 174.23, 172.46, 172.03, 171.86, 171.24, 161.06, 137.11, 136.52, 133.39, 132.60, 132.23, 128.40, 128.33, 127.91, 127.88, 127.85, 127.76, 126.40, 126.20, 125.82, 123.63, 120.66, 112.11, 103.82, 54.84, 52.40, 51.83, 50.03, 37.99, 36.58, 30.22, 26.55. HRMS (ESI) Calcd for C$_{32}$H$_{31}$ClN$_4$O$_9$(M−H)$^−$ 649.1701, found 649.1701.

(S)-4-((S)-3-Carboxy-2-((S)-2-(5-fluoro-1H-indole-2-carboxamido)-3-(naphthalen-2-yl)propanamido)propanamido)-5-methoxy-5-oxopentanoic acid (12). $^1$H NMR (500 MHz, DMSO-d$_6$) δ 12.28 (s, 2H), 11.53 (d, J=2.3 Hz, 1H), 8.74 (d, J=8.5 Hz, 1H), 8.58 (d, J=7.7 Hz, 1H), 8.24 (d, J=7.6 Hz, 1H), 7.99-7.72 (m, 4H), 7.55 (dd, J=8.5, 1.7 Hz, 1H), 7.50-7.30 (m, 4H), 7.20 (d, J=2.1 Hz, 1H), 7.01 (td, J=9.2, 2.6 Hz, 1H), 4.96-4.83 (m, 1H), 4.65 (td, J=8.0, 5.2 Hz, 1H), 4.30 (ddd, J=9.2, 7.5, 5.2 Hz, 1H), 3.63 (s, 3H), 3.31 (s, 1H), 3.14 (dd, J=13.9, 10.9 Hz, 1H), 2.72 (dd, J=16.6, 5.2 Hz, 1H), 2.58 (dd, J=16.6, 8.3 Hz, 1H), 2.38-2.25 (m, 2H), 2.06-1.89 (m, 1H), 1.89-1.74 (m, 1H). $^{13}$C NMR (126 MHz, DMSO-d$_6$) δ 174.24, 172.46, 172.03, 171.87, 171.25, 161.10, 158.48, 156.62, 136.54, 133.58, 133.39, 133.29, 132.23, 128.34, 127.91, 127.88, 127.84, 127.76, 127.51, 127.43, 126.39, 125.82, 113.91, 113.83, 112.63, 112.41, 106.26, 106.08, 103.79, 103.75, 54.84, 52.40, 51.83, 50.02, 37.98, 36.59, 30.22, 26.54. HRMS (ESI) Calcd for C$_{32}$H$_{31}$FN$_4$O$_9$(M−H)$^−$ 633.1997, found 633.2003.

(S)-4-((S)-2-((S)-2-(5-Bromo-1H-indole-2-carboxamido)-3-(naphthalen-2-yl)propanamido)-3-carboxypropanamido)-5-methoxy-5-oxopentanoic acid (13). $^1$H NMR (500 MHz, DMSO-d$_6$) δ 12.28 (s, 2H), 11.64 (d, J=2.3 Hz, 1H), 8.78 (d, J=8.5 Hz, 1H), 8.58 (d, J=7.7 Hz, 1H), 8.24 (d, J=7.6 Hz, 1H), 7.94-7.69 (m, 5H), 7.55 (dd, J=8.5, 1.7 Hz, 1H), 7.42 (pd, J=6.9, 1.6 Hz, 2H), 7.32 (d, J=8.7 Hz, 1H), 7.25 (dd, J=8.7, 1.9 Hz, 1H), 7.20 (d, J=2.1 Hz, 1H), 5.12-4.81 (m, 1H), 4.65 (td, J=7.9, 5.1 Hz, 1H), 4.30 (ddd, J=9.2, 7.5, 5.1 Hz, 1H), 3.63 (s, 3H), 3.38-3.25 (m, 1H), 3.14 (dd, J=13.9, 10.9 Hz, 1H), 2.72 (dd, J=16.6, 5.2 Hz, 1H), 2.57 (dd, J=16.6, 8.4 Hz, 1H), 2.36-2.26 (m, 2H), 2.05-1.93 (m, 1H), 1.83 (ddt, J=13.9, 7.9, 4.2 Hz, 1H). $^{13}$C NMR (126 MHz, DMSO-d$_6$) δ 174.23, 172.46, 172.02, 171.84, 171.24, 161.01, 136.52, 135.44, 133.39, 132.89, 132.22, 129.21, 128.33, 127.91, 127.88, 127.85, 127.76, 126.40, 125.82, 124.18, 114.72, 112.59, 103.19, 54.85, 52.40, 51.82, 50.02, 37.96, 36.58, 30.21, 26.54. HRMS (ESI) Calcd for C$_{32}$H$_{31}$BrN$_4$O$_9$(M−H)$^−$ 693.1196, 695.1176, found 693.1206, 695.1195.

(S)-4-((S)-3-Carboxy-2-((S)-2-(5-methyl-1H-indole-2-carboxamido)-3-(naphthalen-2-yl)propanamido)propanamido)-5-methoxy-5-oxopentanoic acid (14). $^1$H NMR (500 MHz, DMSO-d$_6$) δ 12.28 (s, 2H), 11.28 (d, J=2.2 Hz, 1H), 8.59 (dd, J=20.6, 8.0 Hz, 2H), 8.23 (d, J=7.6 Hz, 1H), 7.92-7.71 (m, 4H), 7.55 (dd, J=8.5, 1.7 Hz, 1H), 7.45-7.33 (m, 3H), 7.25 (d, J=8.3 Hz, 1H), 7.10 (d, J=2.2 Hz, 1H), 6.98 (dd, J=8.4, 1.6 Hz, 1H), 4.87 (ddd, J=11.8, 8.6, 3.7 Hz, 1H), 4.65 (td, J=7.9, 5.2 Hz, 1H), 4.30 (td, J=8.5, 5.4 Hz, 1H), 3.63 (s, 3H), 3.30 (d, J=7.8 Hz, 1H), 3.14 (dd, J=13.9, 10.8 Hz, 1H), 2.72 (dd, J=16.6, 5.2 Hz, 1H), 2.58 (dd, J=16.6, 8.3 Hz, 1H), 2.39-2.24 (m, 5H), 2.09-1.91 (m, 1H), 1.84 (ddd, J=11.6, 8.6, 6.2 Hz, 1H). $^{13}$C NMR (126 MHz, DMSO-d$_6$) δ 174.24, 172.46, 172.04, 171.96, 171.25, 161.46, 136.56, 135.29, 133.39, 132.22, 131.54, 128.69, 128.35, 127.90, 127.89, 127.84, 127.76, 127.65, 126.39, 125.81, 125.69, 121.25, 112.41, 103.32, 54.80, 52.40, 51.83, 50.01, 38.01, 36.59, 30.21, 26.54, 21.60. HRMS (ESI) Calcd for C$_{33}$H$_{34}$N$_4$O$_9$ (M−H)$^−$ 629.2248, found 629.2250.

(S)-4-((S)-3-Carboxy-2-((S)-2-(5-methoxy-1H-indole-2-carboxamido)-3-(naphthalen-2-yl)propanamido)propanamido)-5-methoxy-5-oxopentanoic acid (15). $^1$H NMR (500 MHz, DMSO-d$_6$) δ 12.29 (s, 2H), 11.26 (d, J=2.2 Hz, 1H), 8.59 (dd, J=21.0, 8.0 Hz, 2H), 8.24 (d, J=7.6 Hz, 1H), 7.85-7.70 (m, 4H), 7.55 (dd, J=8.5, 1.7 Hz, 1H), 7.49-7.29 (m, 2H), 7.25 (d, J=8.9 Hz, 1H), 7.09 (dd, J=17.1, 2.3 Hz, 2H), 6.80 (dd, J=8.9, 2.5 Hz, 1H), 4.98-4.80 (m, 1H), 4.65 (td, J=8.0, 5.2 Hz, 1H), 4.30 (ddd, J=9.2, 7.5, 5.2 Hz, 1H), 3.75 (s, 3H), 3.63 (s, 3H), 3.32-3.28 (m, 7H), 3.14 (dd, J=13.9, 10.9 Hz, 1H), 2.72 (dd, J=16.6, 5.2 Hz, 1H), 2.58 (dd, J=16.6, 8.3 Hz, 1H), 2.36-2.24 (m, 2H), 2.09-1.93 (m, 1H), 1.88-1.78 (m, 1H). $^{13}$C NMR (126 MHz, DMSO-$d_6$) δ 174.24, 172.46, 172.04, 171.97, 171.25, 161.36, 154.15, 136.57, 133.39, 132.22, 132.14, 131.88, 128.36, 127.90, 127.82, 127.76, 127.71, 126.38, 125.81, 115.02, 113.50, 103.53, 102.48, 55.70, 54.79, 52.40, 51.84, 50.02, 38.00, 36.59, 30.22, 26.54. HRMS (ESI) Calcd for $C_{33}H_{34}N_4O_{10}$ (M−H)$^-$ 645.2197, found 645.2200.

(S)-4-((S)-3-Carboxy-2-((S)-3-(naphthalen-2-yl)-2-(5-(trifluoromethyl)-1H-indole-2-carboxamido)propanamido)propanamido)-5-methoxy-5-oxopentanoic acid (16). $^1$H NMR (500 MHz, DMSO-$d_6$) δ 12.27 (s, 2H), 11.88 (d, J=2.2 Hz, 1H), 8.88 (d, J=8.6 Hz, 1H), 8.60 (d, J=7.7 Hz, 1H), 8.25 (d, J=7.6 Hz, 1H), 8.08 (d, J=1.7 Hz, 1H), 7.85 (d, J=1.6 Hz, 1H), 7.81-7.71 (m, 3H), 7.59-7.50 (m, 2H), 7.48-7.36 (m, 4H), 5.01-4.74 (m, 1H), 4.66 (td, J=7.9, 5.1 Hz, 1H), 4.31 (ddd, J=9.2, 7.5, 5.1 Hz, 1H), 3.63 (s, 3H), 3.40-3.31 (m, 1H), 3.15 (dd, J=13.8, 10.9 Hz, 1H), 2.72 (dd, J=16.6, 5.2 Hz, 1H), 2.58 (dd, J=16.6, 8.3 Hz, 1H), 2.38-2.25 (m, 2H), 1.99 (td, J=8.2, 4.1 Hz, 1H), 1.88-1.75 (m, 1H). $^{13}$C NMR (126 MHz, DMSO-$d_6$) δ 174.21, 172.45, 172.00, 171.80, 171.23, 160.90, 138.15, 136.51, 133.70, 133.39, 132.23, 128.34, 127.90, 127.84, 127.76, 126.91, 126.71, 126.39, 125.82, 124.76, 121.12, 120.88, 119.98, 104.62, 54.86, 52.39, 51.83, 50.04, 37.98, 36.59, 30.22, 26.56. HRMS (ESI) Calcd for $C_{33}H_{31}F_3N_4O_9$(M−H)$^-$ 683.1965, found 683.1976.

(S)-4-((S)-3-Carboxy-2-((S)-3-(naphthalen-2-yl)-2-(5-nitro-1H-indole-2-carboxamido)propanamido)propanamido)-5-methoxy-5-oxopentanoic acid (17). $^1$H NMR (500 MHz, DMSO-$d_6$) δ 12.21 (s, 2H), 9.03 (d, J=8.6 Hz, 1H), 8.71 (d, J=2.3 Hz, 1H), 8.61 (d, J=7.6 Hz, 1H), 8.30 (d, J=7.5 Hz, 1H), 8.03 (dd, J=9.2, 2.3 Hz, 1H), 7.91-7.70 (m, 4H), 7.56 (dd, J=8.5, 1.7 Hz, 1H), 7.51 (t, J=4.4 Hz, 2H), 7.42 (pd, J=6.8, 1.6 Hz, 2H), 4.92 (ddd, J=11.9, 8.6, 3.6 Hz, 1H), 4.65 (td, J=7.9, 5.1 Hz, 1H), 4.30 (td, J=8.5, 5.4 Hz, 1H), 3.63 (s, 3H), 3.15 (dd, J=13.9, 11.0 Hz, 2H), 2.72 (dd, J=16.6, 5.1 Hz, 1H), 2.58 (dd, J=16.6, 8.4 Hz, 1H), 2.36-2.22 (m, 2H), 2.09-1.91 (m, 1H), 1.83 (ddd, J=14.5, 8.7, 6.4 Hz, 1H). $^{13}$C NMR (126 MHz, DMSO-$d_6$) δ 174.30, 172.47, 172.04, 171.70, 171.23, 160.56, 141.66, 139.71, 136.48, 135.12, 133.39, 132.23, 128.32, 127.91, 127.89, 127.86, 127.76, 126.69, 126.40, 125.83, 119.70, 118.87, 113.22, 106.08, 54.88, 52.40, 51.86, 50.07, 37.95, 36.59, 30.28, 26.54. HRMS (ESI) Calcd for $C_{32}H_{31}N_5O_{11}$ (M−H)$^-$ 660.1942, found 660.1953.

(S)-4-((S)-3-Carboxy-2-((S)-2-(5,7-dichloro-1H-indole-2-carboxamido)-3-(naphthalen-2-yl)propanamido)propanamido)-5-methoxy-5-oxopentanoic acid (18). $^1$H NMR (500 MHz, DMSO-$d_6$) δ 12.30 (s, 2H), 11.90 (s, 1H), 8.90 (d, J=8.4 Hz, 1H), 8.66 (d, J=7.6 Hz, 1H), 8.24 (d, J=7.6 Hz, 1H), 7.93-7.74 (m, 4H), 7.71 (d, J=1.8 Hz, 1H), 7.53 (dd, J=8.5, 1.7 Hz, 1H), 7.47-7.38 (m, 2H), 7.37 (d, J=1.8 Hz, 1H), 7.16 (d, J=1.2 Hz, 1H), 4.93 (ddd, J=10.6, 8.5, 3.8 Hz, 1H), 4.65 (td, J=8.0, 5.0 Hz, 1H), 4.31 (ddd, J=9.2, 7.4, 5.1 Hz, 1H), 3.63 (s, 3H), 3.34 (d, J=11.8 Hz, 1H), 3.09 (dd, J=14.0, 10.7 Hz, 1H), 2.72 (dd, J=16.6, 5.0 Hz, 1H), 2.57 (dd, J=16.6, 8.6 Hz, 1H), 2.38-2.23 (m, 2H), 1.98 (dq, J=10.5, 4.1, 2.6 Hz, 1H), 1.89-1.75 (m, 1H). $^{13}$C NMR (126 MHz, DMSO-$d_6$) δ 174.22, 172.46, 172.01, 171.71, 171.22, 160.06, 136.24, 134.58, 133.39, 132.76, 132.26, 129.40, 128.27, 127.91, 127.89, 127.78, 126.42, 125.86, 124.73, 123.28, 120.43, 117.78, 106.31, 99.99, 54.73, 52.41, 51.83, 50.07, 38.26, 36.57, 30.24, 26.55. HRMS (ESI) Calcd for $C_{32}H_{30}Cl_2N_4O_9$ (M−H)$^-$ 683.1312, found 683.1312.

(S)-4-((S)-3-Carboxy-2-((S)-2-(4,6-dichloro-1H-indole-2-carboxamido)-3-(naphthalen-2-yl)propanamido)propanamido)-5-methoxy-5-oxopentanoic acid (19). $^1$H NMR (500 MHz, DMSO-$d_6$) δ 12.28 (s, 2H), 11.94 (s, 1H), 8.95 (d, J=8.6 Hz, 1H), 8.58 (d, J=7.7 Hz, 1H), 8.24 (d, J=7.6 Hz, 1H), 8.00-7.73 (m, 4H), 7.55 (dd, J=8.5, 1.7 Hz, 1H), 7.47-7.31 (m, 4H), 7.21 (d, J=1.7 Hz, 1H), 5.11-4.82 (m, 1H), 4.65 (td, J=8.0, 5.2 Hz, 1H), 4.30 (ddd, J=9.2, 7.5, 5.1 Hz, 1H), 3.63 (s, 3H), 3.36-3.23 (m, 1H), 3.13 (dd, J=13.9, 11.0 Hz, 1H), 2.72 (dd, J=16.6, 5.1 Hz, 1H), 2.58 (dd, J=16.6, 8.4 Hz, 1H), 2.30 (dt, J=8.0, 3.4 Hz, 2H), 1.98 (dtd, J=13.1, 7.7, 5.1 Hz, 1H), 1.88-1.70 (m, 1H). $^{13}$C NMR (126 MHz, DMSO-$d_6$) δ 174.22, 172.46, 172.02, 171.73, 171.23, 160.58, 137.22, 136.50, 133.38, 133.34, 132.23, 128.28, 128.22, 127.92, 127.88, 127.85, 127.75, 126.82, 126.42, 125.84, 125.15, 119.89, 111.54, 101.93, 54.88, 52.40, 51.83, 50.02, 37.96, 36.58, 30.22, 26.54. HRMS (ESI) Calcd for $C_{32}H_{30}Cl_2N_4O_9$ (M−H)$^-$ 683.1312, found 683.1314.

Synthesis of final products 22-26. The synthetic route for final products 22-26 is shown in Scheme 3.

Scheme 3. Synthesis of Final Compounds 22-26.

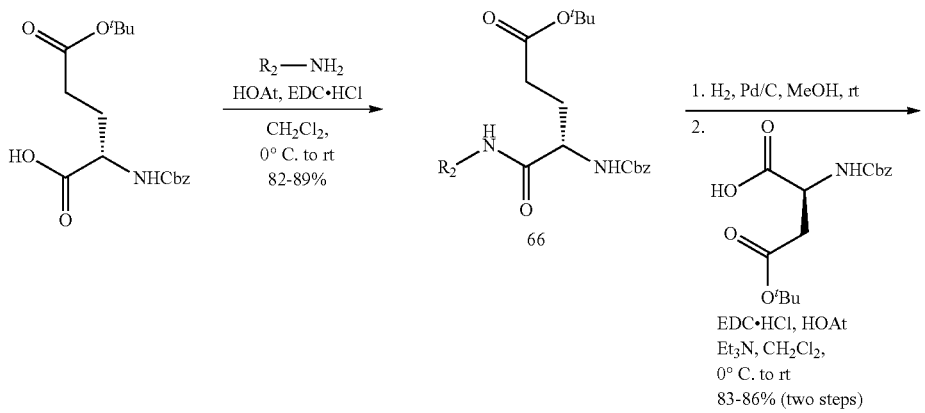

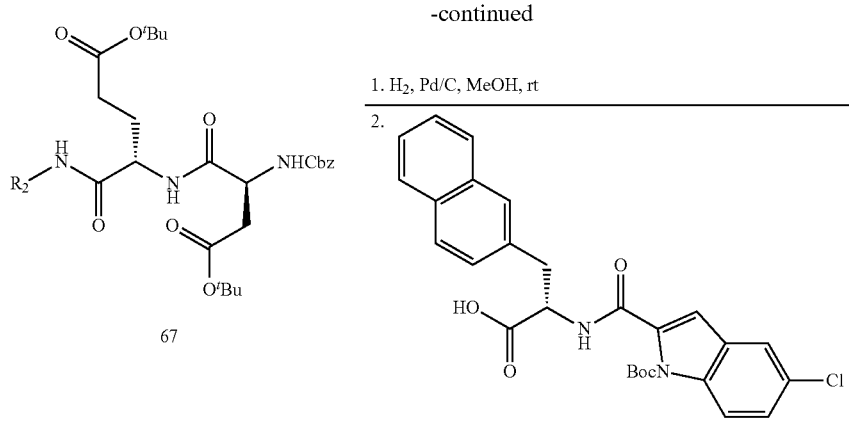

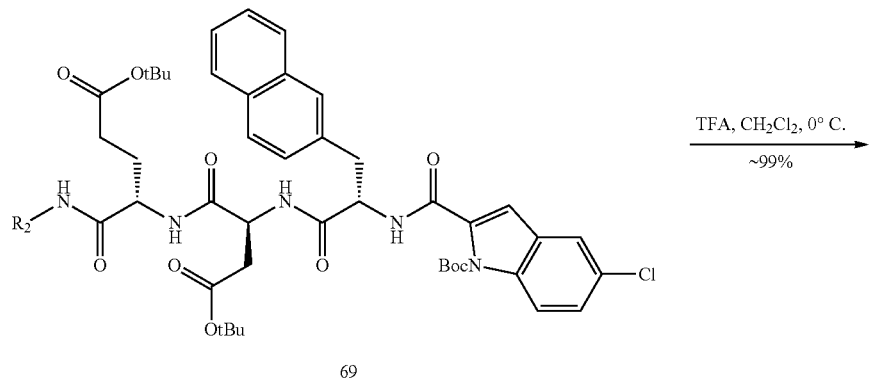

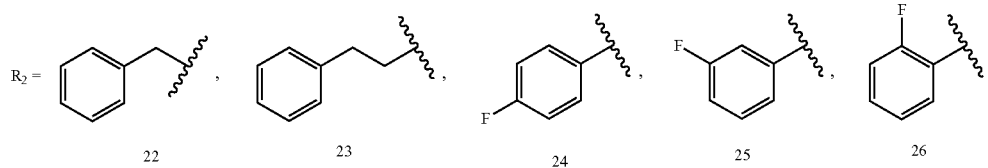

tert-Butyl (S)-5-(benzylamino)-4-(((benzyloxy)carbonyl)amino)-5-oxopentanoate (66a). Yield, 89%. $^1$H NMR (500 MHz, Chloroform-d) δ 7.19 (qd, J=9.1, 7.7, 4.2 Hz, 7H), 7.13-7.09 (m, 3H), 6.99 (d, J=6.1 Hz, 1H), 5.90 (d, J=8.1 Hz, 1H), 4.89 (q, J=12.3 Hz, 2H), 4.25 (tp, J=19.5, 7.1, 6.4 Hz, 3H), 2.32-2.13 (m, 2H), 1.98 (dtd, J=14.5, 7.3, 5.3 Hz, 1H), 1.83 (dt, J=14.8, 7.4 Hz, 1H), 1.31 (s, 9H). $^{13}$C NMR (126 MHz, Chloroform-d) δ 172.65, 171.44, 156.37, 137.98, 136.20, 128.65, 128.50, 128.14, 128.00, 127.60, 127.43, 80.84, 77.18, 66.95, 54.40, 43.44, 31.64, 28.06. MS (ESI) m/z=449.2 [M+Na]$^+$.

tert-Butyl (S)-4-(((benzyloxy)carbonyl)amino)-5-oxo-5-(phenethylamino)pentanoate(66b). Yield, 82%. $^1$H NMR (500 MHz, Chloroform-d) δ 7.52-7.26 (m, 7H), 7.25-7.11 (m, 3H), 6.50 (d, J=6.1 Hz, 1H), 5.82 (d, J=7.9 Hz, 1H), 5.19-4.97 (m, 2H), 4.18 (q, J=7.2 Hz, 1H), 3.72-3.41 (m, 2H), 2.81 (t, J=7.1 Hz, 2H), 2.37 (dt, J=16.4, 7.2 Hz, 1H), 2.25 (dt, J=16.6, 7.0 Hz, 1H), 2.13-1.99 (m, 1H), 1.93 (s, 1H), 1.45 (s, 9H). ¹³C NMR (126 MHz, Chloroform-d) δ 172.75, 171.22, 156.24, 138.66, 136.22, 128.75, 128.61, 128.53, 128.19, 128.03, 126.53, 80.92, 77.11, 66.98, 54.42, 40.71, 35.63, 31.66, 28.07. MS (ESI) m/z=441.3 [M+H]⁺, MS (ESI) m/z=463.2 [M+Na]⁺, MS (ESI) m/z=903.4 [2M+Na]⁺.

tert-Butyl (S)-4-(((benzyloxy)carbonyl)amino)-5-((4-fluorophenyl)amino)-5-oxopentanoate (66c). Yield, 87%. ¹H NMR (500 MHz, Chloroform-d) δ 8.81 (s, 1H), 7.47-7.38 (m, 2H), 7.35-7.21 (m, 5H), 6.93 (t, J=8.7 Hz, 2H), 6.03 (d, J=7.8 Hz, 1H), 5.18-4.95 (m, 2H), 4.38 (t, J=7.4 Hz, 1H), 2.48 (dt, J=16.5, 7.2 Hz, 1H), 2.37 (dt, J=16.7, 6.9 Hz, 1H), 2.21-2.10 (m, 1H), 2.07-1.92 (m, 1H), 1.44 (s, 9H). ¹³C NMR (126 MHz, Chloroform-d) δ 172.99, 169.78, 159.39 (d, J=243.5 Hz), 156.66, 136.05, 133.67, 128.55, 128.23, 127.97, 121.71 (d, J=7.9 Hz), 115.51 (d, J=22.5 Hz), 81.28, 67.22, 54.97, 31.82, 28.06, 28.01. MS (ESI) m/z=453.2 [M+Na]⁺.

tert-Butyl (S)-4-(((benzyloxy)carbonyl)amino)-5-((3-fluorophenyl)amino)-5-oxopentanoate(66 d). Yield, 84%. ¹H NMR (500 MHz, Chloroform-d) δ 8.85 (s, 1H), 7.46 (dt, J=11.0, 2.4 Hz, 1H), 7.32 (q, J=4.3 Hz, 5H), 7.21 (td, J=8.2, 6.3 Hz, 1H), 7.16-7.06 (m, 1H), 6.95-6.59 (m, 1H), 5.92 (d, J=7.7 Hz, 1H), 5.11 (d, J=4.3 Hz, 2H), 4.36 (d, J=7.1 Hz, 1H), 2.59-2.47 (m, 1H), 2.37 (ddd, J=16.7, 7.3, 6.0 Hz, 1H), 2.15 (ddt, J=13.8, 7.8, 6.0 Hz, 1H), 2.06-1.89 (m, 1H), 1.45 (s, 9H). ¹³C NMR (126 MHz, Chloroform-d) δ 173.23, 169.79, 162.91 (d, J=244.7 Hz), 156.64, 139.16 (d, J=10.8 Hz), 136.01, 130.00 (d, J=9.2 Hz), 128.56, 128.27, 128.02, 115.13 (d, J=3.0 Hz), 111.08 (d, J=21.3 Hz), 107.34 (d, J=26.3 Hz), 81.46, 67.30, 55.03, 31.89, 28.06, 28.01. MS (ESI) m/z=297.2 [M+H]⁺, MS (ESI) m/z=453.2 [M+Na]⁺.

tert-Butyl (S)-4-(((benzyloxy)carbonyl)amino)-5-((2-fluorophenyl)amino)-5-oxopentanoate (66e). Yield, 88%. ¹H NMR (500 MHz, Chloroform-d) δ 8.62 (s, 1H), 8.37-8.09 (m, 1H), 7.43-7.28 (m, 5H), 7.06 (dtt, J=14.0, 5.3, 2.6 Hz, 3H), 6.07-5.87 (m, 1H), 5.27-5.01 (m, 2H), 4.47 (t, J=7.3 Hz, 1H), 2.48 (q, J=8.0, 7.2 Hz, 1H), 2.38 (dt, J=16.7, 6.8 Hz, 1H), 2.26-2.10 (m, 1H), 2.08-1.89 (m, 1H), 1.44 (s, 9H). ¹³C NMR (126 MHz, Chloroform-d) δ 172.84, 169.99, 156.55, 152.87 (d, J=243.8 Hz), 136.10, 128.52, 128.19, 128.06, 125.88 (d, J=10.4 Hz), 124.83 (d, J=7.4 Hz), 124.43 (d, J=3.7 Hz), 122.24, 114.96 (d, J=19.2 Hz), 81.21 (d, J=4.1 Hz), 67.24, 55.15, 31.79, 28.05, 27.87. MS (ESI) m/z=453.3 [M+Na]⁺.

tert-Butyl (S)-5-(benzylamino)-4-((S)-2-(((benzyloxy)carbonyl)amino)-4-(tert-butoxy)-4-oxobutanamido)-5-oxopentanoate (67a). Yield, 86%. ¹H NMR (500 MHz, Chloroform-d) δ 7.50 (d, J=7.5 Hz, 1H), 7.44-7.31 (m, 7H), 7.27 (dd, J=10.6, 3.4 Hz, 3H), 7.09 (d, J=8.3 Hz, 1H), 5.89 (d, J=8.3 Hz, 1H), 5.25-5.02 (m, 2H), 4.58-4.31 (m, 4H), 2.89 (dd, J=16.9, 4.8 Hz, 1H), 2.70 (dd, J=16.9, 6.1 Hz, 1H), 2.55-2.39 (m, 1H), 2.33 (dt, J=17.0, 6.5 Hz, 1H), 2.22-2.12 (m, 1H), 2.02 (dt, J=14.0, 7.1 Hz, 1H), 1.44 (s, 9H), 1.40 (s, 9H). ¹³C NMR (126 MHz, Chloroform-d) δ 173.52, 170.95, 170.80, 170.58, 156.07, 138.17, 135.98, 128.61, 128.56, 128.27, 128.15, 127.58, 127.32, 82.00, 81.07, 67.31, 53.31, 51.67, 43.40, 37.33, 31.67, 28.04, 27.99, 26.99. MS (ESI) m/z=620.3 [M+Na]⁺.

tert-Butyl (S)-4-((S)-2-(((benzyloxy)carbonyl)amino)-4-(tert-butoxy)-4-oxobutanamido)-5-oxo-5-(phenethylamino) pentanoate (67b). Yield, 83%. ¹H NMR (500 MHz, Chloroform-d) δ 7.41-7.27 (m, 8H), 7.24-7.12 (m, 3H), 6.62 (s, 1H), 5.84 (d, J=8.4 Hz, 1H), 5.13 (q, J=12.2 Hz, 2H), 4.45 (q, J=7.3, 6.2 Hz, 1H), 4.32 (td, J=8.0, 4.7 Hz, 1H), 3.49 (q, J=7.3 Hz, 2H), 2.90 (dd, J=17.0, 4.6 Hz, 1H), 2.85-2.75 (m, 2H), 2.67 (dd, J=16.9, 5.9 Hz, 1H), 2.36 (ddd, J=17.1, 8.0, 6.1 Hz, 1H), 2.24 (dt, J=17.0, 6.5 Hz, 1H), 2.06 (dt, J=10.4, 5.5 Hz, 1H), 1.91 (dd, J=14.5, 7.4 Hz, 1H), 1.43 (s, 9H), 1.42 (s, 9H). ¹³C NMR (126 MHz, Chloroform-d) δ 173.53, 171.04, 170.69, 170.54, 156.08, 138.78, 135.99, 128.75, 128.57, 128.29, 128.14, 126.46, 81.99, 81.04, 67.35, 53.34, 53.24, 51.60, 40.78, 37.29, 35.63, 31.63, 28.11, 27.99, 26.99. MS (ESI) m/z=612.3 [M+H]⁺, MS (ESI) m/z=634.3 [M+Na]⁺.

tert-Butyl (S)-4-((S)-2-(((benzyloxy)carbonyl)amino)-4-(tert-butoxy)-4-oxobutanamido)-5-((4-fluorophenyl)amino)-5-oxopentanoate (67c). Yield, 86%. ¹H NMR (500 MHz, Chloroform-d) δ 8.78 (s, 1H), 7.61 (d, J=7.5 Hz, 1H), 7.47 (dd, J=8.9, 4.8 Hz, 2H), 7.26-7.12 (m, 5H), 6.94-6.63 (m, 2H), 5.97 (d, J=8.0 Hz, 1H), 5.14-4.95 (m, 2H), 4.47 (dtd, J=11.2, 7.9, 5.4 Hz, 2H), 2.78 (dd, J=16.9, 5.1 Hz, 1H), 2.68 (dd, J=16.8, 6.3 Hz, 1H), 2.43-2.32 (m, 1H), 2.27 (dt, J=17.0, 6.7 Hz, 1H), 2.13 (q, J=6.4, 6.0 Hz, 1H), 2.00-1.90 (m, 1H), 1.34 (s, 9H), 1.31 (s, 9H). ¹³C NMR (126 MHz, Chloroform-d) δ 173.50, 171.25, 170.80, 169.06, 159.33 (d, J=243.3 Hz), 156.24, 135.98, 133.90 (d, J=2.8 Hz), 128.54, 128.26, 128.08, 121.87 (d, J=7.8 Hz), 115.35 (d, J=22.4 Hz), 82.04, 81.19, 67.34, 53.78, 51.82, 37.32, 31.73, 28.04, 27.98, 26.85. MS (ESI) m/z=624.3 [M+Na]⁺.

tert-Butyl (S)-4-((S)-2-(((benzyloxy)carbonyl)amino)-4-(tert-butoxy)-4-oxobutanamido)-5-((3-fluorophenyl)amino)-5-oxopentanoate (67 d). Yield, 84%. ¹H NMR (500 MHz, Chloroform-d) δ 8.91 (s, 1H), 7.67 (d, J=7.3 Hz, 1H), 7.54 (dt, J=11.2, 2.3 Hz, 1H), 7.38-7.25 (m, 6H), 7.21 (td, J=8.2, 6.4 Hz, 1H), 6.77 (tdd, J=8.3, 2.5, 1.0 Hz, 1H), 5.95 (d, J=7.9 Hz, 1H), 5.21-5.03 (m, 2H), 4.67-4.41 (m, 2H), 2.88 (dd, J=16.9, 4.9 Hz, 1H), 2.76 (dd, J=16.9, 6.2 Hz, 1H), 2.48 (ddd, J=17.1, 8.1, 5.9 Hz, 1H), 2.35 (ddd, J=17.1, 7.1, 5.8 Hz, 1H), 2.20 (td, J=8.4, 4.0 Hz, 1H), 2.04 (q, J=5.4, 3.4 Hz, 1H), 1.43 (s, 9H), 1.41 (s, 9H). ¹³C NMR (126 MHz, Chloroform-d) δ 173.75, 171.26, 170.85, 169.19, 162.87 (d, J=244.2 Hz), 156.25, 139.42 (d, J=10.7 Hz), 135.95, 129.84 (d, J=9.3 Hz), 128.56, 128.30, 128.12, 115.39 (d, J=2.8 Hz), 110.90 (d, J=21.3 Hz), 107.48 (d, J=26.3 Hz), 82.17, 81.37, 67.42, 53.94, 51.82, 37.25, 31.79, 28.04, 27.99, 26.69. MS (ESI) m/z=624.3 [M+Na]⁺.

tert-Butyl (S)-4-((S)-2-(((benzyloxy)carbonyl)amino)-4-(tert-butoxy)-4-oxobutanamido)-5-((2-fluorophenyl)amino)-5-oxopentanoate (67e). Yield, 85%. ¹H NMR (500 MHz, Chloroform-d) δ 8.68 (s, 1H), 8.31-8.01 (m, 1H), 7.59 (d, J=7.4 Hz, 1H), 7.43-7.27 (m, 5H), 7.14-6.92 (m, 3H), 5.99 (d, J=8.7 Hz, 1H), 5.24-5.01 (m, 2H), 4.61 (ddt, J=15.7, 10.5, 4.8 Hz, 2H), 2.95 (dd, J=17.1, 4.7 Hz, 1H), 2.67 (dd, J=17.1, 6.0 Hz, 1H), 2.55-2.44 (m, 1H), 2.36 (dt, J=17.0, 6.6 Hz, 1H), 2.23-2.15 (m, 1H), 2.09-1.98 (m, 1H), 1.43 (s, 9H), 1.38 (s, 9H). ¹³C NMR (126 MHz, Chloroform-d) δ 173.26, 171.43, 170.95, 169.29, 156.04, 153.06 (d, J=244.8 Hz), 136.05, 128.53, 128.23, 128.15, 125.90 (d, J=10.7 Hz), 124.88 (d, J=7.4 Hz), 124.32 (d, J=3.6 Hz), 122.63, 114.99 (d, J=19.1 Hz), 81.91, 81.13, 67.32, 53.77, 51.43, 37.42, 31.60, 28.05, 27.97, 27.03. MS (ESI) m/z=624.3 [M+Na]⁺.

tert-Butyl 2-(((S)-1-(((S)-1-(((S)-1-(benzylamino)-5-(tert-butoxy)-1,5-dioxopentan-2-yl)amino)-4-(tert-butoxy)-1,4-dioxobutan-2-yl)amino)-3-(naphthalen-2-yl)-1-oxopropan-2-yl)carbamoyl)-5-chloro-1H-indole-1-carboxylate (69a). Yield, 89%. ¹H NMR (500 MHz, Chloroform-d) δ 7.85-7.64 (m, 4H), 7.64-7.55 (m, 1H), 7.48 (d, J=7.5 Hz, 1H), 7.45-7.32 (m, 4H), 7.26 (dd, J=8.5, 1.8 Hz, 1H), 7.23-7.17 (m, 5H), 7.16-7.06 (m, 2H), 6.76 (d, J=5.9 Hz, 1H), 6.53 (d, J=0.7 Hz, 1H), 4.79-4.57 (m, 2H), 4.40 (ddd, J=21.0, 13.9, 7.3 Hz, 2H), 4.26 (dd, J=14.9, 5.5 Hz, 1H), 3.34 (dd, J=14.4, 5.4 Hz, 1H), 3.16 (dd, J=14.4, 8.3 Hz, 1H), 2.83-2.60 (m, 2H), 2.31-2.06 (m, 3H), 1.97-1.76 (m, 1H), 1.49 (s, 9H), 1.28 (s, 9H), 1.23 (s, 9H). $^{13}$C NMR (126 MHz, Chloroform-d) δ 172.49, 170.96, 170.75, 170.44, 170.29, 162.96, 149.39, 138.37, 134.68, 134.48, 133.45, 133.26, 132.61, 129.15, 129.11, 128.92, 128.82, 128.46, 127.99, 127.91, 127.79, 127.63, 127.10, 126.91, 126.52, 126.03, 121.37, 121.33, 116.58, 116.48, 111.24, 111.09, 86.03, 81.75, 80.43, 55.59, 53.17, 53.13, 50.96, 50.88, 43.30, 37.27, 36.73, 31.89, 28.12, 28.03, 27.92, 27.88, 27.82, 26.96. MS (ESI) m/z=960.4 [M+Na]$^+$.

tert-Butyl 2-(((S)-1-(((S)-4-(tert-butoxy)-1-(((S)-5-(tert-butoxy)-1,5-dioxo-1-(phenethylamino)pentan-2-yl)amino)-1,4-dioxobutan-2-yl)amino)-3-(naphthalen-2-yl)-1-oxopropan-2-yl)carbamoyl)-5-chloro-1H-indole-1-carboxylate (69b). Yield, 84%. $^1$H NMR (500 MHz, Chloroform-d) δ 7.84-7.68 (m, 4H), 7.66-7.58 (m, 1H), 7.46 (d, J=7.6 Hz, 1H), 7.42-7.35 (m, 3H), 7.33-7.24 (m, 2H), 7.24-7.16 (m, 3H), 7.16-7.03 (m, 3H), 6.88-6.65 (m, 2H), 6.56 (d, J=0.7 Hz, 1H), 4.81-4.61 (m, 2H), 4.37-4.20 (m, 1H), 3.57-3.31 (m, 3H), 3.22 (dd, J=14.4, 8.4 Hz, 1H), 2.88-2.64 (m, 4H), 2.13 (ddd, J=11.2, 5.4, 2.5 Hz, 2H), 2.10-2.00 (m, 1H), 1.85-1.73 (m, 1H), 1.50 (s, 9H), 1.31 (s, 9H), 1.22 (s, 9H). $^{13}$C NMR (126 MHz, Chloroform-d) δ 172.47, 171.02, 170.75, 170.35, 170.32, 162.99, 149.45, 139.09, 134.65, 134.48, 133.47, 133.22, 132.64, 129.18, 129.13, 129.00, 128.84, 128.46, 128.02, 127.92, 127.80, 127.70, 127.53, 126.90, 126.87, 126.55, 126.25, 126.09, 121.40, 121.34, 116.60, 116.49, 111.26, 111.11, 86.11, 81.74, 80.37, 55.74, 55.66, 53.29, 53.19, 50.95, 50.88, 40.94, 37.28, 36.64, 35.65, 31.90, 28.20, 28.08, 28.02, 27.97, 27.90, 27.80, 26.82. MS (ESI) m/z=974.4 [M+Na]$^+$.

tert-Butyl 2-(((S)-1-(((S)-4-(tert-butoxy)-1-(((S)-5-(tert-butoxy)-1-((4-fluorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (69c). Yield, 86%. $^1$H NMR (500 MHz, Chloroform-d) δ 8.66 (s, 1H), 7.93-7.75 (m, 4H), 7.74-7.53 (m, 5H), 7.52-7.41 (m, 3H), 7.39 (dd, J=8.4, 1.7 Hz, 1H), 7.30 (dd, J=9.0, 2.1 Hz, 1H), 6.95 (t, J=8.4 Hz, 2H), 6.83 (s, 1H), 6.65 (s, 1H), 4.81 (dq, J=13.4, 6.9, 6.3 Hz, 2H), 4.51 (s, 1H), 3.55 (dd, J=14.4, 5.2 Hz, 1H), 3.30 (dd, J=14.3, 8.6 Hz, 1H), 2.88 (qd, J=16.6, 6.4 Hz, 2H), 2.52-2.20 (m, 3H), 2.04-1.95 (m, 1H), 1.58 (s, 9H), 1.39 (s, 9H), 1.29 (s, 9H). $^{13}$C NMR (126 MHz, Chloroform-d) δ 172.30, 171.38, 170.57, 170.20, 169.14, 163.38, 160.18, 158.25, 149.53, 134.61, 134.31, 134.29, 134.22, 133.46, 132.99, 132.67, 129.31, 129.11, 129.05, 127.93, 127.77, 127.57, 126.76, 126.68, 126.56, 126.16, 121.65, 121.59, 121.44, 116.58, 115.36, 115.18, 111.48, 86.29, 81.87, 80.47, 56.05, 53.79, 51.30, 37.21, 36.50, 31.99, 28.01, 27.96, 27.94, 26.72. MS (ESI) m/z=964.1 [M+Na]$^+$.

tert-Butyl 2-(((S)-1-(((S)-4-(tert-butoxy)-1-(((S)-5-(tert-butoxy)-1-((3-fluorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (69 d). Yield, 88%. $^1$H NMR (500 MHz, Chloroform-d) δ 8.79 (d, J=24.9 Hz, 1H), 8.04-7.75 (m, 4H), 7.68 (d, J=33.8 Hz, 4H), 7.52-7.35 (m, 5H), 7.30 (dd, J=8.9, 2.0 Hz, 1H), 7.18 (s, 1H), 6.75 (t, J=8.0 Hz, 2H), 6.65 (s, 1H), 4.82 (s, 2H), 4.54 (s, 1H), 3.54 (dd, J=14.0, 5.7 Hz, 1H), 3.30 (dd, J=14.4, 8.5 Hz, 1H), 3.05-2.74 (m, 2H), 2.48-2.19 (m, 3H), 2.09-1.89 (m, 1H), 1.57 (s, 9H), 1.39 (s, 9H), 1.31 (s, 9H). $^{13}$C NMR (126 MHz, Chloroform-d) δ 172.28, 171.31, 170.60, 170.20, 169.40, 163.32, 161.89, 149.47, 139.81, 139.72, 134.67, 134.26, 133.47, 133.05, 132.66, 129.79, 129.72, 129.27, 129.09, 129.00, 127.97, 127.76, 127.57, 126.83, 126.66, 126.54, 126.11, 121.42, 116.57, 115.31, 111.46, 110.73, 110.56, 107.43, 107.22, 86.21, 81.90, 80.52, 55.98, 53.81, 51.20, 37.31, 36.62, 31.94, 28.01, 27.95, 26.78. MS (ESI) m/z=964.1 [M+Na]$^+$.

tert-Butyl 2-(((S)-1-(((S)-4-(tert-butoxy)-1-(((S)-5-(tert-butoxy)-1-((2-fluorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (69e). Yield, 84%. $^1$H NMR (500 MHz, Chloroform-d) δ 8.56 (d, J=2.4 Hz, 1H), 8.11-7.98 (m, 1H), 7.78 (d, J=9.0 Hz, 1H), 7.76-7.67 (m, 3H), 7.63 (d, J=1.6 Hz, 1H), 7.50 (dd, J=21.4, 7.8 Hz, 2H), 7.41-7.28 (m, 4H), 7.26-7.15 (m, 1H), 7.10-6.92 (m, 3H), 6.81 (d, J=6.3 Hz, 1H), 6.66-6.35 (m, 1H), 4.85 (dt, J=7.9, 5.8 Hz, 1H), 4.80-4.71 (m, 1H), 4.46 (td, J=8.1, 5.2 Hz, 1H), 3.43 (dd, J=14.3, 5.5 Hz, 1H), 3.25 (dd, J=14.3, 8.1 Hz, 1H), 2.76 (dd, J=6.2, 2.2 Hz, 2H), 2.43-2.02 (m, 3H), 1.86 (dtd, J=14.4, 8.3, 6.0 Hz, 1H), 1.48 (s, 9H), 1.29 (s, 9H), 1.25 (s, 9H). $^{13}$C NMR (126 MHz, Chloroform-d) δ 172.52, 170.95, 170.58, 170.52, 169.30, 162.90, 154.13, 152.18, 149.31, 134.77, 134.59, 133.47, 132.60, 129.10, 129.07, 128.80, 128.03, 127.73, 127.56, 127.02, 126.46, 126.41, 126.05, 125.98, 124.77 (d, J=7.6 Hz), 124.24 (d, J=3.7 Hz), 122.75, 121.31, 116.48, 115.06, 114.91, 111.04, 85.92, 81.75, 80.68, 55.41, 53.86, 50.33, 37.36, 36.88, 31.77, 27.98, 27.97, 27.91, 26.78. MS (ESI) m/z=964.4 [M+Na]$^+$.

(S)-5-(Benzylamino)-4-((S)-3-carboxy-2-((S)-2-(5-chloro-1H-indole-2-carboxamido)-3-(naphthalen-2-yl)propanamido)propanamido)-5-oxopentanoic acid (22). $^1$H NMR (500 MHz, DMSO-d$_6$) δ 12.26 (s, 2H), 11.62 (d, J=2.2 Hz, 1H), 8.80 (d, J=8.6 Hz, 1H), 8.67 (d, J=7.6 Hz, 1H), 8.36 (t, J=6.0 Hz, 1H), 8.02 (d, J=8.0 Hz, 1H), 7.91-7.73 (m, 4H), 7.70 (d, J=2.0 Hz, 1H), 7.55 (dd, J=8.5, 1.7 Hz, 1H), 7.49-7.37 (m, 2H), 7.36 (d, J=8.7 Hz, 1H), 7.31 (dd, J=8.1, 6.9 Hz, 2H), 7.26-7.18 (m, 4H), 7.15 (dd, J=8.7, 2.1 Hz, 1H), 5.00-4.81 (m, 1H), 4.65 (td, J=7.6, 6.0 Hz, 1H), 4.30 (t, J=5.8 Hz, 3H), 3.28 (d, J=3.5 Hz, 1H), 3.15 (dd, J=13.8, 11.0 Hz, 1H), 2.81 (dd, J=16.7, 6.0 Hz, 1H), 2.60 (dd, J=16.7, 7.6 Hz, 1H), 2.26 (ddd, J=9.2, 6.5, 3.0 Hz, 2H), 1.99 (dddd, J=14.0, 9.2, 6.8, 4.9 Hz, 1H), 1.80 (dtd, J=13.7, 9.0, 6.5 Hz, 1H). $^{13}$C NMR (126 MHz, DMSO-d$_6$) δ 174.42, 172.39, 172.03, 171.30, 170.92, 161.04, 139.69, 136.49, 135.23, 133.38, 133.07, 132.23, 128.73, 128.46, 128.33, 127.91, 127.90, 127.84, 127.76, 127.48, 127.21, 126.40, 125.83, 124.63, 123.91, 121.10, 114.28, 103.31, 54.80, 52.62, 50.17, 42.53, 37.97, 36.38, 30.49, 27.82. HRMS (ESI) Calcd for C$_{38}$H$_{36}$ClN$_5$O$_8$(M−H)$^−$ 724.2174, found 724.2178.

(S)-4-((S)-3-Carboxy-2-((S)-2-(5-chloro-1H-indole-2-carboxamido)-3-(naphthalen-2-yl)propanamido)propanamido)-5-oxo-5-(phenethylamino)pentanoic acid (23). $^1$H NMR (500 MHz, DMSO-d$_6$) δ 12.25 (s, 2H), 11.62 (d, J=2.2 Hz, 1H), 8.80 (d, J=8.6 Hz, 1H), 8.67 (d, J=7.5 Hz, 1H), 7.92 (dd, J=6.7, 4.9 Hz, 2H), 7.85 (d, J=1.6 Hz, 1H), 7.83-7.74 (m, 3H), 7.70 (d, J=2.1 Hz, 1H), 7.56 (dd, J=8.5, 1.7 Hz, 1H), 7.46-7.38 (m, 2H), 7.36 (d, J=8.7 Hz, 1H), 7.27 (dd, J=8.1, 6.7 Hz, 2H), 7.22-7.17 (m, 4H), 7.17-7.09 (m, 1H), 5.00-4.79 (m, 1H), 4.63 (td, J=7.5, 6.1 Hz, 1H), 4.21 (td, J=8.2, 5.1 Hz, 1H), 3.27 (qd, J=7.4, 6.7, 5.0 Hz, 3H), 3.18-3.05 (m, 1H), 2.79 (dd, J=16.7, 6.1 Hz, 1H), 2.71 (t, J=7.4 Hz, 2H), 2.60 (dd, J=16.6, 7.5 Hz, 1H), 2.20 (t, J=8.0 Hz, 2H), 1.92 (dtd, J=16.3, 8.0, 5.1 Hz, 1H), 1.79-1.65 (m, 1H). $^{13}$C NMR (126 MHz, DMSO-d$_6$) δ 174.43, 172.40, 172.04, 171.30, 170.74, 161.04, 139.74, 136.49, 135.23, 133.38, 133.07, 132.23, 129.09, 128.74, 128.46, 128.33, 127.91, 127.90, 127.84, 127.76, 126.55, 126.40, 125.83, 124.63, 123.91, 121.10, 114.28, 103.32, 54.81, 52.50, 50.15, 40.70, 37.96, 36.39, 35.49, 30.40, 27.88. HRMS (ESI) Calcd for C$_{39}$H$_{38}$ClN$_5$O$_8$(M−H)$^−$ 738.2331, found 738.2337.

(S)-4-((S)-3-Carboxy-2-((S)-2-(5-chloro-1H-indole-2-carboxamido)-3-(naphthalen-2-yl)propanamido)propanamido)-5-((4-fluorophenyl)amino)-5-oxopentanoic acid (24). $^1$H NMR (500 MHz, DMSO-d$_6$) δ 12.31 (s, 2H), 11.80-11.30 (m, 1H), 9.93 (s, 1H), 8.84 (d, J=8.5 Hz, 1H), 8.67 (d, J=7.6 Hz, 1H), 8.18 (d, J=7.7 Hz, 1H), 7.89-7.73 (m, 4H), 7.70 (d, J=2.0 Hz, 1H), 7.66-7.61 (m, 2H), 7.56 (dd, J=8.5, 1.7 Hz, 1H), 7.42 (pd, J=6.9, 1.6 Hz, 2H), 7.36 (d, J=8.7 Hz, 1H), 7.21 (d, J=2.0 Hz, 1H), 7.18-7.07 (m, 3H), 4.91 (ddd, J=11.7, 8.6, 3.7 Hz, 1H), 4.66 (q, J=7.1 Hz, 1H), 4.39 (td, J=8.2, 5.0 Hz, 1H), 3.29 (d, J=3.7 Hz, 1H), 3.16 (dd, J=13.9, 10.9 Hz, 1H), 2.80 (dd, J=16.6, 6.1 Hz, 1H), 2.62 (dd, J=16.6, 7.4 Hz, 1H), 2.31 (pt, J=9.0, 4.9 Hz, 2H), 2.05 (td, J=8.8, 5.0 Hz, 1H), 1.88 (ddt, J=13.5, 8.7, 4.6 Hz, 1H). $^{13}$C NMR (126 MHz, DMSO-$d_6$) δ 174.38, 172.47, 172.03, 171.16, 170.23, 161.06, 159.54, 157.63, 136.50, 135.52, 135.50, 135.25, 133.39, 133.09, 132.23, 128.46, 128.32, 127.91, 127.89, 127.85, 127.76, 126.40, 125.83, 124.63, 123.91, 121.75, 121.69, 121.09, 115.80, 115.62, 114.30, 103.35, 54.85, 53.34, 50.24, 37.96, 36.61, 30.61, 27.67. HRMS (ESI) Calcd for $C_{37}H_{33}ClFN_5O_8$(M−H)$^-$ 728.1923, found 728.1936.

(S)-4-((S)-3-Carboxy-2-((S)-2-(5-chloro-1H-indole-2-carboxamido)-3-(naphthalen-2-yl)propanamido)propanamido)-5-((3-fluorophenyl)amino)-5-oxopentanoic acid (25). $^1$H NMR (500 MHz, DMSO-$d_6$) δ 12.31 (s, 2H), 11.62 (d, J=2.2 Hz, 1H), 10.08 (s, 1H), 8.81 (d, J=8.5 Hz, 1H), 8.67 (d, J=7.5 Hz, 1H), 8.17 (d, J=7.7 Hz, 1H), 7.93-7.73 (m, 4H), 7.70 (d, J=2.1 Hz, 1H), 7.65-7.49 (m, 2H), 7.48-7.39 (m, 2H), 7.37-7.28 (m, 3H), 7.21 (d, J=2.1 Hz, 1H), 7.15 (dd, J=8.8, 2.1 Hz, 1H), 7.05-6.82 (m, 1H), 4.91 (ddd, J=11.7, 8.5, 3.6 Hz, 1H), 4.67 (td, J=7.6, 5.9 Hz, 1H), 4.41 (td, J=8.3, 5.1 Hz, 1H), 3.30 (d, J=3.5 Hz, 1H), 3.16 (dd, J=13.9, 11.0 Hz, 1H), 2.81 (dd, J=16.7, 5.8 Hz, 1H), 2.63 (dd, J=16.7, 7.7 Hz, 1H), 2.42-2.20 (m, 2H), 2.05 (ddt, J=14.7, 9.7, 5.7 Hz, 1H), 1.88 (ddt, J=14.5, 9.1, 4.5 Hz, 1H). $^{13}$C NMR (126 MHz, DMSO-$d_6$) δ 174.26, 172.36, 172.08, 171.16, 170.69, 163.50, 161.59, 161.07, 140.86, 140.77, 136.48, 135.24, 133.39, 133.06, 132.23, 130.87, 130.80, 128.47, 128.31, 127.91, 127.88, 127.85, 127.76, 126.40, 125.83, 124.64, 123.93, 121.10, 115.65, 115.65, 114.29, 110.55, 110.38, 106.79, 106.58, 103.34, 54.84, 53.43, 50.15, 37.97, 36.41, 30.50, 27.58. HRMS (ESI) Calcd for $C_{37}H_{33}ClFN_5O_8$(M−H)$^-$ 728.1923, found 728.1929.

(S)-4-((S)-3-Carboxy-2-((S)-2-(5-chloro-1H-indole-2-carboxamido)-3-(naphthalen-2-yl)propanamido)propanamido)-5-((2-fluorophenyl)amino)-5-oxopentanoic acid (26). $^1$H NMR (500 MHz, DMSO-$d_6$) δ 12.29 (s, 2H), 11.62 (d, J=2.2 Hz, 1H), 9.72 (s, 1H), 8.80 (d, J=8.5 Hz, 1H), 8.67 (d, J=7.5 Hz, 1H), 8.15 (d, J=7.7 Hz, 1H), 7.93-7.74 (m, 5H), 7.70 (d, J=2.0 Hz, 1H), 7.56 (dd, J=8.6, 1.7 Hz, 1H), 7.42 (pd, J=6.9, 1.6 Hz, 2H), 7.36 (d, J=8.7 Hz, 1H), 7.28-7.01 (m, 5H), 4.91 (ddd, J=11.8, 8.6, 3.5 Hz, 1H), 4.68 (td, J=7.6, 5.6 Hz, 1H), 4.55 (td, J=8.2, 5.0 Hz, 1H), 3.30 (d, J=3.4 Hz, 1H), 3.15 (dd, J=13.8, 11.0 Hz, 1H), 2.80 (dd, J=16.7, 5.6 Hz, 1H), 2.61 (dd, J=16.6, 7.8 Hz, 1H), 2.34 (dq, J=16.6, 10.6 Hz, 2H), 2.05 (ddt, J=14.9, 10.3, 5.5 Hz, 1H), 1.90 (ddt, J=13.8, 8.8, 4.7 Hz, 1H). $^{13}$C NMR (126 MHz, DMSO-$d_6$) δ 174.37, 172.24, 172.00, 171.16, 170.73, 161.03, 155.39, 153.44, 136.51, 135.23, 133.39, 133.08, 132.23, 128.47, 128.33, 127.90, 127.90, 127.84, 127.76, 126.40, 126.24, 126.11, 126.01, 125.83, 125.03, 124.82, 124.79, 124.63, 123.91, 121.10, 116.10, 115.94, 114.28, 103.31, 54.80, 53.01, 50.09, 38.00, 36.43, 30.51, 27.80. HRMS (ESI) Calcd for $C_{37}H_{33}ClFN_5O_8$(M−H)$^-$ 728.1923, found 728.1929.

Synthesis of final products 27-29. The synthetic route for final products 27-29 is shown in Scheme 4.

Scheme 4. Synthesis of Final Compounds 27-29.

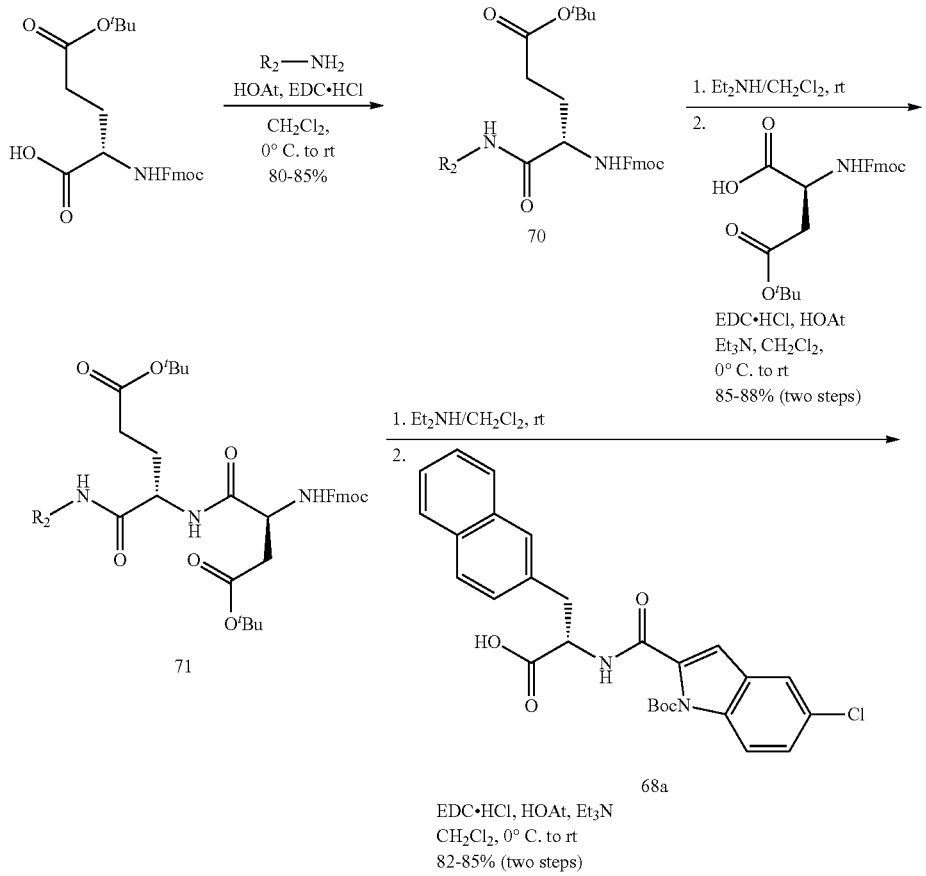

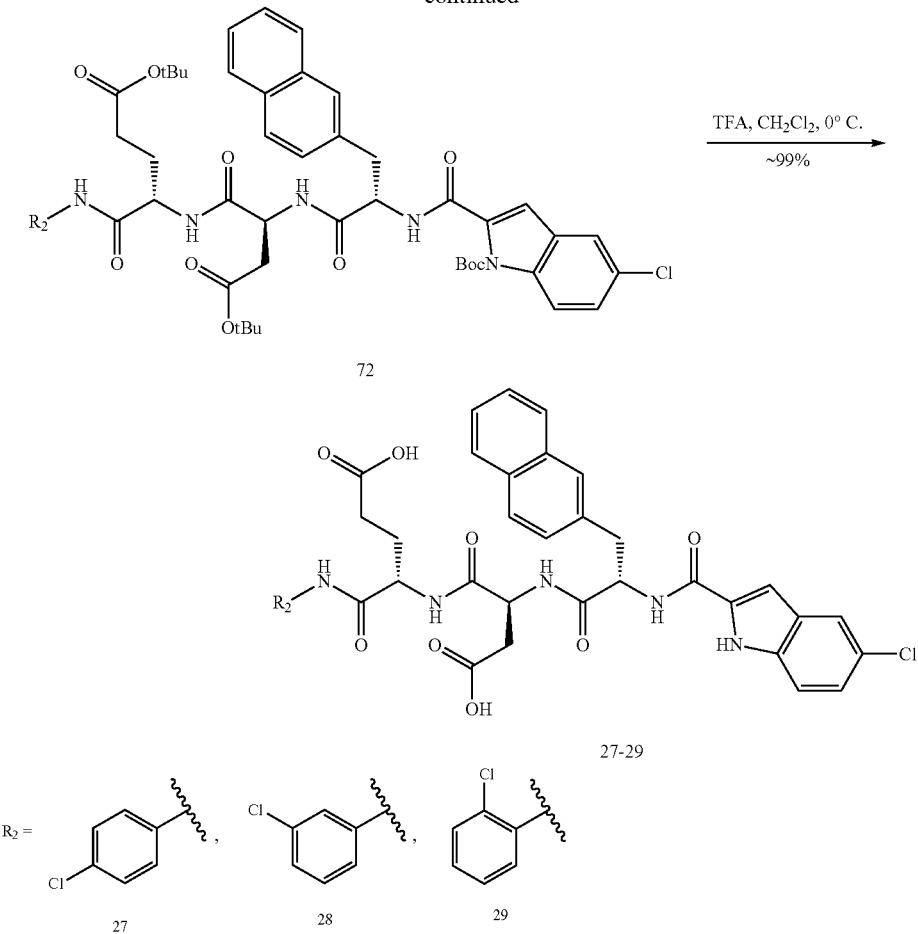

tert-Butyl (S)-4-((((9H-fluoren-9-yl)methoxy)carbonyl)amino)-5-((4-chlorophenyl)amino)-5-oxopentanoate (70a). Yield, 85%. $^1$H NMR (500 MHz, Chloroform-d) δ 8.80 (s, 1H), 7.64 (d, J=7.6 Hz, 2H), 7.55-7.41 (m, 2H), 7.40-7.32 (m, 2H), 7.28 (t, J=7.5 Hz, 2H), 7.23-7.01 (m, 4H), 6.02 (d, J=7.7 Hz, 1H), 4.29 (dd, J=19.2, 7.0 Hz, 3H), 4.07 (t, J=7.2 Hz, 1H), 2.57-2.37 (m, 1H), 2.29 (dt, J=16.4, 6.7 Hz, 1H), 2.16-2.04 (m, 1H), 2.00-1.78 (m, 1H), 1.35 (s, 9H). $^{13}$C NMR (126 MHz, Chloroform-d) δ 173.12, 169.88, 156.70, 143.69, 143.54, 141.29, 136.25, 129.43, 128.95, 127.80, 127.12, 127.09, 125.06, 125.03, 121.19, 120.04, 81.42, 67.41, 55.00, 47.04, 31.85, 28.09. MS (ESI) m/z=557.3 [M+Na]$^+$.

tert-Butyl (S)-4-((((9H-fluoren-9-yl)methoxy)carbonyl)amino)-5-((3-chlorophenyl)amino)-5-oxopentanoate (70b). Yield, 82%. $^1$H NMR (500 MHz, Chloroform-d) δ 8.93 (s, 1H), 7.68-7.53 (m, 3H), 7.43 (dd, J=13.0, 7.5 Hz, 2H), 7.29-7.18 (m, 3H), 7.15-7.07 (m, 2H), 7.02 (t, J=8.1 Hz, 1H), 6.92 (d, J=7.5 Hz, 1H), 6.14 (d, J=7.9 Hz, 1H), 4.29 (dd, J=42.7, 7.2 Hz, 3H), 4.13-3.89 (m, 1H), 2.37 (q, J=7.9, 7.2 Hz, 1H), 2.28 (dt, J=16.5, 6.8 Hz, 1H), 2.14-2.01 (m, 1H), 1.94 (h, J=5.9, 4.6 Hz, 1H), 1.32 (s, 9H). $^{13}$C NMR (126 MHz, Chloroform-d) δ 172.96, 170.16, 156.78, 143.72, 143.54, 141.29, 138.86, 134.56, 129.91, 127.80, 127.79, 127.14, 127.10, 125.10, 125.05, 124.46, 120.11, 120.02, 117.95, 81.33, 67.46, 55.08, 47.04, 31.78, 28.10, 28.02. MS (ESI) m/z=557.4 [M+Na]$^+$.

tert-Butyl (S)-4-((((9H-fluoren-9-yl)methoxy)carbonyl)amino)-5-((2-chlorophenyl)amino)-5-oxopentanoate (70c). Yield, 80%. $^1$H NMR (500 MHz, Chloroform-d) δ 8.52 (s, 1H), 8.21 (dd, J=8.3, 1.6 Hz, 1H), 7.65 (d, J=7.6 Hz, 2H), 7.49 (d, J=7.4 Hz, 2H), 7.32-7.23 (m, 3H), 7.23-7.10 (m, 3H), 6.95 (td, J=7.7, 1.6 Hz, 1H), 5.95 (d, J=7.4 Hz, 1H), 4.59-4.26 (m, 3H), 4.12 (t, J=6.9 Hz, 1H), 2.41 (q, J=8.2, 6.9 Hz, 1H), 2.30 (dt, J=16.8, 6.6 Hz, 1H), 2.15 (dd, J=14.5, 7.3 Hz, 1H), 2.00-1.88 (m, 1H), 1.37 (s, 9H). $^{13}$C NMR (126 MHz, Chloroform-d) δ 172.93, 169.76, 156.51, 143.75, 143.66, 141.31, 134.20, 129.14, 127.76, 127.63, 127.11, 127.09, 125.14, 125.07, 123.63, 122.05, 120.02, 120.01, 81.31, 67.35, 55.61, 47.15, 31.84, 28.10, 27.53. MS (ESI) m/z=557.3 [M+Na]$^+$.

tert-Butyl (S)-4-((S)-2-((((9H-fluoren-9-yl)methoxy)carbonyl)amino)-4-(tert-butoxy)-4-oxobutanamido)-5-((4-chlorophenyl)amino)-5-oxopentanoate (71a). Yield, 88%. $^1$H NMR (500 MHz, DMSO-d$_6$) δ 10.05 (s, 1H), 8.16 (d, J=7.7 Hz, 1H), 7.89 (d, J=7.6 Hz, 2H), 7.69 (q, J=6.2, 5.3 Hz, 2H), 7.62 (d, J=8.5 Hz, 2H), 7.51-7.14 (m, 6H), 4.64-4.14 (m, 5H), 2.69 (dd, J=16.2, 5.0 Hz, 1H), 2.50 (s, 1H), 2.36-2.16 (m, 2H), 2.00-1.93 (m, 1H), 1.84 (ddt, J=13.6, 8.7, 4.6 Hz, 1H), 1.36 (s, 9H), 1.34 (s, 9H). $^{13}$C NMR (126 MHz, DMSO-d$_6$) δ 171.93, 171.30, 170.43, 169.80, 156.28, 144.26, 144.17, 141.18, 138.09, 129.07, 128.11, 127.52, 125.69, 121.36, 120.58, 80.67, 80.21, 66.25, 53.32, 51.81, 47.07, 37.86, 31.59, 31.16, 28.15, 27.49. MS (ESI) m/z=728.3 [M+Na]$^+$.

tert-Butyl (S)-4-((S)-2-((((9H-fluoren-9-yl)methoxy)carbonyl)amino)-4-(tert-butoxy)-4-oxobutanamido)-5-((3-chlorophenyl)amino)-5-oxopentanoate (71b). Yield, 85%. $^1$H NMR (500 MHz, Chloroform-d) δ 8.89 (s, 1H), 7.87-7.65 (m, 4H), 7.59 (d, J=7.5 Hz, 2H), 7.56-7.50 (m, 1H), 7.40 (ddd, J=9.4, 7.4, 1.8 Hz, 2H), 7.30 (tdd, J=7.4, 2.4, 1.2 Hz, 2H), 7.20 (t, J=8.1 Hz, 1H), 7.06 (ddd, J=8.0, 2.1, 1.0 Hz, 1H), 5.90 (d, J=7.8 Hz, 1H), 4.72-4.35 (m, 4H), 4.23 (t, J=6.9 Hz, 1H), 2.89 (dd, J=16.8, 4.8 Hz, 1H), 2.80 (dd, J=16.9, 6.3 Hz, 1H), 2.58-2.49 (m, 1H), 2.38 (dt, J=17.2, 6.7 Hz, 1H), 2.22 (tt, J=9.0, 4.5 Hz, 1H), 2.14-2.07 (m, 1H), 1.44 (s, 9H), 1.44 (s, 9H). $^{13}$C NMR (126 MHz, Chloroform-d) δ 174.01, 171.15, 170.93, 169.14, 156.25, 143.68, 143.61, 141.31, 139.06, 134.41, 129.81, 127.80, 127.11, 125.03, 124.27, 120.14, 120.04, 118.06, 82.32, 81.51, 67.45, 54.10, 51.85, 47.11, 37.39, 31.91, 29.29, 28.05, 26.53. MS (ESI) m/z=728.3 [M+Na]$^+$.

tert-Butyl (S)-4-((S)-2-((((9H-fluoren-9-yl)methoxy)carbonyl)amino)-4-(tert-butoxy)-4-oxobutanamido)-5-((2-chlorophenyl)amino)-5-oxopentanoate (71c). Yield, 85%. $^1$H NMR (500 MHz, Chloroform-d) δ 8.62 (s, 1H), 8.24 (dd, J=8.3, 1.5 Hz, 1H), 7.76 (d, J=7.6 Hz, 2H), 7.62 (d, J=8.0 Hz, 3H), 7.48-7.28 (m, 5H), 7.27-7.19 (m, 1H), 7.04 (td, J=7.7, 1.6 Hz, 1H), 5.98 (d, J=8.8 Hz, 1H), 4.68-4.57 (m, 2H), 4.44 (d, J=7.1 Hz, 2H), 4.24 (t, J=7.0 Hz, 1H), 3.20-2.97 (m, 1H), 2.76-2.59 (m, 1H), 2.54 (ddd, J=17.1, 8.1, 5.8 Hz, 1H), 2.39 (ddd, J=17.2, 7.1, 5.7 Hz, 1H), 2.24 (ddd, J=13.5, 8.4, 5.6 Hz, 1H), 2.13-2.05 (m, 1H), 1.45 (s, 9H), 1.43 (s, 9H). $^{13}$C NMR (126 MHz, Chloroform-d) δ 173.39, 171.43, 171.14, 169.15, 156.04, 143.82, 143.67, 141.32, 141.31, 134.32, 129.15, 127.77, 127.50, 127.12, 127.09, 125.12, 123.90, 122.38, 120.01, 120.00, 82.01, 81.20, 67.41, 54.12, 51.37, 47.16, 37.45, 31.61, 28.09, 28.04, 26.71. MS (ESI) m/z=728.3 [M+Na]$^+$.

tert-Butyl 2-(((S)-1-(((S)-4-(tert-butoxy)-1-(((S)-5-(tert-butoxy)-1-((4-chlorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (72a). Yield, 85%. $^1$H NMR (500 MHz, Chloroform-d) δ 8.65 (s, 1H), 7.92-7.74 (m, 4H), 7.74-7.66 (m, 3H), 7.60 (dd, J=17.5, 7.5 Hz, 2H), 7.52-7.46 (m, 2H), 7.45 (d, J=2.1 Hz, 1H), 7.39 (dd, J=8.4, 1.8 Hz, 1H), 7.31 (dd, J=9.0, 2.1 Hz, 1H), 7.25 (d, J=8.2 Hz, 2H), 6.75 (d, J=5.0 Hz, 1H), 6.65 (d, J=0.7 Hz, 1H), 4.78 (t, J=8.1, 3.8 Hz, 2H), 4.48 (td, J=9.4, 8.8, 3.4 Hz, 1H), 3.56 (dd, J=14.4, 5.2 Hz, 1H), 3.30 (dd, J=14.4, 8.8 Hz, 1H), 2.97-2.77 (m, 2H), 2.40-2.22 (m, 3H), 2.05-1.84 (m, 1H), 1.58 (s, 9H), 1.39 (s, 9H), 1.29 (s, 9H). $^{13}$C NMR (126 MHz, Chloroform-d) δ 172.33, 171.45, 170.59, 170.21, 169.27, 163.44, 149.59, 136.89, 134.58, 134.16, 133.46, 132.92, 132.69, 129.35, 129.13, 129.13, 128.89, 128.72, 127.91, 127.78, 127.57, 126.71, 126.69, 126.61, 126.21, 121.46, 121.26, 116.61, 111.53, 86.38, 81.90, 80.49, 56.17, 53.85, 51.43, 37.06, 36.31, 32.00, 29.28, 28.02, 27.98, 27.93, 26.54. MS (ESI) m/z=980.1 [M+Na]$^+$.

tert-Butyl 2-(((S)-1-(((S)-4-(tert-butoxy)-1-(((S)-5-(tert-butoxy)-1-((3-chlorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (72b). Yield, 83%. $^1$H NMR (500 MHz, Chloroform-d) δ 8.80 (s, 1H), 7.88-7.76 (m, 5H), 7.73-7.52 (m, 4H), 7.51-7.35 (m, 4H), 7.30 (dd, J=9.0, 2.1 Hz, 1H), 7.16 (t, J=8.1 Hz, 1H), 7.08-6.96 (m, 1H), 6.86 (s, 1H), 6.65 (s, 1H), 4.88 (s, 1H), 4.85-4.70 (m, 1H), 4.55 (s, 1H), 3.55 (dd, J=14.3, 5.3 Hz, 1H), 3.30 (dd, J=14.4, 8.4 Hz, 1H), 2.87 (qd, J=16.6, 6.4 Hz, 2H), 2.48-2.16 (m, 3H), 2.07-1.87 (m, 1H), 1.57 (s, 9H), 1.39 (s, 9H), 1.31 (s, 9H). $^{13}$C NMR (126 MHz, Chloroform-d) δ 172.30, 171.29, 170.59, 170.22, 169.39, 163.30, 149.46, 139.41, 134.67, 134.31, 134.25, 133.47, 133.06, 132.66, 129.71, 129.26, 129.09, 128.99, 127.98, 127.76, 127.57, 126.84, 126.65, 126.52, 126.11, 124.00, 121.41, 120.01, 117.95, 116.58, 111.44, 86.20, 81.93, 80.55, 55.96, 53.78, 51.19, 37.35, 36.62, 31.91, 28.02, 27.97, 27.94, 26.78. MS (ESI) m/z=980.4 [M+Na]$^+$.

tert-Butyl 2-(((S)-1-(((S)-4-(tert-butoxy)-1-(((S)-5-(tert-butoxy)-1-((2-chlorophenyl)amino)-1,5-dioxopentan-2-yl)amino)-1,4-dioxobutan-2-yl)amino)-3-(naphthalen-2-yl)-1-oxopropan-2-yl)carbamoyl)-5-chloro-1H-indole-1-carboxylate (72c). Yield, 82%. $^1$H NMR (500 MHz, Chloroform-d) δ 8.54 (s, 1H), 8.13 (dd, J=8.2, 1.5 Hz, 1H), 7.78 (d, J=8.9 Hz, 1H), 7.75-7.66 (m, 3H), 7.66-7.58 (m, 1H), 7.49 (d, J=8.3 Hz, 1H), 7.45-7.30 (m, 5H), 7.27 (dd, J=8.1, 1.5 Hz, 1H), 7.23-7.17 (m, 1H), 7.14 (td, J=8.4, 8.0, 1.5 Hz, 1H), 6.95 (td, J=7.7, 1.5 Hz, 1H), 6.78 (d, J=6.3 Hz, 1H), 6.55 (s, 1H), 4.82 (dt, J=8.1, 5.8 Hz, 2H), 4.47-4.32 (m, 1H), 3.44 (dd, J=14.3, 5.6 Hz, 1H), 3.26 (dd, J=14.3, 8.1 Hz, 1H), 2.86-2.70 (m, 2H), 2.42-2.06 (m, 3H), 1.89-1.71 (m, 1H), 1.48 (s, 9H), 1.29 (s, 9H), 1.25 (s, 9H). $^{13}$C NMR (126 MHz, Chloroform-d) δ 172.54, 171.04, 170.64, 170.41, 169.18, 162.88, 149.33, 134.75, 134.60, 134.46, 133.49, 133.47, 132.59, 129.11, 129.09, 128.82, 128.02, 127.74, 127.56, 127.38, 127.01, 126.47, 126.43, 126.00, 125.02, 124.15, 122.60, 121.31, 116.49, 111.04, 85.98, 81.70, 80.66, 55.45, 54.08, 50.19, 37.19, 36.79, 31.75, 27.99, 27.93, 26.52. MS (ESI) m/z=980.0 [M+Na]$^+$.

(S)-4-((S)-3-Carboxy-2-((S)-2-(5-chloro-1H-indole-2-carboxamido)-3-(naphthalen-2-yl)propanamido)propanamido)-5-((4-chlorophenyl)amino)-5-oxopentanoic acid (27). $^1$H NMR (500 MHz, DMSO-d$_6$) δ 12.30 (s, 2H), 11.62 (d, J=2.2 Hz, 1H), 10.00 (s, 1H), 8.80 (d, J=8.5 Hz, 1H), 8.67 (d, J=7.5 Hz, 1H), 8.15 (d, J=7.7 Hz, 1H), 7.92-7.73 (m, 4H), 7.70 (d, J=2.0 Hz, 1H), 7.67-7.60 (m, 2H), 7.56 (dd, J=8.6, 1.7 Hz, 1H), 7.42 (pd, J=6.9, 1.6 Hz, 2H), 7.39-7.29 (m, 3H), 7.21 (d, J=2.1 Hz, 1H), 7.15 (dd, J=8.7, 2.1 Hz, 1H), 4.91 (ddd, J=11.8, 8.6, 3.6 Hz, 1H), 4.67 (td, J=7.5, 5.8 Hz, 1H), 4.40 (td, J=8.3, 5.1 Hz, 1H), 3.29 (d, J=3.5 Hz, 1H), 3.16 (dd, J=13.9, 11.0 Hz, 1H), 2.80 (dd, J=16.7, 5.8 Hz, 1H), 2.63 (dd, J=16.7, 7.7 Hz, 1H), 2.40-2.18 (m, 2H), 2.04 (ddt, J=14.9, 10.7, 5.7 Hz, 1H), 1.88 (ddt, J=13.4, 8.7, 4.6 Hz, 1H). $^{13}$C NMR (126 MHz, DMSO-d$_6$) δ 174.27, 172.36, 172.08, 171.13, 170.46, 161.06, 138.06, 136.49, 135.24, 133.39, 133.06, 132.23, 129.08, 128.46, 128.32, 127.91, 127.89, 127.86, 127.76, 127.56, 126.41, 125.84, 124.64, 123.93, 121.46, 121.10, 114.29, 103.33, 54.84, 53.40, 50.15, 37.97, 36.40, 30.52, 27.62. HRMS (ESI) Calcd for C$_{37}$H$_{33}$Cl$_2$N$_5$O$_8$ (M−H)$^−$ 744.1628, found 744.1632.

(S)-4-((S)-3-Carboxy-2-((S)-2-(5-chloro-1H-indole-2-carboxamido)-3-(naphthalen-2-yl)propanamido)propanamido)-5-((3-chlorophenyl)amino)-5-oxopentanoic acid (28). $^1$H NMR (500 MHz, DMSO-d$_6$) δ 12.31 (s, 2H), 11.73-11.41 (m, 1H), 10.06 (s, 1H), 8.80 (d, J=8.5 Hz, 1H), 8.67 (d, J=7.5 Hz, 1H), 8.16 (d, J=7.6 Hz, 1H), 7.93-7.73 (m, 5H), 7.70 (d, J=2.1 Hz, 1H), 7.60-7.50 (m, 1H), 7.52-7.22 (m, 5H), 7.21 (d, J=2.2 Hz, 1H), 7.14 (ddd, J=10.7, 8.4, 2.2 Hz, 2H), 4.91 (ddd, J=11.9, 8.6, 3.8 Hz, 1H), 4.67 (q, J=7.1 Hz, 1H), 4.40 (td, J=8.2, 5.2 Hz, 1H), 3.30 (d, J=3.6 Hz, 1H), 3.16 (dd, J=13.9, 11.0 Hz, 1H), 2.80 (dd, J=16.7, 5.8 Hz, 1H), 2.63 (dd, J=16.6, 7.8 Hz, 1H), 2.32 (dq, J=16.5, 10.4 Hz, 2H), 2.04 (ddt, J=15.0, 10.7, 5.8 Hz, 1H), 1.89 (dtd, J=14.5, 9.1, 5.9 Hz, 1H). $^{13}$C NMR (126 MHz, DMSO-d$_6$) δ 174.25, 172.33, 172.08, 171.16, 170.71, 161.07, 140.54, 136.49, 135.24, 133.51, 133.39, 133.06, 132.23, 130.90, 128.47, 128.31, 127.91, 127.88, 127.88, 127.76, 126.40, 125.83, 124.64, 123.93, 123.71, 121.10, 119.37, 118.31, 114.29, 103.34, 54.84, 53.45, 50.16, 37.97, 36.42, 30.49, 27.55. HRMS (ESI) Calcd for $C_{37}H_{33}Cl_2N_5O_8$ (M−H)⁻ 744.1628, found 744.1627.

(S)-4-((S)-3-Carboxy-2-((S)-2-(5-chloro-1H-indole-2-carboxamido)-3-(naphthalen-2-yl)propanamido)propanamido)-5-((2-chlorophenyl)amino)-5-oxopentanoic acid (29). ¹H NMR (500 MHz, DMSO-d₆) δ 12.51-12.07 (m, 2H), 11.85-11.18 (m, 1H), 9.51 (s, 1H), 8.80 (d, J=8.5 Hz, 1H), 8.68 (d, J=7.6 Hz, 1H), 8.20 (d, J=7.7 Hz, 1H), 8.02-7.62 (m, 6H), 7.62-7.26 (m, 6H), 7.25-6.85 (m, 3H), 4.91 (ddd, J=11.9, 8.4, 3.6 Hz, 1H), 4.70 (q, J=7.1 Hz, 1H), 4.54 (td, J=8.2, 4.9 Hz, 1H), 3.32-3.27 (m, 1H), 3.16 (dd, J=13.9, 11.0 Hz, 1H), 2.81 (dd, J=16.7, 5.7 Hz, 1H), 2.62 (dd, J=16.7, 7.8 Hz, 1H), 2.36 (tq, J=16.7, 8.8, 7.1 Hz, 2H), 2.09 (ddt, J=15.0, 10.5, 5.7 Hz, 1H), 1.92 (dq, J=13.6, 5.7, 3.1 Hz, 1H). ¹³C NMR (126 MHz, DMSO-d₆) δ 174.43, 172.22, 171.99, 171.28, 170.61, 161.05, 136.50, 135.23, 134.91, 133.39, 133.07, 132.23, 129.94, 128.47, 128.33, 127.94, 127.90, 127.90, 127.84, 127.76, 127.10, 127.01, 126.47, 126.40, 125.83, 124.64, 123.92, 121.10, 114.29, 103.32, 54.83, 53.06, 50.10, 37.99, 36.47, 30.49, 27.56. HRMS (ESI) Calcd for $C_{37}H_{33}Cl_2N_5O_8$ (M−H)⁻ 744.1628, found 744.1632.

Synthesis of final product 39. The synthetic route for final product 39 is shown in Scheme 5.

Scheme 5. Synthesis of Final Compound 39.

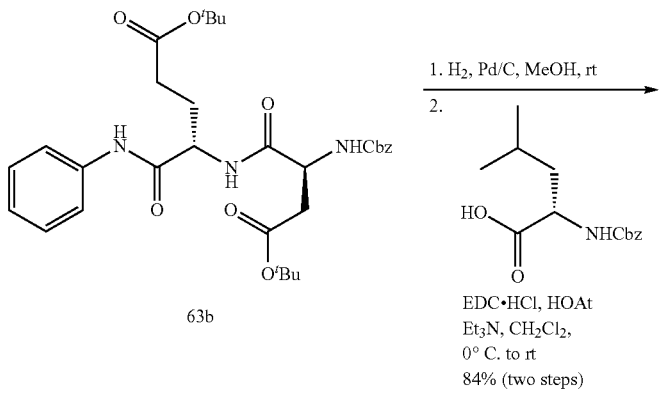

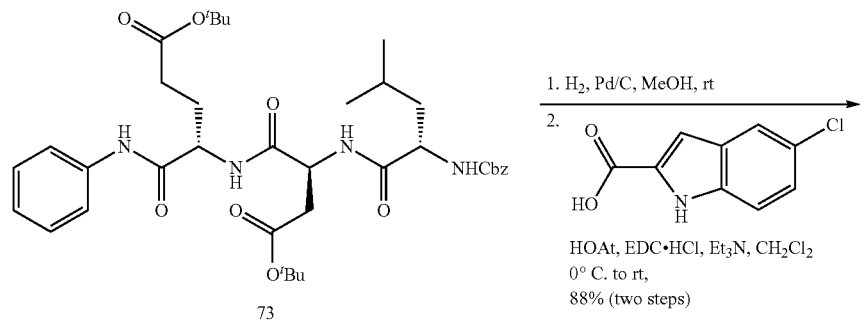

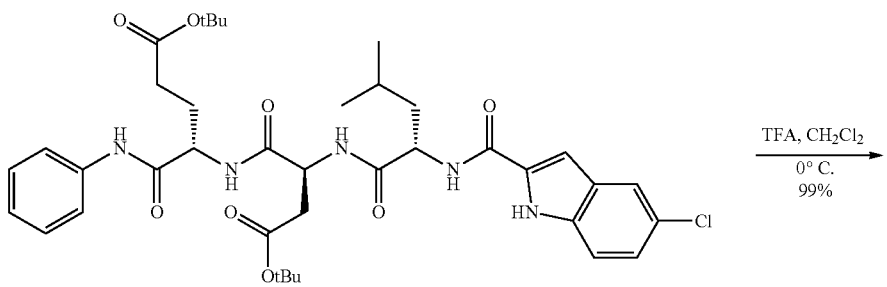

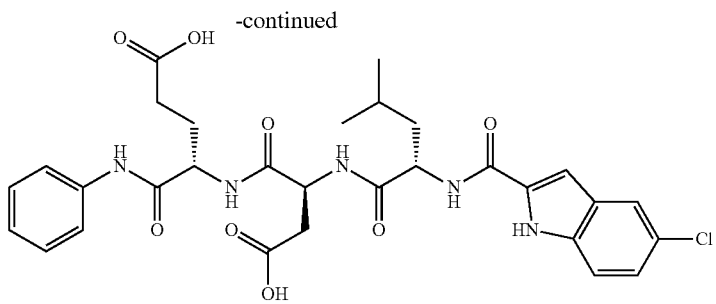

39 tert-Butyl (5S,8S,11S)-8-(2-(tert-butoxy)-2-oxoethyl)-5-isobutyl-3,6,9-trioxo-1-phenyl-11-(phenylcarbamoyl)-2-oxa-4,7,10-triazatetradecan-14-oate (73). Yield, 84%. $^1$H NMR (500 MHz, DMSO-$d_6$) δ 9.84 (s, 1H), 8.32 (d, J=7.9 Hz, 1H), 7.90 (d, J=7.9 Hz, 1H), 7.68-7.56 (m, 2H), 7.50 (d, J=7.7 Hz, 1H), 7.40-7.23 (m, 7H), 7.12-6.93 (m, 1H), 5.02 (q, J=12.6 Hz, 2H), 4.57 (td, J=7.9, 5.8 Hz, 1H), 4.38 (td, J=8.3, 5.1 Hz, 1H), 4.04 (ddd, J=9.3, 7.6, 5.7 Hz, 1H), 2.73 (dd, J=16.1, 5.8 Hz, 1H), 2.60-2.51 (m, 1H), 2.35-2.16 (m, 2H), 2.06-1.93 (m, 1H), 1.89-1.79 (m, 1H), 1.69-1.59 (m, 1H), 1.52-1.42 (m, 2H), 0.86 (dd, J=9.6, 6.6 Hz, 6H). $^{13}$C NMR (126 MHz, DMSO-$d_6$) δ 173.00, 171.95, 170.74, 170.05, 169.89, 156.54, 139.09, 137.39, 129.16, 128.78, 128.26, 128.17, 123.98, 119.77, 80.75, 80.20, 65.92, 53.67, 53.23, 50.08, 41.07, 37.39, 31.62, 28.18, 28.09, 27.72, 24.62, 23.36, 22.02. MS (ESI) m/z=719.2 [M+Na]$^+$.

tert-Butyl (S)-4-((S)-4-(tert-butoxy)-2-((S)-2-(5-chloro-1H-indole-2-carboxamido)-4-methylpentanamido)-4-oxobutanamido)-5-oxo-5-(phenylamino)pentanoate (74). Yield, 88%. $^1$H NMR (500 MHz, Chloroform-d) δ 10.97 (s, 1H), 9.00 (s, 1H), 8.65 (s, 1H), 8.54 (s, 1H), 7.66 (d, J=8.0 Hz, 3H), 7.50 (s, 1H), 7.35-7.25 (m, 1H), 7.25-7.15 (m, 3H), 7.12-6.99 (m, 2H), 5.04 (d, J=39.7 Hz, 2H), 4.80 (s, 1H), 3.14-2.75 (m, 2H), 2.47 (q, J=8.6, 7.9 Hz, 3H), 2.38-2.23 (m, 1H), 1.85 (dtd, J=36.5, 12.4, 11.5, 6.7 Hz, 3H), 1.47 (s, 9H), 1.21 (s, 9H), 1.02 (dd, J=18.9, 5.9 Hz, 6H). $^{13}$C NMR (126 MHz, Chloroform-d) δ 173.38, 172.67, 171.53, 170.36, 169.91, 162.19, 137.68, 135.54, 130.96, 128.71, 128.24, 125.96, 125.01, 124.52, 121.12, 120.62, 113.60, 103.98, 81.84, 81.23, 54.14, 53.23, 50.34, 41.57, 37.05, 32.63, 28.09, 27.81, 27.74, 25.22, 22.59, 22.53. MS (ESI) m/z=762.1 [M+Na]$^+$.

(S)-4-((S)-3-Carboxy-2-((S)-2-(5-chloro-1H-indole-2-carboxamido)-4-methylpentanamido)propanamido)-5-oxo-5-(phenylamino)pentanoic acid (39). $^1$H NMR (500 MHz, DMSO-d6) δ 12.19 (s, 2H), 11.66 (d, J=2.2 Hz, 1H), 9.75 (s, 1H), 8.53 (d, J=8.1 Hz, 1H), 8.40 (d, J=7.6 Hz, 1H), 7.90 (d, J=7.8 Hz, 1H), 7.64 (d, J=2.0 Hz, 1H), 7.60-7.50 (m, 2H), 7.37 (d, J=8.8 Hz, 1H), 7.31-7.17 (m, 3H), 7.12 (dd, J=8.7, 2.1 Hz, 1H), 7.08-6.90 (m, 1H), 4.72-4.42 (m, 2H), 4.31 (dt, J=8.4, 4.3 Hz, 1H), 2.71 (dd, J=16.7, 6.2 Hz, 1H), 2.51 (dd, J=16.7, 7.5 Hz, 1H), 2.20 (td, J=10.4, 6.0 Hz, 2H), 2.07-1.92 (m, 1H), 1.79 (dt, J=10.1, 5.3 Hz, 1H), 1.71-1.57 (m, 2H), 1.54-1.44 (m, 1H), 0.84 (dd, J=13.6, 6.2 Hz, 6H). $^{13}$C NMR (126 MHz, DMSO-$d_6$) δ 174.29, 172.88, 172.39, 171.05, 170.19, 161.16, 139.08, 135.30, 133.22, 129.17, 128.55, 124.66, 123.98 (d, J=3.5 Hz), 121.09, 119.88, 114.33, 103.61, 53.27, 51.80, 50.01, 40.92, 36.13, 30.50, 27.79, 24.82, 23.50, 21.86. HRMS (ESI) Calcd for $C_{30}H_{34}ClN_5O_8$ (M−H)$^-$ 626.2018, found 626.2014.

Synthesis of final products 40-45. The synthetic route for final products 40-45 is shown in Scheme 6.

Scheme 6. Synthesis of Final Compounds 40-45.

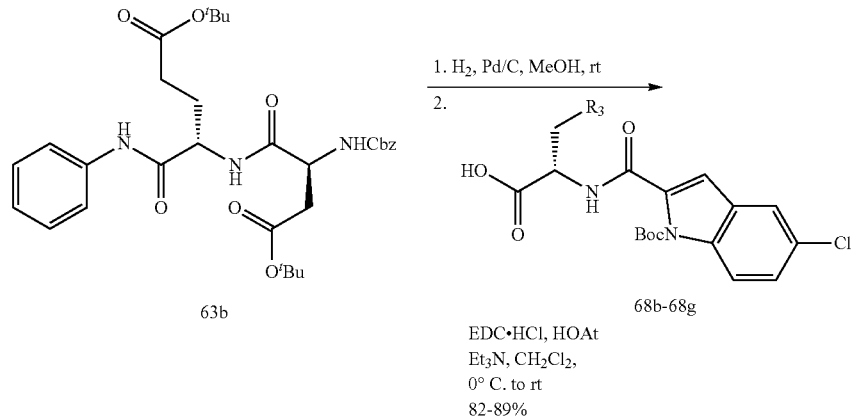

-continued

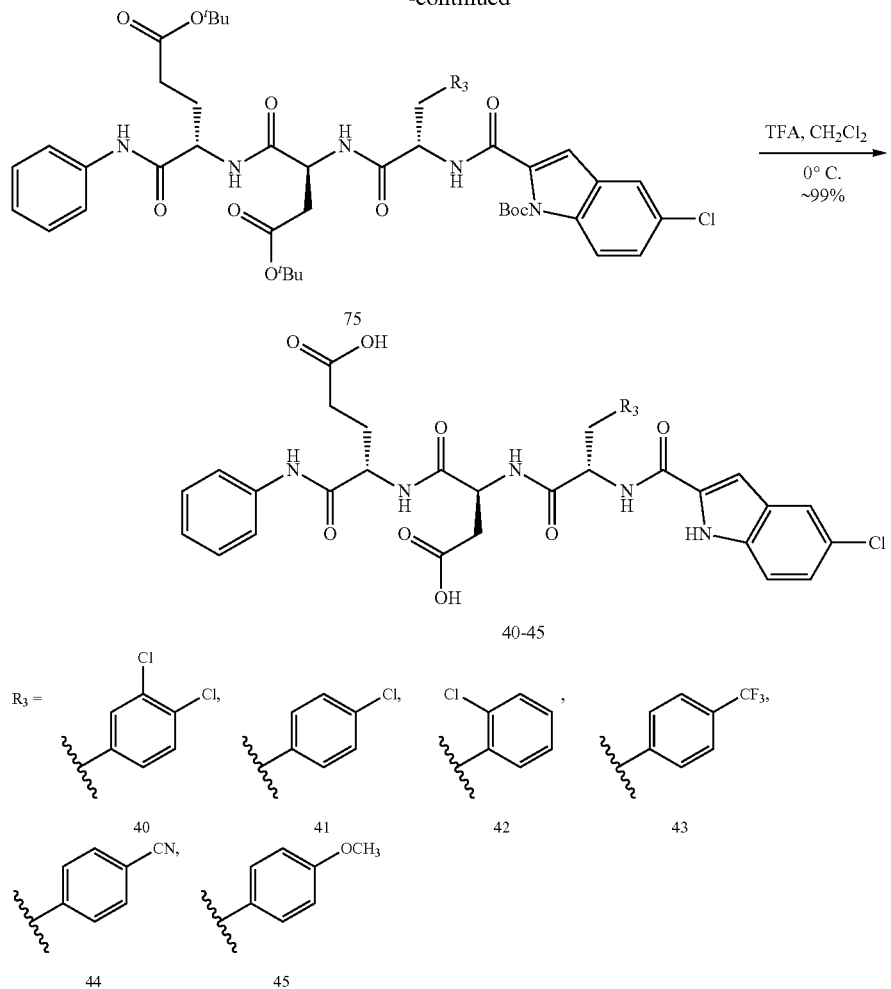

tert-Butyl 2-(((S)-1-(((S)-4-(tert-butoxy)-1-(((S)-5-(tert-butoxy)-1,5-dioxo-1-(phenylamino)pentan-2-yl)amino)-1,4-dioxobutan-2-yl)amino)-3-(3,4-dichlorophenyl)-1-oxopropan-2-yl)carbamoyl)-5-chloro-1H-indole-1-carboxylate (75a). Yield, 82%. $^1$H NMR (500 MHz, Chloroform-d) δ 9.52 (s, 1H), 8.44 (s, 2H), 7.89 (d, J=8.9 Hz, 1H), 7.53 (s, 1H), 7.44 (d, J=8.1 Hz, 1H), 7.36-7.09 (m, 6H), 6.80 (d, J=22.8 Hz, 4H), 5.58-4.98 (m, 3H), 3.36 (td, J=19.5, 16.8, 7.8 Hz, 2H), 2.89-2.70 (m, 2H), 2.58-1.93 (m, 4H), 1.51 (s, 9H), 1.41 (s, 9H), 1.29 (s, 9H). $^{13}$C NMR (126 MHz, Chloroform-d) δ 172.07, 170.60, 170.14, 169.77, 169.20, 162.42, 148.67, 137.73, 136.65, 135.04, 134.71, 132.31, 131.77, 131.02, 130.51, 129.05, 128.91, 128.81, 128.39, 126.34, 123.85, 121.30, 119.32, 116.24, 111.47, 85.23, 81.48, 80.73, 54.17, 53.28, 49.58, 38.80, 38.13, 31.86, 29.07, 28.06, 27.92, 27.81. MS (ESI) m/z=964.3 [M+Na]$^+$.

tert-Butyl 2-(((S)-1-(((S)-4-(tert-butoxy)-1-(((S)-5-(tert-butoxy)-1,5-dioxo-1-(phenylamino)pentan-2-yl)amino)-1,4-dioxobutan-2-yl)amino)-3-(4-chlorophenyl)-1-oxopropan-2-yl)carbamoyl)-5-chloro-1H-indole-1-carboxylate (75b). Yield, 89%. $^1$H NMR (500 MHz, Chloroform-d) δ 9.16 (s, 1H), 8.08 (s, 1H), 7.84 (d, J=8.9 Hz, 1H), 7.40-7.04 (m, 10H), 6.96-6.78 (m, 3H), 6.68 (s, 1H), 5.28-4.76 (m, 3H), 3.27 (dd, J=14.1, 6.3 Hz, 1H), 3.15 (dd, J=14.0, 6.9 Hz, 1H), 2.84-2.53 (m, 2H), 2.36 (dd, J=9.7, 6.4 Hz, 2H), 2.28-2.17 (m, 1H), 2.09-2.05 (m, 1H), 1.47 (s, 9H), 1.30 (s, 9H), 1.23 (s, 9H). $^{13}$C NMR (126 MHz, Chloroform-d) δ 172.14, 170.58, 170.29, 169.90, 169.12, 162.62, 148.99, 137.91, 135.06, 134.62, 134.59, 133.05, 130.82, 128.99, 128.96, 128.87, 128.54, 126.48, 123.94, 121.34, 119.47, 116.36, 111.44, 85.51, 81.64, 80.72, 54.73, 53.37, 49.88, 38.23, 38.00, 31.92, 28.48, 28.04, 27.94, 27.88. MS (ESI) m/z=930.3 [M+Na]$^+$.

tert-Butyl 2-(((S)-1-(((S)-4-(tert-butoxy)-1-(((S)-5-(tert-butoxy)-1,5-dioxo-1-(phenylamino)pentan-2-yl)amino)-1,4-dioxobutan-2-yl)amino)-3-(2-chlorophenyl)-1-oxopropan-2-yl)carbamoyl)-5-chloro-1H-indole-1-carboxylate (75c). Yield, 87%. $^1$H NMR (500 MHz, Chloroform-d) δ 9.17 (s, 1H), 8.16 (s, 1H), 7.86 (d, J=8.9 Hz, 1H), 7.37-7.04 (m, 10H), 6.78 (s, 3H), 6.67 (s, 1H), 5.51-4.79 (m, 3H), 3.43 (dd, J=14.2, 6.4 Hz, 1H), 3.32 (dd, J=14.0, 7.1 Hz, 1H), 2.88-2.61 (m, 2H), 2.36 (s, 2H), 2.19 (t, J=8.1 Hz, 1H), 2.07 (d, J=6.9 Hz, 1H), 1.44 (s, 9H), 1.29 (s, 9H), 1.22 (s, 9H). $^{13}$C NMR (126 MHz, Chloroform-d) δ 172.09, 170.42, 170.28, 169.82, 169.23, 162.63, 148.98, 137.92, 135.14, 134.73, 134.40, 134.19, 131.84, 129.70, 128.98, 128.94, 128.78, 128.44, 127.23, 126.40, 123.82, 121.32, 119.41, 116.36, 111.34, 85.44, 81.41, 80.45, 54.18, 53.22, 50.01, 38.32, 36.06, 31.84, 28.55, 28.04, 27.95, 27.84. MS (ESI) m/z=930.3 [M+Na]$^+$.

tert-Butyl 2-(((S)-1-(((S)-4-(tert-butoxy)-1-(((S)-5-(tert-butoxy)-1,5-dioxo-1-(phenylamino)pentan-2-yl)amino)-1, 4-dioxobutan-2-yl)amino)-1-oxo-3-(4-(trifluoromethyl)phenyl)propan-2-yl)carbamoyl)-5-chloro-1H-indole-1-carboxylate (75 d). Yield, 84%. $^1$H NMR (500 MHz, Chloroform-d) δ 9.51-8.25 (m, 2H), 7.79 (d, J=9.0 Hz, 1H), 7.49 (d, J=8.0 Hz, 2H), 7.39 (d, J=8.0 Hz, 2H), 7.25-7.02 (m, 6H), 6.71 (d, J=26.1 Hz, 4H), 5.70-4.91 (m, 3H), 3.37 (dd, J=14.2, 5.7 Hz, 1H), 3.25 (dd, J=14.3, 7.4 Hz, 1H), 2.73 (dt, J=38.6, 11.1 Hz, 2H), 2.48-2.18 (m, 3H), 2.12-2.03 (m, 1H), 1.39 (s, 9H), 1.28 (s, 9H), 1.18 (s, 9H). $^{13}$C NMR (126 MHz, Chloroform-d) δ 172.04, 170.81, 170.31, 169.74, 169.29, 162.50, 148.69, 140.56, 137.78, 135.08, 134.70, 129.97, 128.92, 128.81, 128.44, 126.35, 125.50 (d, J=3.6 Hz), 125.33, 123.94, 123.17, 121.28, 119.41, 116.23, 111.54, 85.17, 81.45, 80.75, 54.19, 53.24, 49.63, 38.73, 31.76, 28.99, 28.22, 27.94, 27.89, 27.77. MS (ESI) m/z=964.3 [M+Na]$^+$.

tert-Butyl 2-(((S)-1-(((S)-4-(tert-butoxy)-1-(((S)-5-(tert-butoxy)-1,5-dioxo-1-(phenylamino)pentan-2-yl)amino)-1,4-dioxobutan-2-yl)amino)-3-(4-cyanophenyl)-1-oxopropan-2-yl)carbamoyl)-5-chloro-1H-indole-1-carboxylate (75e). Yield, 87%. $^1$H NMR (500 MHz, Chloroform-d) δ 9.80-8.38 (m, 2H), 7.79-7.71 (m, 1H), 7.56 (d, J=7.8 Hz, 2H), 7.45 (d, J=7.8 Hz, 2H), 7.25-6.87 (m, 5H), 6.79-6.37 (m, 5H), 5.21 (s, 3H), 3.51-3.24 (m, 2H), 2.94-2.63 (m, 2H), 2.50-2.24 (m, 3H), 2.17-2.11 (m, 1H), 1.39 (s, 9H), 1.33 (s, 9H), 1.17 (dd, J=4.9, 2.5 Hz, 9H). $^{13}$C NMR (126 MHz, Chloroform-d) δ 172.11, 170.84, 170.52, 170.14, 169.61, 169.21, 162.46, 148.47, 142.10, 137.69, 134.95, 134.71, 132.38, 130.52, 128.91, 128.75, 128.37, 123.89, 121.26, 119.15, 118.84, 116.14, 111.49, 110.86, 85.14, 81.38, 81.04, 53.81, 53.06, 49.43, 39.19, 31.76, 29.70, 29.28, 28.05, 27.87, 27.82. MS (ESI) m/z=921.3 [M+Na]$^+$.

tert-Butyl 2-(((S)-1-(((S)-4-(tert-butoxy)-1-(((S)-5-(tert-butoxy)-1,5-dioxo-1-(phenylamino)pentan-2-yl)amino)-1,4-dioxobutan-2-yl)amino)-3-(4-methoxyphenyl)-1-oxopropan-2-yl)carbamoyl)-5-chloro-1H-indole-1-carboxylate (75f). Yield, 88%. $^1$H NMR (500 MHz, Chloroform-d) δ 8.57 (s, 1H), 7.81 (d, J=9.0 Hz, 1H), 7.60 (d, J=8.0 Hz, 2H), 7.48 (dd, J=45.3, 4.2 Hz, 3H), 7.26 (dd, J=9.0, 2.1 Hz, 1H), 7.22-7.15 (m, 2H), 7.13-7.04 (m, 2H), 7.02-6.91 (m, 1H), 6.86-6.73 (m, 2H), 6.63 (d, J=0.7 Hz, 2H), 4.73 (td, J=7.3, 5.3 Hz, 1H), 4.64 (dd, J=8.1, 5.5 Hz, 1H), 4.48 (td, J=8.6, 3.7 Hz, 1H), 3.70 (s, 3H), 3.25 (dd, J=14.4, 5.4 Hz, 1H), 3.01 (dd, J=14.4, 8.3 Hz, 1H), 2.80 (qd, J=16.5, 6.4 Hz, 2H), 2.33-2.13 (m, 3H), 2.04-1.85 (m, 1H), 1.54 (s, 9H), 1.33 (s, 9H), 1.23 (s, 9H). $^{13}$C NMR (126 MHz, Chloroform-d) δ 172.39, 171.23, 170.58, 170.27, 169.14, 163.17, 158.98, 149.46, 138.16, 134.69, 134.44, 130.15, 129.27, 129.15, 128.74, 127.37, 126.63, 124.04, 121.43, 119.98, 116.58, 114.47, 111.18, 86.20, 81.85, 80.48, 56.06, 55.24, 53.82, 51.10, 36.67, 36.32, 31.97, 28.03, 27.99, 27.95, 26.89. MS (ESI) m/z=926.3 [M+Na]$^+$.

(S)-4-((S)-3-Carboxy-2-((S)-2-(5-chloro-1H-indole-2-carboxamido)-3-(3,4-dichlorophenyl)propanamido)propanamido)-5-oxo-5-(phenylamino)pentanoic acid (40). $^1$H NMR (500 MHz, DMSO-d$_6$) δ 12.30 (s, 2H), 11.69 (s, 1H), 9.86 (s, 1H), 8.77 (d, J=8.6 Hz, 1H), 8.62 (d, J=7.6 Hz, 1H), 8.15 (d, J=7.8 Hz, 1H), 7.80-7.55 (m, 4H), 7.50 (d, J=8.2 Hz, 1H), 7.42-7.25 (m, 4H), 7.24-7.12 (m, 2H), 7.06 (t, J=7.4 Hz, 1H), 4.80 (ddd, J=11.9, 8.6, 3.6 Hz, 1H), 4.64 (q, J=7.1 Hz, 1H), 4.41 (td, J=8.2, 4.9 Hz, 1H), 3.13 (dd, J=13.9, 3.5 Hz, 1H), 3.05-2.89 (m, 1H), 2.78 (dd, J=16.7, 5.9 Hz, 1H), 2.60 (dd, J=16.7, 7.7 Hz, 1H), 2.31 (pt, J=10.6, 4.5 Hz, 2H), 2.04 (ddt, J=15.2, 10.7, 5.8 Hz, 1H), 1.88 (qd, J=8.8, 4.5 Hz, 1H). $^1$H NMR (500 MHz, DMSO-d$_6$) δ 11.69 (s, 2H), 9.86 (s, 1H), 8.77 (d, J=8.6 Hz, 1H), 8.62 (d, J=7.6 Hz, 1H), 8.15 (d, J=7.8 Hz, 1H), 7.80-7.55 (m, 4H), 7.50 (d, J=8.2 Hz, 1H), 7.42-7.25 (m, 4H), 7.24-7.12 (m, 2H), 7.06 (t, J=7.4 Hz, 1H), 4.80 (ddd, J=11.9, 8.6, 3.6 Hz, 1H), 4.64 (q, J=7.1 Hz, 1H), 4.41 (td, J=8.2, 4.9 Hz, 1H), 3.13 (dd, J=13.9, 3.5 Hz, 1H), 3.05-2.89 (m, 1H), 2.78 (dd, J=16.7, 5.9 Hz, 1H), 2.60 (dd, J=16.7, 7.7 Hz, 1H), 2.31 (pt, J=10.6, 4.5 Hz, 2H), 2.04 (ddt, J=15.2, 10.7, 5.8 Hz, 1H), 1.88 (qd, J=8.8, 4.5 Hz, 1H). HRMS (ESI) Calcd for C$_{33}$H$_{30}$Cl$_3$N$_5$O$_8$ (M−H)$^-$ 728.1082, 730.1052, found 728.1092, 730.1069.

(S)-4-((S)-3-Carboxy-2-((S)-2-(5-chloro-1H-indole-2-carboxamido)-3-(4-chlorophenyl)propanamido)propanamido)-5-oxo-5-(phenylamino)pentanoic acid (41). $^1$H NMR (500 MHz, DMSO-d$_6$) δ 12.30 (s, 2H), 11.96-11.32 (m, 1H), 9.85 (s, 1H), 8.75 (d, J=8.6 Hz, 1H), 8.62 (d, J=7.6 Hz, 1H), 8.11 (d, J=7.8 Hz, 1H), 7.71 (d, J=2.1 Hz, 1H), 7.60 (d, J=7.9 Hz, 2H), 7.39 (dd, J=8.5, 5.9 Hz, 3H), 7.29 (d, J=8.0 Hz, 4H), 7.23-7.12 (m, 2H), 7.06 (t, J=7.4 Hz, 1H), 4.78 (ddd, J=11.8, 8.6, 3.7 Hz, 1H), 4.64 (q, J=7.1 Hz, 1H), 4.41 (td, J=8.3, 5.0 Hz, 1H), 3.12 (dd, J=13.9, 3.7 Hz, 1H), 2.97 (dd, J=13.8, 11.1 Hz, 1H), 2.78 (dd, J=16.7, 5.9 Hz, 1H), 2.60 (dd, J=16.7, 7.7 Hz, 1H), 2.30 (pd, J=16.5, 7.4 Hz, 2H), 2.04 (td, J=9.1, 4.9 Hz, 1H), 1.87 (dtd, J=14.5, 9.3, 5.9 Hz, 1H). $^{13}$C NMR (126 MHz, DMSO-d$_6$) δ 174.29, 172.33, 171.86, 171.02, 170.24, 161.05, 139.08, 137.79, 135.27, 133.02, 131.52, 131.43, 129.18, 128.48, 128.45, 124.67, 123.99, 123.98, 121.12, 119.90, 114.32, 103.34, 54.58, 53.30, 50.13, 37.09, 36.40, 30.54, 27.78). HRMS (ESI) Calcd for C$_{33}$H$_{31}$Cl$_2$N$_5$O$_8$ (M−H)$^-$ 694.1471, found 694.1470.

(S)-4-((S)-3-Carboxy-2-((S)-2-(5-chloro-1H-indole-2-carboxamido)-3-(2-chlorophenyl)propanamido)propanamido)-5-oxo-5-(phenylamino)pentanoic acid (42). $^1$H NMR (500 MHz, DMSO-d$_6$) δ 12.26 (s, 2H), 11.68 (s, 1H), 9.83 (s, 1H), 8.78 (d, J=8.5 Hz, 1H), 8.47 (d, J=7.6 Hz, 1H), 8.08 (d, J=7.8 Hz, 1H), 7.71 (s, 1H), 7.60 (d, J=8.0 Hz, 2H), 7.49-7.36 (m, 3H), 7.30 (t, J=7.7 Hz, 2H), 7.24-7.14 (m, 4H), 7.06 (t, J=7.4 Hz, 1H), 4.90 (td, J=9.6, 4.2 Hz, 1H), 4.64 (q, J=7.0 Hz, 1H), 4.39 (td, J=8.1, 4.9 Hz, 1H), 3.32 (m, 1H), 3.13 (dd, J=14.4, 10.6 Hz, 1H), 2.78 (dd, J=16.7, 5.9 Hz, 1H), 2.62 (dd, J=16.6, 7.3 Hz, 1H), 2.30 (tq, J=16.5, 6.7, 5.4 Hz, 2H), 2.03 (ddq, J=17.0, 11.9, 5.9 Hz, 1H), 1.87 (dq, J=8.7, 4.5, 3.6 Hz, 1H). $^{13}$C NMR (126 MHz, DMSO-d$_6$) δ 174.31, 172.43, 171.52, 170.94, 170.25, 161.09, 139.10, 135.90, 135.29, 133.89, 132.96, 131.76, 129.55, 129.16, 128.75, 128.47, 127.32, 124.68, 124.01, 123.97, 121.12, 119.89, 114.33, 103.45, 53.39, 52.69, 50.19, 36.29, 35.33, 30.57, 27.72. HRMS (ESI) Calcd for C$_{33}$H$_{31}$Cl$_2$N$_5$O$_8$ (M−H)$^-$ 694.1471, found 694.1477.

(S)-4-((S)-3-Carboxy-2-((S)-2-(5-chloro-1H-indole-2-carboxamido)-3-(4-(trifluoromethyl)phenyl)propanamido)propanamido)-5-oxo-5-(phenylamino)pentanoic acid (43). $^1$H NMR (500 MHz, DMSO-d$_6$) δ 12.27 (s, 2H), 11.67 (d, J=2.2 Hz, 1H), 9.86 (s, 1H), 8.80 (d, J=8.6 Hz, 1H), 8.66 (d, J=7.6 Hz, 1H), 8.13 (d, J=7.8 Hz, 1H), 7.71 (d, J=2.0 Hz, 1H), 7.60 (q, J=8.3 Hz, 6H), 7.39 (d, J=8.7 Hz, 1H), 7.30 (t, J=7.9 Hz, 2H), 7.21 (d, J=2.1 Hz, 1H), 7.17 (dd, J=8.7, 2.1 Hz, 1H), 7.06 (t, J=7.4 Hz, 1H), 4.85 (ddd, J=11.9, 8.6, 3.6 Hz, 1H), 4.66 (td, J=7.5, 5.9 Hz, 1H), 4.42 (td, J=8.3, 5.0 Hz, 1H), 3.22 (dd, J=13.8, 3.6 Hz, 1H), 3.08 (dd, J=13.8, 11.1 Hz, 1H), 2.79 (dd, J=16.7, 5.9 Hz, 1H), 2.61 (dd, J=16.7, 7.6 Hz, 1H), 2.39-2.22 (m, 2H), 2.08-1.98 (m, 1H), 1.90-1.80 (m, 1H). $^{13}$C NMR (126 MHz, DMSO-d$_6$) δ 174.29, 172.33, 171.75, 171.03, 170.24, 161.09, 143.73, 139.08, 135.28, 132.96, 130.45, 129.18, 128.47, 127.49 (d, J=31.7 Hz), 125.35 (d, J=4.2 Hz), 124.85 (d, J=270.0 Hz), 124.68, 124.00, 121.13, 119.90, 114.32, 103.38, 54.34, 53.31, 50.16, 37.54, 36.41, 30.54, 27.79. HRMS (ESI) Calcd for C$_{34}$H$_{31}$ClF$_3$N$_5$O$_8$ (M−H)$^-$ 728.1735, found 728.1733.

(S)-4-((S)-3-Carboxy-2-((S)-2-(5-chloro-1H-indole-2-carboxamido)-3-(4-cyanophenyl)propanamido)propanamido)-5-oxo-5-(phenylamino)pentanoic acid (44). $^1$H NMR (500 MHz, DMSO-$d_6$) δ 12.28 (s, 2H), 11.67 (d, J=2.2 Hz, 1H), 9.85 (s, 1H), 8.80 (d, J=8.7 Hz, 1H), 8.64 (d, J=7.5 Hz, 1H), 8.13 (d, J=7.8 Hz, 1H), 7.83-7.66 (m, 3H), 7.58 (ddd, J=18.4, 7.5, 1.6 Hz, 4H), 7.39 (d, J=8.7 Hz, 1H), 7.30 (dd, J=8.5, 7.4 Hz, 2H), 7.23-7.14 (m, 2H), 7.06 (dd, J=8.1, 6.7 Hz, 1H), 4.84 (ddd, J=12.0, 8.8, 3.6 Hz, 1H), 4.65 (td, J=7.6, 5.9 Hz, 1H), 4.41 (td, J=8.3, 5.1 Hz, 1H), 3.21 (dd, J=13.8, 3.6 Hz, 1H), 3.07 (dd, J=13.7, 11.1 Hz, 1H), 2.79 (dd, J=16.7, 5.9 Hz, 1H), 2.61 (dd, J=16.7, 7.7 Hz, 1H), 2.31 (dq, J=16.6, 10.5 Hz, 2H), 2.04 (td, J=9.0, 5.0 Hz, 1H), 1.88 (ddt, J=13.5, 8.7, 4.7 Hz, 1H). $^{13}$C NMR (126 MHz, DMSO-$d_6$) δ 174.29, 172.31, 171.63, 171.00, 170.24, 161.07, 144.84, 139.08, 135.29, 132.91, 132.42, 130.75, 129.18, 128.46, 124.69, 124.00, 121.14, 119.90, 119.37, 114.32, 109.67, 103.37, 54.17, 53.30, 50.16, 37.84, 36.40, 30.54, 27.78. HRMS (ESI) Calcd for $C_{34}H_{31}ClN_6O_8(M-H)^-$ 685.1814, found 685.1812.

(S)-4-((S)-3-Carboxy-2-((S)-2-(5-chloro-1H-indole-2-carboxamido)-3-(4-methoxyphenyl)propanamido)propanamido)-5-oxo-5-(phenylamino)pentanoic acid (45). $^1$H NMR (500 MHz, DMSO-$d_6$) δ 12.27 (s, 2H), 11.66 (s, 1H), 9.84 (s, 1H), 8.69 (d, J=8.4 Hz, 1H), 8.58 (d, J=7.6 Hz, 1H), 8.07 (d, J=7.8 Hz, 1H), 7.79-7.65 (m, 1H), 7.60 (d, J=8.0 Hz, 2H), 7.40 (d, J=8.7 Hz, 1H), 7.34-7.23 (m, 4H), 7.22-7.11 (m, 2H), 7.06 (t, J=7.4 Hz, 1H), 6.79 (d, J=8.2 Hz, 2H), 4.72 (ddd, J=11.8, 8.3, 3.6 Hz, 1H), 4.64 (q, J=7.1 Hz, 1H), 4.41 (td, J=8.3, 5.1 Hz, 1H), 3.66 (s, 3H), 3.06 (dd, J=13.9, 3.7 Hz, 1H), 2.92 (dd, J=14.0, 10.9 Hz, 1H), 2.78 (dd, J=16.6, 6.1 Hz, 1H), 2.60 (dd, J=16.7, 7.5 Hz, 1H), 2.30 (td, J=10.0, 6.1 Hz, 2H), 2.04 (td, J=9.2, 5.1 Hz, 1H), 1.87 (dt, J=15.0, 4.8 Hz, 1H). $^{13}$C NMR (126 MHz, DMSO-$d_6$) δ 174.30, 172.36, 172.17, 171.05, 170.23, 161.05, 158.20, 139.09, 135.26, 133.16, 130.63, 130.55, 129.17, 128.50, 124.65, 123.99, 123.92, 121.10, 119.92, 114.31, 113.92, 103.34, 55.33, 55.09, 53.32, 50.11, 36.88, 36.41, 30.54, 27.79. HRMS (ESI) Calcd for $C_{34}H_{34}ClN_5O_9(M-H)^-$ 690.1967, found 690.1963.

Synthesis of final product 46. The synthetic route for final product 46 is shown in Scheme 7.

Scheme 7. Synthesis of Final Compound 46.

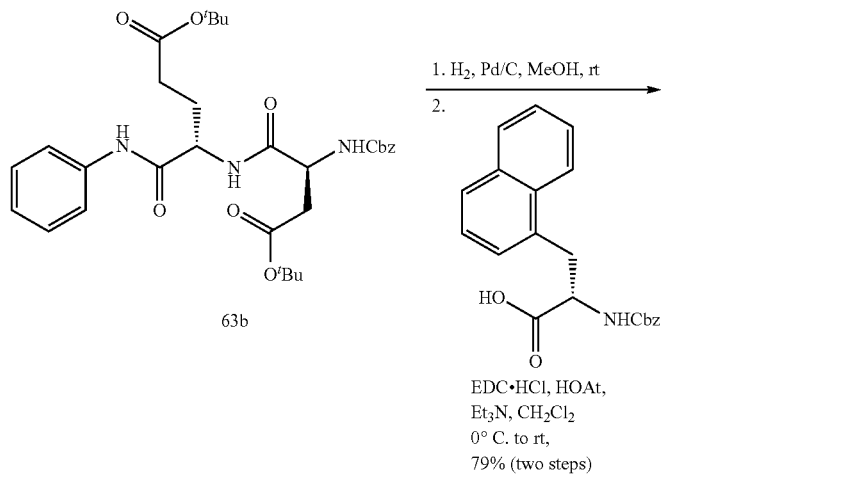

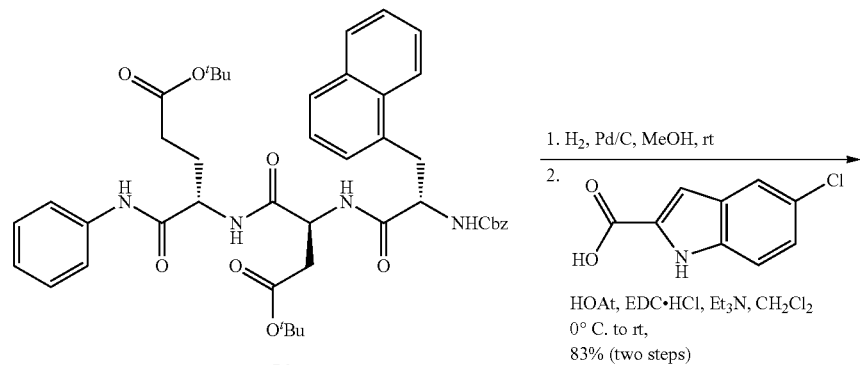

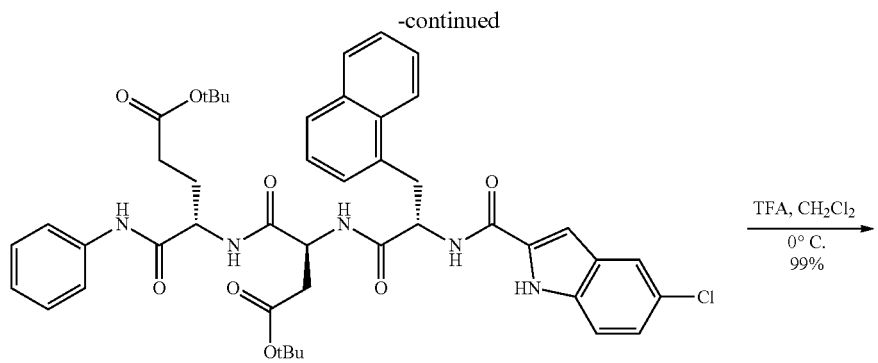

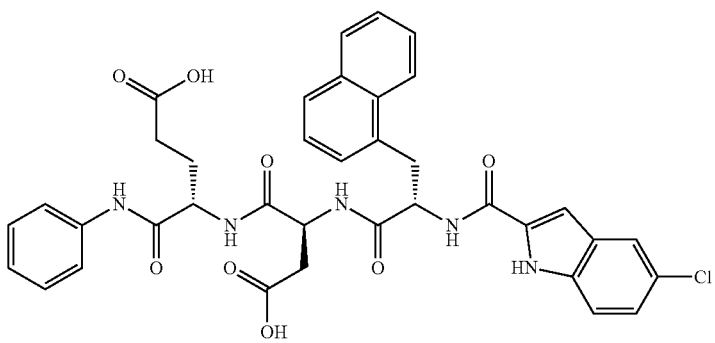

tert-Butyl (5S,8S,11S)-8-(2-(tert-butoxy)-2-oxoethyl)-5-(naphthalen-1-ylmethyl)-3,6,9-trioxo-1-phenyl-11-(phenylcarbamoyl)-2-oxa-4,7,10-triazatetradecan-14-oate (76). Yield, 79%. $^1$H NMR (500 MHz, Chloroform-d) δ 8.71 (s, 1H), 8.01 (d, J=8.2 Hz, 1H), 7.89-7.79 (m, 1H), 7.77-7.66 (m, 2H), 7.64-7.51 (m, 3H), 7.39-7.26 (m, 2H), 7.25-7.05 (m, 9H), 7.02-6.84 (m, 1H), 6.10-5.65 (m, 1H), 4.87 (s, 2H), 4.67 (dt, J=21.2, 5.7 Hz, 2H), 4.50 (td, J=8.9, 8.4, 4.2 Hz, 1H), 3.63 (dd, J=14.4, 4.8 Hz, 1H), 3.26 (dd, J=14.4, 9.1 Hz, 1H), 2.74 (dd, J=17.3, 4.6 Hz, 1H), 2.56-2.39 (m, 1H), 2.17 (dt, J=12.9, 6.6 Hz, 3H), 1.88 (d, J=17.7 Hz, 1H), 1.25 (d, J=6.9 Hz, 18H). $^{13}$C NMR (126 MHz, Chloroform-d) δ 172.31, 172.17, 170.89, 170.66, 169.37, 156.83, 138.16, 135.78, 133.97, 132.22, 131.87, 128.98, 128.77, 128.52, 128.27, 128.17, 127.68, 126.58, 125.93, 125.38, 124.17, 123.39, 120.23, 82.06, 80.53, 67.44, 56.37, 53.67, 50.26, 36.74, 35.44, 31.89, 28.07, 28.00, 27.10. MS (ESI) m/z=803.3 [M+Na]$^+$.

tert-Butyl (S)-4-((S)-4-(tert-butoxy)-2-((S)-2-(5-chloro-1H-indole-2-carboxamido)-3-(naphthalen-1-yl)propanamido)-4-oxobutanamido)-5-oxo-5-(phenylamino)pentanoate (77). Yield, 83%. $^1$H NMR (500 MHz, Chloroform-d) δ 10.70 (s, 1H), 8.70 (s, 1H), 8.25 (s, 1H), 8.09 (d, J=7.3 Hz, 1H), 7.90-7.77 (m, 1H), 7.56 (dd, J=27.2, 8.7 Hz, 4H), 7.48-7.40 (m, 1H), 7.30-7.05 (m, 9H), 6.97 (t, J=7.4 Hz, 1H), 6.64 (s, 1H), 5.06-4.90 (m, 1H), 4.80-4.66 (m, 1H), 4.47 (dt, J=9.1, 5.0 Hz, 1H), 3.68 (dd, J=14.5, 5.9 Hz, 1H), 3.30 (dd, J=14.2, 8.6 Hz, 1H), 2.77-2.54 (m, 2H), 2.35 (ddt, J=17.3, 13.7, 4.7 Hz, 3H), 2.16 (d, J=8.6 Hz, 1H), 1.34 (s, 9H), 1.08 (s, 9H). $^{13}$C NMR (126 MHz, Chloroform-d) δ 173.83, 171.87, 171.03, 170.68, 169.43, 162.33, 137.85, 135.61, 133.94, 132.07, 131.72, 130.58, 128.95, 128.77, 128.31, 128.14, 127.50, 126.50, 126.02, 125.84, 125.23, 125.16, 124.42, 123.00, 121.04, 120.43, 113.74, 102.99, 82.16, 81.45, 55.19, 54.38, 50.30, 36.89, 34.96, 32.65, 28.07, 27.76, 27.52. MS (ESI) m/z=846.4 [M+Na]$^+$.

(S)-4-((S)-3-Carboxy-2-((S)-2-(5-chloro-1H-indole-2-carboxamido)-3-(naphthalen-1-yl)propanamido)propanamido)-5-oxo-5-(phenylamino)pentanoic acid (46). $^1$H NMR (500 MHz, DMSO-d$_6$) δ 12.27 (s, 2H), 11.62 (d, J=2.2 Hz, 1H), 9.86 (s, 1H), 8.83 (d, J=8.4 Hz, 1H), 8.67 (d, J=7.5 Hz, 1H), 8.32 (d, J=8.5 Hz, 1H), 8.09 (d, J=7.8 Hz, 1H), 7.89 (dd, J=8.3, 1.4 Hz, 1H), 7.74 (d, J=8.2 Hz, 1H), 7.70 (d, J=2.0 Hz, 1H), 7.64-7.47 (m, 5H), 7.42-7.33 (m, 2H), 7.33-7.27 (m, 2H), 7.23-7.18 (m, 1H), 7.16 (dd, J=8.7, 2.1 Hz, 1H), 7.11-7.02 (m, 1H), 4.96 (ddd, J=10.7, 8.4, 3.9 Hz, 1H), 4.69 (td, J=7.5, 5.9 Hz, 1H), 4.43 (td, J=8.3, 5.1 Hz, 1H), 3.70 (dd, J=14.4, 3.8 Hz, 1H), 3.42 (dd, J=14.5, 10.6 Hz, 1H), 2.82 (dd, J=16.7, 5.9 Hz, 1H), 2.65 (dd, J=16.7, 7.6 Hz, 1H), 2.40-2.24 (m, 2H), 2.16-2.01 (m, 1H), 1.91 (ddt, J=13.7, 8.7, 4.7 Hz, 1H). $^{13}$C NMR (126 MHz, DMSO-d$_6$) δ 174.32, 172.40, 172.04, 171.00, 170.27, 161.08, 139.10, 135.25, 134.32, 133.82, 133.01, 132.07, 129.17, 129.01, 128.46, 127.75, 127.50, 126.56, 126.00, 125.76, 124.66, 124.32, 123.99, 123.96, 121.10, 119.91, 114.29, 103.42, 53.85, 53.35, 50.30, 36.33, 34.91, 30.56, 27.81. HRMS (ESI) Calcd for $C_{37}H_{34}ClN_5O_8$(M−H)$^-$ 710.2018, found 710.2016.

Synthesis of final products 47-49. The synthetic route for final products 47-49 is shown in Scheme 8.
Scheme 8. Synthesis of Final Compounds 47-49.
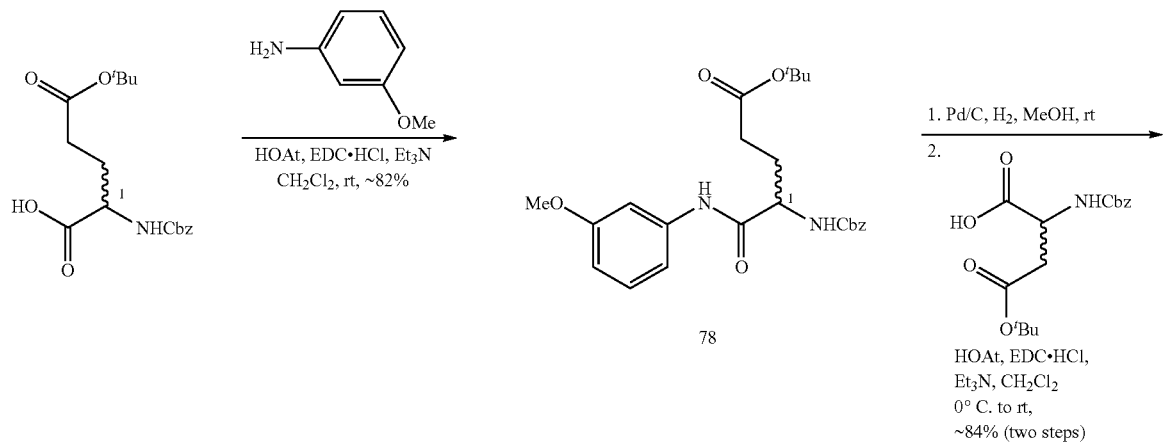
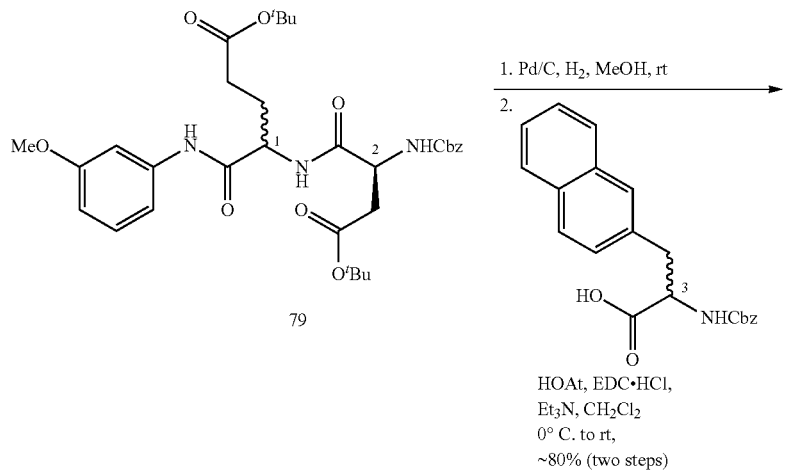
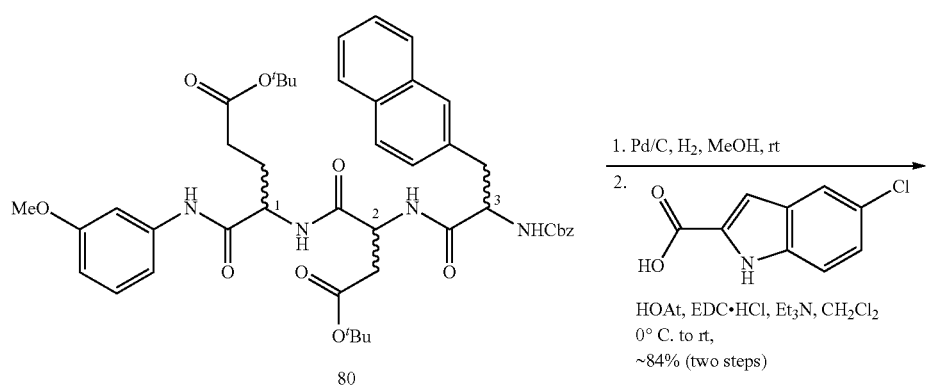

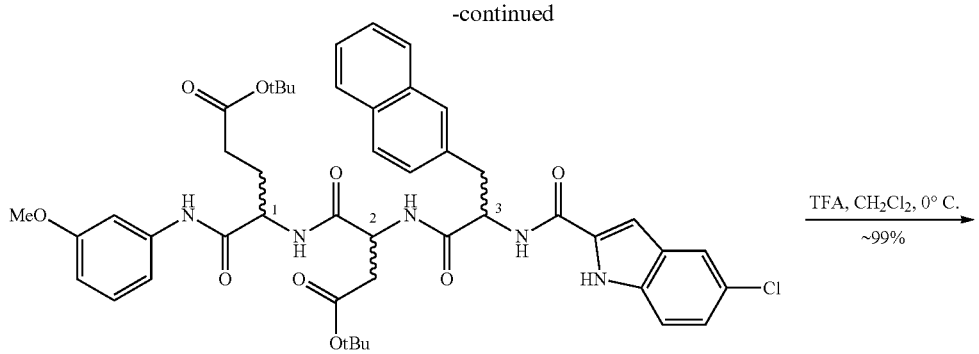

81

TFA, CH₂Cl₂, 0° C.
~99%

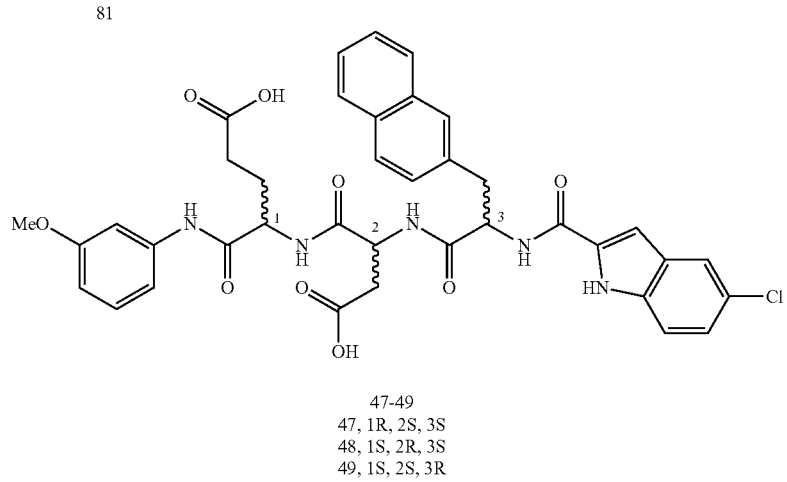

47-49
47, 1R, 2S, 3S
48, 1S, 2R, 3S
49, 1S, 2S, 3R tert-Butyl (R)-4-(((benzyloxy)carbonyl)amino)-5-((3-methoxyphenyl)amino)-5-oxopentanoate (78). $^1$H NMR (500 MHz, Chloroform-d) δ 8.70 (s, 1H), 7.34-7.12 (m, 6H), 7.06 (t, J=8.2 Hz, 1H), 6.90-6.70 (m, 1H), 6.55 (dd, J=8.3, 2.4 Hz, 1H), 5.95 (d, J=8.0 Hz, 1H), 5.00 (q, J=12.3 Hz, 2H), 4.33 (q, J=7.3 Hz, 1H), 3.65 (s, 3H), 2.37 (td, J=9.3, 4.8 Hz, 1H), 2.28 (dt, J=16.6, 6.9 Hz, 1H), 2.12-2.03 (m, 1H), 2.01-1.85 (m, 1H), 1.35 (s, 9H). $^{13}$C NMR (126 MHz, Chloroform-d) δ 172.93, 169.86, 160.08, 156.62, 138.87, 136.08, 129.60, 128.53, 128.19, 128.00, 112.14, 110.47, 105.54, 81.18, 67.21, 55.23, 31.81, 28.07. MS (ESI) m/z=443.2 [M+H]⁺, MS (ESI) m/z=465.3 [M+Na]⁺.

tert-Butyl (R)-4-((S)-2-(((benzyloxy)carbonyl)amino)-4-(tert-butoxy)-4-oxobutanamido)-5-((3-methoxyphenyl)amino)-5-oxopentanoate (79a). $^1$H NMR (500 MHz, Chloroform-d) δ 8.65 (s, 1H), 7.78 (d, J=7.5 Hz, 1H), 7.50-7.27 (m, 6H), 7.24-6.97 (m, 2H), 6.63 (ddd, J=8.1, 2.5, 1.1 Hz, 1H), 5.89 (d, J=8.7 Hz, 1H), 5.19-5.01 (m, 2H), 4.64-4.33 (m, 2H), 3.76 (s, 3H), 3.05 (dd, J=17.3, 5.0 Hz, 1H), 2.69 (dd, J=17.3, 5.2 Hz, 1H), 2.54-2.42 (m, 1H), 2.36 (dt, J=17.2, 6.5 Hz, 1H), 2.26-2.13 (m, 1H), 2.12-2.04 (m, 1H), 1.42 (s, 9H), 1.36 (s, 9H). $^{13}$C NMR (126 MHz, Chloroform-d) δ 173.64, 171.28, 171.23, 169.05, 160.00, 156.17, 138.97, 135.87, 129.35, 128.58, 128.34, 128.18, 112.54, 110.27, 105.95, 82.21, 81.24, 67.49, 55.27, 53.85, 51.63, 37.41, 31.92, 28.03, 27.96, 26.64. MS (ESI) m/z=614.4 [M+H]⁺, MS (ESI) m/z=636.3 [M+Na]⁺.

tert-Butyl (S)-4-((R)-2-(((benzyloxy)carbonyl)amino)-4-(tert-butoxy)-4-oxobutanamido)-5-((3-methoxyphenyl)amino)-5-oxopentanoate (79b). $^1$H NMR (500 MHz, Chloroform-d) δ 8.60 (s, 1H), 7.79 (d, J=7.3 Hz, 1H), 7.47-7.30 (m, 6H), 7.17 (t, J=8.1 Hz, 1H), 7.10 (d, J=8.0 Hz, 1H), 6.64 (ddd, J=8.1, 2.5, 1.0 Hz, 1H), 5.80 (d, J=8.9 Hz, 1H), 5.19 (d, J=12.1 Hz, 1H), 5.12 (d, J=12.2 Hz, 1H), 4.56 (ddd, J=12.5, 8.4, 4.6 Hz, 2H), 3.79 (s, 3H), 3.10 (dd, J=17.4, 4.8 Hz, 1H), 2.69 (dd, J=17.4, 5.0 Hz, 1H), 2.56-2.41 (m, 1H), 2.38 (ddd, J=17.1, 7.2, 5.2 Hz, 1H), 2.28-2.13 (m, 1H), 2.09 (dd, J=14.3, 7.0 Hz, 1H), 1.44 (s, 9H), 1.37 (s, 9H). $^{13}$C NMR (126 MHz, Chloroform-d) δ 173.84, 171.45, 171.22, 168.97, 160.01, 156.14, 138.95, 135.83, 129.34, 128.61, 128.39, 128.22, 112.55, 110.30, 105.95, 82.32, 81.35, 67.56, 55.30, 53.92, 51.60, 37.38, 31.99, 28.04, 27.97, 26.54. MS (ESI) m/z=614.4 [M+H]⁺, MS (ESI) m/z=636.3 [M+Na]⁺.

tert-Butyl (5S,8S,11R)-8-(2-(tert-butoxy)-2-oxoethyl)-11-((3-methoxyphenyl)carbamoyl)-5-(naphthalen-2-ylmethyl)-3,6,9-trioxo-1-phenyl-2-oxa-4,7,10-triazatetradecan-14-oate (80a). $^1$H NMR (500 MHz, Chloroform-d) δ 8.64 (s, 1H), 7.84 (s, 1H), 7.57-7.34 (m, 5H), 7.13 (dq, J=13.1, 7.1, 6.1 Hz, 8H), 7.03 (d, J=7.0 Hz, 2H), 6.91-6.79 (m, 1H), 6.79-6.69 (m, 1H), 6.45 (dd, J=8.2, 2.4 Hz, 1H), 5.23-4.60 (m, 5H), 3.51 (d, J=7.1 Hz, 3H), 3.17 (dd, J=14.0, 4.6 Hz, 1H), 3.10-2.89 (m, 2H), 2.75 (s, 1H), 2.19 (dt, J=56.9, 7.5 Hz, 3H), 1.92 (d, J=5.4 Hz, 1H), 1.32 (s, 9H), 1.27 (d, J=11.9 Hz, 9H). $^{13}$C NMR (126 MHz, Chloroform-d) δ 172.23, 171.28, 170.76, 169.30, 159.89, 156.76, 139.13, 135.82, 133.58, 133.29, 132.36, 129.32, 128.46, 128.08, 127.83, 127.60, 127.45, 127.09, 126.07, 125.56, 112.11, 109.95, 105.49, 81.85, 80.51, 67.19, 56.30, 55.07, 53.49, 53.34, 49.46, 39.52, 38.18, 31.67, 28.11, 28.02. MS (ESI) m/z=811.4 [M+H]⁺, MS (ESI) m/z=833.4 [M+Na]⁺.

tert-Butyl (5S,8R,11S)-8-(2-(tert-butoxy)-2-oxoethyl)-11-((3-methoxyphenyl)carbamoyl)-5-(naphthalen-2-ylmethyl)-3,6,9-trioxo-1-phenyl-2-oxa-4,7,10-triazatetradecan-14-oate (80b). ¹H NMR (500 MHz, Chloroform-d) δ 8.54 (s, 1H), 7.84-7.69 (m, 4H), 7.62 (d, J=1.7 Hz, 1H), 7.55-7.45 (m, 2H), 7.43 (t, J=2.2 Hz, 1H), 7.38-7.20 (m, 4H), 7.19-6.98 (m, 2H), 6.94 (d, J=9.1 Hz, 1H), 6.63 (ddd, J=8.1, 2.5, 1.1 Hz, 1H), 5.67 (d, J=5.7 Hz, 1H), 5.09 (d, J=12.2 Hz, 1H), 4.99 (d, J=12.2 Hz, 1H), 4.76 (dt, J=9.2, 4.6 Hz, 1H), 4.56 (ddd, J=8.5, 6.6, 3.5 Hz, 1H), 4.31 (q, J=7.1 Hz, 1H), 3.75 (s, 3H), 3.32 (dd, J=13.5, 7.8 Hz, 1H), 3.19 (dd, J=13.4, 7.3 Hz, 1H), 2.99 (dd, J=17.4, 4.2 Hz, 1H), 2.51-2.25 (m, 3H), 2.22-2.10 (m, 1H), 2.10-1.93 (m, 1H), 1.41 (s, 9H), 1.25 (s, 9H). ¹³C NMR (126 MHz, Chloroform-d) δ 172.61, 171.49, 171.19, 171.02, 169.23, 159.98, 156.62, 139.16, 135.73, 133.42, 132.45, 129.27, 128.51 (d, J=2.0 Hz), 128.25, 128.14, 128.02, 127.69, 127.56, 127.03, 126.43, 125.96, 112.47, 110.08, 105.90, 82.14, 80.69, 67.51, 57.79, 55.25, 53.76, 49.04, 37.51, 36.37, 31.99, 28.06, 27.78, 26.30. MS (ESI) m/z=811.4 [M+H]⁺, MS (ESI) m/z=833.4 [M+Na]⁺.

tert-Butyl (5R,8S,11S)-8-(2-(tert-butoxy)-2-oxoethyl)-11-((3-methoxyphenyl)carbamoyl)-5-(naphthalen-2-ylmethyl)-3,6,9-trioxo-1-phenyl-2-oxa-4,7,10-triazatetradecan-14-oate (80c). ¹H NMR (500 MHz, Chloroform-d) δ 8.53 (s, 1H), 7.87-7.72 (m, 4H), 7.64 (d, J=1.6 Hz, 1H), 7.48 (qt, J=7.1, 3.3 Hz, 3H), 7.39-7.21 (m, 5H), 7.21-7.03 (m, 4H), 6.85-6.45 (m, 1H), 5.73 (d, J=5.8 Hz, 1H), 4.99 (d, J=12.0 Hz, 1H), 4.76 (d, J=12.1 Hz, 1H), 4.70 (dt, J=8.1, 5.0 Hz, 1H), 4.67-4.56 (m, 1H), 4.44 (d, J=6.8 Hz, 1H), 3.77 (s, 3H), 3.32 (dd, J=13.5, 7.3 Hz, 1H), 3.20 (dd, J=13.6, 7.7 Hz, 1H), 2.90 (dd, J=17.1, 4.3 Hz, 1H), 2.40-2.29 (m, 3H), 2.24-2.17 (m, 1H), 2.09-1.97 (m, 1H), 1.42 (s, 9H), 1.37 (s, 9H). ¹³C NMR (126 MHz, Chloroform-d) δ 172.63, 172.16, 170.91, 170.46, 169.19, 160.03, 156.68, 139.29, 135.56, 133.41, 132.46, 129.52, 128.54, 128.44, 128.26, 128.24, 128.06, 127.67, 127.54, 127.00, 126.41, 125.95, 112.05, 110.32, 105.26, 82.09, 80.56, 67.55, 57.41, 55.22, 53.65, 50.18, 37.81, 35.68, 31.99, 28.09, 27.94, 26.81. MS (ESI) m/z=833.4 [M+Na]⁺.

tert-Butyl (R)-4-((S)-4-(tert-butoxy)-2-((S)-2-(5-chloro-1H-indole-2-carboxamido)-3-(naphthalen-2-yl)propanamido)-4-oxobutanamido)-5-((3-methoxyphenyl)amino)-5-oxopentanoate (81a). ¹H NMR (500 MHz, Chloroform-d) δ 10.18 (s, 1H), 8.61 (s, 1H), 7.96 (s, 1H), 7.71-7.47 (m, 4H), 7.42 (d, J=1.9 Hz, 1H), 7.30-7.10 (m, 5H), 7.07 (dd, J=8.7, 2.0 Hz, 1H), 6.88 (d, J=8.2 Hz, 2H), 6.62 (s, 1H), 6.40 (dt, J=7.3, 2.2 Hz, 1H), 4.75 (d, J=126.2 Hz, 3H), 3.46 (s, 3H), 3.34 (dd, J=14.1, 4.9 Hz, 1H), 3.20 (dd, J=13.5, 8.1 Hz, 1H), 2.95 (dd, J=17.2, 5.8 Hz, 1H), 2.71 (d, J=16.9 Hz, 1H), 2.31 (dt, J=44.6, 6.9 Hz, 3H), 2.13-1.99 (m, 1H), 1.34 (s, 9H), 1.13 (s, 9H). ¹³C NMR (126 MHz, Chloroform-d) δ 173.01, 171.06, 170.71, 169.77, 162.43, 159.77, 138.77, 135.33, 133.37, 132.44, 130.45, 129.30, 128.72, 128.16, 127.92, 127.59, 127.35, 126.86, 126.38, 126.19, 125.87, 125.27, 121.04, 113.54, 112.15, 109.89, 105.77, 103.22, 81.88, 81.03, 69.55, 55.72, 54.96, 53.84, 53.65, 49.85, 32.11, 29.29, 28.08, 27.79. MS (ESI) m/z=876.4 [M+Na]⁺.

tert-Butyl (S)-4-((R)-4-(tert-butoxy)-2-((S)-2-(5-chloro-1H-indole-2-carboxamido)-3-(naphthalen-2-yl)propanamido)-4-oxobutanamido)-5-((3-methoxyphenyl)amino)-5-oxopentanoate (81b). ¹H NMR (500 MHz, Chloroform-d) δ 10.03 (d, J=2.1 Hz, 1H), 8.41 (s, 1H), 8.02 (d, J=6.4 Hz, 1H), 7.84 (d, J=4.9 Hz, 1H), 7.77-7.67 (m, 3H), 7.67-7.55 (m, 1H), 7.50-7.35 (m, 4H), 7.34-7.24 (m, 2H), 7.09 (dd, J=8.8, 2.0 Hz, 1H), 6.99 (t, J=8.1 Hz, 1H), 6.91 (ddd, J=8.1, 1.9, 1.0 Hz, 1H), 6.75 (s, 1H), 6.64 (d, J=9.9 Hz, 1H), 6.49 (ddd, J=8.2, 2.5, 1.0 Hz, 1H), 4.80 (dt, J=9.9, 4.0 Hz, 1H), 4.35-4.26 (m, 2H), 3.64 (d, J=9.2 Hz, 2H), 2.98 (dd, J=17.7, 3.8 Hz, 1H), 2.50-2.36 (m, 1H), 2.35-2.15 (m, 2H), 1.87-1.68 (m, 2H), 1.36 (s, 9H), 0.96 (s, 9H). ¹³C NMR (126 MHz, Chloroform-d) δ 173.86, 171.64, 171.58, 171.46, 169.08, 162.53, 159.90, 138.97, 135.54, 133.43, 133.08, 132.49, 130.42, 129.13, 128.63, 128.09, 128.02, 127.77, 127.54, 126.94, 126.68, 126.17, 125.86, 124.86, 120.88, 113.91, 112.63, 110.15, 105.97, 103.44, 82.20, 80.90, 58.57, 55.23, 54.42, 48.36, 37.10, 36.28, 32.22, 28.11, 27.54, 26.63. MS (ESI) m/z=876.3 [M+Na]⁺.

tert-Butyl (S)-4-((S)-4-(tert-butoxy)-2-((R)-2-(5-chloro-1H-indole-2-carboxamido)-3-(naphthalen-2-yl)propanamido)-4-oxobutanamido)-5-((3-methoxyphenyl)amino)-5-oxopentanoate (81c). ¹H NMR (500 MHz, Chloroform-d) δ 10.33 (s, 1H), 8.42 (s, 1H), 8.06 (s, 1H), 7.74-7.60 (m, 3H), 7.57 (d, J=1.6 Hz, 1H), 7.50-7.29 (m, 4H), 7.27-7.21 (m, 2H), 7.18 (d, J=4.1 Hz, 1H), 7.08 (dd, J=8.8, 2.0 Hz, 1H), 7.03-6.99 (m, 1H), 6.99-6.91 (m, 2H), 6.59 (d, J=2.1 Hz, 1H), 6.41 (ddd, J=7.6, 2.5, 1.5 Hz, 1H), 4.81-4.37 (m, 3H), 3.55 (s, 3H), 3.36 (dd, J=13.5, 7.6 Hz, 1H), 3.26 (dd, J=13.5, 7.8 Hz, 1H), 2.78 (dd, J=17.0, 4.5 Hz, 1H), 2.46-2.20 (m, 3H), 2.18-2.05 (m, 2H), 1.35 (s, 9H), 1.22 (s, 9H). ¹³C NMR (126 MHz, Chloroform-d) δ 173.71, 171.75, 170.93, 170.73, 169.49, 162.64, 159.81, 138.89, 135.40, 133.52, 133.43, 132.46, 130.38, 129.29, 128.58, 128.17, 128.04, 127.65, 127.48, 126.99, 126.47, 126.06, 125.97, 125.15, 121.01, 113.59, 112.23, 110.00, 105.69, 103.09, 82.06, 81.13, 57.05, 55.09, 54.00, 50.26, 37.30, 35.73, 32.25, 28.10, 27.89, 27.32. MS (ESI) m/z=876.4 [M+Na]⁺.

(R)-4-((S)-3-Carboxy-2-((S)-2-(5-chloro-1H-indole-2-carboxamido)-3-(naphthalen-2-yl)propanamido)propanamido)-5-((3-methoxyphenyl)amino)-5-oxopentanoic acid (47). ¹H NMR (500 MHz, DMSO-d₆) δ 12.28 (s, 2H), 11.62 (s, 1H), 9.80 (s, 1H), 8.76 (d, J=8.3 Hz, 1H), 8.66 (d, J=7.2 Hz, 1H), 8.21 (d, J=8.1 Hz, 1H), 7.95-7.72 (m, 4H), 7.72-7.63 (m, 1H), 7.53 (d, J=8.5 Hz, 1H), 7.48-7.25 (m, 4H), 7.16 (ddd, J=19.7, 9.6, 5.0 Hz, 4H), 6.78-6.42 (m, 1H), 4.89 (td, J=9.7, 8.6, 3.7 Hz, 1H), 4.64 (q, J=7.0 Hz, 1H), 4.43 (td, J=8.5, 4.8 Hz, 1H), 3.67 (s, 3H), 3.46-3.24 (m, 1H), 3.16 (dd, J=13.9, 10.6 Hz, 1H), 2.78 (dd, J=16.5, 6.1 Hz, 1H), 2.64 (dd, J=16.5, 7.6 Hz, 1H), 2.30 (ddt, J=20.0, 16.4, 10.4 Hz, 2H), 2.06 (td, J=9.3, 5.1 Hz, 1H), 1.88 (dq, J=9.4, 5.0, 4.4 Hz, 1H). ¹³C NMR (126 MHz, DMSO-d₆) δ 174.31, 172.17, 172.13, 171.00, 170.31, 161.12, 159.91, 140.25, 136.37, 135.25, 133.38, 133.04, 132.23, 129.91, 128.46, 128.27, 127.87, 127.85, 127.75, 126.37, 125.81, 124.65, 123.94, 121.08, 114.29, 112.19, 109.39, 105.73, 103.36, 55.38, 54.89, 53.28, 50.50, 37.86, 36.52, 30.59, 27.70. HRMS (ESI) Calcd for C₃₈H₃₆ClN₅O₉(M–H)⁻ 740.2123, found 740.2121.

(S)-4-((R)-3-Carboxy-2-((S)-2-(5-chloro-1H-indole-2-carboxamido)-3-(naphthalen-2-yl)propanamido)propanamido)-5-((3-methoxyphenyl)amino)-5-oxopentanoic acid (48). ¹H NMR (500 MHz, DMSO-d₆) δ 12.26 (s, 2H), 11.56 (s, 1H), 9.77 (s, 1H), 8.77 (d, J=8.2 Hz, 1H), 8.67 (d, J=7.5 Hz, 1H), 8.26 (d, J=8.1 Hz, 1H), 8.01-7.73 (m, 4H), 7.69 (s, 1H), 7.54 (d, J=8.5 Hz, 1H), 7.49-7.32 (m, 4H), 7.28-7.00 (m, 4H), 6.79-6.41 (m, 1H), 5.04-4.84 (m, 1H), 4.75-4.59 (m, 1H), 4.41 (dt, J=8.7, 4.2 Hz, 1H), 3.68 (s, 3H), 3.46-3.24 (m, 1H), 3.17 (dd, J=13.8, 10.4 Hz, 1H), 2.71 (dd, J=16.5, 5.9 Hz, 1H), 2.58 (dd, J=16.5, 7.7 Hz, 1H), 2.38-2.15 (m, 2H), 2.07 (ddd, J=14.7, 10.0, 5.3 Hz, 1H), 1.90 (ddd, J=14.1, 9.6, 5.3 Hz, 1H). ¹³C NMR (126 MHz, DMSO-d₆) δ 174.34, 172.12, 172.03, 171.04, 170.33, 161.19, 159.88, 140.23, 136.28, 135.26, 133.39, 132.98, 132.25, 129.90, 128.45, 128.30, 127.91, 127.89, 127.77, 126.41, 125.85, 124.66, 123.95, 121.09, 114.32, 112.21, 109.37, 105.73, 103.43, 55.40, 55.14, 53.38, 50.28, 37.92, 36.75, 30.55, 27.62. HRMS (ESI) Calcd for $C_{38}H_{36}ClN_5O_9(M-H)^-$ 740.2123, found 740.2123.

(S)-4-((S)-3-Carboxy-2-((R)-2-(5-chloro-1H-indole-2-carboxamido)-3-(naphthalen-2-yl)propanamido)propanamido)-5-((3-methoxyphenyl)amino)-5-oxopentanoic acid (49). $^1$H NMR (500 MHz, DMSO-$d_6$) δ 12.27 (s, 2H), 11.55 (s, 1H), 9.75 (s, 1H), 8.80 (d, J=8.1 Hz, 1H), 8.67 (d, J=7.9 Hz, 1H), 8.14 (d, J=7.7 Hz, 1H), 7.98-7.76 (m, 4H), 7.69 (d, J=2.1 Hz, 1H), 7.54 (dd, J=8.5, 1.7 Hz, 1H), 7.48-7.34 (m, 3H), 7.29 (t, J=2.3 Hz, 1H), 7.25-6.98 (m, 4H), 6.61 (dd, J=8.3, 2.4 Hz, 1H), 4.89 (ddd, J=10.6, 8.2, 4.4 Hz, 1H), 4.69 (td, J=7.8, 5.3 Hz, 1H), 4.36 (td, J=8.3, 5.2 Hz, 1H), 3.70 (s, 3H), 3.46-3.24 (m, 1H), 3.17 (dd, J=13.8, 10.3 Hz, 1H), 2.73 (dd, J=16.6, 5.4 Hz, 1H), 2.62-2.51 (m, 1H), 2.36-2.22 (m, 2H), 2.06-1.99 (m, 1H), 1.92 (tt, J=9.8, 5.3 Hz, 1H). $^{13}$C NMR (126 MHz, DMSO-$d_6$) δ 174.41, 172.29, 171.96, 171.10, 170.32, 161.19, 159.91, 140.25, 136.29, 135.24, 133.40, 133.01, 132.26, 129.91, 128.47, 128.32, 127.91, 127.89, 127.78, 126.41, 125.86, 124.66, 123.96, 121.11, 114.29, 112.14, 109.41, 105.64, 103.48, 55.42, 55.13, 53.58, 50.06, 37.90, 36.60, 30.69, 27.60. HRMS (ESI) Calcd for $C_{38}H_{36}ClN_5O_9(M-H)^-$ 740.2123, found 740.2121.

Synthesis of final product 50. The synthetic route for final product 50 is shown in Scheme 9.

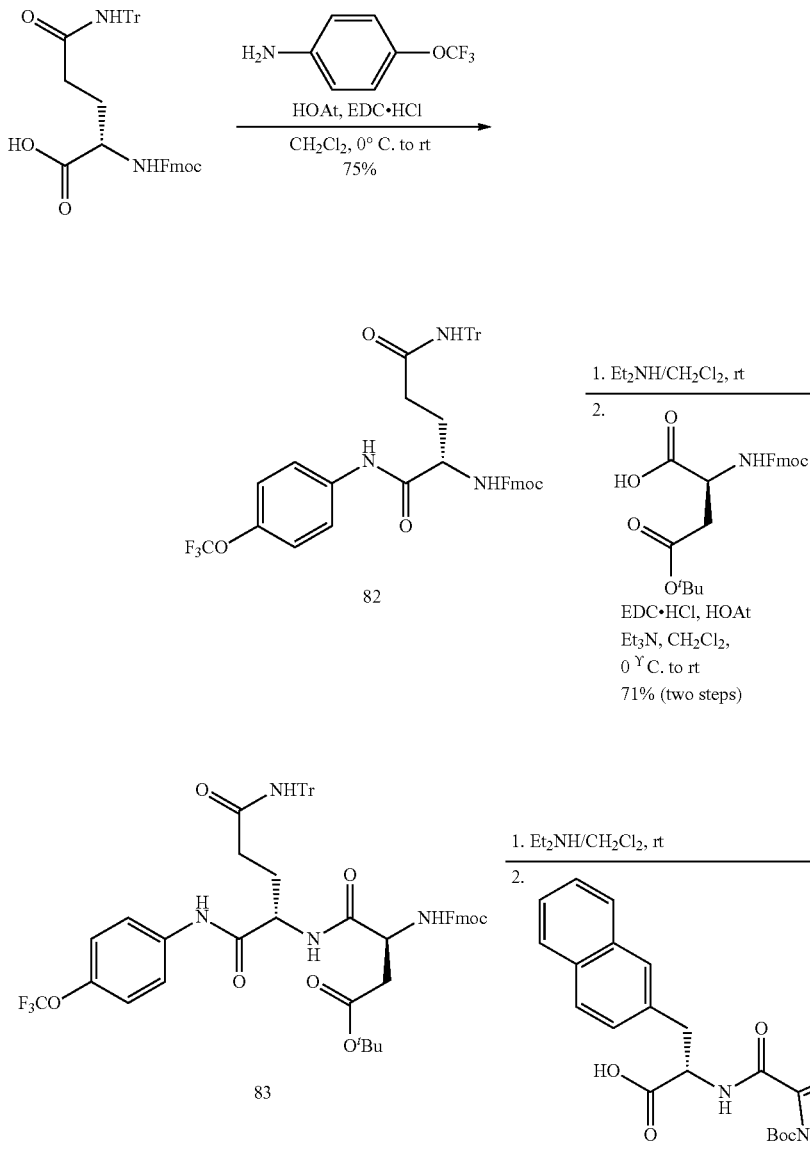

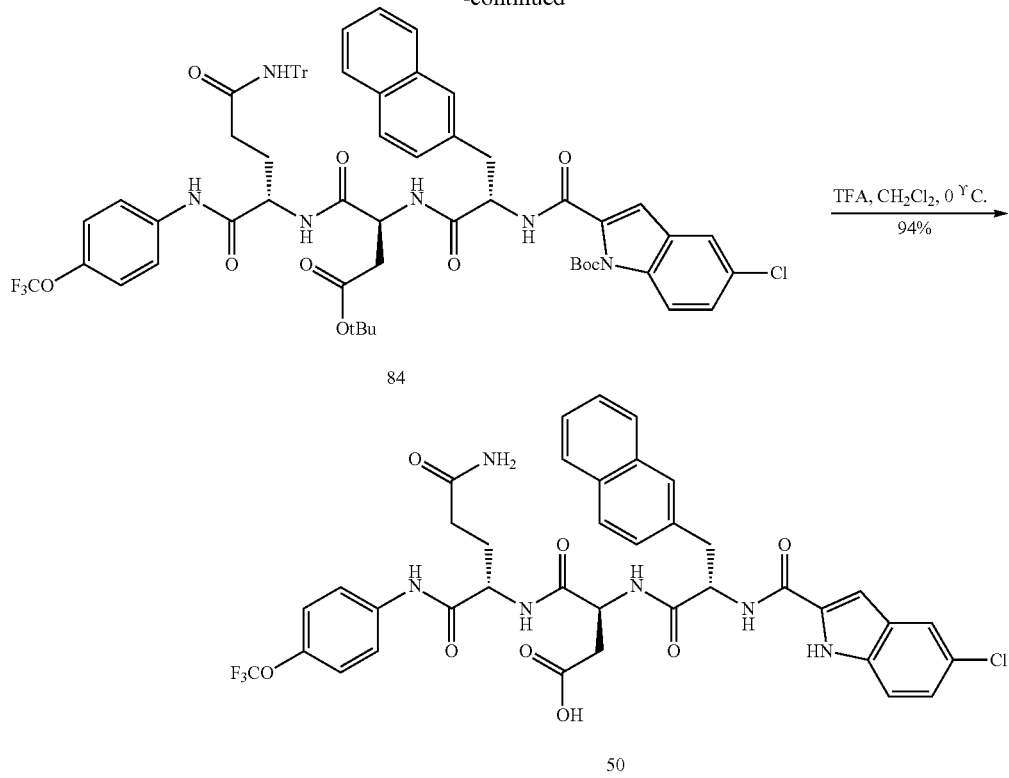

(9H-Fluoren-9-yl)methyl (S)-(1,5-dioxo-1-((4-(trifluoromethoxy)phenyl)amino)-5-(tritylamino)pentan-2-yl)carbamate (82). Yield, 75%. 1H NMR (500 MHz, Chloroform-d) δ 9.12 (s, 1H), 7.65 (dd, J=8.2, 3.5 Hz, 2H), 7.49 (d, J=7.5 Hz, 2H), 7.36-7.05 (m, 21H), 7.01-6.89 (m, 2H), 6.88 (s, 1H), 6.00 (d, J=7.0 Hz, 1H), 4.30 (t, J=6.1 Hz, 2H), 4.11 (t, J=7.1 Hz, 1H), 4.03 (q, J=7.1 Hz, 1H), 2.59-2.49 (m, 1H), 2.42-2.31 (m, 1H), 2.13-1.99 (m, 1H), 1.90-1.85 (m, 1H). 13C NMR (126 MHz, Chloroform-d) δ 172.54, 169.54, 156.26, 145.08, 145.06, 144.19, 143.82, 143.72, 141.34, 141.33, 136.50, 128.69, 128.11, 127.77, 127.76, 127.23, 127.10, 125.11, 121.45, 120.90, 120.04, 119.48, 70.99, 67.02, 54.35, 47.19, 34.05, 30.49. MS (ESI) m/z=792.3 [M+Na]+.

tert-Butyl (S)-3-((((9H-fluoren-9-yl)methoxy)carbonyl)amino)-4-(((S)-1,5-dioxo-1-((4-(trifluoromethoxy)phenyl)amino)-5-(tritylamino)pentan-2-yl)amino)-4-oxobutanoate (83). Yield, 71%. 1H NMR (500 MHz, Chloroform-d) δ 9.03 (s, 1H), 7.97 (d, J=6.5 Hz, 1H), 7.67 (dd, J=7.5, 4.7 Hz, 2H), 7.47 (dt, J=6.4, 3.1 Hz, 4H), 7.31 (td, J=7.4, 3.7 Hz, 2H), 7.23-7.04 (m, 17H), 7.00 (d, J=8.6 Hz, 2H), 6.88 (s, 1H), 5.66 (d, J=7.3 Hz, 1H), 4.44-4.18 (m, 4H), 4.10 (t, J=7.1 Hz, 1H), 2.86-2.52 (m, 3H), 2.40 (ddd, J=15.8, 7.4, 4.2 Hz, 1H), 2.20-2.00 (m, 1H), 1.65 (s, 1H), 1.34 (s, 9H). 13C NMR (126 MHz, Chloroform-d) δ 173.05, 170.91, 170.64, 169.26, 156.15, 145.11, 144.18, 143.83, 143.65, 141.29, 136.69, 128.65, 128.07, 127.75, 127.24, 127.09, 127.08, 125.09, 121.51, 121.38, 121.15, 120.01, 82.07, 70.91, 67.27, 53.96, 51.79, 47.08, 37.44, 33.92, 28.21, 28.04.

tert-Butyl 2-(((S)-1-(((S)-4-(tert-butoxy)-1-(((S)-1,5-dioxo-1-((4-(trifluoromethoxy)phenyl)amino)-5-(tritylamino)pentan-2-yl)amino)-1,4-dioxobutan-2-yl)amino)-3-(naphthalen-2-yl)-1-oxopropan-2-yl)carbamoyl)-5-chloro-1H-indole-1-carboxylate (84). Yield, 65%. 1H NMR (500 MHz, Chloroform-d) δ 8.76 (s, 1H), 7.75 (dd, J=7.2, 3.3 Hz, 2H), 7.70 (dd, J=9.5, 4.7 Hz, 2H), 7.60 (td, J=5.9, 5.0, 3.3 Hz, 4H), 7.50 (d, J=7.4 Hz, 1H), 7.46 (s, 1H), 7.41 (dd, J=6.3, 3.3 Hz, 2H), 7.30-7.21 (m, 3H), 7.03-6.91 (m, 11H), 6.90-6.82 (m, 6H), 6.72 (d, J=5.8 Hz, 1H), 5.90 (s, 1H), 4.74 (td, J=7.9, 5.1 Hz, 1H), 4.61 (dt, J=10.7, 5.3 Hz, 1H), 4.22 (ddd, J=10.7, 6.6, 3.6 Hz, 1H), 3.46 (dd, J=14.4, 4.8 Hz, 1H), 3.16 (dd, J=14.4, 9.1 Hz, 1H), 2.91 (dd, J=16.3, 5.1 Hz, 1H), 2.63 (dd, J=16.3, 8.4 Hz, 1H), 2.42 (td, J=8.9, 5.3 Hz, 1H), 2.29-2.15 (m, 2H), 2.04 (dt, J=10.4, 3.8 Hz, 1H), 1.48 (s, 9H), 1.31 (s, 9H). 13C NMR (126 MHz, Chloroform-d) δ 171.98, 171.16, 170.47, 169.97, 169.47, 163.63, 149.65, 145.03 (d, J=2.0 Hz), 144.37, 136.91, 134.39, 133.72, 133.49, 133.44, 132.66, 129.43, 129.14, 129.00, 128.66, 128.60, 127.91, 127.79, 127.70, 127.57, 126.85, 126.76, 126.62, 126.20, 121.62, 121.55, 121.44, 121.03, 116.44, 111.22, 86.70, 81.70, 70.21, 56.36, 54.48, 51.25, 36.75, 36.47, 34.41, 28.97, 28.04, 27.96.

(S)-4-(((S)-5-Amino-1,5-dioxo-1-((4-(trifluoromethoxy)phenyl)amino)pentan-2-yl)amino)-3-((S)-2-(5-chloro-1H-indole-2-carboxamido)-3-(naphthalen-2-yl)propanamido)-4-oxobutanoic acid (50). 1H NMR (500 MHz, DMSO-d6) δ 12.45 (s, 1H), 11.84-11.29 (m, 1H), 10.09 (s, 1H), 8.82 (d, J=8.3 Hz, 1H), 8.63 (d, J=7.5 Hz, 1H), 8.13 (d, J=7.5 Hz, 1H), 7.94-7.64 (m, 7H), 7.56 (d, J=8.4 Hz, 1H), 7.48-7.35 (m, 3H), 7.31 (d, J=8.7 Hz, 3H), 7.21 (d, J=2.1 Hz, 1H), 7.15 (dd, J=8.7, 2.1 Hz, 1H), 6.85 (s, 1H), 4.89 (ddd, J=11.9, 8.4, 3.8 Hz, 1H), 4.65 (q, J=7.2 Hz, 1H), 4.35 (q, J=7.3 Hz, 1H), 3.30-3.32 (m, 1H), 3.16 (dd, J=13.9, 10.9 Hz, 1H), 2.81 (dd, J=16.7, 5.5 Hz, 1H), 2.63 (dd, J=16.6, 8.0 Hz, 1H), 2.18 (t, J=8.2 Hz, 2H), 2.01 (q, J=7.2, 6.7 Hz, 1H), 1.92 (p, J=7.5, 7.0 Hz, 1H). 13C NMR (126 MHz, DMSO-d6) δ 174.13, 172.36, 172.11, 171.06, 170.70, 161.21, 144.14, 138.38, 136.47, 135.26, 133.39, 133.01, 132.24, 128.45, 128.30, 127.91, 127.88, 127.77, 126.41, 125.84, 124.66, 123.95, 122.07, 121.19, 121.10, 120.58 (t, J=253.7 Hz), 114.32, 103.37, 55.04, 53.85, 50.24, 37.86, 36.38, 31.79, 28.17.
HRMS (ESI) Calcd for $C_{38}H_{34}ClF_3N_6O_8$ (M–H)⁻ 793.2000, found 793.1999.
Synthesis of final product 51. The synthetic route for final product 51 is shown in Scheme 10.
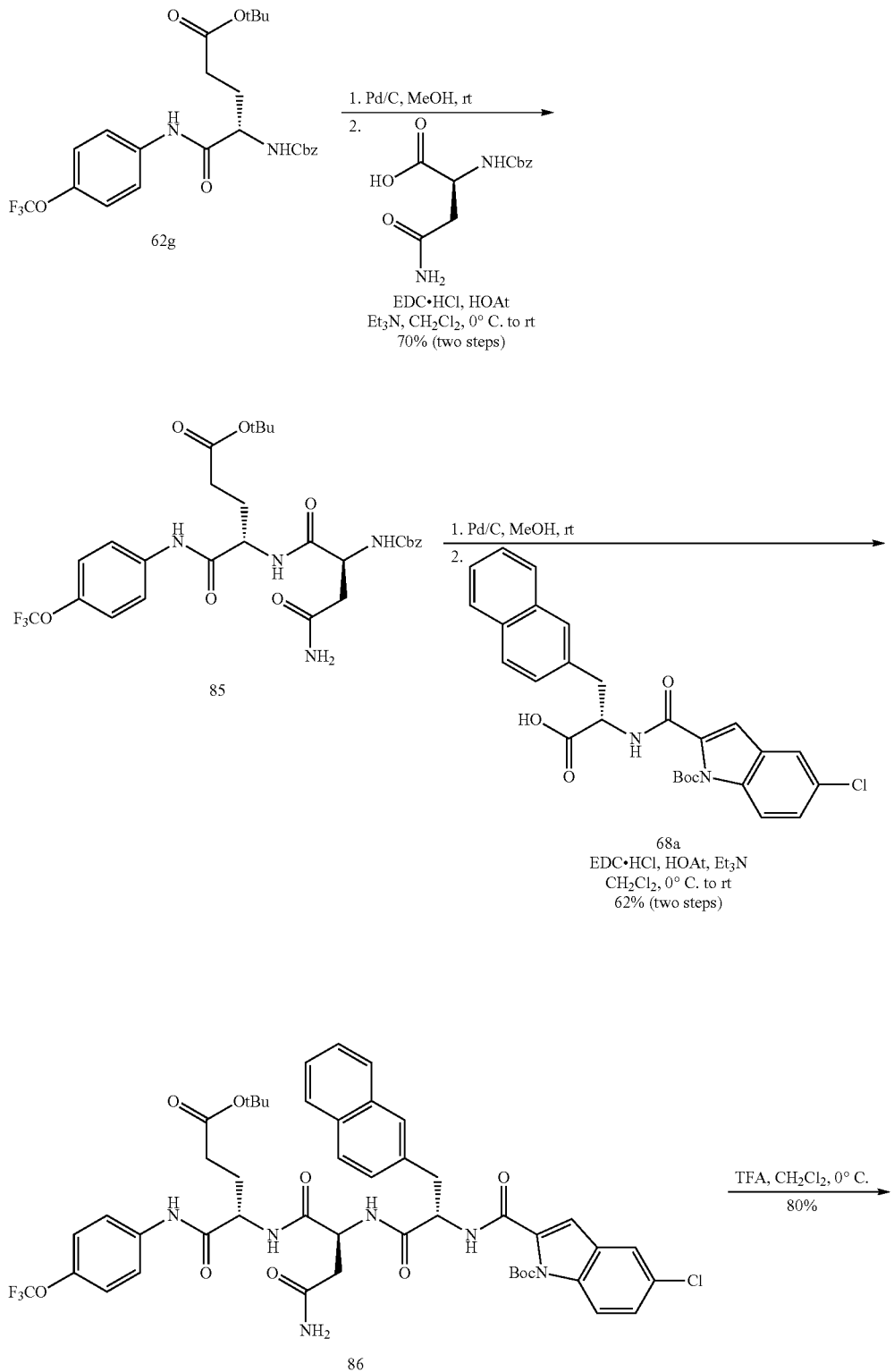
Scheme 10. Synthesis of Final Compound 51.

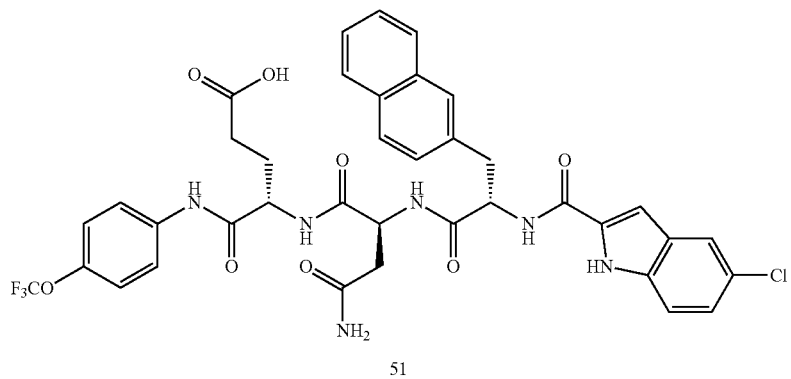

51 tert-Butyl (S)-4-((S)-4-amino-2-(((benzyloxy)carbonyl)amino)-4-oxobutanamido)-5-oxo-5-((4-(trifluoromethoxy)phenyl)amino)pentanoate (85). Yield, 70%. $^1$H NMR (500 MHz, Acetone-$d_6$) δ 9.57 (s, 1H), 7.93 (dd, J=28.0, 8.6 Hz, 3H), 7.47-7.27 (m, 5H), 7.26-7.10 (m, 3H), 6.95-6.49 (m, 2H), 5.11 (d, J=1.8 Hz, 2H), 4.51 (tdd, J=11.2, 7.8, 4.6 Hz, 2H), 3.10-2.71 (m, 2H), 2.39 (dddd, J=16.6, 14.0, 10.4, 6.1 Hz, 3H), 2.01-1.87 (m, 1H), 1.42 (s, 9H). $^{13}$C NMR (126 MHz, Acetone-$d_6$) δ 172.75, 171.90, 171.43, 170.07, 156.09, 144.39, 138.38, 137.08, 128.35, 127.81, 127.76, 121.62, 121.22, 121.06, 79.62, 66.15, 53.39, 52.14, 36.89, 31.47, 27.37, 26.61. MS (ESI) m/z=611.3 [M+H]$^+$, 633.3 [M+Na]$^+$.

tert-Butyl 2-(((S)-1-(((S)-4-amino-1-(((S)-5-(tert-butoxy)-1,5-dioxo-1-((4-(trifluoromethoxy)phenyl)amino)pentan-2-yl)amino)-1,4-dioxobutan-2-yl)amino)-3-(naphthalen-2-yl)-1-oxopropan-2-yl)carbamoyl)-5-chloro-1H-indole-1-carboxylate (86). Yield, 62%. $^1$H NMR (500 MHz, Acetone-$d_6$) δ 9.41 (s, 1H), 8.32 (d, J=6.6 Hz, 1H), 8.24 (d, J=7.0 Hz, 1H), 8.11-7.93 (m, 3H), 7.91-7.82 (m, 4H), 7.80 (d, J=8.0 Hz, 1H), 7.61 (d, J=2.1 Hz, 1H), 7.55 (dd, J=8.3, 1.8 Hz, 1H), 7.51-7.40 (m, 2H), 7.37 (dd, J=8.9, 2.1 Hz, 1H), 7.32-7.11 (m, 3H), 6.95 (d, J=0.8 Hz, 1H), 6.71 (s, 1H), 4.93 (ddd, J=9.1, 6.5, 4.8 Hz, 1H), 4.71 (q, J=6.1 Hz, 1H), 4.48 (dt, J=9.5, 5.6 Hz, 1H), 3.51 (dd, J=14.2, 4.8 Hz, 1H), 3.35 (dd, J=14.2, 9.2 Hz, 1H), 2.89 (d, J=6.0 Hz, 2H), 2.47-2.21 (m, 3H), 1.98-1.85 (m, 1H), 1.44 (s, 9H), 1.33 (s, 9H).

(S)-4-((S)-4-Amino-2-((S)-2-(5-chloro-1H-indole-2-carboxamido)-3-(naphthalen-2-yl)propanamido)-4-oxobutanamido)-5-oxo-5-((4-(trifluoromethoxy)phenyl)amino)pentanoic acid (51). Yield, 80%. $^1$H NMR (500 MHz, DMSO-$d_6$) δ 12.12 (s, 1H), 11.64 (s, 1H), 9.97 (s, 1H), 8.80 (d, J=8.5 Hz, 1H), 8.61 (d, J=7.5 Hz, 1H), 8.36 (d, J=7.7 Hz, 1H), 7.94-7.75 (m, 5H), 7.69 (d, J=2.1 Hz, 1H), 7.63-7.52 (m, 2H), 7.42 (pd, J=6.8, 1.6 Hz, 2H), 7.36 (d, J=8.7 Hz, 1H), 7.29 (d, J=8.6 Hz, 2H), 7.20 (d, J=2.1 Hz, 1H), 7.16-7.06 (m, 2H), 4.93 (ddd, J=11.9, 8.7, 3.7 Hz, 1H), 4.64 (q, J=7.1 Hz, 1H), 4.38 (ddd, J=9.3, 7.6, 4.6 Hz, 1H), 3.28 (dd, J=14.8, 4.7 Hz, 1H), 3.15 (dd, J=13.9, 11.0 Hz, 1H), 2.69 (dd, J=15.6, 7.6 Hz, 1H), 2.58 (dd, J=15.5, 6.0 Hz, 1H), 2.33 (pt, J=8.8, 5.2 Hz, 2H), 2.12 (dq, J=9.7, 6.1 Hz, 1H), 1.86 (ddt, J=13.5, 9.0, 4.7 Hz, 1H). $^{13}$C NMR (126 MHz, DMSO-$d_6$) δ 174.39, 172.44, 171.84, 171.67, 170.72, 161.03, 144.17, 138.37, 136.48, 135.24, 133.38, 133.08, 132.23, 128.46, 128.33, 127.90, 127.83, 127.77, 126.39, 125.83, 124.63, 123.91, 121.94, 121.47, 121.09, 120.59 (d, J=253.7 Hz), 114.29, 103.31, 99.99, 54.77, 53.34, 50.36, 37.94, 37.38, 30.56, 27.22. HRMS (ESI) Calcd for $C_{38}H_{34}ClF_3N_6O_8$ (M−H)$^-$ 793.2000, found 793.1998.

Synthesis of final product 52. The synthetic route for final product 52 is shown in Scheme 11.

Scheme 11. Synthesis of Final Compound 52.

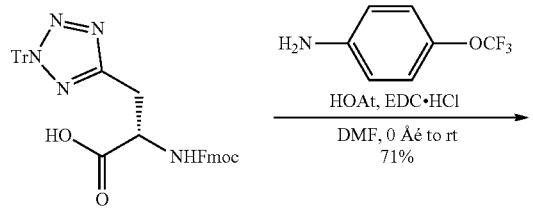

-continued
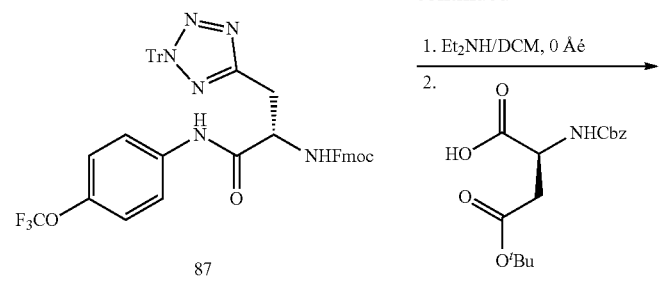
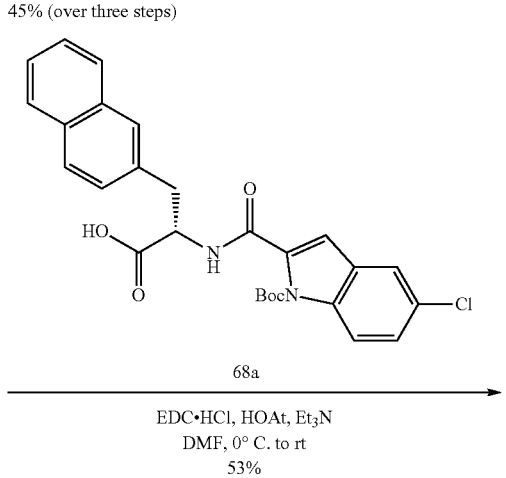
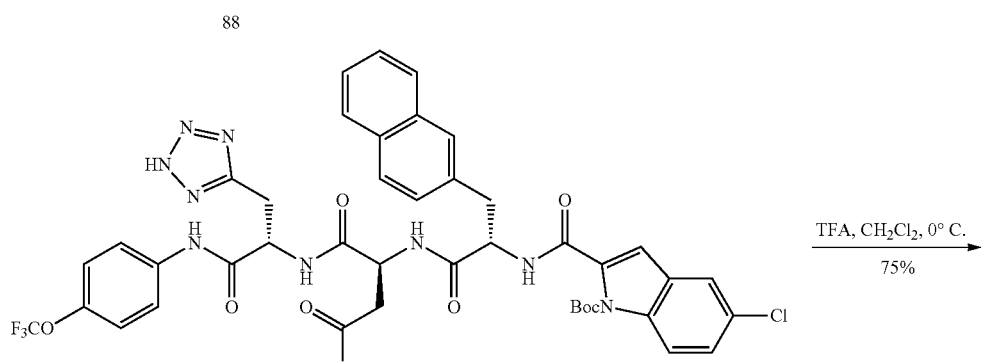
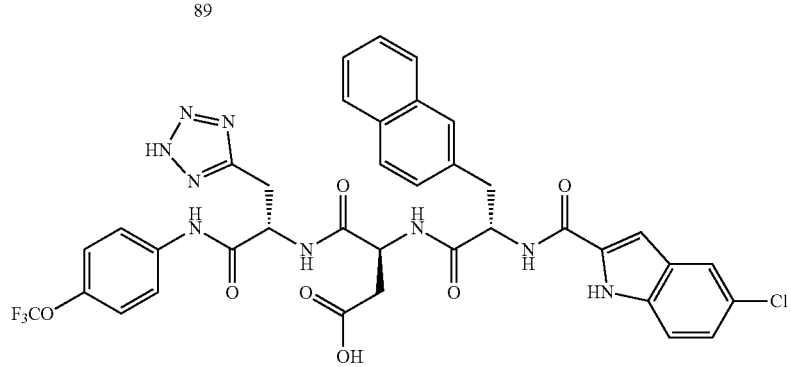

(9H-fluoren-9-yl)methyl (S)-(1-oxo-1-((4-(trifluoromethoxy)phenyl)amino)-3-(2-trityl-2H-tetrazol-5-yl)propan-2-yl)carbamate (87). Yield, 71%. $^1$H NMR (500 MHz, Chloroform-d) δ 8.62 (s, 1H), 7.76 (d, J=7.6 Hz, 2H), 7.54 (t, J=5.7 Hz, 2H), 7.43-7.35 (m, 4H), 7.35-7.31 (m, 3H), 7.31-7.21 (m, 8H), 7.18-6.81 (m, 8H), 6.17 (d, J=8.3 Hz, 1H), 4.97 (d, J=8.8 Hz, 1H), 4.41 (h, J=8.6, 7.2 Hz, 2H), 4.18 (t, J=6.9 Hz, 1H), 3.60 (dd, J=16.0, 6.0 Hz, 1H), 3.46 (dd, J=15.5, 6.3 Hz, 1H). $^{13}$C NMR (126 MHz, Chloroform-d) δ 168.39, 161.76, 156.37, 145.43, 143.52, 143.49, 141.29, 141.03, 135.97, 130.14, 128.47, 127.83, 127.14, 124.99, 121.62, 121.50, 121.26, 120.05, 119.46, 83.39, 67.48, 53.74, 47.04, 28.47. MS (ESI) m/z=803.2 [M+Na]$^+$.

tert-Butyl (S)-3-amino-4-oxo-4-(((S)-1-oxo-3-(2H-tetrazol-5-yl)-1-((4-(trifluoromethoxy)phenyl)amino)propan-2-yl)amino)butanoate (88). Yield, 45%. $^1$H NMR (500 MHz, Methanol-d$_4$) δ 7.81-7.60 (m, 1H), 7.34-7.22 (m, 2H), 7.22-7.13 (m, 2H), 7.13-6.99 (m, 2H), 4.87-4.78 (m, 1H), 3.87 (dd, J=7.3, 5.5 Hz, 1H), 3.43 (dd, J=14.8, 5.2 Hz, 1H), 3.34 (d, J=8.5 Hz, 1H), 2.80 (dd, J=17.0, 5.5 Hz, 1H), 2.63 (dd, J=17.1, 7.5 Hz, 1H), 1.42 (s, 9H).

tert-Butyl 2-(((S)-1-(((S)-4-(tert-butoxy)-1,4-dioxo-1-(((S)-1-oxo-3-(2H-tetrazol-5-yl)-1-((4-(trifluoromethoxy)phenyl)amino)propan-2-yl)amino)butan-2-yl)amino)-3-(naphthalen-2-yl)-1-oxopropan-2-yl)carbamoyl)-5-chloro-1H-indole-1-carboxylate (89). Yield, 53%. $^1$H NMR (500 MHz, Acetone-d$_6$) δ 9.41 (s, 1H), 8.46 (d, J=6.5 Hz, 1H), 8.38 (d, J=6.9 Hz, 1H), 8.10 (d, J=8.1 Hz, 1H), 7.99 (d, J=8.9 Hz, 1H), 7.91-7.77 (m, 6H), 7.67-7.52 (m, 2H), 7.51-7.42 (m, 2H), 7.37 (dd, J=8.9, 2.2 Hz, 1H), 7.24 (d, J=8.6 Hz, 2H), 6.78 (s, 1H), 4.93 (dtd, J=12.4, 8.7, 7.9, 4.9 Hz, 2H), 4.69 (q, J=6.7 Hz, 1H), 3.66 (dd, J=15.4, 4.8 Hz, 1H), 3.60-3.42 (m, 2H), 3.35 (dd, J=14.2, 9.5 Hz, 1H), 2.97 (dd, J=16.6, 6.0 Hz, 1H), 2.76 (dd, J=16.6, 7.2 Hz, 1H), 1.50 (s, 9H), 1.41 (s, 9H).

(S)-3-((S)-2-(5-Chloro-1H-indole-2-carboxamido)-3-(naphthalen-2-yl)propanamido)-4-oxo-4-(((S)-1-oxo-3-(2H-tetrazol-5-yl)-1-((4-(trifluoromethoxy)phenyl)amino)propan-2-yl)amino)butanoic acid (52). Yield, 75%. $^1$H NMR (500 MHz, DMSO-d$_6$) δ 11.66 (s, 1H), 10.03 (s, 1H), 8.74 (dd, J=40.3, 7.8 Hz, 2H), 8.42 (d, J=7.6 Hz, 1H), 7.98-7.59 (m, 8H), 7.55 (d, J=8.4 Hz, 1H), 7.46-7.35 (m, 3H), 7.28 (d, J=8.5 Hz, 2H), 7.23-7.07 (m, 2H), 4.94-4.79 (m, 2H), 4.61 (q, J=7.0 Hz, 1H), 3.45 (dd, J=15.1, 6.3 Hz, 2H), 3.15 (d, J=12.1 Hz, 1H), 2.77 (dd, J=16.7, 5.5 Hz, 1H), 2.69-2.58 (m, 2H). $^{13}$C NMR (126 MHz, DMSO-d$_6$) δ 172.34, 172.27, 171.14, 168.99, 161.15, 144.31, 138.08, 136.46, 135.25, 133.38, 133.03, 132.23, 128.44, 128.32, 127.88, 127.75, 126.39, 125.82, 124.65, 123.94, 121.99, 121.45, 121.07, 114.30, 103.34, 54.88, 52.72, 50.44, 37.82, 36.37, 26.12. HRMS (ESI) Calcd for $C_{37}H_{31}ClF_3N_9O_7$ (M−H)$^-$ 804.1909, found 793.1919.

Synthesis of final products 53, 56, and 57. The synthetic routes for 53, 56, and 57 are shown in Scheme 12. All the amide coupling reaction in Scheme 2 used DMF as the solvent. The amide bond coupling reaction between N-Cbz-L-glutamic acid 5-tert-butyl ester or N-Cbz-L-glutamic acid 5-ethyl ester and various amines produced intermediate 62 g or 90, which underwent hydrogenation reaction to remove the Cbz protecting group and then coupled with (S)-2-((((9H-fluoren-9-yl)methoxy)carbonyl)amino)-3-(2H-tetrazol-5-yl)propanoic acid to yield 91. Removal of the Fmoc protecting group under basic condition and then coupling with 68a or 68 h gave 92, in which the Boc (and tert-butyl) protecting group(s) was removed by TFA in $CH_2Cl_2$ solution to offer the final products.

Scheme 12. Synthesis of 53, 56, and 57.

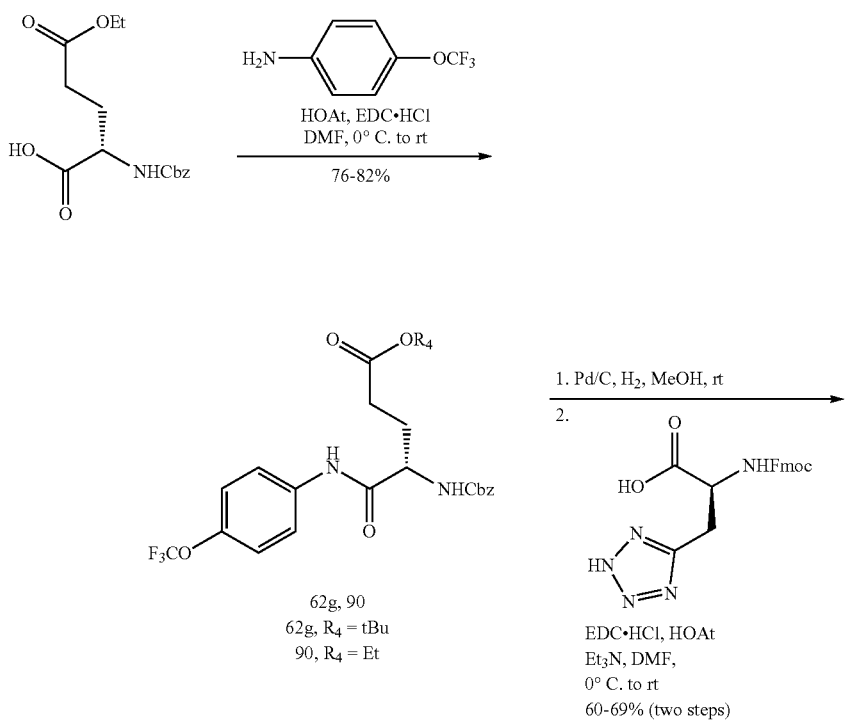

-continued
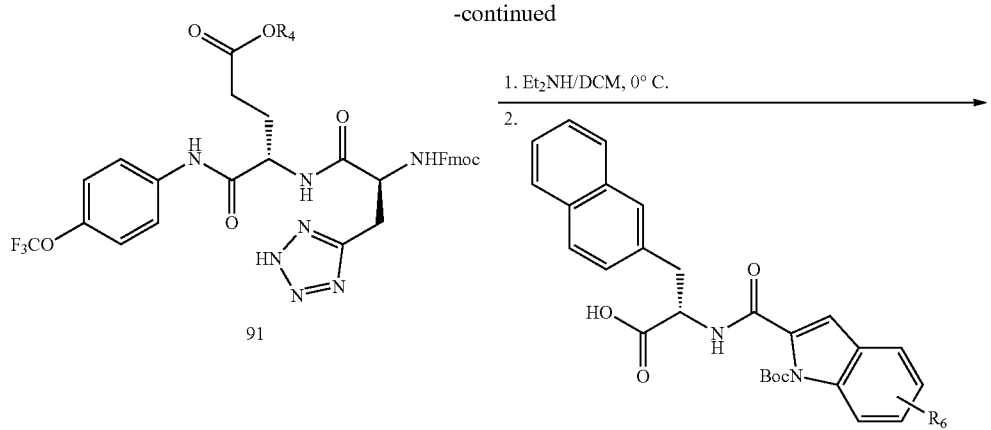
91
68a or 68h
EDC·HCl, HOAt, Et₃N
DMF, 0° C. to rt
53-58% (two steps)
1. Et₂NH/DCM, 0° C.
2.
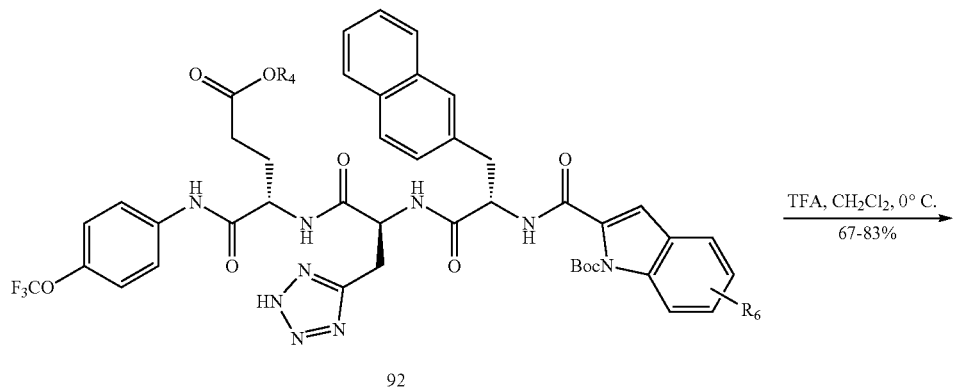
92
TFA, CH₂Cl₂, 0° C.
67-83%
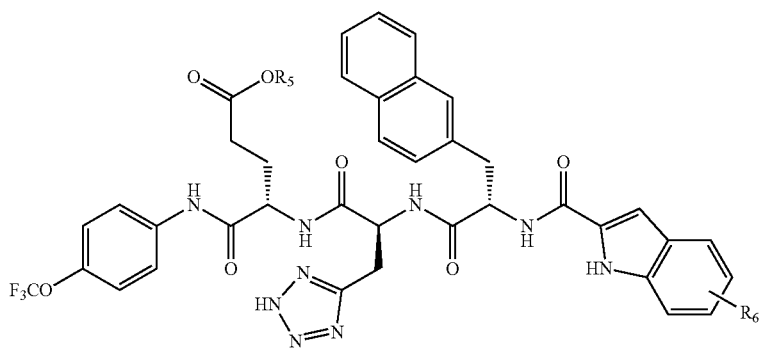
53, R₅ = H, R₆ = 5-Cl
56, R₅ = Et, R₆ = 5-Cl
57, R₅ = H, R₆ = 4,6-diCl
Ethyl (S)-4-(((benzyloxy)carbonyl)amino)-5-oxo-5-((4-(trifluoromethoxy)phenyl)amino)pentanoate (90). Yield, 76%. $^1$H NMR (500 MHz, DMSO-d$_6$) δ 10.25 (s, 1H), 8.09-7.58 (m, 3H), 7.53-7.15 (m, 6H), 5.33-4.85 (m, 2H), 4.16 (td, J=8.3, 5.6 Hz, 1H), 4.02 (qd, J=7.1, 1.3 Hz, 2H), 2.38 (ddd, J=8.5, 6.6, 3.8 Hz, 2H), 1.98 (pd, J=6.1, 2.4 Hz, 1H), 1.94-1.78 (m, 1H), 1.14 (t, J=7.1 Hz, 3H). $^{13}$C NMR (126 MHz, DMSO-d$_6$) δ 172.55, 171.08, 156.51, 144.10, 138.49, 137.38, 128.80, 128.29, 128.19, 122.07, 121.61, 121.13, 119.58, 66.00, 60.39, 55.16, 30.63, 27.39, 14.50. MS (ESI) m/z=469.2 [M+H]⁺.

tert-Butyl (S)-4-((S)-2-((((9H-fluoren-9-yl)methoxy)carbonyl)amino)-3-(2H-tetrazol-5-yl)propanamido)-5-oxo-5-((4-(trifluoromethoxy)phenyl)amino)pentanoate (91a). Yield, 60%. $^1$H NMR (500 MHz, DMSO-$d_6$) δ 10.26 (s, 1H), 8.35 (d, J=7.5 Hz, 1H), 7.88 (d, J=7.5 Hz, 2H), 7.80 (d, J=8.2 Hz, 1H), 7.75-7.69 (m, 2H), 7.66 (t, J=8.4 Hz, 2H), 7.41 (tt, J=7.5, 1.5 Hz, 2H), 7.31 (tt, J=7.4, 1.3 Hz, 4H), 4.58 (td, J=8.6, 5.3 Hz, 1H), 4.39 (td, J=8.1, 5.1 Hz, 1H), 4.29-4.15 (m, 3H), 3.39-3.34 (m, 1H), 3.23 (dd, J=15.3, 9.1 Hz, 1H), 2.37-2.18 (m, 2H), 1.99 (ddd, J=9.9, 8.4, 5.2 Hz, 1H), 1.86 (dtd, J=14.1, 9.2, 5.7 Hz, 1H), 1.33 (s, 9H). $^{13}$C NMR (126 MHz, DMSO-$d_6$) δ 171.93, 170.82, 170.52, 156.23, 144.18, 141.14, 138.35, 128.10, 127.57, 127.54, 125.77, 125.69, 122.06, 121.60, 121.31, 120.57, 119.57, 80.21, 66.37, 55.38, 53.49, 53.28, 47.00, 31.57, 28.14, 27.48. MS (ESI) m/z=724.3 [M+H]$^+$, 746.2 [M+Na]$^+$, 722.3 [M−H]$^−$.

Ethyl (S)-4-((S)-2-((((9H-fluoren-9-yl)methoxy)carbonyl)amino)-3-(2H-tetrazol-5-yl)propanamido)-5-oxo-5-((4-(trifluoromethoxy)phenyl)amino)pentanoate (91b). Yield, 69%. $^1$H NMR (500 MHz, DMSO-$d_6$) δ 10.23 (s, 1H), 8.34 (d, J=7.5 Hz, 1H), 7.88 (d, J=7.5 Hz, 2H), 7.78 (d, J=8.1 Hz, 1H), 7.74-7.69 (m, 2H), 7.66 (t, J=8.4 Hz, 2H), 7.40 (tt, J=7.6, 1.5 Hz, 2H), 7.31 (tt, J=7.4, 1.4 Hz, 5H), 4.57 (td, J=8.5, 5.4 Hz, 1H), 4.39 (td, J=8.2, 5.4 Hz, 1H), 4.31-4.13 (m, 3H), 3.98 (qd, J=7.1, 1.8 Hz, 2H), 3.22 (dd, J=15.3, 9.0 Hz, 2H), 2.41-2.25 (m, 2H), 2.04 (ddt, J=14.9, 9.8, 5.8 Hz, 1H), 1.95-1.82 (m, 1H), 1.10 (t, J=7.1 Hz, 3H). MS (ESI) m/z=696.2 [M+H]$^+$.

tert-Butyl 2-(((S)-1-(((S)-1-(((S)-5-(tert-butoxy)-1,5-dioxo-1-((4-(trifluoromethoxy)phenyl)amino)pentan-2-yl)amino)-1-oxo-3-(2H-tetrazol-5-yl)propan-2-yl)amino)-3-(naphthalen-2-yl)-1-oxopropan-2-yl)carbamoyl)-5-chloro-1H-indole-1-carboxylate (92a). Yield, 56%. $^1$H NMR (500 MHz, DMSO-d6) δ 10.34 (s, 1H), 9.02 (d, J=8.3 Hz, 1H), 8.65 (d, J=7.7 Hz, 1H), 8.34 (d, J=7.5 Hz, 1H), 7.84 (td, J=41.5, 40.5, 8.7 Hz, 8H), 7.60-7.18 (m, 6H), 6.78 (s, 1H), 5.00-4.72 (m, 2H), 4.40 (q, J=7.3 Hz, 1H), 3.31-2.87 (m, 4H), 2.28 (ddt, J=20.7, 15.7, 7.7 Hz, 2H), 2.01 (p, J=7.4, 6.9 Hz, 1H), 1.85 (h, J=6.8, 6.2 Hz, 1H), 1.31 (s, 9H), 1.26 (s, 9H).

tert-Butyl 5-chloro-2-(((S)-1-(((S)-1-(((S)-5-ethoxy-1,5-dioxo-1-((4-(trifluoromethoxy)phenyl)amino)pentan-2-yl)amino)-1-oxo-3-(2H-tetrazol-5-yl)propan-2-yl)amino)-3-(naphthalen-2-yl)-1-oxopropan-2-yl)carbamoyl)-1H-indole-1-carboxylate (92b). Yield, 58%. $^1$H NMR (500 MHz, DMSO-$d_6$) δ 10.39 (d, J=35.1 Hz, 1H), 9.00 (dd, J=30.5, 8.3 Hz, 1H), 8.70 (dd, J=48.7, 7.8 Hz, 1H), 8.39 (dd, J=36.7, 7.4 Hz, 1H), 8.08-7.61 (m, 8H), 7.61-7.22 (m, 6H), 6.76 (d, J=25.8 Hz, 1H), 4.99-4.70 (m, 2H), 4.40 (qd, J=7.9, 4.9 Hz, 1H), 4.15-3.81 (m, 2H), 3.32-2.86 (m, 4H), 2.37 (qd, J=9.5, 8.7, 4.3 Hz, 2H), 2.05 (d, J=10.5 Hz, 1H), 1.98-1.77 (m, 1H), 1.26 (s, 9H), 1.17-0.91 (m, 3H). MS (ESI) m/z=948.3 [M+H]$^+$, 970.3 [M+H]$^+$, 946.3 [M−H]$^−$.

tert-Butyl (S)-4-((S)-2-((S)-2-(4,6-dichloro-1H-indole-2-carboxamido)-3-(naphthalen-2-yl)propanamido)-3-(2H-tetrazol-5-yl)propanamido)-5-oxo-5-((4-(trifluoromethoxy)phenyl)amino)pentanoate (92c). Yield, 53%. $^1$H NMR (500 MHz, DMSO-$d_6$) δ 11.94 (d, J=2.3 Hz, 1H), 10.29 (s, 1H), 8.97 (d, J=8.4 Hz, 1H), 8.71 (d, J=7.6 Hz, 1H), 8.31 (d, J=7.5 Hz, 1H), 7.96-7.63 (m, 4H), 7.53 (dd, J=8.5, 1.7 Hz, 1H), 7.48-7.25 (m, 4H), 7.21 (dd, J=4.7, 1.7 Hz, 1H), 4.98-4.67 (m, 2H), 4.41 (td, J=8.1, 5.1 Hz, 1H), 3.44 (dd, J=15.3, 6.3 Hz, 1H), 3.30-3.28 (m, 2H), 3.14 (dd, J=13.9, 11.0 Hz, 1H), 2.29 (qdd, J=16.2, 11.8, 3.9 Hz, 2H), 2.02 (ddd, J=15.2, 10.2, 5.4 Hz, 1H), 1.94-1.74 (m, 1H), 1.31 (d, J=1.8 Hz, 9H).

(S)-4-((S)-2-((S)-2-(5-Chloro-1H-indole-2-carboxamido)-3-(naphthalen-2-yl)propanamido)-3-(2H-tetrazol-5-yl)propanamido)-5-oxo-5-((4-(trifluoromethoxy)phenyl)amino)pentanoic acid (53). Yield, 82%. $^1$H NMR (500 MHz, DMSO-$d_6$) δ 12.14 (s, 1H), 11.69-11.53 (m, 1H), 10.25 (s, 1H), 8.79 (d, J=8.3 Hz, 1H), 8.69 (d, J=7.5 Hz, 1H), 8.31 (d, J=7.4 Hz, 1H), 7.90-7.64 (m, 8H), 7.53 (d, J=8.4 Hz, 1H), 7.49-7.26 (m, 5H), 7.25-7.09 (m, 2H), 4.94-4.73 (m, 2H), 4.40 (td, J=8.0, 5.1 Hz, 1H), 3.56-3.41 (m, 2H), 3.14 (dd, J=13.9, 10.8 Hz, 2H), 2.39-2.22 (m, 2H), 2.04 (ddt, J=15.1, 10.6, 5.7 Hz, 1H), 1.89 (dtd, J=14.5, 9.0, 5.8 Hz, 1H). $^{13}$C NMR (126 MHz, DMSO-$d_6$) δ 174.23, 172.08, 170.55, 170.38, 161.16, 144.26, 138.24, 136.35, 135.26, 133.38, 132.97, 132.24, 128.44, 128.25, 127.88, 127.76, 126.41, 125.85, 124.67, 123.97, 122.04, 121.52, 121.09, 114.31, 103.39, 54.98, 53.60, 51.72, 37.78, 30.49, 27.59. HRMS (ESI) Calcd for $C_{38}H_{33}ClF_3N_9O_7$ (M−H)$^−$ 818.2065, found 818.2065.

Ethyl (S)-4-((S)-2-((S)-2-(5-chloro-1H-indole-2-carboxamido)-3-(naphthalen-2-yl)propanamido)-3-(2H-tetrazol-5-yl)propanamido)-5-oxo-5-((4-(trifluoromethoxy)phenyl)amino)pentanoate (56). Yield, 67%. $^1$H NMR (500 MHz, DMSO-$d_6$) δ 11.76-11.50 (m, 1H), 10.26-10.22 (m, 1H), 8.91-8.63 (m, 2H), 8.37-8.33 (m, 1H), 8.01-7.61 (m, 7H), 7.55-7.25 (m, 6H), 7.23-7.05 (m, 2H), 4.85 (ddt, J=29.7, 14.3, 5.9 Hz, 2H), 4.41 (tt, J=8.7, 4.5 Hz, 1H), 4.13-3.86 (m, 2H), 3.62-2.91 (m, 4H), 2.38 (qd, J=9.9, 9.3, 4.4 Hz, 2H), 2.07 (td, J=8.7, 4.8 Hz, 1H), 1.91 (dtd, J=14.3, 8.9, 5.8 Hz, 1H), 1.08 (t, J=7.0 Hz, 3H). $^{13}$C NMR (126 MHz, DMSO-$d_6$) δ 172.57, 172.10, 170.42, 161.17, 144.28, 138.24, 136.34, 135.27, 133.38, 132.97, 132.24, 128.45, 128.24, 127.91, 127.75, 126.43, 125.86, 124.67, 123.97, 122.05, 121.47, 121.38, 121.09, 119.57, 114.32, 103.38, 60.38, 55.02, 53.45, 51.72, 37.80, 30.41, 27.49, 14.44. HRMS (ESI) Calcd for $C_{40}H_{37}ClF_3N_9O_7$ (M−H)$^−$ 846.2378, found 846.2375.

(S)-4-((S)-2-((S)-2-(4,6-Dichloro-1H-indole-2-carboxamido)-3-(naphthalen-2-yl)propanamido)-3-(2H-tetrazol-5-yl)propanamido)-5-oxo-5-((4-(trifluoromethoxy)phenyl)amino)pentanoic acid (57). Yield, 83%. $^1$H NMR (500 MHz, DMSO-$d_6$) δ 11.90 (d, J=36.1 Hz, 1H), 10.23 (d, J=28.1 Hz, 1H), 8.95 (t, J=7.8 Hz, 1H), 8.73 (dd, J=28.2, 7.8 Hz, 1H), 8.35 (dd, J=42.8, 7.3 Hz, 1H), 7.92-7.64 (m, 6H), 7.59-7.16 (m, 8H), 5.00-4.76 (m, 2H), 4.40 (p, J=7.0 Hz, 1H), 3.31-2.97 (m, 4H), 2.33 (ttd, J=16.5, 12.7, 9.8, 6.1 Hz, 2H), 2.06 (dt, J=13.7, 6.2 Hz, 1H), 2.00-1.81 (m, 1H). $^{13}$C NMR (126 MHz, DMSO-$d_6$) δ 174.25, 174.22, 171.99, 171.85, 170.55, 170.43, 170.38, 160.69, 144.26, 138.25, 137.24, 137.20, 136.37, 136.34, 133.38, 133.25, 132.24, 128.25, 128.21, 127.92, 127.86, 127.75, 126.84, 126.43, 125.86, 125.15, 122.03, 121.97, 121.60, 121.51, 121.41, 119.92, 119.57, 111.55, 101.98, 54.98, 54.93, 53.71, 53.60, 51.74, 51.56, 37.78, 30.60, 30.49, 27.59, 27.46, 26.18. HRMS (ESI) Calcd for $C_{38}H_{32}Cl_2F_3N_9O_7$(M−H)$^−$ 852.1676, found 852.1686.

Synthesis of final product 54. The synthetic route for final product 54 is shown in Scheme 13.
Scheme 13. Synthesis of Final Compound 54.
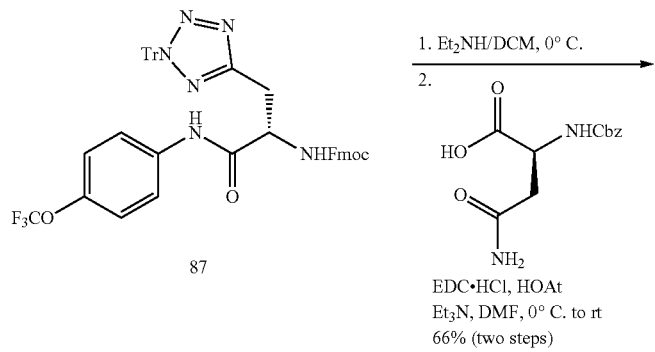
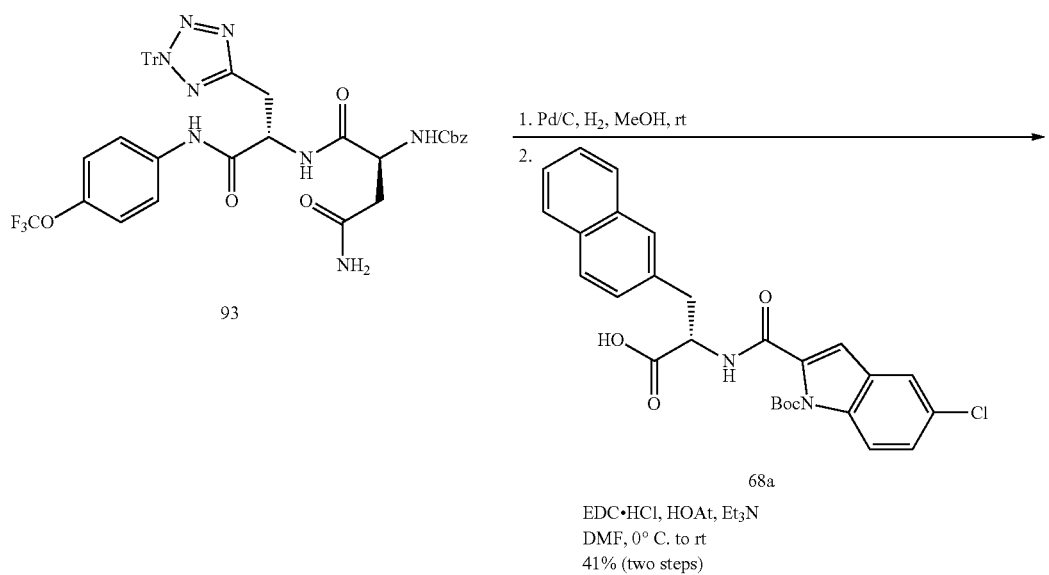
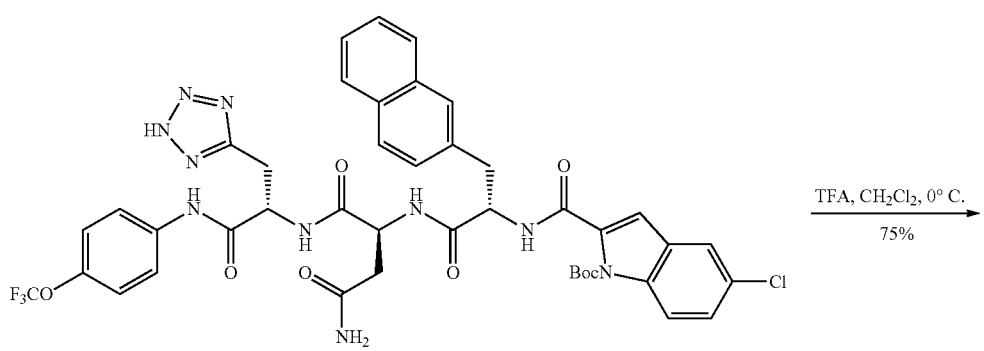

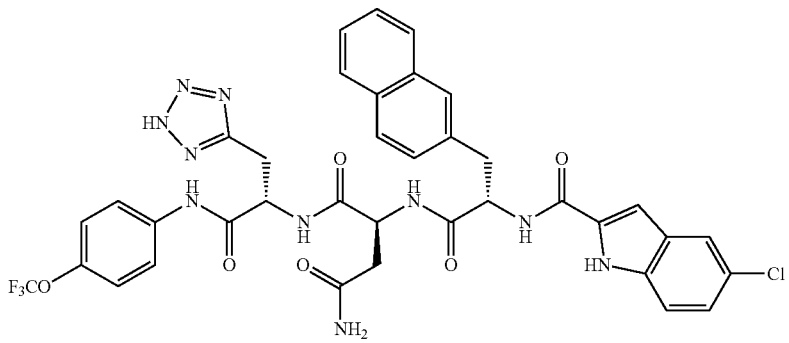

54

Benzyl ((S)-4-amino-1,4-dioxo-1-(((S)-1-oxo-1-((4-(trifluoromethoxy)phenyl)amino)-3-(2-trityl-2H-tetrazol-5-yl)propan-2-yl)amino)butan-2-yl)carbamate (93). Yield, 62%. $^1$H NMR (500 MHz, Chloroform-d) δ 8.88 (s, 1H), 7.84 (d, J=8.4 Hz, 1H), 7.53 (d, J=8.5 Hz, 2H), 7.34-7.09 (m, 13H), 7.02 (d, J=8.6 Hz, 2H), 6.96-6.80 (m, 7H), 6.13 (d, J=6.4 Hz, 1H), 5.64 (s, 1H), 5.30 (s, 1H), 5.09-4.94 (m, 2H), 4.90 (d, J=12.1 Hz, 1H), 4.32 (q, J=5.9 Hz, 1H), 3.70 (dd, J=15.9, 5.3 Hz, 1H), 3.26 (dd, J=15.8, 5.0 Hz, 1H), 2.66 (d, J=5.7 Hz, 2H). MS (ESI) m/z=829.3 [M+Na]$^+$.

tert-Butyl 2-(((S)-1-(((S)-4-amino-1,4-dioxo-1-(((S)-1-oxo-3-(2H-tetrazol-5-yl)-1-((4-(trifluoromethoxy)phenyl)amino)propan-2-yl)amino)butan-2-yl)amino)-3-(naphthalen-2-yl)-1-oxopropan-2-yl)carbamoyl)-5-chloro-1H-indole-1-carboxylate (94). Yield, 40%. $^1$H NMR (500 MHz, DMSO-d$_6$) δ 9.96 (s, 1H), 8.94 (d, J=8.5 Hz, 1H), 8.60 (t, J=7.6 Hz, 2H), 7.92 (d, J=8.9 Hz, 1H), 7.87-7.71 (m, 6H), 7.66 (s, 1H), 7.55 (dd, J=8.4, 1.7 Hz, 1H), 7.50-7.35 (m, 3H), 7.29 (d, J=8.5 Hz, 2H), 7.19 (d, J=8.3 Hz, 1H), 6.74 (s, 1H), 4.86 (dddd, J=19.4, 11.5, 8.1, 4.7 Hz, 2H), 4.59 (q, J=7.0 Hz, 1H), 3.52 (dd, J=15.3, 5.7 Hz, 1H), 3.29-3.24 (m, 1H), 3.16 (s, 1H), 3.02 (dd, J=14.0, 10.8 Hz, 1H), 2.69 (dd, J=15.9, 7.5 Hz, 1H), 2.57 (dd, J=15.7, 5.8 Hz, 1H), 1.26 (s, 9H). MS (ESI) m/z=905.3 [M+H]$^+$, 903.3 [M−H]$^−$.

(S)-2-((S)-2-(5-Chloro-1H-indole-2-carboxamido)-3-(naphthalen-2-yl)propanamido)-N$^1$—((S)-1-oxo-3-(2H-tetrazol-5-yl)-1-((4-(trifluoromethoxy)phenyl)amino)propan-2-yl)succinamide (54). Yield, 75%. $^1$H NMR (500 MHz, DMSO-d$_6$) δ 11.63 (d, J=2.2 Hz, 1H), 9.99 (s, 1H), 8.75 (d, J=8.5 Hz, 1H), 8.59 (t, J=8.2 Hz, 2H), 7.94-7.73 (m, 6H), 7.69 (d, J=2.0 Hz, 1H), 7.64 (s, 1H), 7.56 (d, J=8.4 Hz, 1H), 7.48-7.33 (m, 3H), 7.29 (d, J=8.6 Hz, 2H), 7.22-7.06 (m, 3H), 5.00-4.75 (m, 2H), 4.60 (q, J=6.9 Hz, 1H), 3.52 (dd, J=15.2, 5.8 Hz, 1H), 3.24 (dd, J=14.0, 3.7 Hz, 2H), 3.12 (dd, J=14.0, 11.0 Hz, 1H), 2.69 (dd, J=15.7, 7.2 Hz, 1H), 2.59 (dd, J=15.7, 5.9 Hz, 1H). $^{13}$C NMR (126 MHz, DMSO-d$_6$) δ 172.53, 171.97, 171.48, 161.09, 144.34, 138.13, 136.50, 135.24, 133.38, 133.05, 132.23, 128.45, 128.35, 127.90, 127.82, 127.76, 126.38, 125.81, 124.65, 123.93, 121.90, 121.65, 121.08, 120.57 (d, J=253.8 Hz), 114.29, 103.31, 54.79, 52.45, 50.40, 37.86, 37.45, 25.95. HRMS (ESI) Calcd for C$_{37}$H$_{32}$ClF$_3$N$_{10}$O$_6$ (M−H)$^−$ 803.2069, found 803.2065.

Synthesis of final product 55. The synthetic route for 55 is shown in Scheme 14. The amide bond coupling reaction between N-Cbz-L-glutamine and 4-(trifluoromethoxy) aniline and then the deprotection of the Cbz protecting group produced 95, which coupled with (S)-2-(((((9H-fluoren-9-yl)methoxy)carbonyl)amino)-3-(2H-tetrazol-5-yl)propanoic acid afforded 96. Removal of the Fmoc group in 96 and then coupling with intermediate 86a gave 97. The Boc deprotection yielded final product Scheme 14. Synthesis of 55.

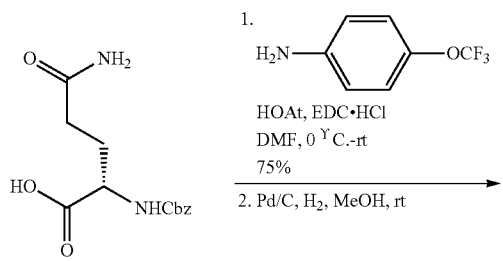

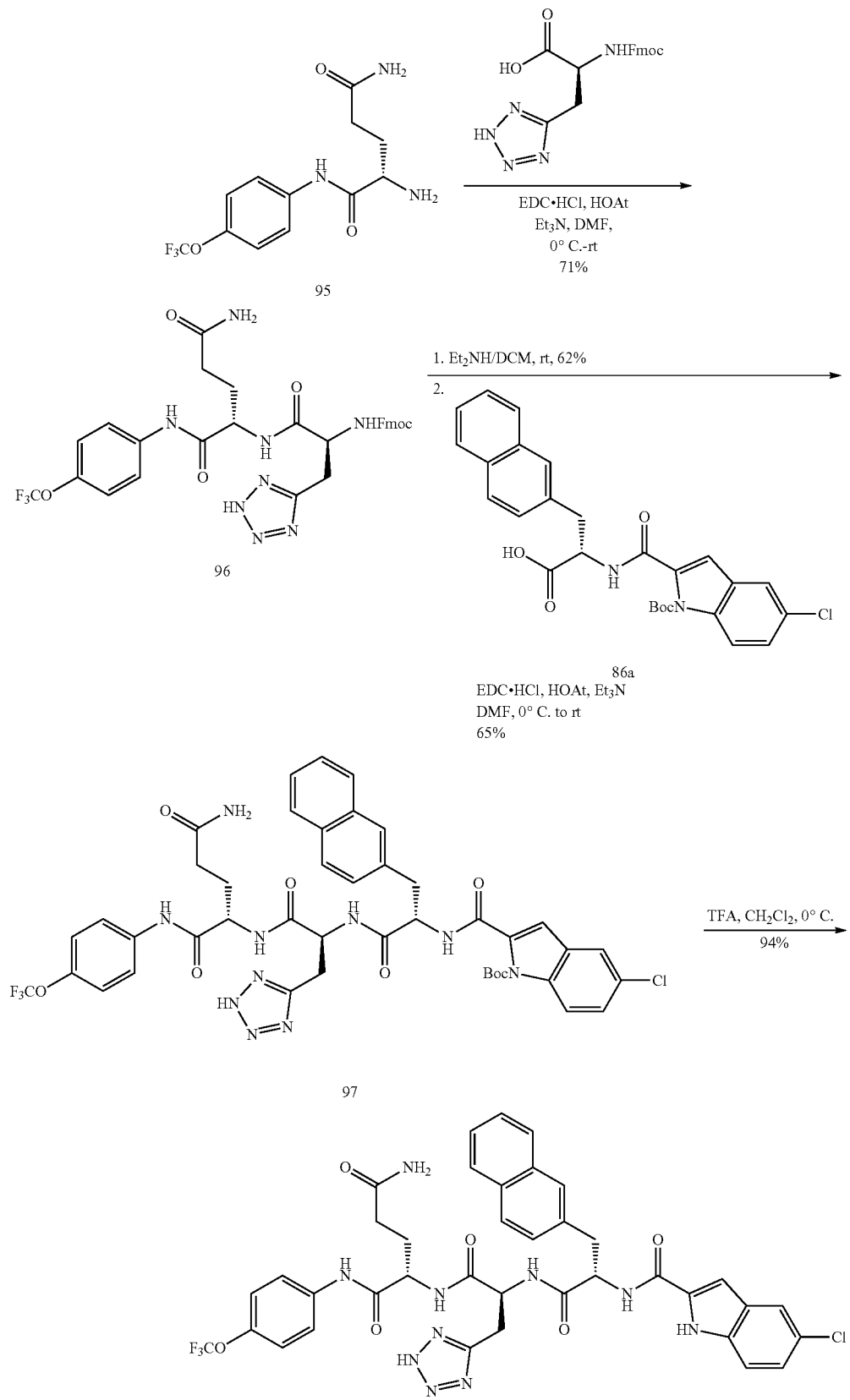

(S)-2-Amino-N[1]-(4-(trifluoromethoxy)phenyl)pentanediamide (95). Yield, 75%. $^1$H NMR (500 MHz, DMSO-$d_6$) δ 7.91-7.62 (m, 2H), 7.43-7.12 (m, 3H), 6.71 (s, 1H), 3.45-3.15 (m, 3H), 2.26-2.05 (m, 2H), 1.86 (dddd, J=13.4, 9.3, 6.6, 5.4 Hz, 1H), 1.75-1.58 (m, 1H). MS (ESI) m/z=306.1 [M+H]$^+$, 304.2 [M−H]$^−$.

(9H-Fluoren-9-yl)methyl ((S)-1-(((S)-5-amino-1,5-dioxo-1-((4-(trifluoromethoxy)phenyl)amino)pentan-2-yl)amino)-1-oxo-3-(2H-tetrazol-5-yl)propan-2-yl)carbamate (96). Yield, 71%. $^1$H NMR (500 MHz, DMSO-$d_6$) δ 10.34 (s, 1H), 8.36 (d, J=7.3 Hz, 1H), 7.88 (d, J=7.6 Hz, 2H), 7.74 (dd, J=8.5, 6.2 Hz, 3H), 7.67 (t, J=8.2 Hz, 2H), 7.53-7.37 (m, 2H), 7.37-7.07 (m, 5H), 7.01-6.61 (m, 1H), 4.55 (td, J=8.4, 5.4 Hz, 1H), 4.40-4.14 (m, 4H), 3.22 (dd, J=15.3, 8.9 Hz, 2H), 2.15 (dt, J=9.3, 6.3 Hz, 2H), 1.99 (s, 1H), 1.87-1.73 (m, 1H). $^{13}$C NMR (126 MHz, DMSO-$d_6$) δ 173.93, 170.90, 170.84, 156.24, 144.19, 141.13, 138.41, 128.11, 127.60, 127.58, 125.79, 125.71, 122.03, 121.61, 121.41, 120.56, 119.58, 66.38, 60.22, 53.44, 47.01, 31.75, 28.04. MS (ESI) m/z=667.3 [M+H]$^+$, 665.3 [M−H]$^−$.

tert-Butyl 2-(((S)-1-(((S)-1-(((S)-5-amino-1,5-dioxo-1-((4-(trifluoromethoxy)phenyl)amino)pentan-2-yl)amino)-1-oxo-3-(2H-tetrazol-5-yl)propan-2-yl)amino)-3-(naphthalen-2-yl)-1-oxopropan-2-yl)carbamoyl)-5-chloro-1H-indole-1-carboxylate (97). Yield, 65%. $^1$H NMR (500 MHz, DMSO-$d_6$) δ 10.33 (s, 1H), 9.01 (d, J=8.4 Hz, 1H), 8.63 (d, J=7.6 Hz, 1H), 8.39 (d, J=7.3 Hz, 1H), 7.99-7.62 (m, 8H), 7.56-7.20 (m, 7H), 6.93-6.62 (m, 2H), 4.81 (dt, J=7.6, 4.2 Hz, 2H), 4.37 (td, J=7.8, 5.6 Hz, 1H), 3.43-3.03 (m, 4H), 2.30-2.12 (m, 2H), 2.03-1.99 (m, 1H), 1.88 (ddt, J=11.8, 8.0, 3.6 Hz, 1H), 1.25 (s, 9H). MS (ESI) m/z=919.3 [M+H]$^+$, 917.2 [M−H]$^−$.

(S)-2-((S)-2-((S)-2-(5-Chloro-1H-indole-2-carboxamido)-3-(naphthalen-2-yl)propanamido)-3-(2H-tetrazol-5-yl)propanamido)-N[1]-(4-(trifluoromethoxy)phenyl)pentanediamide (55). Yield, 75%. $^1$H NMR (500 MHz, DMSO-d6) δ 11.65 (s, 1H), 10.27 (s, 1H), 8.81 (d, J=8.1 Hz, 1H), 8.65 (d, J=7.5 Hz, 1H), 8.29 (d, J=7.1 Hz, 1H), 7.97-7.66 (m, 7H), 7.52 (d, J=8.4 Hz, 1H), 7.49-7.26 (m, 6H), 7.21-7.07 (m, 2H), 6.85 (s, 1H), 4.83 (ddd, J=21.3, 12.4, 5.4 Hz, 2H), 4.35 (q, J=7.0 Hz, 1H), 3.44 (dd, J=15.3, 6.0 Hz, 1H), 3.39-3.22 (m, 2H), 3.15 (dd, J=13.9, 10.7 Hz, 1H), 2.18 (t, J=8.0 Hz, 2H), 2.01 (p, J=7.6 Hz, 1H), 1.92 (dq, J=15.2, 8.0 Hz, 1H). $^{13}$C NMR (126 MHz, DMSO-$d_6$) δ 174.10, 172.10, 170.73, 170.32, 161.31, 144.22, 138.33, 136.36, 135.29, 133.39, 132.94, 132.24, 128.44, 128.23, 127.91, 127.85, 127.77, 126.41, 125.86, 124.68, 123.99, 122.05, 121.42, 121.11, 120.59 (d, J=255.0 Hz), 114.34, 103.43, 55.17, 54.03, 51.81, 37.68, 31.73, 28.14, 26.16. HRMS (ESI) Calcd for $C_{38}H_{34}ClF_3N_{10}O_6$ (M−H)$^−$ 817.2225, found 817.2226.

Synthesis of intermediates 68a-68 h. The synthetic route for intermediates 68a-68 h is shown in Scheme 15.

Scheme 15. Synthesis of Intermediates 68a-68h.

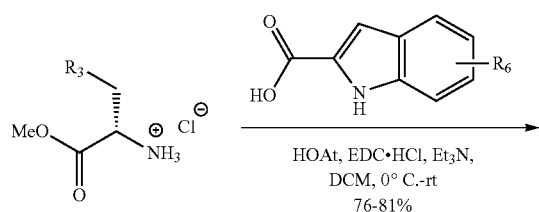

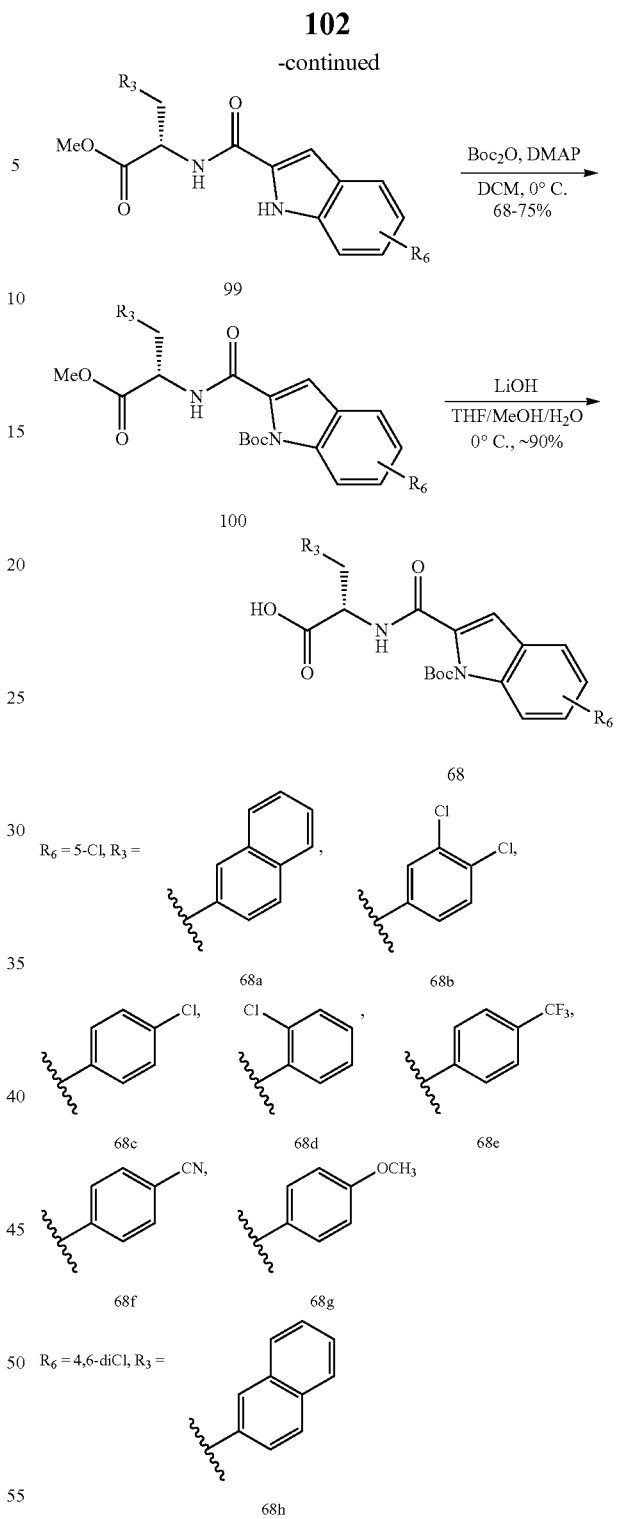

Methyl (S)-2-(5-chloro-1H-indole-2-carboxamido)-3-(naphthalen-2-yl)propanoate (99a). $^1$H NMR (500 MHz, Chloroform-d) δ 9.66 (s, 1H), 7.91-7.71 (m, 3H), 7.63-7.59 (m, 1H), 7.57 (d, J=1.9 Hz, 1H), 7.51-7.42 (m, 2H), 7.35 (dt, J=8.8, 0.8 Hz, 1H), 7.28 (dd, J=8.4, 1.8 Hz, 1H), 7.23 (dd, J=8.7, 2.0 Hz, 1H), 6.84-6.71 (m, 2H), 5.21 (dt, J=7.9, 5.7 Hz, 1H), 3.78 (s, 3H), 3.60-3.31 (m, 2H). $^{13}$C NMR (126 MHz, Chloroform-d) δ 171.81, 160.82, 134.79, 133.47, 133.06, 132.58, 131.15, 128.48, 128.47, 128.16, 127.71, 127.58, 127.25, 126.34, 125.94, 125.24, 121.24, 113.11, 102.36, 53.40, 52.63, 38.28. MS (ESI) m/z=429.1 [M+Na]$^+$.

Methyl (S)-2-(5-chloro-1H-indole-2-carboxamido)-3-(3,4-dichlorophenyl)propanoate (99b). $^1$H NMR (500 MHz, Chloroform-d) δ 10.27 (s, 1H), 7.54 (d, J=2.0 Hz, 1H), 7.35-7.30 (m, 2H), 7.29 (d, J=2.1 Hz, 1H), 7.21 (dd, J=8.8, 2.0 Hz, 1H), 7.14 (d, J=7.8 Hz, 1H), 7.01 (dd, J=8.2, 2.1 Hz, 1H), 6.81 (dd, J=2.3, 0.9 Hz, 1H), 5.12 (dt, J=7.7, 6.1 Hz, 1H), 3.82 (s, 3H), 3.27 (dd, J=14.0, 5.8 Hz, 1H), 3.18 (dd, J=14.0, 6.4 Hz, 1H). $^{13}$C NMR (126 MHz, Chloroform-d) δ 171.90, 161.37, 136.01, 135.13, 132.67, 131.55, 131.23, 130.81, 130.62, 128.62, 128.31, 126.27, 125.23, 121.19, 113.27, 102.77, 53.38, 52.90, 37.16. MS (ESI) m/z=447.0 [M+Na]$^+$.

Methyl (S)-2-(5-chloro-1H-indole-2-carboxamido)-3-(4-chlorophenyl)propanoate (99c). $^1$H NMR (500 MHz, Chloroform-d) δ 10.18 (s, 1H), 7.47 (d, J=2.1 Hz, 1H), 7.24 (d, J=8.7 Hz, 1H), 7.17-7.08 (m, 3H), 7.05-6.96 (m, 2H), 6.92 (d, J=7.8 Hz, 1H), 6.75-6.46 (m, 1H), 5.03 (dt, J=7.7, 6.0 Hz, 1H), 3.71 (s, 3H), 3.20 (dd, J=14.0, 5.7 Hz, 1H), 3.12 (dd, J=14.0, 6.2 Hz, 1H). $^{13}$C NMR (126 MHz, Chloroform-d) δ 171.96, 161.23, 135.10, 134.14, 133.31, 130.94, 130.60, 128.90, 128.34, 126.26, 125.18, 121.18, 113.29, 102.58, 53.48, 52.78, 37.39. MS (ESI) m/z=391.1 [M+H]$^+$, 413.1 [M+Na]$^+$, 389.0 [M−H]$^-$.

Methyl (S)-2-(5-chloro-1H-indole-2-carboxamido)-3-(2-chlorophenyl)propanoate (99 d). $^1$H NMR (500 MHz, Chloroform-d) δ 10.43 (s, 1H), 7.56 (d, J=2.1 Hz, 1H), 7.40 (dd, J=5.8, 3.5 Hz, 1H), 7.37-7.06 (m, 6H), 6.83 (d, J=2.0 Hz, 1H), 5.22 (qd, J=7.0, 6.1, 2.4 Hz, 1H), 3.82 (s, 3H), 3.50 (dd, J=14.0, 5.7 Hz, 1H), 3.38 (dd, J=13.9, 8.3 Hz, 1H). $^{13}$C NMR (126 MHz, Chloroform-d) δ 172.41, 161.53, 135.15, 134.35, 133.97, 131.36, 130.99, 129.81, 128.87, 128.29, 127.15, 126.08, 124.96, 121.08, 113.44, 102.59, 102.56, 52.90, 52.80, 35.61. MS (ESI) m/z=391.1 [M+H]$^+$, 413.1 [M+Na]$^+$.

Methyl (S)-2-(5-chloro-1H-indole-2-carboxamido)-3-(4-(trifluoromethyl)phenyl)propanoate (99e). $^1$H NMR (500 MHz, Acetone-d$_6$) δ 11.09 (s, 1H), 8.26 (d, J=8.3 Hz, 1H), 7.72-7.48 (m, 6H), 7.23 (dd, J=8.7, 2.0 Hz, 1H), 7.17 (dd, J=2.2, 0.9 Hz, 1H), 5.06 (ddd, J=9.4, 8.2, 5.3 Hz, 1H), 3.72 (s, 3H), 3.43 (dd, J=14.0, 5.3 Hz, 1H), 3.29 (dd, J=14.0, 9.4 Hz, 1H). $^{13}$C NMR (126 MHz, Acetone-d$_6$) δ 171.53, 161.11, 142.26, 135.32, 132.24, 130.02, 128.69, 128.51, 128.25, 125.61, 125.32, 125.17 (q, J=3.8 Hz), 124.19, 123.45, 120.88, 113.78, 102.63, 53.67, 51.75, 36.86. MS (ESI) m/z=425.1 [M+H]$^+$, 447.1 [M+Na]$^+$.

Methyl (S)-2-(5-chloro-1H-indole-2-carboxamido)-3-(4-cyanophenyl)propanoate (99f). $^1$H NMR (500 MHz, Chloroform-d) δ 10.36 (d, J=2.2 Hz, 1H), 7.40 (dd, J=8.7, 2.1 Hz, 3H), 7.33-7.14 (m, 4H), 7.09 (dd, J=8.7, 2.0 Hz, 1H), 6.74 (dd, J=2.3, 0.9 Hz, 1H), 5.04 (td, J=7.4, 5.7 Hz, 1H), 3.70 (s, 3H), 3.28 (dd, J=13.9, 5.7 Hz, 1H), 3.16 (dd, J=13.9, 7.1 Hz, 1H). $^{13}$C NMR (126 MHz, Chloroform-d) δ 171.87, 161.50, 141.64, 135.21, 132.37, 130.80, 130.08, 128.27, 126.20, 125.14, 121.17, 118.65, 113.39, 111.11, 102.92, 53.39, 52.95, 38.05. MS (ESI) m/z=382.1 [M+H]$^+$, 404.1 [M+Na]$^+$, 380.1 [M−H]$^-$.

Methyl (S)-2-(5-chloro-1H-indole-2-carboxamido)-3-(4-methoxyphenyl)propanoate (99 g). $^1$H NMR (500 MHz, Chloroform-d) δ 10.82 (d, J=2.3 Hz, 1H), 7.52 (d, J=1.9 Hz, 1H), 7.41 (d, J=7.9 Hz, 1H), 7.34 (dt, J=8.7, 0.8 Hz, 1H), 7.21 (dd, J=8.7, 2.0 Hz, 1H), 7.18 (s, 1H), 7.16 (s, 1H), 7.05-6.68 (m, 3H), 5.16 (ddd, J=7.9, 6.9, 5.7 Hz, 1H), 3.82 (s, 3H), 3.76 (s, 3H), 3.31 (dd, J=14.0, 5.6 Hz, 1H), 3.23 (dd, J=14.0, 7.0 Hz, 1H). $^{13}$C NMR (126 MHz, Chloroform-d) δ 172.76, 161.68, 158.85, 135.33, 131.20, 130.29, 128.32, 127.80, 125.97, 124.85, 121.05, 114.21, 113.52, 102.70, 55.20, 54.11, 52.70, 37.08. MS (ESI) m/z=387.1 [M+H]$^+$, 409.1 [M+Na]$^+$.

tert-Butyl (S)-5-chloro-2-((1-methoxy-3-(naphthalen-2-yl)-1-oxopropan-2-yl)carbamoyl)-1H-indole-1-carboxylate (100a). To the solution of methyl (S)-2-(5-chloro-1H-indole-2-carboxamido)-3 (naphthalen-2-yl)propanoate (1 eq) in DCM at 0° C. was added Boc$_2$O (1.5 eq) and DMAP (0.01 eq). The mixture was stirred at 0° C. for 4 hrs. Water was added to the mixture. The organic layer was concentrated and the residue was further purified by silica column. $^1$H NMR (500 MHz, Chloroform-d) δ 8.02 (d, J=8.9 Hz, 1H), 7.89-7.70 (m, 3H), 7.67-7.54 (m, 1H), 7.52-7.39 (m, 3H), 7.31 (ddd, J=9.1, 7.6, 1.9 Hz, 2H), 6.62 (d, J=0.7 Hz, 1H), 6.59-6.50 (m, 1H), 5.16 (dt, J=7.9, 5.7 Hz, 1H), 3.79 (s, 3H), 3.50 (dd, J=13.9, 5.8 Hz, 1H), 3.39 (dd, J=13.9, 5.5 Hz, 1H), 1.58 (s, 9H). $^{13}$C NMR (126 MHz, Chloroform-d) δ 171.65, 161.30, 148.82, 135.47, 135.14, 133.43, 133.12, 132.59, 128.82, 128.77, 128.40, 128.32, 127.73, 127.52, 127.29, 126.40, 126.35, 125.92, 121.05, 116.35, 110.45, 85.16, 53.45, 52.55, 38.04, 27.78. MS (ESI) m/z=529.2 [M+Na]$^+$, 505.2 [M−H]$^-$. Hydrolysis of 100a yielded compound 68a.

tert-Butyl (S)-5-chloro-2-((3-(3,4-dichlorophenyl)-1-methoxy-1-oxopropan-2-yl)carbamoyl)-1H-indole-1-carboxylate (100b). $^1$H NMR (500 MHz, Chloroform-d) δ 7.98 (d, J=8.9 Hz, 1H), 7.50 (d, J=2.1 Hz, 1H), 7.36 (d, J=8.2 Hz, 1H), 7.33-7.27 (m, 2H), 7.03 (dd, J=8.2, 2.1 Hz, 1H), 6.88-6.43 (m, 2H), 5.03 (dt, J=7.5, 5.6 Hz, 1H), 3.78 (s, 3H), 3.30 (dd, J=14.0, 5.7 Hz, 1H), 3.15 (dd, J=14.0, 5.4 Hz, 1H), 1.60 (s, 10H). $^{13}$C NMR (126 MHz, Chloroform-d) δ 171.16, 161.38, 148.83, 136.05, 135.32, 134.92, 132.53, 131.52, 131.48, 130.54, 128.89, 128.80, 128.76, 126.48, 121.15, 116.38, 110.63, 85.31, 53.29, 52.70, 36.89, 27.83. MS (ESI) m/z=547.1 [M+Na]$^+$, 523.1 [M−H]$^-$. Hydrolysis of 100b yielded compound 68b.

tert-Butyl (S)-5-chloro-2-((3-(4-chlorophenyl)-1-methoxy-1-oxopropan-2-yl)carbamoyl)-1H-indole-1-carboxylate (100c). $^1$H NMR (500 MHz, Chloroform-d) δ 8.02 (d, J=8.9 Hz, 1H), 7.52 (d, J=2.0 Hz, 1H), 7.37-7.23 (m, 3H), 7.18-7.03 (m, 2H), 6.68 (d, J=21.6 Hz, 2H), 5.07 (dt, J=7.7, 5.6 Hz, 1H), 3.78 (s, 3H), 3.31 (dd, J=14.0, 5.8 Hz, 1H), 3.20 (dd, J=14.0, 5.5 Hz, 1H), 1.61 (s, 9H). $^{13}$C NMR (126 MHz, Chloroform-d) δ 171.41, 161.31, 148.83, 135.38, 135.03, 134.19, 133.26, 130.75, 128.87, 128.79, 128.77, 126.44, 121.12, 116.36, 110.46, 85.24, 53.32, 52.59, 37.25, 27.80. MS (ESI) m/z=513.1 [M+Na]$^+$, 489.2 [M−H]$^-$. Hydrolysis of 100c yielded compound 68c.

tert-Butyl (S)-5-chloro-2-((3-(2-chlorophenyl)-1-methoxy-1-oxopropan-2-yl)carbamoyl)-1H-indole-1-carboxylate (100 d). $^1$H NMR (500 MHz, Chloroform-d) δ 7.90 (d, J=9.0 Hz, 1H), 7.37 (d, J=2.1 Hz, 1H), 7.32-7.25 (m, 1H), 7.23-7.16 (m, 2H), 7.15-7.01 (m, 2H), 6.72 (d, J=8.3 Hz, 1H), 6.58 (d, J=0.7 Hz, 1H), 5.02 (td, J=7.9, 6.1 Hz, 1H), 3.65 (s, 3H), 3.30 (d, J=6.1 Hz, 1H), 3.21 (dd, J=13.9, 7.6 Hz, 1H), 1.44 (s, 9H). $^{13}$C NMR (126 MHz, Chloroform-d) δ 171.76, 161.45, 148.79, 135.43, 134.99, 134.46, 133.92, 131.51, 129.72, 128.80, 128.73, 128.71, 127.03, 126.29, 121.05, 116.26, 110.40, 85.08, 52.61, 52.52, 35.58, 27.67. MS (ESI) m/z=513.1 [M+Na]$^+$, Hydrolysis of 100 d yielded compound 68d.

tert-Butyl (S)-5-chloro-2-((1-methoxy-1-oxo-3-(4-(trifluoromethyl)phenyl)propan-2-yl)carbamoyl)-1H-indole-1-carboxylate (100e). $^1$H NMR (500 MHz, Acetone-d$_6$) δ 8.22 (d, J=8.3 Hz, 1H), 8.05 (d, J=8.8 Hz, 1H), 7.78-7.50 (m, 5H), 7.37 (dd, J=8.9, 2.2 Hz, 1H), 6.85 (s, 1H), 5.01 (td, J=8.7, 5.3 Hz, 1H), 3.74 (s, 3H), 3.41 (dd, J=13.9, 5.3 Hz, 1H), 3.25 (dd, J=13.9, 8.9 Hz, 1H), 1.49 (s, 9H). $^{13}$C NMR (126 MHz, Acetone-$d_6$) δ 171.36, 161.34, 148.79, 142.00, 135.75, 135.32, 130.18, 129.10, 128.53 (d, J=32.0 Hz), 128.16, 125.79, 125.63, 125.23 (q, J=3.8 Hz), 123.48, 121.07, 115.94, 109.89, 84.63, 53.74, 51.76, 37.12, 26.85. MS (ESI) m/z=547.1 [M+Na]$^+$, 523.1 [M−H]$^−$, Hydrolysis of 100e yielded compound 68e.

tert-Butyl (S)-5-chloro-2-((3-(4-cyanophenyl)-1-methoxy-1-oxopropan-2-yl)carbamoyl)-1H-indole-1-carboxylate (100f). $^1$H NMR (500 MHz, Chloroform-d) δ 7.82 (dd, J=9.0, 2.4 Hz, 1H), 7.46 (dd, J=8.3, 2.0 Hz, 2H), 7.33 (d, J=2.2 Hz, 1H), 7.26-7.19 (m, 2H), 7.16 (dt, J=9.0, 2.3 Hz, 1H), 6.94 (t, J=7.4 Hz, 1H), 6.56 (d, J=2.0 Hz, 1H), 4.95 (dt, J=8.0, 6.0 Hz, 1H), 3.64 (d, J=2.0 Hz, 3H), 3.25 (ddd, J=14.0, 5.9, 2.2 Hz, 1H), 3.11 (dd, J=13.9, 6.4 Hz, 1H), 1.47 (d, J=2.4 Hz, 9H). $^{13}$C NMR (126 MHz, Chloroform-d) δ 171.09, 161.51, 148.77, 141.72, 135.17, 134.83, 132.24, 130.24, 128.73, 128.69, 126.33, 121.06, 118.64, 116.24, 111.03, 110.52, 85.24, 53.19, 52.65, 37.87, 27.74. MS (ESI) m/z=504.2 [M+Na]$^+$, 480.2 [M−H]$^−$, Hydrolysis of 100f yielded compound 68f.

tert-Butyl (S)-5-chloro-2-((1-methoxy-3-(4-methoxyphenyl)-1-oxopropan-2-yl)carbamoyl)-1H-indole-1-carboxylate (100 g). $^1$H NMR (500 MHz, Chloroform-d) δ 8.20-7.82 (m, 1H), 7.48 (d, J=2.0 Hz, 1H), 7.30 (dd, J=8.9, 2.1 Hz, 1H), 7.12-7.00 (m, 2H), 6.92-6.74 (m, 2H), 6.69-6.50 (m, 2H), 5.03 (dt, J=8.0, 5.6 Hz, 1H), 3.77 (s, 3H), 3.76 (s, 3H), 3.23 (dd, J=14.0, 5.7 Hz, 1H), 3.15 (dd, J=14.0, 5.6 Hz, 1H), 1.58 (s, 9H). $^{13}$C NMR (126 MHz, Chloroform-d) δ 171.72, 161.29, 158.85, 148.82, 135.42, 135.19, 130.39, 128.78, 128.76, 127.53, 126.32, 121.05, 116.32, 114.07, 110.28, 85.13, 55.23, 53.52, 52.46, 37.07, 27.76. MS (ESI) m/z=509.1 [M+Na]$^+$, Hydrolysis of 100 g yielded compound 68g.

Methyl (S)-2-(4,6-dichloro-1H-indole-2-carboxamido)-3-(naphthalen-2-yl)propanoate (99 h). $^1$H NMR (500 MHz, DMSO-$d_6$) δ 12.04 (s, 1H), 9.15 (d, J=8.0 Hz, 1H), 7.91-7.77 (m, 4H), 7.55-7.41 (m, 3H), 7.41-7.31 (m, 2H), 7.23 (d, J=1.7 Hz, 1H), 4.86 (ddd, J=10.1, 8.0, 5.3 Hz, 1H), 3.66 (s, 3H), 3.38 (dd, J=13.9, 5.3 Hz, 1H), 3.26 (dd, J=13.9, 10.1 Hz, 1H). $^{13}$C NMR (126 MHz, DMSO-$d_6$) δ 172.35, 160.73, 137.33, 135.64, 133.43, 133.01, 132.32, 128.41, 128.16, 128.01, 127.93, 127.87, 127.85, 126.89, 126.52, 126.02, 125.14, 120.01, 111.59, 101.95, 54.36, 52.57, 37.01. MS (ESI) m/z=463.1 [M+Na]$^+$ (S)-2-(4,6-Dichloro-1H-indole-2-carboxamido)-3-(naphthalen-2-yl)propanoic acid (68 h). $^1$H NMR (500 MHz, DMSO-$d_6$) δ 14.01 (s, 1H), 8.86 (s, 1H), 7.82-7.66 (m, 4H), 7.60 (d, J=6.4 Hz, 1H), 7.49-7.30 (m, 3H), 7.14 (d, J=1.7 Hz, 1H), 6.96 (d, J=3.2 Hz, 1H), 4.70-4.45 (m, 1H), 3.37-3.32 (m, 1H), 3.14 (dd, J=13.5, 8.0 Hz, 1H). MS (ESI) m/z=449.1 [M+Na]$^+$ Biochemical Characterizations: Fluorescence polarization (FP) assays to determine the inhibitory activities of final products 2-55 for disruption of the β-catenin/Tcf protein-protein interaction and the inhibitory selectivities for β-catenin/Tcf over β-catenin/E-cadherin and β-catenin/APC interactions.

Peptides, and Protein Expression and Purification. Wild-type human β-catenin (residues 138-781) were cloned into a pET-28b vector carrying a C-terminal 6× histidine (Novagen) and transformed into Escherichia coli BL21 DE3 (Novagen). Cells were cultured in LB medium with 30 µg/mL kanamycin until the $OD_{600}$ was approximately 0.8. The protein expression was then induced with 400 µM of IPTG at 16° C. overnight. Cells were lysed by sonication. The proteins were purified by two steps of chromatography, including Ni-NTA affinity chromatography (30210, Qiagen) and size-exclusion chromatography with a HiLoad 26/600 Superdex 200 µg column (28-9893-36, GE Healthcare Life Science) using an AKTA Pure FPLC system (GE Healthcare Life Science). Protein was eluted in a buffer containing 20 mM Tris (pH 8.5), 100 mM NaCl, and 2 mM DTT. The purity of β-catenin was greater than 95% as determined by SDS-PAGE gel analysis.

Thermal-shift assay was performed on an CFX96 Real Time System (Bio-Rad) to monitor protein stability and detect protein aggregation. Protein unfolding was evaluated through measuring the fluorescence changes of fluorescent dye Sypro Orange when interacting with wild-type or mutant β-catenin proteins. A temperature increment of 1°/min was applied. All proteins were stable, and no aggregation was observed under storage or assay conditions. Proteins were aliquoted and stored at −80° C.

C-terminally fluorescein-labeled human Tcf4 (residues 7-51), C-terminally fluorescein-labeled human E-cadherin (residues 819-873), and C-terminally fluorescein-labeled human APC-R3 (residues 1477-1519) were synthesized by InnoPep, Inc. (http://www.innopep.com/) and HPLC purified with purity >95%. The structures were validated by LC/MS (liquid chromatography/mass spectrometry). The sequences of these peptides were reported in the previous paper.

FP Competitive Inhibition Assays. Experiments were performed in 96-well Microfluor 2 black plates on a Synergy 2 plate reader (Biotek). The polarization was measured at room temperature with an excitation wavelength at 485 nm and an emission wavelength at 535 nm. The FP experiments were performed in an assay buffer of 25 mM Hepes (pH 7.4), 100 mM NaCl, 0.01% Triton X-100, and 100 µg/ml γ-globulin. The final reaction volume was set to 100 µL. For the β-catenin/Tcf assay, 10 nM human β-catenin (residues 138-781) was incubated with 2.5 nM C-terminally fluorescein-labeled human Tcf4 (residues 7-51) for 30 min at 4° C., and then different concentrations of the compound in assay buffer were added. The negative control (equivalent to 0% inhibition) refers to 2.5 nM Tcf4 fluorescence tracer and 10 nM β-catenin in assay buffer without the tested compound. The positive control (equivalent to 100% inhibition) refers to only 2.5 nM Tcf4 fluorescence tracer in assay buffer. For the β-catenin/cadherin assay, 150 nM human β-catenin (residues 138-781) was incubated with 5 nM C-terminally fluorescent-labeled human E-cadherin (residues 819-873) in assay buffer for 30 min at 4° C. The negative control refers to 5 nM E-cadherin fluorescence tracer and 150 nM β-catenin in assay buffer with no inhibitor presenting. The positive control refers to 5 nM E-cadherin fluorescence tracer in assay buffer. For the β-catenin/APC-R3 assay, 2000 nM human β-catenin (residues 138-781) was incubated with 5 nM of C-terminally fluorescent-labeled human APC-R3 (residues 1477-1519) in assay buffer for 30 min at 4° C. The negative control refers to 5 nM APC-R3 fluorescence tracer and 2,000 nM β-catenin in assay buffer without the tested compound. The positive control refers to 5 nM APC-R3 fluorescence tracer in assay buffer. Each assay plate was covered black and gently mixed on an orbital shaker at 4° C. for 2.5 h to reach equilibrium before the polarization values were read. The background of the tested inhibitors was corrected by subtracting the raw intensity values of the sample background well (all components except probe) from the raw intensity values of the corresponding test wells (all components). The $IC_{50}$ values were determined by GraphPad Prism 5.0. The $K_i$ values were derived from the $IC_{50}$ values. All of the experiments were performed in triplicate and carried out in the presence of 1% DMSO for small-molecule inhibitors. The results were expressed as mean±standard deviation. The Tcf/cahderin selectivity ratios were calculated on the basis of the respective $K_i$ value of the β-catenin/E-cadherin interaction over that of the β-catenin/Tcf4 interaction. The Tcf/APC selectivity ratios were calculated on the basis of the respective $K_i$ value of the β-catenin/APC-R3 interaction over that of the β-catenin/Tcf4 interaction.

The results are shown in Tables 1-5.

TABLE 1

FP Competitive Inhibition Assay Results of Inhibitors 9-19.[a]

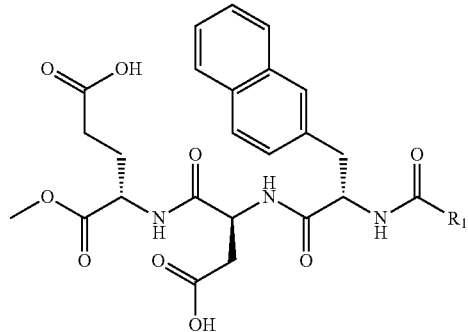

| No. | $R_1$ | $K_i \pm$ SD (μM) | No. | $R_1$ | $K_i \pm$ SD (μM) |
|---|---|---|---|---|---|
| | | | 11 | [indole-6-Cl] | 89 ± 8.6 |
| | | | 12 | [indole-5-F] | 89 ± 8.6 |
| | | | 13 | [indole-5-Br] | 16 ± 1.7 |
| | | | 14 | [indole-5-C] | >100 |
| | | | 15 | [indole] | >100 |
| | | | 16 | [indole-5-] | 12 ± 1.0 |
| | | | 17 | [indole-5-N] | 17 ± 1.5 |
| | | | 18 | [indole-5-,7-Cl] | 9.7 ± 1.0 |

TABLE 1-continued

FP Competitive Inhibition Assay Results of Inhibitors 9-19.[a]

| No. | R₁ | $K_i \pm SD$ (μM) | No. | R₁ | $K_i \pm SD$ (μM) |
|---|---|---|---|---|---|
| 9 | (2,3-divinyl-1H-pyrrol-2-yl) | 11 ± 0.92 | 19 | 4-chloro-6-methyl-1H-indol-2-yl | 4.3 ± 0.34 |
| 10 | 4-chloro-1H-indol-2-yl | 15 ± 1.3 | | | |

[a]Each set of data was expressed as mean ± standard deviation (n = 3)

TABLE 2

FP Competitive Inhibition Assay Results of Inhibitors 20-38.[a]

| No. | R₂ | $K_i \pm SD$ (μM) | No. | R₂ | $K_i \pm SD$ (μM) |
|---|---|---|---|---|---|
| 20 | isohexyl | 8.5 ± 0.98 | 30 | 4-(trifluoromethyl)phenyl | 1.9 ± 0.20 |
| 21 | phenyl | 3.3 ± 0.64 | 31 | 3-(trifluoromethyl)phenyl | 2.3 ± 0.17 |

TABLE 2-continued
FP Competitive Inhibition Assay Results of Inhibitors 20-38.[a]
| No. | R₂ | $K_i \pm$ SD (µM) | No. | R₂ | $K_i \pm$ SD (µM) |
|---|---|---|---|---|---|
| 22 |  | 7.6 ± 0.94 | 32 |  | 2.6 ± 0.37 |
| 23 | 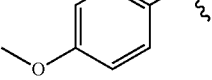 | 8.9 ± 0.91 | 33 |  | 2.4 ± 0.31 |
| 24 |  | 4.5 ± 0.88 | 34 | 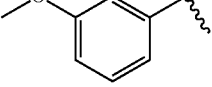 | 1.9 ± 0.13 |
| 25 |  | 3.3 ± 0.37 | 35 |  | 2.2 ± 0.15 |
| 26 |  | 3.6 ± 0.74 | 36 | 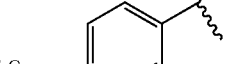 | 3.3 ± 0.26 |
| 27 |  | 2.7 ± 0.50 | 37 |  | 2.6 ± 0.20 |
| 28 |  | 3.1 ± 0.51 | 38 | 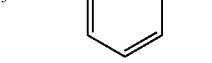 | 2.5 ± 0.83 |

TABLE 2-continued
FP Competitive Inhibition Assay Results of Inhibitors 20-38.[a]
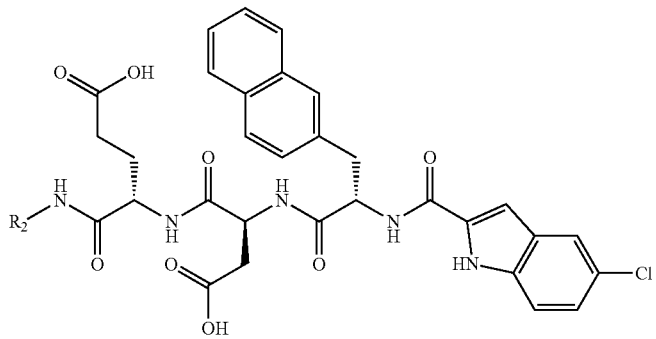
| No. | R₂ | $K_i$ ± SD (μM) | No. | R₂ | $K_i$ ± SD (μM) |
|---|---|---|---|---|---|
| 29 | 2-Cl-phenyl | 9.6 ± 2.1 | | | |
[a]Each set of data was expressed as mean ± standard deviation (n = 3).
TABLE 3
FP Competitive Inhibition Assay Results of Inhibitors 39-46.[a]
| No. | R₃ | $K_i$ ± SD (μM) | No. | R₃ | $K_i$ ± SD (μM) |
|---|---|---|---|---|---|
| 39 | isopropyl | 70 ± 9.5 | 3 | 4-CF₃-phenyl | 9.3 ± 1.2 |
| 40 | 3,4-diCl-phenyl | 3.7 ± 0.58 | 4 | 4-CN-phenyl | 20 ± 1.7 |
| 41 | 4-Cl-phenyl | 11 ± 1.0 | 5 | 4-OCH₃-phenyl | 25 ± 1.9 |

TABLE 3-continued
FP Competitive Inhibition Assay Results of Inhibitors 39-46.[a]
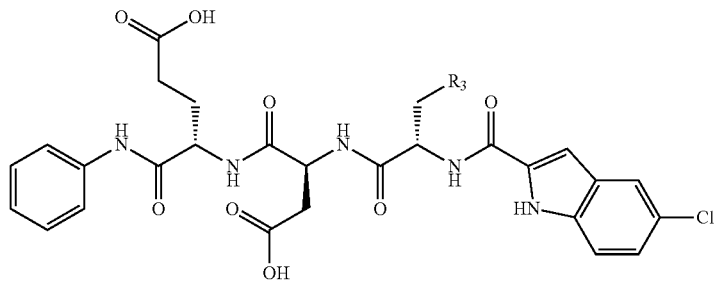
| No. | R$_3$ | K$_i$ ± SD (μM) | No. | R$_3$ | K$_i$ ± SD (μM) |
|---|---|---|---|---|---|
| 42 | 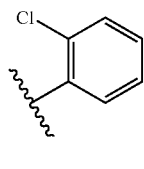 [SMILES: *c1ccccc1Cl] | 14 ± 0.89 | 6 | 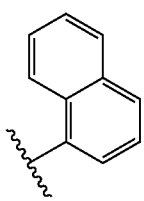 [SMILES: *c1cccc2ccccc12] | 2.9 ± 0.45 |
[a] Each set of data is expressed as mean ± standard deviation (n = 3)
Table 4
FP Competitive Inhibition Assay Results of Inhibitors 47-49.[a]
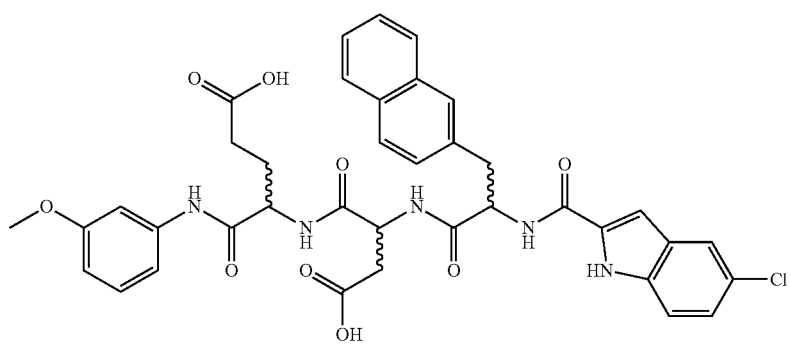 [SMILES: COc1cccc(NC(=O)C(CCC(=O)O)NC(=O)C(CC(=O)O)NC(=O)C(Cc2ccc3ccccc3c2)NC(=O)c2cc3cc(Cl)ccc3[nH]2)c1]
| No. | R,S | K$_i$ ± SD (μM) |
|---|---|---|
| 47 | R, S, S | 10 ± 0.73 |
| 48 | S, R, S | 6.6 ± 0.42 |
| 49 | S, S, R | 8.0 ± 0.42 |
[a] Each set of data is expressed as mean ± standard deviation (n = 3)

TABLE 5
FP Competitive Inhibition Assay Results of Inhibitors 50-57.[a]
| No. | $R_4$ | $R_5$ | $K_i \pm$ SD (μM) |
|---|---|---|---|
| 50 | $CH_2CONH_2$ | COOH | 6.7 ± 0.60 |
| 51 | $CH_2COOH$ | $CONH_2$ | 10 ± 0.88 |
| 52 | 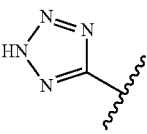 | COOH | 1.5 ± 0.066 |
| 53 | $CH_2COOH$ | 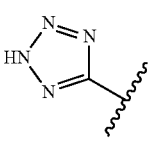 | 0.64 ± 0.12 |
| 54 | 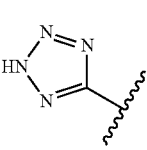 | $CONH_2$ | 4.9 ± 0.58 |
| 55 | $CH_2CONH_2$ | 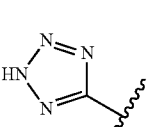 | 3.9 ± 0.16 |
| 56 | $CH_2COOEt$ | 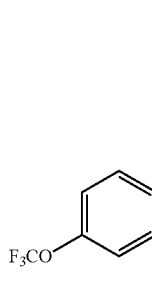 | 5.2 ± 0.070 |
| 57 | 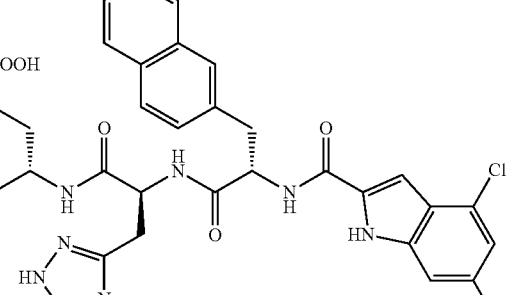 | | 0.44 ± 0.098 |
[a]Each set of data was expressed as mean ± standard deviation (n = 3).

Inhibitor selectivity between β-catenin/Tcf, β-catenin/E-cadherin, and β-catenin/APC PPIs. β-Catenin not only interacts with Tcf/Lef, BCL9/B9L, CBP/p300, etc. to culminate Wnt/β-catenin signaling, but also forms the complexes with E-cadherin and APC, respectively, to play the specific roles in cells. The PPI between β-catenin and E-cadherin is essential for cell-cell adhesion, while the β-catenin/APC PPI is critical for β-catenin phosphorylation and degradation. The crystallographic analyses of β-catenin in complexes with Tcf, E-cadherin, and APC indicated that β-catenin uses the same armadillo repeats to bind Tcf/Lef, cadherin, and APC. Biochemical analyses confirmed that the binding mode of Tcf, cadherin, and APC to β-catenin is identical and mutually exclusive. The selectivities of 53 and 57 between β-catenin/Tcf4, β-catenin/Ecadherin, and β-catenin/APC-R3 interactions were quantified using the FP selectivity assay. As shown in Table 6, the selectivities of 53 and 57 for β-catenin/Tcf4 over β-catenin/E-cadherin interactions and β-catenin/APC-R3 interactions are 50-, 137-, and 30-, 395-fold, respectively.

TABLE 6

The selectivities of 53 and 57 for β-catenin/Tcf over β-catenin/E-cadherin interactions and β-catenin/APC interactions. [a]

| Compounds | $K_i \pm SD$ (μM) | | | Selectivity | |
|---|---|---|---|---|---|
| | β-catenin/ TCF | β-catenin/ E-cadherin | β-catenin/ APC | TCF/ E-cadherin | TCF/ APC |
| 53 | 0.64 ± 0.12 | 32 ± 2.8 | 88 ± 7.3 | 50 | 137 |
| 57 | 0.44 ± 0.098 | 13 ± 0.60 | 173 ± 15 | 31 | 395 |

[a] Each set of data was expressed as mean ± standard deviation (n = 3).

Cell-Based Characterization.

MTS cell viability assay. Colorectal cancer cells (SW480 and HCT116), breast cancer cells (MDA-MB-231, MDA-MB-468, and BT-20), and lung cancer cells A549 were seeded in 96-well plates at $5 \times 10^3$ cells/well, maintained overnight at 37° C., and incubated with the tested compounds at various concentrations. Cell viability was monitored after 72 h using a freshly prepared mixture of 1 part phenazine methosulfate (PMS, Sigma) solution (0.92 mg/mL) and 19 parts 3-(4,5-dimethylthiazol-2-yl)-5-(3-carboxymethoxyphenyl)-2-(4-sulfophenyl)-2H-tetrazolium (MTs, Promega) solution (2 mg/mL). Cells were incubated in 10 μL of this solution at 37° C. for 3 h, and $A_{490}$ was measured. The effect of each compound is expressed as the concentration required to reduce $A_{490}$ by 50% ($IC_{50}$) relative to DMSO-treated cells. Experiments were performed in triplicate.

MTS tetrazolium cell viability assays were performed to evaluate the effect of β-catenin/Tcf inhibitors on growth of different cancer cell lines with hyperactive Wnt signaling, including colorectal cancer cells (SW480 and HCT116) and TNBC cells (MDA-MB-231, MDA-MB-468, and BT-20), and one cancer cell line with normal Wnt signaling, A549. The half maximal inhibitory concentrations ($IC_{50}$) of two representative compounds (55 and 56) are shown in Table 7. Both compounds inhibited viability of Wnt/pt-catenin hyperactive cancer cells. Compound 56 is selective for Wnt/β-catenin hyperactive cancer cells over Wnt/β-catenin normal cancer cells.

TABLE 7

The MTS assay to monitor the inhibitory activities of 55 and 56 on viability of cancer cells. [a]

MTs $IC_{50} \pm SD$ (μM)

| No. | Wnt/β-catenin hyperactive | | | | | Wnt/β-catenin normal |
|---|---|---|---|---|---|---|
| | SW480 | HCT116 | MDA-MB-231 | MDA-MB-468 | BT-20 | A549 |
| 5 | 28.2 ± 4.63 | 63.9 ± 7.48 | 34.3 ± 6.42 | 29.2 ± 4.02 | 38.4 ± 3.99 | 60.3 ± 10.5 |
| 6 | 14.1 ± 2.86 | 69.4 ± 7.21 | 12.3 ± 2.16 | 7.25 ± 0.72 | 16.5 ± 2.23 | 86.4 ± 8.58 |

[a] Each set of data was expressed as mean ± standard deviation (n = 3).

Cell transfection and luciferase assay. FuGENE 6 (E2962, Promega) in a 96-well plate format was used for the transfection of HEK293 cells according to the manufacturer's instructions. HEK293 cells were co-transfected with 45 ng of the TOPFlash or FOPFlash reporter gene, 135 ng of pcDNA3.1-β-catenin and 20 ng of pCMV-RL normalization reporter gene. Cells were cultured in DMEM and 10% fatal bovine serum at 37° C. for 24 h, and different concentrations of inhibitors were then added. After 24 h, the luciferase reporter activity was measured using the Dual-Glo system (E2940, Promega). Normalized luciferase activity in response to the treatment with the inhibitors was compared with that obtained from the cells treated with DMSO. Experiments were performed in triplicate.

The suppressing effect of the inhibitors on transactivation of β-catenin signaling was evaluated by the TOPFlash/FOPFlash luciferase reporter assay. As shown in FIG. 1, compounds 55 and 56 inhibited the TOPFlash (in which the luciferase reporter has three wild-type Tcf4 binding sites) luciferase activities in a dose-dependent manner, while did not inhibit the FOPFlash (with three mutant Tcf4 binding sites) luciferase reporter activities, indicating they are specific for the Wnt/β-catenin signaling pathway.

Co—IP experiments. Two sets of co-IP experiments were conducted: one is the inhibitor was added onto the cell lysates, and the second is the inhibitor was added onto the live cells. For the cell lysate co-IP experiments, SW480 cells were lysed in buffer A containing 50 mM Tris, pH 7.4, 150 mM NaCl, 1% Nonidet P-40, 2 mM EDTA, and protease inhibitors. Different concentrations of the inhibitor were incubated with the SW480 cell lysates at 4° C. for 4 h. For the whole cell co-IP experiments, HCT116 cells at $1 \times 10^6$/mL were treated with different concentrations of the inhibitor for 24 h. Cells were then lysed in buffer containing 50 mM Tris, pH 7.4, 150 mM NaCl, 1% Nonidet P-40, 2 mM EDTA, and protease inhibitors. For both cell lysate and whole cell co-IP experiments, the lysates were preadsorbed to A/G plus agarose (sc-2003, Santa Cruz Biotechnology, Inc.) at 4° C. for 1 h. Preadsorbed lysates were incubated with a specific primary antibody overnight at 4° C. A/G plus agarose was then added to the lysates mixture and incubated for 3 h. The beads were washed 5 times with the lysis buffer at 4° C. The bound protein was eluted by boiling in the SDS sample buffer and loaded onto 8% SDS polyacrylamide gel for electrophoretic analysis. Separated proteins were transferred onto nitrocellulose membranes for immunoblot analysis. The primary antibodies were against β-catenin (610153, BD Biosciences) and Tcf4 (05-511, Millipore), E-cadherin (610404, BD Biosciences), and APC (MAB3785, Millipore). IRDye 680LT goat antimouse IgG (827-11080, LiCOR) was used as the secondary antibody. The images were detected by the Odyssey infrared imaging system (LiCOR). Experiments were performed in duplicate.

Figures 2A, 2B, 2C, 2D:
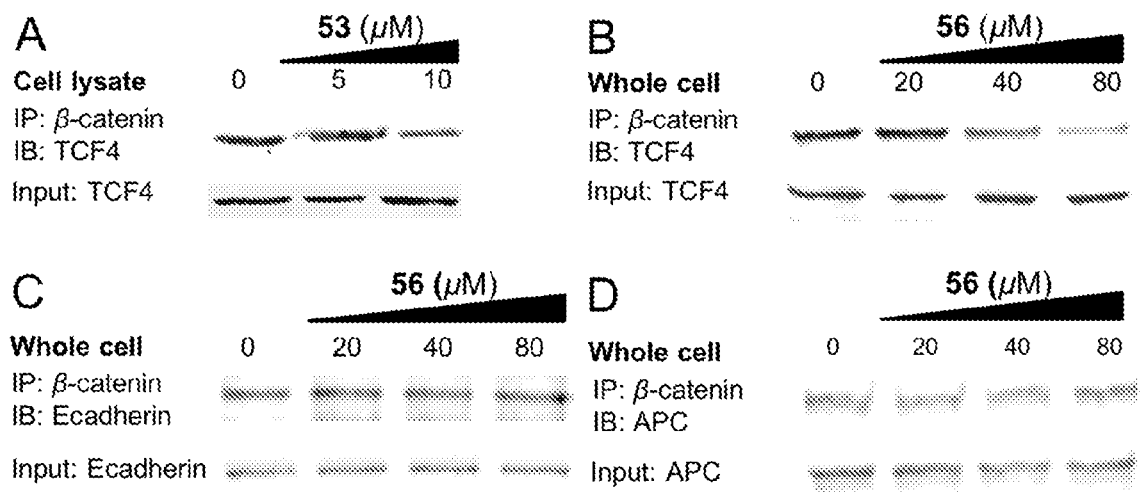
FIGS. 2A-2D show co-IP experiments to evaluate the disruption of the β-catenin/TCF PPI by inhibitor 53 in SW480 cell lysate (FIG. 2A), and co-IP experiments to evaluate the disruption of the β-catenin/Tcf PPI by inhibitor 56 and the inhibitory selectivity of inhibitor 56 for β-catenin/Tcf over β-catenin/E-cadherin and β-catenin/APC PPIs using HCT116 cells. IP, immunoprecipitation; IB, immunoblotting; input, 10% of cell lysate. Each experiment was performed in duplicate.

The co-immunoprecipitation (co-IP) experiments were conducted to assess the effect of the inhibitors for disruption of the interaction between β-catenin and Tcf using SW480 cell lysates. The results were shown in FIG. 2. Compound 53 can disrupt the interaction between full-length β-catenin and full-length Tcf in a dose-dependent manner after 4 h incubation with SW480 cell lysates. The effect of 56, the prodrug form of 53, on disruption of the β-catenin/Tcf PPI and on the selectivity between three PPIs in the cellular context were also evaluated by the co-IP experiments using HCT116 cells. As shown in FIG. 2, compound 56 dose-dependently inhibited the β-catenin/Tcf PPI, but had no effect on the β-catenin/E-cadherin and β-catenin/APC PPIs at the concentrations that were sufficient to disrupt the β-catenin/Tcf PPI.

Scratch wound healing assay. To the confluent monolayer of MDA-MB-231 cells in 24-well plates, wounds will be made by scraping a sterile 200 μL pipette tip. Cells were maintained in DMEM containing 10% FBS with 10 μg/mL mitomycin to inhibit cell proliferation. Images of wounds were taken immediately and 14 h after wounding.

Figures 3A, 3B:
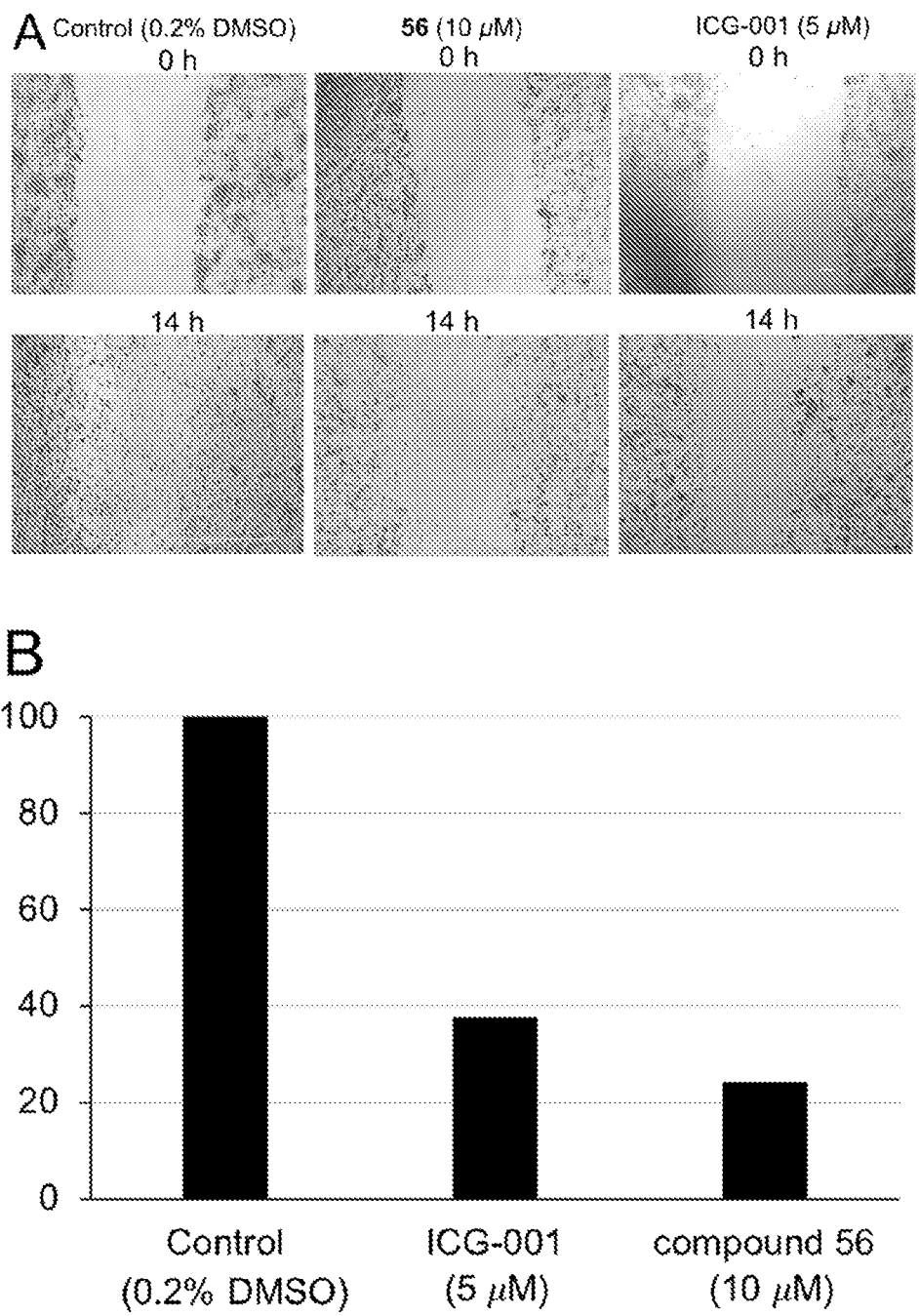
FIGS. 3A-3B show wound-healing assays demonstrating that inhibitor 56 (10 μM) inhibited the migration of human TNBC MDA-MB-231 cells induced by serum (10% in media) (FIG. 3A). Control, 0.2% DMSO in 10% FBS. The β-catenin/CBP inhibitor ICG-001 (5 μM) was assessed in parallel. In all experiments, mitomycin (10 μg/mL) was added to inhibit cell proliferation and allow examination of the effects on cell migration.

Matrigel invasion assay. MDA-MB-231 cells ($5 \times 10^4$) suspended in 200 μL starvation medium were added to the upper chamber of a Matrigel coated insert (6.5 mm diameter, 8 mm pore size; Corning 353097), and the insert was placed in a 24-well plate containing 600 mL DMEM medium with 10% FBS. Inhibitors were added to both upper and the lower chambers. Invasion assays were performed for 24 h and cells were fixed with 3.7% formaldehyde. Cells were stained with crystal violet staining solution. The cells on the upper side of the insert were removed with a cotton swab. Five randomly selected fields (×10 objectives) on the lower side of the insert were photographed, and the invaded cells were counted.

β-Catenin signaling induces and maintains migration, invasion and metastasis of cancer cells, including TNBC cells. Scratch wound healing and Matrigel invasion assays using TNBC MDA-MB-231 cells were conducted. As shown in FIG. 3, compound 56 can effectively inhibit TNBC cell migration (FIG. 3A) and invasion (FIG. 3B) at 10 μM. The effects are comparable to that of the β-catenin/CBP inhibitor ICG-001 at 5 μM.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound having Formula I,

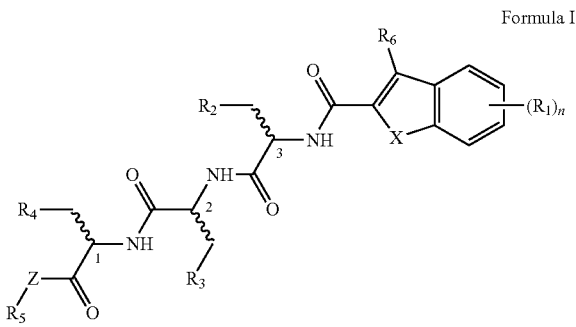

wherein

X is N—$R_a$, wherein $R_a$ is selected from hydrogen or $C_1$-$C_3$ alkyl;

Z is selected from O or N—$R_a$, wherein $R_a$ is selected from hydrogen or $C_1$-$C_3$ alkyl;

$R_1$ is absent or independently for each occurrence, selected from halogen, $C_1$-$C_3$ alkyl, $C_1$-$C_3$ alkoxy, $C_1$-$C_3$ haloalkyl, $C_1$-$C_3$ haloalkoxy, $C_1$-$C_3$ alkoxy, hydroxyl, amino, cyano, nitro, or isocyano;

$R_2$ is $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, alkylaryl, alkylheteroaryl, wherein $R_2$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ and $R_4$ are independently halogen, hydroxyl, amino, —CN, $C_1$-$C_6$ alkyl, $C_1$-$C_6$ haloalkyl, —R'CO$_2$H, —R'CONH$_2$, —R'CONHR'', —R'CONR''R''', —R'CO$_2$R''', —R'SO$_3$H, —R'SO$_2$NHCOR'', —R'CONHSO$_2$R'', —R'CONHOH, —R'CONHCN, —R'SO$_2$NHR'', $C_3$-$C_6$ cycloalkyl, $C_1$-$C_8$ heterocycloalkyl, $C_5$-$C_{10}$ aryl, $C_1$-$C_8$ heteroaryl, wherein $R_3$ and $R_4$ are optionally substituted with halogen, hydroxyl, amino, cyano, nitro, isocyano, carboxyl, hydroxyl, alkyl, alkoxy, alkenyl, haloalkyl, haloalkoxy, cyclopropyl, and wherein R', R'', and R''' are independently absent or is hydrogen, halogen, $C_1$-$C_6$ alkyl, $C_1$-$C_6$ alkoxy, $C_1$-$C_6$ haloalkyl;

$R_5$ is $C_1$-$C_6$ alkyl, $C_1$-$C_6$ alkoxy, $C_3$-$C_8$ cycloalkyl, a $C_1$-$C_7$ heterocycloalkyl, $C_5$-$C_{10}$ aryl, alkylaryl, $C_1$-$C_8$ heteroaryl, alkylheteroaryl, wherein $R_5$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_6$ is hydrogen, $C_1$-$C_6$ alkyl, $C_1$-$C_6$ alkoxy, halogen, or $C_1$-$C_3$ haloalkyl, n is 0, 1, 2, 3, or 4;

wherein positions labeled 1, 2, and 3 indicate chiral positions; or a pharmaceutically acceptable salt or ester thereof.

2. The compound of claim 1, having a structure as represented by Formula I-A:

Formula I-A

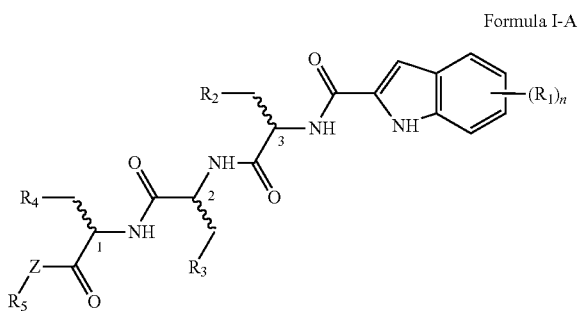

wherein

Z is selected from O or N—$R_a$, wherein $R_a$ is selected from hydrogen or $C_1$-$C_3$ alkyl;

$R_1$ is absent or independently for each occurrence, selected from halogen, $C_1$-$C_3$ alkyl, $C_1$-$C_3$ alkoxy, $C_1$-$C_3$ haloalkyl, $C_1$-$C_3$ haloalkoxy, $C_1$-$C_3$ alkoxy, hydroxyl, amino, cyano, nitro, or isocyano;

$R_2$ is $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, alkylaryl, alkylheteroaryl, wherein $R_2$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_3$ and $R_4$ are independently halogen, hydroxyl, amino, —CN, $C_1$-$C_6$ alkyl, $C_1$-$C_6$ haloalkyl, —R'CO$_2$H, —R'CONH$_2$, —R'CONHR", —R'CONR"R''' ", —R'CO$_2$R''', —R'SO$_3$H, —R'SO$_2$NHCOR", —R'CONHSO$_2$R", —R'CONHOH, —R'CONHCN, —R'SO$_2$NHR", $C_3$-$C_6$ cycloalkyl, $C_1$-$C_8$ heterocycloalkyl, $C_5$-$C_{10}$ aryl, $C_1$-$C_8$ heteroaryl, wherein $R_3$ and $R_4$ are optionally substituted with halogen, hydroxyl, amino, cyano, nitro, isocyano, carboxyl, hydroxyl, alkyl, alkoxy, alkenyl, haloalkyl, haloalkoxy, cyclopropyl, and wherein R', R", and R''' are independently absent or is hydrogen, halogen, $C_1$-$C_6$ alkyl, $C_1$-$C_6$ alkoxy, $C_1$-$C_6$ haloalkyl;

$R_5$ is $C_1$-$C_6$ alkyl, $C_1$-$C_6$ alkoxy, $C_3$-$C_8$ cycloalkyl, a $C_1$-$C_7$ heterocycloalkyl, $C_5$-$C_{10}$ aryl, alkylaryl, $C_1$-$C_8$ heteroaryl, alkylheteroaryl, wherein $R_5$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

n is 0, 1, 2, 3, or 4;

wherein positions labeled 1, 2, and 3 indicate chiral positions; or a pharmaceutically acceptable salt or ester thereof.

3. The compound of claim 1, wherein X is N—H.

4. The compound of claim 1, wherein Z is selected from O or N—H.

5. The compound of claim 1, wherein $R_1$, independently for each occurrence, is selected from a halogen, $C_1$-$C_3$ alkoxy, $C_1$-$C_3$ haloalkyl, $C_1$-$C_3$ alkoxy, $C_1$-$C_3$ alkyl, or nitro.

6. The compound of claim 1, wherein $R_1$ is absent.

7. The compound of claim 1, wherein $R_2$ is a $C_6$-$C_{10}$ aryl, wherein $R_2$ is optionally substituted with one or more groups selected from halogen, $C_1$-$C_6$ haloalkyl, $C_1$-$C_6$ haloalkoxy, or cyano.

8. The compound of claim 1, wherein $R_2$ is $C_1$-$C_6$ alkyl.

9. The compound of claim 1, wherein $R_3$ is selected from $C_1$-$C_5$ heterocycloalkyl, $C_1$-$C_5$ heteroaryl, R'CO$_2$H, or R'CONH$_2$, wherein R' is absent or selected from a $C_1$-$C_6$ alkyl.

10. The compound of claim 1, wherein $R_3$ is selected from an imidazole, pyrazole, triazole, or tetrazole.

11. The compound of claim 1, wherein $R_3$ is selected from CO$_2$H, or CONH$_2$.

12. The compound of claim 1, wherein $R_4$ is selected from $C_1$-$C_5$ heterocycloalkyl, $C_1$-$C_5$ heteroaryl, R'CO$_2$H, R'CO$_2$R", or R'CONH$_2$, wherein R' and R" are independently absent or selected from hydrogen, a $C_1$-$C_6$ alkyl or a halogen.

13. The compound of claim 1, wherein $R_4$ is selected from an imidazole, pyrazole, triazole, or tetrazole.

14. The compound of claim 1, wherein $R_4$ is R'CO$_2$H, —R'CO$_2$R", or R'CONH$_2$, wherein R' and R" are independently hydrogen, $C_1$-$C_6$ alkyl or a halogen.

15. The compound of claim 1, wherein $R_5$ is $C_1$-$C_6$ alkoxy, $C_1$-$C_6$ alkyl, $C_5$-$C_8$ aryl, alkylaryl, $C_2$-$C_8$ heteroaryl, or alkylheteroalkyl, wherein $R_5$ is optionally substituted with one or more groups selected from halogen, hydroxyl, amino, cyano, carboxyl, hydroxyl, alkyl, alkoxy, alkenyl, haloalkyl, haloalkoxy, cycloalkyl, heterocycloalkyl, aryl, or heteroaryl.

16. The compound of claim 1, wherein $R_5$ is phenyl or benzyl, wherein $R_5$ is optionally substituted with one or more groups selected from halogen, hydroxyl, $C_1$-$C_6$ alkoxy, $C_1$-$C_6$ haloalkyl, or $C_1$-$C_6$ haloalkoxy.

17. The compound of claim 1, having a chiral designation of 1S,2S,3R; 1S,2R,3S; or 1R,2S,3S.

18. A pharmaceutical composition comprising a therapeutically effective amount of a compound of claim 1, or a pharmaceutically acceptable salt thereof, and a pharmaceutically acceptable carrier.

* * * * *